United States Patent
Walsh et al.

(10) Patent No.: US 10,165,941 B2
(45) Date of Patent: *Jan. 1, 2019

(54) OPTICAL COHERENCE TOMOGRAPHY-BASED OPHTHALMIC TESTING METHODS, DEVICES AND SYSTEMS

(71) Applicant: DOHENY EYE INSTITUTE, Los Angeles, CA (US)

(72) Inventors: Alexander C. Walsh, Los Angeles, CA (US); Paul G. Updike, Santa Barbara, CA (US); Srinivas R. Sadda, Pasadena, CA (US)

(73) Assignee: Doheny Eye Institute, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/349,970

(22) Filed: Nov. 11, 2016

(65) Prior Publication Data

US 2017/0119247 A1     May 4, 2017

Related U.S. Application Data

(63) Continuation of application No. 14/472,161, filed on Aug. 28, 2014, now Pat. No. 9,492,079, which is a
(Continued)

(51) Int. Cl.
*A61B 3/10*      (2006.01)
*A61B 3/117*     (2006.01)
(Continued)

(52) U.S. Cl.
CPC ............ *A61B 3/102* (2013.01); *A61B 3/0025* (2013.01); *A61B 3/0033* (2013.01);
(Continued)

(58) Field of Classification Search
CPC .......... A61B 3/14; A61B 3/0025; A61B 3/12; A61B 3/102; A61B 3/0058
(Continued)

(56) References Cited

U.S. PATENT DOCUMENTS 4,154,114 A    5/1979   Katz et al.
4,237,901 A    12/1980   Taenzer
(Continued)

FOREIGN PATENT DOCUMENTS

CA       2595324      7/2006
CA       2678506      8/2008
(Continued)

OTHER PUBLICATIONS

US 8,979,269, 03/2015, Walsh et al. (withdrawn)
(Continued)

*Primary Examiner* — Mohammed Hasan
(74) *Attorney, Agent, or Firm* — Knobbe Martens Olson & Bear LLP

(57) ABSTRACT

In accordance with one aspect of the present invention, an optical coherence tomography-based ophthalmic testing center system includes an optical coherence tomography instrument comprising an eyepiece for receiving at least one eye of a user or subject; a light source that outputs light that is directed through the eyepiece into the user's or subject's eye, an interferometer configured to produce optical interference using light reflected from the user's/subject's eye, an optical detector disposed so as to detect said optical interference; and a processing unit coupled to the detector. The ophthalmic testing center system can be configured to perform a multitude of self-administered functional and/or structural ophthalmic tests and output the test data.

19 Claims, 67 Drawing Sheets

Related U.S. Application Data continuation of application No. 13/054,481, filed as application No. PCT/US2009/051073 on Jul. 17, 2009, now Pat. No. 8,820,931, application No. 15/349,970, which is a continuation-in-part of application No. 15/249,151, filed on Aug. 26, 2016, which is a continuation of application No. 14/521,392, filed on Oct. 22, 2014, now abandoned, which is a continuation of application No. 13/717,508, filed on Dec. 17, 2012, now Pat. No. 9,149,182, which is a continuation of application No. 12/111,894, filed on Apr. 29, 2008, now Pat. No. 8,348,429.

(60) Provisional application No. 61/082,171, filed on Jul. 18, 2008, provisional application No. 61/082,175, filed on Jul. 18, 2008, provisional application No. 61/168,340, filed on Apr. 10, 2009, provisional application No. 61/180,837, filed on May 23, 2009, provisional application No. 61/221,552, filed on Jun. 29, 2009, provisional application No. 61/222,080, filed on Jun. 30, 2009, provisional application No. 61/040,084, filed on Mar. 27, 2008.

(51) Int. Cl.
  *A61B 5/00* (2006.01)
  *A61B 3/00* (2006.01)
  *A61B 3/113* (2006.01)
  *A61B 3/08* (2006.01)
  *A61B 3/028* (2006.01)
  *A61B 3/18* (2006.01)

(52) U.S. Cl.
  CPC .......... *A61B 3/0041* (2013.01); *A61B 3/0091* (2013.01); *A61B 3/028* (2013.01); *A61B 3/085* (2013.01); *A61B 3/113* (2013.01); *A61B 3/117* (2013.01); *A61B 3/18* (2013.01); *A61B 5/0066* (2013.01); *A61B 5/0073* (2013.01)

(58) Field of Classification Search
  USPC .................................................. 351/200–246
  See application file for complete search history.

(56) References Cited

U.S. PATENT DOCUMENTS

| | | |
|---|---|---|
| 4,393,366 A | 7/1983 | Hill |
| 4,479,931 A | 10/1984 | Lambrecht et al. |
| 4,764,006 A | 8/1988 | Hamano et al. |
| H574 H | 2/1989 | Merkel |
| 4,848,340 A | 7/1989 | Bille et al. |
| 4,872,217 A | 10/1989 | Kitayama |
| 4,930,512 A | 6/1990 | Henriksen et al. |
| 5,005,966 A | 4/1991 | Handler et al. |
| 5,056,522 A | 10/1991 | Matsumura et al. |
| 5,129,109 A | 7/1992 | Runckel |
| 5,141,302 A | 8/1992 | Arai et al. |
| 5,214,455 A | 5/1993 | Penney et al. |
| 5,369,454 A | 11/1994 | Reinstein et al. |
| 5,442,412 A | 8/1995 | Frey et al. |
| 5,467,104 A | 11/1995 | Furness, III et al. |
| 5,491,524 A | 2/1996 | Hellmuth et al. |
| 5,493,109 A | 2/1996 | Wei et al. |
| 5,543,866 A | 8/1996 | Van de Velde |
| 5,557,350 A | 9/1996 | Yano |
| 5,644,642 A | 7/1997 | Kirschbaum |
| 5,776,068 A | 7/1998 | Silverman et al. |
| 5,838,424 A | 11/1998 | Wawro et al. |
| 5,914,772 A | 6/1999 | Dyer |
| 6,019,103 A | 2/2000 | Carroll |
| 6,086,205 A | 7/2000 | Svetliza |
| 6,112,114 A | 8/2000 | Dreher |
| 6,293,674 B1 | 9/2001 | Huang et al. |
| 6,367,932 B1 | 4/2002 | Donaldson |
| 6,439,720 B1 | 8/2002 | Graves et al. |
| 6,450,643 B1 | 9/2002 | Wilson |
| 6,592,223 B1 | 7/2003 | Stern et al. |
| 6,609,794 B2 | 8/2003 | Levine |
| 6,619,799 B1 | 9/2003 | Blum et al. |
| 6,656,131 B2 | 12/2003 | Alster et al. |
| 6,687,389 B2 | 2/2004 | McCartney et al. |
| 6,692,436 B1 | 2/2004 | Bluth et al. |
| 6,705,726 B2 | 3/2004 | Tanassi et al. |
| 6,820,979 B1 | 11/2004 | Stark et al. |
| 6,939,298 B2 | 9/2005 | Brown et al. |
| 7,008,116 B2 | 3/2006 | Kobayashi et al. |
| 7,219,996 B2 | 5/2007 | Ichikawa |
| 7,233,312 B2 | 6/2007 | Stern et al. |
| 7,237,898 B1 | 7/2007 | Hohla et al. |
| 7,350,921 B2 | 4/2008 | Ridings |
| 7,370,966 B2 | 5/2008 | Fukuma et al. |
| 7,384,146 B2 | 6/2008 | Covannon et al. |
| 7,445,335 B2 | 11/2008 | Su et al. |
| 7,458,685 B2 | 12/2008 | Liang et al. |
| 7,549,752 B2 | 6/2009 | Peyman et al. |
| 7,614,747 B2 | 11/2009 | Foster |
| 7,618,372 B2 | 11/2009 | dela Houssaye |
| 7,744,221 B2 | 6/2010 | Wei et al. |
| 7,815,310 B2 | 10/2010 | Su et al. |
| 7,982,881 B2 | 7/2011 | Fercher et al. |
| 7,997,728 B2 | 8/2011 | Huang et al. |
| 8,002,410 B2 | 8/2011 | Shea |
| 8,079,711 B2 | 12/2011 | Stetson et al. |
| 8,100,530 B2 | 1/2012 | Zhou et al. |
| 8,348,429 B2 | 1/2013 | Walsh et al. |
| 8,372,411 B2 | 2/2013 | Meinke et al. |
| 8,381,729 B2 | 2/2013 | Freitag et al. |
| 8,820,931 B2 | 9/2014 | Walsh et al. |
| 9,149,182 B2 | 10/2015 | Walsh et al. |
| 9,226,856 B2 | 1/2016 | Walsh et al. |
| 9,492,079 B2 | 11/2016 | Walsh et al. |
| 2001/0025226 A1 | 9/2001 | Lavery |
| 2002/0021411 A1 | 2/2002 | Wilson |
| 2002/0080329 A1 | 6/2002 | Kasahara |
| 2002/0099305 A1 | 7/2002 | Fukushima et al. |
| 2002/0159030 A1 | 10/2002 | Frey et al. |
| 2003/0065636 A1 | 4/2003 | Peyrelevade |
| 2003/0232015 A1 | 12/2003 | Brown et al. |
| 2004/0019032 A1 | 1/2004 | North et al. |
| 2004/0036838 A1 | 2/2004 | Podoleanu et al. |
| 2004/0141152 A1 | 7/2004 | Marino et al. |
| 2004/0196432 A1 | 10/2004 | Su et al. |
| 2004/0254154 A1 | 12/2004 | Ashton |
| 2004/0260183 A1 | 12/2004 | Lambert et al. |
| 2005/0001980 A1 | 1/2005 | Spector |
| 2005/0041200 A1 | 2/2005 | Rich |
| 2005/0105044 A1 | 5/2005 | Warden et al. |
| 2005/0140981 A1 | 6/2005 | Waelti |
| 2006/0077347 A1 | 4/2006 | Liang et al. |
| 2006/0077348 A1 | 4/2006 | Gorin |
| 2006/0092376 A1 | 5/2006 | Baek et al. |
| 2006/0109423 A1 | 5/2006 | Wang |
| 2006/0119858 A1 | 6/2006 | Knighton et al. |
| 2006/0135859 A1 | 6/2006 | Iliff |
| 2006/0158655 A1 | 7/2006 | Everett et al. |
| 2006/0187462 A1 | 8/2006 | Srinivasan et al. |
| 2006/0195076 A1 | 8/2006 | Blumenkranz et al. |
| 2006/0203195 A1 | 9/2006 | Squire et al. |
| 2006/0257451 A1 | 11/2006 | Varner et al. |
| 2006/0284813 A1 | 12/2006 | Yamamoto et al. |
| 2006/0290885 A1 | 12/2006 | Covannon et al. |
| 2007/0008116 A1 | 1/2007 | Bergman et al. |
| 2007/0024868 A1 | 2/2007 | Izatt et al. |
| 2007/0030450 A1 | 2/2007 | Liang et al. |
| 2007/0032782 A1 | 2/2007 | Youssefi et al. |
| 2007/0055222 A1 | 3/2007 | Hohla et al. |
| 2007/0073113 A1 | 3/2007 | Squilla et al. |
| 2007/0081165 A1 | 4/2007 | Kilic et al. |
| 2007/0081166 A1 | 4/2007 | Brown et al. |
| 2007/0153233 A1 | 7/2007 | Campin et al. |
| 2007/0177104 A1 | 8/2007 | Lacombe et al. |

(56) References Cited

U.S. PATENT DOCUMENTS

| | | |
|---|---|---|
| 2007/0195269 A1 | 8/2007 | Wei et al. |
| 2007/0216909 A1 | 9/2007 | Everett et al. |
| 2007/0263171 A1 | 11/2007 | Ferguson et al. |
| 2007/0273831 A1 | 11/2007 | Liang et al. |
| 2007/0282313 A1 | 12/2007 | Huang et al. |
| 2007/0287932 A1 | 12/2007 | Huang et al. |
| 2007/0291228 A1 | 12/2007 | Huang et al. |
| 2007/0291277 A1 | 12/2007 | Everett et al. |
| 2008/0007694 A1 | 1/2008 | Wei et al. |
| 2008/0049186 A1* | 2/2008 | MacDougall ......... A61B 3/113 351/206 |
| 2008/0106696 A1 | 5/2008 | Buckland et al. |
| 2009/0141240 A1 | 6/2009 | Weitz et al. |
| 2009/0153796 A1 | 6/2009 | Rabner |
| 2010/0033678 A1* | 2/2010 | Foster ..................... A61B 3/18 351/223 |
| 2010/0100238 A1 | 4/2010 | Torian |
| 2010/0110377 A1 | 5/2010 | Maloca et al. |
| 2010/0277668 A1 | 11/2010 | Frank et al. |
| 2011/0047682 A1 | 3/2011 | Hedayat |
| 2012/0075584 A1* | 3/2012 | Stetson ............... A61B 5/0059 351/206 |
| 2012/0133888 A1 | 5/2012 | Gray et al. |
| 2012/0274897 A1 | 11/2012 | Narasimha-Iyer et al. |
| 2013/0010259 A1 | 1/2013 | Carnevale |
| 2013/0194545 A1 | 8/2013 | Ono |
| 2013/0308099 A1 | 11/2013 | Stack |
| 2014/0046193 A1 | 2/2014 | Stack |
| 2014/0185012 A1 | 7/2014 | Kanazawa et al. |
| 2015/0138503 A1 | 5/2015 | Walsh |
| 2016/0278630 A1 | 9/2016 | Walsh |
| 2017/0049318 A1 | 2/2017 | Walsh |
| 2017/0127932 A1 | 5/2017 | Walsh |
| 2017/0311796 A1 | 11/2017 | Walsh |
| 2017/0332899 A1 | 11/2017 | Walsh |

FOREIGN PATENT DOCUMENTS

| | | |
|---|---|---|
| CN | 1593329 A | 3/2005 |
| CN | 200 980 154 Y | 11/2007 |
| CN | 201 491 234 U | 5/2010 |
| DE | 10 2005 058220 | 6/2007 |
| EP | 0 697 611 | 2/1996 |
| EP | 1 775 545 | 4/2007 |
| EP | 1 858 402 | 11/2007 |
| EP | 1 864 608 | 12/2007 |
| EP | 2 124 713 | 12/2009 |
| JP | S55-10492 | 1/1980 |
| JP | S 57-29204 | 2/1982 |
| JP | S 57-153635 | 9/1982 |
| JP | 05-220113 | 8/1993 |
| JP | 11-225958 | 8/1999 |
| JP | 2004-528111 | 9/2004 |
| JP | 2005-803954 | 3/2005 |
| JP | 2005-531346 | 11/2005 |
| JP | 2012-161595 | 8/2012 |
| WO | WO 1999/57507 | 11/1999 |
| WO | WO 2002/088684 | 11/2002 |
| WO | WO 2004/002298 | 1/2004 |
| WO | WO 2005/079655 | 9/2005 |
| WO | WO 2006/078802 | 7/2006 |
| WO | WO 2007/065493 | 6/2007 |
| WO | WO 2007/139927 | 12/2007 |
| WO | WO 2007/142960 | 12/2007 |
| WO | WO 2008/101359 | 8/2008 |
| WO | WO 2009/095473 | 8/2009 |
| WO | WO 2009/120543 | 10/2009 |
| WO | WO 2009/120544 | 10/2009 |
| WO | WO 2009/128912 | 10/2009 |
| WO | WO 2009/131701 | 10/2009 |
| WO | WO 2010/009447 | 1/2010 |
| WO | WO 2010/009450 | 1/2010 |
| WO | WO 2010/117386 | 10/2010 |
| WO | WO 2003/073922 | 9/2013 |
| WO | WO 2014/074590 | 5/2014 |
| WO | WO 2014/158658 | 10/2014 |
| WO | WO 2017/048873 | 3/2017 |
| WO | WO 2017/190071 | 11/2017 |
| WO | WO 2017/190097 | 11/2017 |

OTHER PUBLICATIONS

"3D OCT-1000 | Topcon," Press Release Mar. 31, 2008, available from internet at http://www.topcon.co.jp/news/20080331-508.html, site visited Apr. 14, 2015.

"A New Level for Retinal Imaging: Topcon's 3D OCT-1000," Vision Care Product New Nov./Dec. 2007 pp. 1-2.

"American National Standard Occupational and Educational Personal Eye and Face Protection Devices," available from internet at https://law.resource.org/pub/us/cfr/ibr/002/ansi.z87.1.2003.html, apparently available Jun. 2003, site visited Nov. 23, 2015.

"Topcon Medical Systems Releases 3D OCT-1000 TrueMapTM Software Version 2.12," Topcon Press Release Feb. 8, 2008, pp. 1-2.

Bachmann, et al., Heterodyne Fourier domain optical coherence tomography for full range probing with high axial resolution; Optics Express; vol. 14; Issue No. 4; pp. 1487-1496, Feb. 20, 2006.

Bigelow, et al., Compact multimodal adaptive-optics spectral-domain optical coherence tomography instrument for retinal imaging; J.Opt. Soc., Am. A.; vol. 24; Issue No. 5; pp. 1327-1336, May 2007.

Bowd, C., et al., "Bayesian Machine Learning Classifiers for Combining Structural and Functional Measurements to Classify Healthy and Glaucomatous Eyes," Investigative Ophthalmology & Visual Science, Mar. 2008, 49(3): 945-953.

Boyer, K.L., et al. "Automatic Recovery of the Optic Nervehead Geometry in Optical Coherence Tomography," IEEE Transactions on Medical Imaging, May 2006, 25(5): 553-570.

Brochure for Optical Coherence Tomography 3D OCT-1000 Mark II, in 12 pages.

Brochure for Optical Coherence Tomography 3D OCT-1000 Mark II, in 11 pages. Copyright 2008.

Bu, et al., Full-range parallel Fourier-domain optical coherence tomography using sinusoidal phase-modulating interferometry; Journal of Optics A: Pure and Applied Optics; vol. 9; pp. 422-426, Mar. 2007.

Burgansky-Eliash, et al., Optical Coherence Tomography Machine Learning Classifiers for Glaucoma Detection: A Preliminary Study, Investigative Ophthalmology & Visual Science; vol. 46; No. 11; pp. 4147-4152, Nov. 2005.

Chang, et al.; New developments in optical coherence tomography for glaucoma, CUff Opin Ophthalmol; vol. 19; Issue No. 2; pp. 127-135; Mar. 2008.

Drexler, et al., State-of-the-art retinal optical coherence tomography; Progress in Retinal and Eye Research; vol. 27; Issue 1; pp. 45-88; Jan. 2008.

Fernandez, Delineating Fluid-Filled Region Boundaries in Optical Coherence Tomography Images of the Retina; IEEE Transactions on Medical Imaging; vol. 24; Issue No. 8; pp. 929-945, Aug. 2005.

Ghosn, et al., Nondestructive Quantification of Analyte Diffusion in Cornea and Sclera Using Optical Coherence Tomography; investigative Ophthalmology & Visual Science; vol. 48, No. 6, pp. 2726-2733, Jun. 2007.

Guo et al., "En face optical coherence tomography" a new method to analyse structural changes of the optic nerve head in rat glaucoma, British Journal of Ophthalmology, Sep. 2005, vol. 89, Issue 9, pp. 1210-1216.

Huang, et al., Development and Comparison of Automated Classifiers for Glaucoma Diagnosis Using Stratus Optical Coherence Tomography; Investigative Ophthalmology & Visual Science; vol. 46; Issue No. 11; pp. 4121-4129, Nov. 2005.

Keystone View; Computer Controlled vision Screeners http://www.keystoneview.com?p=cv&id=39, 2 pages, 2003.

(56) References Cited

OTHER PUBLICATIONS

Koizumi et al: "Three-Dimensional Evaluation of Vitreonacular Traction and Epiretinal Membrane Using Spectral-Domain Optical Coherence Tomography" American Journal of Ophthalmology, Ophthalmic Publ, Chicago, IL, US, vol. 145, No. 3, Jan. 11, 2008, pp. 509-517.el.
Koozekanani, et al., Retinal Thickness Measurements from Optical Coherence Tomography Using a Markov Boundary Model. IEEE Transactions on Medical Imaging; vol. 20; No. 9; pp. 900-916, Sep. 2001.
Lavanya, et al, Screening for Narrow Angles in the Singapore Population: Evaluation of New Noncontact Screening Methods; vol. 115; Issue No. 10, pp. 1720-1727e2, Oct. 2008.
Manassakorn, et al., Comparison of Retinal Nerve Fiber Layer Thickness and Optic Disk Algorithms with Optical Coherence Tomography to Detect Glaucoma; Am J Ophthalmol; vol. No. 141; pp. 105-115; Jan. 2006.
Parikh, M.D., et al., Diagnostic Capability of Optical Coherence Tomography (Stratus OCT 3) in Early Glaucoma; American Academy of Ophthalmology; vol. 114, Issue No. 12; pp. 2238-2243, Dec. 2007.
Prevent Blindness America. SureSight Vision Screener. Prevent Blindness Tri-State. http://www.preventblindness.org/tristate/suresight.htrnl, 2 pages, 2006.
Sadda, Srinivas R., et al., Automated Detection of Clinically Significant Macular Edema by Grid Scanning Optical Coherence Tomography. American Academy of Ophthalmology, vol. 113, No. 7, pp. 1187 e.I-1187 e.12, Jul. 2006.
Sarunic et al., "New Imaging Device Can Detect Glaucoma Risk", Duke Medicine News and Communications, Jun. 2008.
Stein, et al., A new quality assessment parameter for optical coherence tomography; British Journal of Ophthalmology; vol. 90, Issue No. 2; pp. 186-190; Feb. 2006.
Stereo Optical Co., Inc. The Optec® 5500/5500 P-Industry Standard for Visual Screening and Vision Testing Devices. http://www.stereooptical.com/html/optec-5500.html, 3 pages, 2007.
Stereo Optical Co., Inc. The Optec® Functional VisionAnalyzer™ Contrast Sensitivity Tests with Two Glare Levels Under Four Testing Conditions. http://www.stereooptical.com/html/functional_vision_analyzer.html, 3 pages, 2007.
STRATUS OCT™ Software version 4.0 Real Answers in Real Time. [Online] Jan. 2006, XP002530105 Retrieved from the Internet: URL: http://www.meditec.zeiss.com/88256DE3007B916B/0/C26634DOCFF04511882571BI005DECFD/$file/stratusocLen.pdf>[retrieved on May 28, 2009] the whole document.
Topcon Medical Systems Receives FDA Clearance to Market the 3D OCT-1000, the World's First Combination of Fourier Domain OCT and a Color Non-Mydriatic Retinal Camera, Topcon Press Release Jul. 2, 2007, pp. 1-2.
Topcon Optical Coherence Tomography 3D OCT-1000 Brochure, 7 pages, 2008.
Vakhtin, et al, Common-path interferometer for frequency-domain optical coherence tomography; Applied Optics; vol. 42, Issue No. 34; pp. 6953-6958, 2003.
Vakhtin, et al., Demonstration of complex-conjugate-resolved harmonic Fourier-domain optical coherence tomography imaging of biological samples; Applied Optics; vol. 46; Issue No. 18; pp. 3870-3877, Jun. 20, 2007.
Walsh, A. "3D-OCT in the Evaluation of Retinal Disease," Highlights of Ophthalmology, Jul. 2006, 34(3): 9-10.
Walsh, A. M.D., "Next-generation OCT: What to Look for in a Fourier Domain OCT Instrument," Retinal Physician, pp. 1-6, May 1, 2007.
Xu, et al., Anterior Chamber Depth and Chamber Angle and Their Associations with Ocular and General Parameters: The Beijing Eye Study. American Journal of Ophthalmology, vol. 145, pp. 929-936el, May 2008.
Yasuno, et al., One-shot-phase-shifting Fourier domain optical coherence tomography by reference wavefront tilting; Optics Express; vol. 12; Issue No. 25; pp. 6184-6191, Dec. 13, 2004.
Zhang, et al., Full range polarization-sensitive Fourier domain optical coherence tomography; Optics Express; vol. 12; Issue No. 24; pp. 6033-6039, Nov. 29, 2004.
Zhou et al., "Biometric measurement of the mouse eye using optical coherence tomography with focal plane advancement", Vision Research, Apr. 2008, vol. 48, pp. 1137-1143.
Final Office Action in U.S. Appl. No. 14/521,392 dated Feb. 29, 2016.
Office Action in U.S. Appl. No. 14/521,392 dated Sep. 25, 2015.
Amendment in U.S. Appl. No. 14/521,392 dated Jan. 25, 2016.
Chinese First Office Action, re CN Application No. 200980119252.3, dated Aug. 29, 2012.
Chinese Fourth Office Action, re CN Application No. 200980119252.3, dated Oct. 28, 2014.
Chinese Second Office Action, re CN Application No. 200980119252.3, dated Jul. 25, 2013.
Chinese Third Office Action, re CN Application No. 200980119252.3, dated Apr. 15, 2014.
Chinese Fifth Office Action, re CN Application No. 200980119252.3, dated Jul. 10, 2010.
Chinese Sixth Office Action and Search Report, re CN Application No. 200980119252.3, dated Feb. 3, 2016.
European Exam Report, re EP Application No. 09 724 806.6, dated Aug. 20, 2012.
European Exam Report, re EP Application No. 09 724 806.6, dated Feb. 13, 2015.
Japanese Office Action for Japanese Application No. JP 2011-501911, dated May 1, 2013.
Japanese Decision of Rejection for Japanese Application No. JP 2014-016709, dated Mar. 1, 2016.
Japanese Office Action for Japanese Application No. JP 2014-016709, dated Feb. 17, 2015.
PCT International Preliminary Report on Patentability dated Sep. 28, 2010 for PCT Application No. PCT/US2009/037449.
PCT International Search Report and Written Opinion re PCT Application No. PCT/US2009/037449, dated Aug. 27, 2009.
PCT International Preliminary Report on Patentability dated Sep. 28, 2010 for PCT Application No. PCTIUS2009/037448.
PCT International Search Report and Written Opinion re PCT Application No. PCT/US2009/037448, dated Jun. 12, 2009.
PCT International Preliminary Report on Patentability dated Jan. 18, 2011 for PCT Application No. PCTIUS2009/051077.
PCT International Search Report and Written Opinion re PCT Application No. PCT/US2009/051077, dated Oct. 13, 2009.
Amendment in U.S. Appl. No. 13/717,508, dated Aug. 23, 2013.
Amendment in U.S. Appl. No. 13/717,508, dated Jun. 20, 2014.
U.S. Appl. No. 14/472,161, including its prosecution history, and the references cited and the Office Actions therein, Not Yet Published, Walsh, et al.
EPO Supplementary European Search Report for Application No. 090798839.8, dated Jan. 30, 2012.
Amendment in U.S. Appl. No. 13/054,481, dated Jan. 28, 2014.
Amendment in U.S. Appl. No. 13/054,481, dated May 2, 2013.
Amendment in U.S. Appl. No. 13/054,481, dated Nov. 16, 2012.
PCT International Preliminary Report of Patentability dated Jan. 18, 2011 for PCT Application No. PCTIUS2009/051073.
PCT International Search Report and Written Opinion re PCT Application No. PCT/US2009/051073, dated Jan. 13, 2010.
PCT International Preliminary Report of Patentability dated Oct. 11, 2011 for PCT Application No. PCTIUS2009/059133 filed on Sep. 30, 2009.
PCT International Search Report and Written Opinion re PCT Application No. PCT/US2009/059133, dated Jan. 21, 2010.
Office Action dated Apr. 24, 2015 in U.S. Appl. No. 13/802,727.
Amendment in U.S. Appl. No. 13/802,727 dated Jul. 24, 2015.
International Search Report and Written Opinion, re PCT/US2014/019150, dated Dec. 4, 2014.
International Report on Patentability and Written Opinion, re PCT/US2014/019150, dated Sep. 15, 2015.
Joeres, et al.: "Reproducibility of Quantitative Optical Coherence Tomography Subanalysis in Neovascular Age-Related Macular Degeneration," IOVS, Sep. 2007, vol. 48., No. 9.

(56) References Cited

OTHER PUBLICATIONS

Sandhu, et al.: "Correlation of optical coherence tomography, with or without additional colour fundus photography, with stereo fundus fluorescein angiography in diagnosing choroidal neovascular membranes," downloaded from gttp://bjo.bmj.com/ on Nov. 27, 2016. Br J Ophthalmol 2005; 89:967-970.

Shields, et al.: "Photoreceptor Loss Overlying Congenital Hypertrophy of the Retinal Pigment Epithelium by Optical Coherence Tomography," Ophthalmology vol. 113, No. 4, Apr. 2006.

Van de Moere, et al.: "Correlation of optical coherence tomography and fundus fluorescein angiography following photodynamic therapy for choroidal neovascular membranes," downloaded from http://bjo.bmj.com/ on Nov. 27, 2016. Br J. Ophthalmol 2006; 90:304-306.

Zhang, et al.: "Optical Coherence Tomography Reader Agreement in Neovascular Age-related Macular Degeneration," American Journal of Ophthalmology, ol. 144, No. 1, Jul. 2007, pp. 37-44.e1.

Chinese Rejection Decision, re CN Application No. 200980119252. 3, dated Aug. 2, 2016.

European Notice of Opposition, re EP Application No. 09 724 806.6, dated Dec. 23, 2016.

Preliminary Amendment for U.S. Appl. No. 14/472,161, dated Dec. 8, 2014.

Preliminary Amendment in U.S. Appl. No. 13/054,481, dated Feb. 14, 2011.

Preliminary Amendment of U.S. Appl. No. 13/802,727, dated Jun. 24, 2013.

International Search Report and Written Opinion, re PCT/US2016/051778, dated Jan. 5, 2017.

\* cited by examiner

Diagram of A-Scan and B-Scan
FIG. 6A
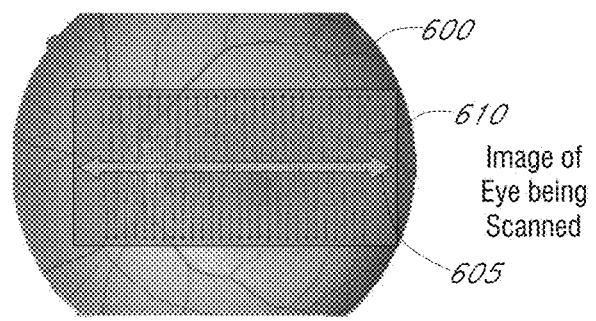
600
610
Image of Eye being Scanned
605
FIG. 6B
A-Scan (stretched horizontally)
FIG. 6C
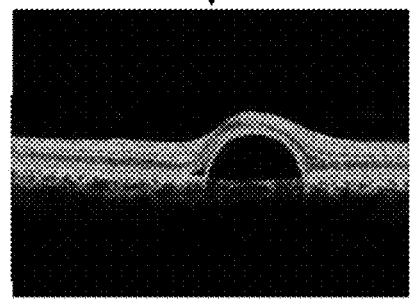
B-Scan

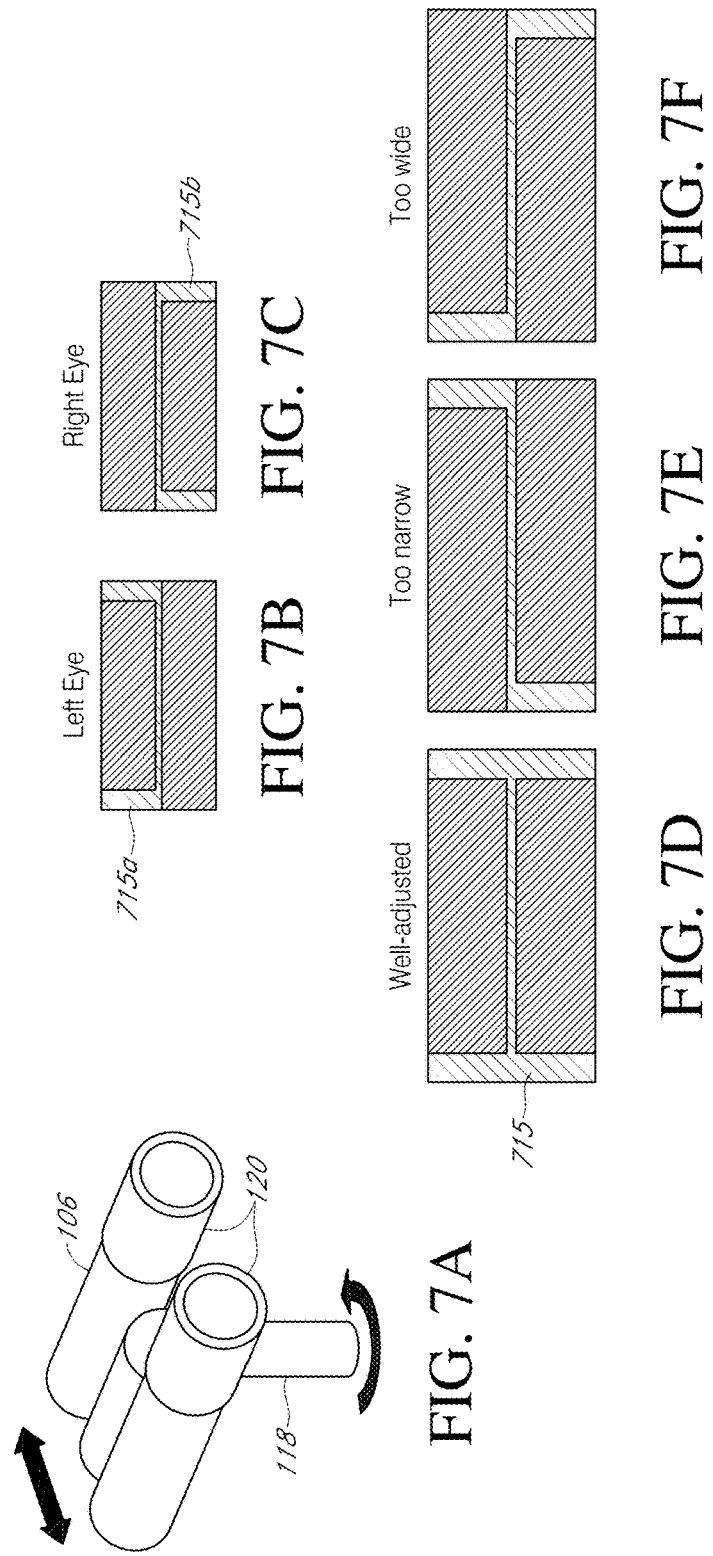

| Eye Health Grades | | |
|---|---|---|
| | Left | Right |
| Macular Health | 25 | 65 |
| Optic Nerve Health | 75 | 80 |
| Clarity | 45 | 90 |

| Recommendations | ABCD-EFGH |
|---|---|

① Within 2 weeks, see either

- Dr. John
  123 Main Street
  Los Angeles, CA or

- Dr. Bob
  456 Main Street
  Los Angeles, CA

② Within 6 months, see

- Dr. Ellie
  999 Main Street
  Los Angeles, CA

See an eye doctor at least once per year

FIG. 11A

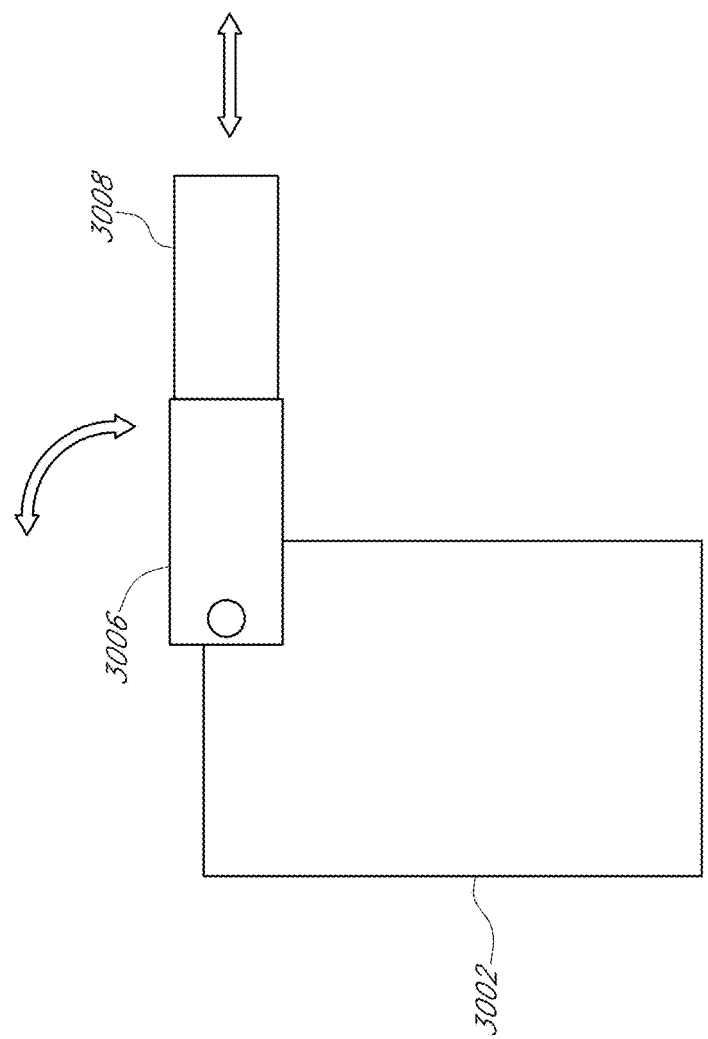

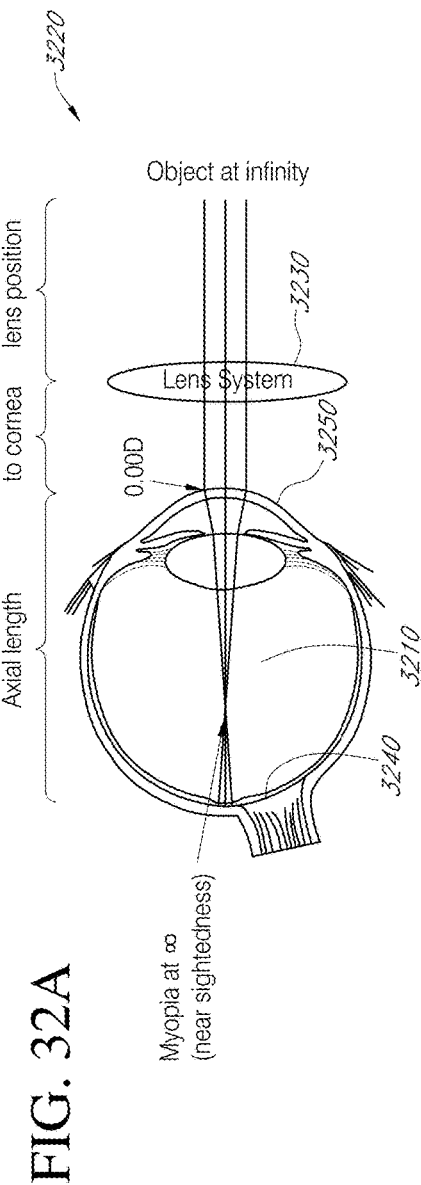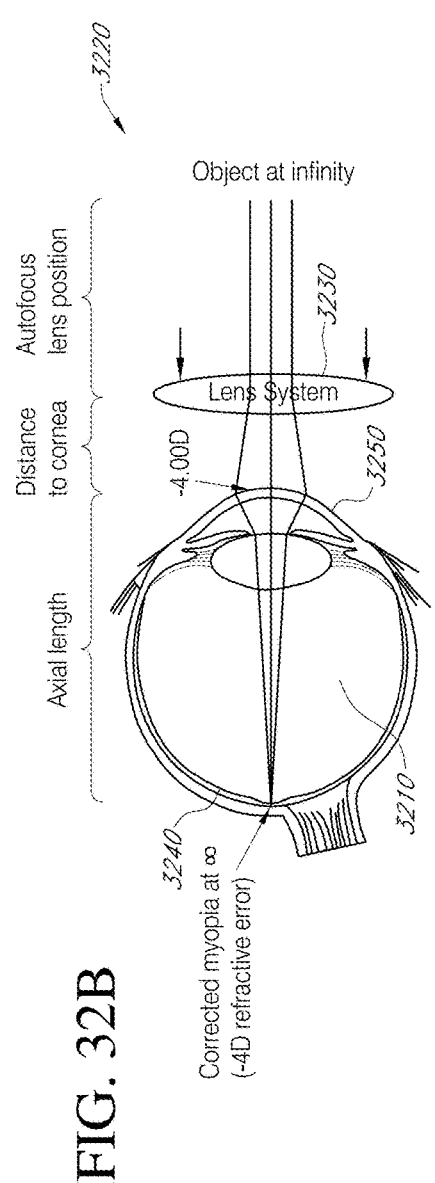

FIG. 35A
Iris Plane Analysis for Gaze Direction
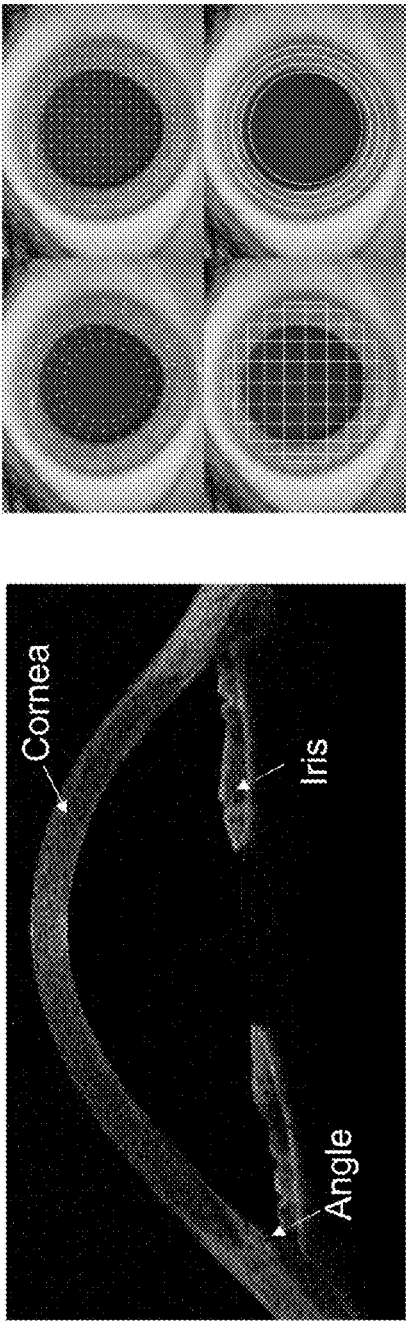
Anterior Segment OCT
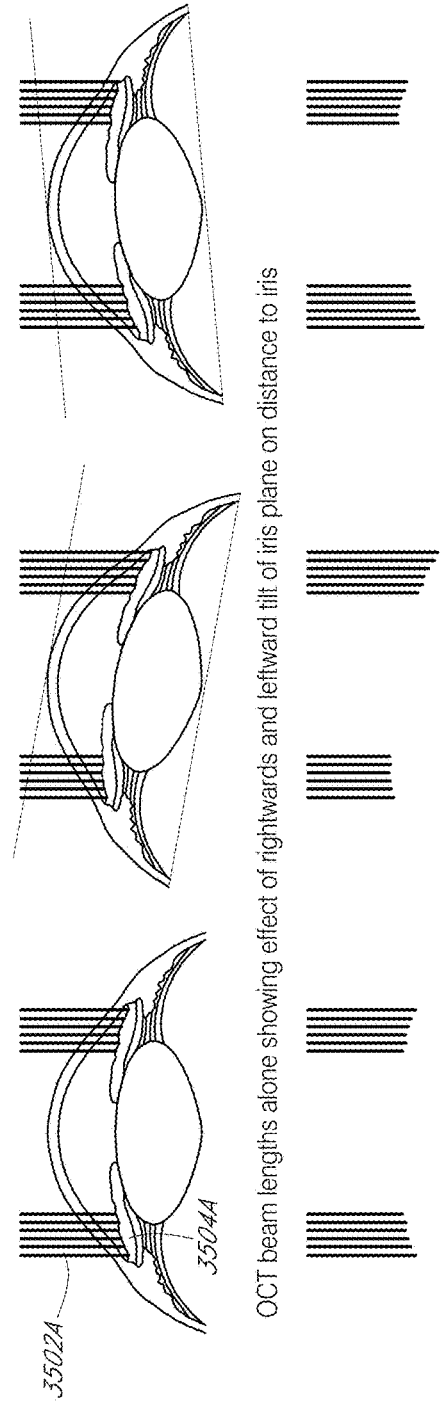
Examples of Scanning Protocols on Human Irises (each dot represents an A-scan)
Side Diagram of Iris and OCT beams (vertical lines) intersecting iris tissue
OCT beam lengths alone showing effect of rightwards and leftward tilt of iris plane on distance to iris FIG. 35B
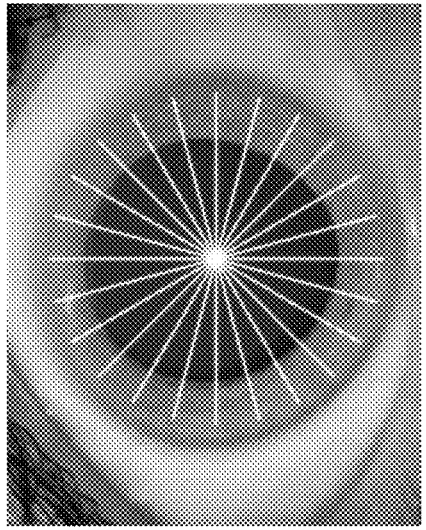
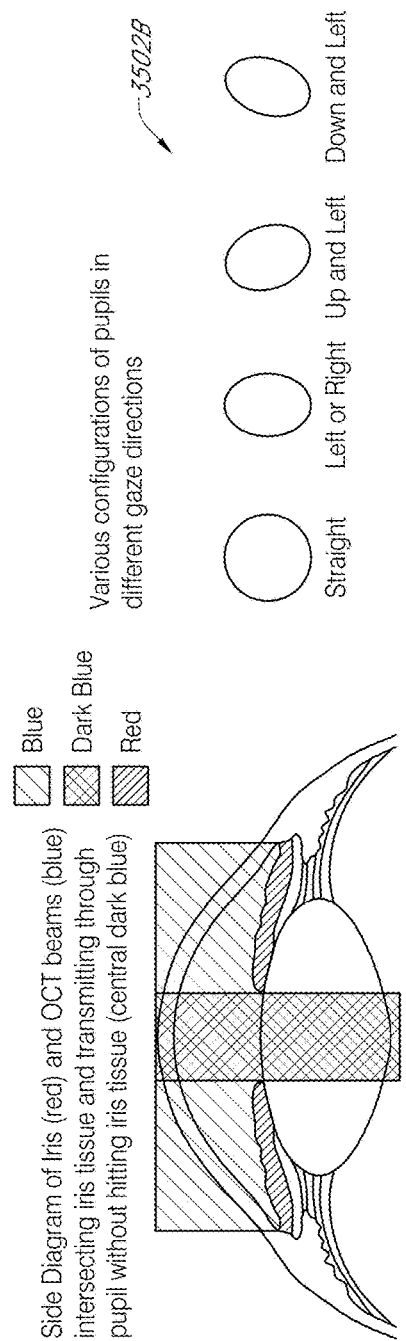

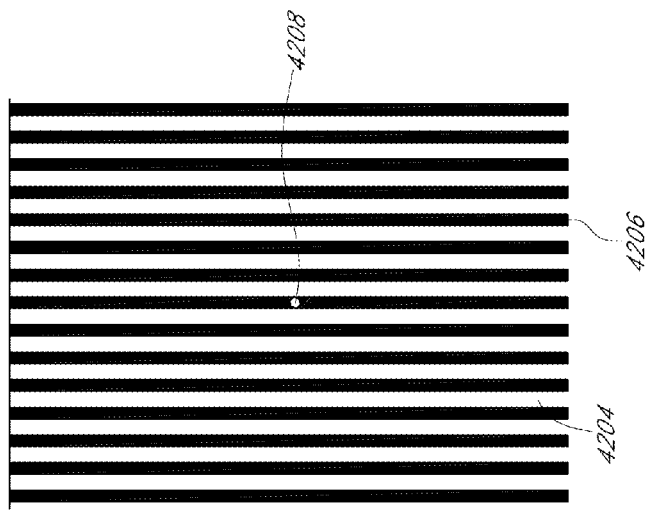
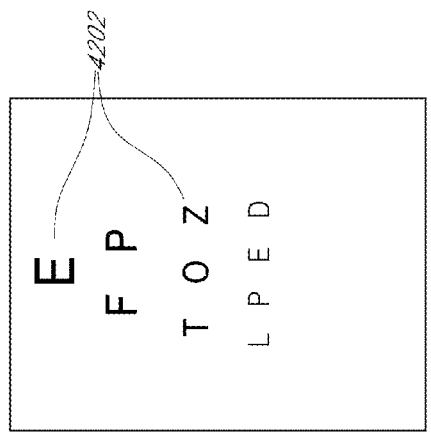
FIG. 42

OPTICAL COHERENCE TOMOGRAPHY-BASED OPHTHALMIC TESTING METHODS, DEVICES AND SYSTEMS

CROSS-REFERENCE TO RELATED APPLICATIONS

The present application is a continuation of U.S. patent application Ser. No. 14/472,161, now U.S. Pat. No. 9,492,079, filed Aug. 28, 2014, which is a continuation of U.S. patent application Ser. No. 13/054,481, now U.S. Pat. No. 8,820,931, filed May 3, 2011, which is a national phase filing of PCT Application No. PCT/US2009/051073, filed Jul. 17, 2009, which claims the benefit under 35 U.S.C. 119 to U.S. Provisional Application No. 61/082,171, filed Jul. 18, 2008, U.S. Provisional Application No. 61/082,175, filed Jul. 18, 2008, U.S. Provisional Application No. 61/168,340, filed Apr. 10, 2009, U.S. Provisional Application No. 61/180,837, filed May 23, 2009, U.S. Provisional Application No. 61/221,552, filed Jun. 29, 2009, U.S. Provisional Application No. 61/222,080, filed Jun. 30, 2009. The present application is also a continuation-in-part of U.S. patent application Ser. No. 15/249,151, filed Aug. 26, 2016, which is a continuation of U.S. patent application Ser. No. 14/521,392, filed Oct. 22, 2014, now abandoned, which is a continuation of U.S. patent application Ser. No. 13/717,508, now U.S. Pat. No. 9,149,182, filed on Dec. 17, 2012, which is a continuation of U.S. patent application Ser. No. 12/111,894, now U.S. Pat. No. 8,348,429, filed on Apr. 29, 2008, which claims priority benefit under 35 U.S.C. § 119(e) to U.S. Provisional Application No. 61/040,084, filed Mar. 27, 2008. Each of the foregoing applications is hereby incorporated by reference in its entirety, including specifically but not limited to the systems and method relating to optical coherence tomography-based systems.

BACKGROUND

Field

Embodiments of the invention relate to the field of optical coherence tomography and, in particular, to devices, systems, methods of utilizing such optical coherence tomography data to perform precision measurements on eye tissue for the detection of eye diseases.

Description of the Related Art

Many industrial, medical, and other applications exist for optical coherence tomography (OCT), which generally refers to an interferometric, non-invasive optical tomographic imaging technique offering millimeter penetration (approximately 2-3 mm in tissue) with micrometer-scale axial and lateral resolution. For example, in medical applications, doctors generally desire a non-invasive, in vivo imaging technique for obtaining sub-surface, cross-sectional and/or three-dimensional images of translucent and/or opaque materials at a resolution equivalent to low-power microscopes. Accordingly, in the coming years, it is projected that there will be 20 million OCT scans performed per year on patients. Most of these will probably occur in the field of ophthalmology. In current optical coherence tomography systems, doctors or other medical professionals administer the OCT scans in the doctors' medical office or medical facilities.

SUMMARY

Various embodiments of the present invention relate to the utilization of optical coherence tomography, in conjunction with one or more display devices, one or more input devices, and a central processor to perform a multitude of ophthalmic diagnostic tests and other testing in one single, small instrument that are currently completed by many separate instruments. Generally, various embodiments of the optical coherence tomography instruments, devices, systems, and methods disclosed herein can be self-administered and/or administered with the assistance of a layperson, and the eyepiece can be a binocular system.

In various embodiments, an optical coherence tomography-based system comprises an optical coherence tomography device configured to obtain an optical coherence tomography scan of at least one first anterior eye region and at least one of a second intermediate or posterior eye region; a processor configured to analyze the optical coherence tomography scan or to generate an optical coherence tomography-based image based on the optical coherence tomography scan; and an output device configured to output on the output device a report based on the analysis of the optical coherence tomography scan or the optical coherence tomography-based image.

In various embodiments, an optical coherence tomography-based system comprises an optical coherence tomography device configured to obtain an optical coherence tomography scan of at least one first posterior eye region and at least one of a second intermediate or anterior eye region; a processor configured to analyze the optical coherence tomography scan or to generate an optical coherence tomography-based image based on the optical coherence tomography scan; and an output device configured to output on the output device a report based on the analysis of the optical coherence tomography scan or the optical coherence tomography-based image.

In various embodiments, an optical coherence tomography-based biomicroscopy system comprises an optical coherence tomography device configured to obtain an optical coherence tomography scan along substantially an entire axis of an eye of a subject, said axis extending between at least a corneal structure to at least a retina; a processor configured to analyze the optical coherence tomography scan or to generate an optical coherence tomography-based biomicroscopy image based on the optical coherence tomography scan; and an output device configured to output on the output device a report based on the analysis of the optical coherence tomography scan or the optical coherence tomography-based biomicroscopy image.

In various embodiments, an optical coherence tomography-based system comprises an optical coherence tomography device configured to obtain a first optical coherence tomography scan of an eye of a subject, and a second optical coherence tomography scan of the eye, wherein the first and second optical coherence tomography scans are arranged along an axis, the axis extending between an anterior region of the eye to a posterior region of the eye, the first scan being anterior to the second scan; a processor configured to analyze the first and second optical coherence tomography scans or to generate an optical coherence tomography-based image based on the first and second optical coherence tomography scans; and an output device configured to output on the output device a report based on the analysis of the first and second optical coherence tomography scans or the optical coherence tomography-based image.

In various embodiments, an optical coherence tomography-based ophthalmic testing system comprises an optical coherence tomography device configured to obtain an anterior optical coherence tomography scan imaging an anterior region of an eye of a user and to obtain a posterior optical coherence tomography scan imaging a posterior region of the eye of the user, the optical coherence tomography device configured to enable the user to self-administer the scan by using the device; a processor configured to analyze the anterior and posterior optical coherence tomography scans to generate an optical coherence tomography-based image; and an output device configured to output on the output device the optical coherence tomography-based image.

In various embodiments, an optical coherence tomography-based ophthalmic testing system comprises an optical coherence tomography device configured to obtain an optical coherence tomography scan imaging a region of a vitreous of an eye of a user, the optical coherence tomography device configured to enable the user to self-administer the scan by using the device; a processor configured to generate an optical coherence tomography-based biomicroscopy image of the vitreous based on the optical coherence tomography scan; and an output device configured to output on the output device the optical coherence tomography-based image of the vitreous.

In various embodiments, an optical coherence tomography-based ophthalmic testing system comprises an optical coherence tomography device configured to obtain a first optical coherence tomography scan of a region of an eye of a user at a first time period and a second optical coherence tomography scan of the region of the eye of the user at a second time period; a processor configured to perform movement tracking of at least one structural element of the eye between the first and second optical coherence tomography scans, and the processor configured to perform at least one of an ophthalmic functional test based on the movement tracking or a structural test; and an output device configured to generate an output on the output device based on the at least one ophthalmic functional test or the structural test.

In various embodiments, an ophthalmic testing system comprises an imaging device configured to obtain a first image of a region of an eye of a subject at a first time period and a second image of the region of the eye of the subject at a second time period; a processor configured to perform movement tracking of at least one structural element of the eye between the first and second images, and the processor configured to perform at least one ophthalmic functional test based on the movement tracking; and an output device configured to generate an output on the output device based on the at least one ophthalmic functional test.

In various embodiments, an optical coherence tomography-based ophthalmic testing system comprises an optical coherence tomography device configured to obtain an optical coherence tomography scan of a region of an eye; a processor configured to conduct a binocular extraocular motility test on the eye based on the optical coherence tomography scan; and an output device configured to generate an output on the output device based on the test.

In various embodiments, an optical coherence tomography-based ophthalmic testing system comprises an optical coherence tomography device configured to obtain an optical coherence tomography scan of a region of an eye; a processor configured to conduct a pupillometry test on the eye based on the optical coherence tomography scan; and an output device configured to generate an output on the output device based on the test.

In various embodiments, an optical coherence tomography-based ophthalmic testing system comprises an optical coherence tomography device configured to obtain an optical coherence tomography scan of a region of an eye; a processor configured to conduct an exophthalmometry test on the eye based on the optical coherence tomography scan; and an output device configured to generate an output on the output device based on the test.

In various embodiments, an optical coherence tomography-based ophthalmic testing system comprises an optical coherence tomography device configured to obtain an optical coherence tomography scan of a region of an eye; a processor configured to conduct a foveal suppression test on the eye based on the optical coherence tomography scan; and an output device configured to generate an output on the output device based on the test.

In various embodiments, an optical coherence tomography-based ophthalmic testing system comprises an optical coherence tomography device configured to obtain an optical coherence tomography scan of a region of an eye; a processor configured to conduct a stereoacuity test on the eye based on the optical coherence tomography scan; and an output device configured to generate an output on the output device based on the test.

In various embodiments, an optical coherence tomography-based ophthalmic testing system comprises an optical coherence tomography device configured to obtain an optical coherence tomography scan of a region of an eye; a processor configured to conduct an ocular alignment test on the eye based on the optical coherence tomography scan; and an output device configured to generate an output on the output device based on the test.

In various embodiments, an optical coherence tomography-based ophthalmic testing system comprises an optical coherence tomography device configured to obtain an optical coherence tomography scan of a region of an eye; a processor configured to conduct a visual acuity test on the eye based on the optical coherence tomography scan; and an output device configured to generate an output on the output device based on the test.

In various embodiments, an optical coherence tomography-based ophthalmic testing system comprises an optical coherence tomography device configured to obtain an optical coherence tomography scan of a region of an eye; a processor configured to conduct a static perimetry test on the eye based on the optical coherence tomography scan; and an output device configured to generate an output on the output device based on the test.

In various embodiments, an optical coherence tomography-based ophthalmic testing system comprises an optical coherence tomography device configured to obtain an optical coherence tomography scan of a region of an eye; a processor configured to conduct a kinetic perimetry test on the eye based on the optical coherence tomography scan; and an output device configured to generate an output on the output device based on the test.

In various embodiments, an optical coherence tomography-based ophthalmic testing system comprises an optical coherence tomography device configured to obtain an optical coherence tomography scan of a region of an eye; a processor configured to conduct a refractive error measurement on the eye based on the optical coherence tomography scan; and an output device configured to generate an output on the output device based on the test.

In various embodiments, an optical coherence tomography-based ophthalmic testing system comprises an optical coherence tomography device configured to obtain an optical coherence tomography scan of a region of an eye; a processor configured to conduct an ocular motility test on the eye based on the optical coherence tomography scan; and an output device configured to generate an output on the output device based on the test.

In various embodiment, an optical coherence tomography-based ophthalmic testing system comprises an optical coherence tomography device configured to obtain an optical coherence tomography scan of a region of an eye; a processor configured to conduct a contrast sensitivity test on the eye based on the optical coherence tomography scan; and an output device configured to generate an output on the output device based on the test.

In various embodiments, an optical coherence tomography-based ophthalmic testing system comprises an optical coherence tomography device configured to obtain an optical coherence tomography scan of a region of an eye; a processor configured to conduct a color vision test on the eye based on the optical coherence tomography scan; and an output device configured to generate an output on the output device based on the test.

In various embodiments, an optical coherence tomography-based ophthalmic testing system comprises an optical coherence tomography device configured to obtain an optical coherence tomography scan of a region of an eye; a processor configured to conduct a central visual distortion test on the eye based on the optical coherence tomography scan; and an output device configured to generate an output on the output device based on the test.

In various embodiments, an optical coherence tomography-based ophthalmic testing system comprises an optical coherence tomography device configured to obtain an optical coherence tomography scan of a region of an eye; a processor configured to conduct a reading speed test on the eye based on the optical coherence tomography scan; and an output device configured to generate an output on the output device based on the test.

In various embodiments, an optical coherence tomography-based ophthalmic testing system comprises an optical coherence tomography device configured to obtain an optical coherence tomography scan of a region of an eye of a user, wherein the optical coherence tomography device is configured to enable the user to self-administer the scan by using the device; a processor configured to conduct a corneal topography test on the eye based on the optical coherence tomography scan; and an output device configured to generate an output on the output device based on the test.

In various embodiments, an optical coherence tomography-based ophthalmic testing system comprises an optical coherence tomography device configured to obtain an optical coherence tomography scan of a region of an eye of a user, wherein the optical coherence tomography device is configured to enable the user to self-administer the scan by using the device; a processor configured to conduct a corneal pachymetry test on the eye based on the optical coherence tomography scan; and an output device configured to generate an output on the output device based on the test.

In various embodiments, an optical coherence tomography-based ophthalmic testing system comprises an optical coherence tomography device configured to obtain an optical coherence tomography scan of a region of an eye of a user, wherein the optical coherence tomography device is configured to enable the user to self-administer the scan by using the device; a processor configured to conduct a gonioscopy test on the eye based on the optical coherence tomography scan; and an output device configured to generate an output on the output device based on the test.

In various embodiments, an optical coherence tomography-based ophthalmic testing system comprises an optical coherence tomography device configured to obtain an anterior optical coherence tomography scan of a anterior region of an eye of a subject, and to obtain a posterior optical coherence tomography scan of a posterior region of the eye, and to obtain an intermediate optical coherence tomography scan of a region in between the anterior region and posterior region of the eye; a processor configured to analyze the anterior, posterior, and intermediate optical coherence tomography scans or to the generate an optical coherence tomography-based image based on the optical coherence tomography scans; and an output device configured to generate an output on the output device a report based on the analysis or the optical coherence tomography-based image.

In various embodiments, an optical coherence tomography-based ophthalmic testing system for conducting a best fixating retina verification comprises an optical coherence tomography device configured to identify a region for a best fixating retina detection, and the optical coherence tomography device configured to generate a scan of the region; a processor configured to analyze the optical coherence tomography scan to determine the presence of a fovea; and an output device configured to generate an output on the output device based on the analysis.

In various embodiments, an optical coherence tomography-based ophthalmic testing system for conducting a best fixating retina search comprises an optical coherence tomography device configured to generate a three-dimensional optical coherence tomography scan of a region; a processor configured to analyze the three-dimensional optical coherence tomography scan to determine the location of a best fixating retina; and an output device configured to generate an output on the output device based on the analysis.

In various embodiments, an optical coherence tomography-based biomicroscopy system comprises an optical coherence tomography device configured perform coherence tomography scans; a processor configured to obtain a first set of optical coherence tomography data from a first optical coherence tomography scan and a set of second optical coherence tomography data from said first optical coherence tomography scan or from a second optical coherence tomography scan, said processor further configured to logically operate on the first set of optical coherence tomography data with the second set of optical coherence tomography data to produce a resultant optical coherence tomography scan with less ghost imagery than said first optical coherence tomography scan; and an output device configured to generate an output on the output device based on the resultant scan.

In various embodiments, an optical coherence tomography-based method comprises obtaining an optical coherence tomography scan, using an optical coherence tomography device, of at least one first anterior eye region and at least one of a second intermediate or posterior eye region; using a processor to analyze the optical coherence tomography scan or to generate an optical coherence tomography-based image based on the optical coherence tomography scan; and outputting on an output device a report based on the analysis of the optical coherence tomography scan or the optical coherence tomography-based image.

In various embodiments, an optical coherence tomography-based method comprises obtaining an optical coherence tomography scan, using an optical coherence tomography device, of at least one first posterior eye region and at least one of a second intermediate or anterior eye region; using a processor to analyze the optical coherence tomography scan or to generate an optical coherence tomography-based image based on the optical coherence tomography scan; and outputting on an output device a report based on the analysis of the optical coherence tomography scan or the optical coherence tomography-based image.

In various embodiments, an optical coherence tomography-based biomicroscopy method comprises obtaining an optical coherence tomography scan, using an optical coherence tomography device, along substantially an entire axis of an eye of a subject, said axis extending between at least a corneal structure to at least a retina; using a processor to analyze the optical coherence tomography scan or to generate an optical coherence tomography-based biomicroscopy image based on the optical coherence tomography scan; and outputting on an output device a report based on the analysis of the optical coherence tomography scan or the optical coherence tomography-based biomicroscopy image.

In various embodiments, an optical coherence tomography-based method comprises obtaining, using an optical coherence tomography device, a first optical coherence tomography scan of an eye of a subject, and a second optical coherence tomography scan of the eye, wherein the first and second optical coherence tomography scans are arranged along an axis, the axis extending between an anterior region of the eye to a posterior region of the eye, the first scan being anterior to the second scan; using a processor to analyze the first and second optical coherence tomography scans or to generate an optical coherence tomography-based image based on the first and second optical coherence tomography scans; and outputting on an output device a report based on the analysis of the first and second optical coherence tomography scans or the optical coherence tomography-based image.

In various embodiments, an optical coherence tomography-based ophthalmic testing method comprises obtaining, using an optical coherence tomography device, an anterior optical coherence tomography scan imaging an anterior region of an eye of a user and to obtain a posterior optical coherence tomography scan imaging a posterior region of the eye of the user, wherein the user self-administers the scan by using the device; using a processor to analyze the anterior and posterior optical coherence tomography scans to generate an optical coherence tomography-based image; and outputting on an output device the optical coherence tomography-based image.

In various embodiments, an optical coherence tomography-based ophthalmic testing method comprises obtaining, using an optical coherence tomography device, an optical coherence tomography scan imaging a region of a vitreous of an eye of a user, the optical coherence tomography device configured to enable the user to self-administer the scan by using the device; using a processor to generate an optical coherence tomography-based image of the vitreous based on the optical coherence tomography scan; and outputting on an output device the optical coherence tomography-based image of the vitreous.

In various embodiments, an optical coherence tomography-based ophthalmic testing method comprises obtaining, using an optical coherence tomography device, a first optical coherence tomography scan of a region of an eye of a user at a first time period and a second optical coherence tomography scan of the region of the eye of the user at a second time period; using a processor to perform movement tracking of at least one structural element of the eye between the first and second optical coherence tomography scans, and to perform at least one of an ophthalmic functional test based on the movement tracking or a structural test; and outputting on an output device an output based on the at least one ophthalmic functional test or the structural test.

In various embodiments, an ophthalmic testing method comprises obtaining, using an imaging device, a first image of a region of an eye of a subject at a first time period and a second image of the region of the eye of the subject at a second time period; using a processor to perform movement tracking of at least one structural element of the eye between the first and second images, and to perform at least one ophthalmic functional test based on the movement tracking; and outputting on an output device an output based on the at least one ophthalmic functional test.

In various embodiments, an optical coherence tomography-based ophthalmic testing method comprises obtaining, using an optical coherence tomography device, an optical coherence tomography scan of a region of an eye; using a processor to conduct a binocular extraocular motility test on the eye based on the optical coherence tomography scan; and outputting on an output device an output based on the test.

In various embodiments, an optical coherence tomography-based ophthalmic testing method comprises obtaining, using an optical coherence tomography device, an optical coherence tomography scan of a region of an eye; using a processor to conduct a pupillometry test on the eye based on the optical coherence tomography scan; and outputting on an output device an output based on the test.

In various embodiments, an optical coherence tomography-based ophthalmic testing method comprises obtaining, using an optical coherence tomography device, an optical coherence tomography scan of a region of an eye; using a processor to conduct an exophthalmometry test on the eye based on the optical coherence tomography scan; and outputting on an output device an output based on the test.

In various embodiments, an optical coherence tomography-based ophthalmic testing method comprises obtaining, using an optical coherence tomography device, an optical coherence tomography scan of a region of an eye; using a processor to conduct a foveal suppression test on the eye based on the optical coherence tomography scan; and outputting on an output device an output based on the test.

In various embodiments, an optical coherence tomography-based ophthalmic testing method comprises obtaining, using an optical coherence tomography device, an optical coherence tomography scan of a region of an eye; using a processor to conduct a stereoacuity test on the eye based on the optical coherence tomography scan; and outputting on an output device an output based on the test.

In various embodiments, an optical coherence tomography-based ophthalmic testing method comprises obtaining, using an optical coherence tomography device, an optical coherence tomography scan of a region of an eye; using a processor to conduct an ocular alignment test on the eye based on the optical coherence tomography scan; and outputting on an output device an output based on the test.

In various embodiments, an optical coherence tomography-based ophthalmic testing method comprises obtaining, using an optical coherence tomography device, an optical coherence tomography scan of a region of an eye; using a processor to conduct a visual acuity test on the eye based on the optical coherence tomography scan; and outputting on an output device an output based on the test.

In various embodiments, an optical coherence tomography-based ophthalmic testing method comprises obtaining, using an optical coherence tomography device, an optical coherence tomography scan of a region of an eye; using a processor to conduct a static perimetry test on the eye based on the optical coherence tomography scan; and outputting on an output device an output based on the test.

In various embodiments, an optical coherence tomography-based ophthalmic testing method comprises obtaining, using an optical coherence tomography device, an optical coherence tomography scan of a region of an eye; using a processor to conduct a kinetic perimetry test on the eye based on the optical coherence tomography scan; and outputting on an output device an output based on the test.

In various embodiments, an optical coherence tomography-based ophthalmic testing method comprises obtaining, using an optical coherence tomography device, an optical coherence tomography scan of a region of an eye; using a processor to conduct a refractive error measurement on the eye based on the optical coherence tomography scan; and outputting on an output device an output based on the test.

In various embodiments, an optical coherence tomography-based ophthalmic testing method comprises obtaining, using an optical coherence tomography device, an optical coherence tomography scan of a region of an eye; using a processor to conduct an ocular motility test on the eye based on the optical coherence tomography scan; and outputting on an output device an output based on the test.

In various embodiments, an optical coherence tomography-based ophthalmic testing method comprises obtaining, using an optical coherence tomography device, an optical coherence tomography scan of a region of an eye; using a processor to conduct a contrast sensitivity test on the eye based on the optical coherence tomography scan; and outputting on an output device an output based on the test.

In various embodiments, an optical coherence tomography-based ophthalmic testing method comprises obtaining, using an optical coherence tomography device, an optical coherence tomography scan of a region of an eye; using a processor to conduct a color vision test on the eye based on the optical coherence tomography scan; and outputting on an output device an output based on the test.

In various embodiments, an optical coherence tomography-based ophthalmic testing method comprises obtaining, using an optical coherence tomography device, an optical coherence tomography scan of a region of an eye; using a processor to conduct a central visual distortion test on the eye based on the optical coherence tomography scan; and outputting on an output device an output based on the test.

In various embodiments, an optical coherence tomography-based ophthalmic testing method comprises obtaining, using an optical coherence tomography device, an optical coherence tomography scan of a region of an eye; using a processor to conduct a reading speed test on the eye based on the optical coherence tomography scan; and outputting on an output device an output based on the test.

In various embodiments, an optical coherence tomography-based ophthalmic testing method comprises obtaining, using an optical coherence tomography device, an optical coherence tomography scan of a region of an eye of a user, wherein the optical coherence tomography device is configured to enable the user to self-administer the scan by using the device; using a processor to conduct a corneal topography test on the eye based on the optical coherence tomography scan; and outputting on an output device an output based on the test.

In various embodiments, an optical coherence tomography-based ophthalmic testing method comprises obtaining, using an optical coherence tomography device, an optical coherence tomography scan of a region of an eye of a user, wherein the optical coherence tomography device is configured to enable the user to self-administer the scan by using the device; using a processor to conduct a corneal pachymetry test on the eye based on the optical coherence tomography scan; and outputting on an output device an output based on the test.

In various embodiments, an optical coherence tomography-based ophthalmic testing method comprises obtaining, using an optical coherence tomography device, an optical coherence tomography scan of a region of an eye of a user, wherein the optical coherence tomography device is configured to enable the user to self-administer the scan by using the device; using a processor to conduct a gonioscopy test on the eye based on the optical coherence tomography scan; and outputting on an output device an output based on the test.

In various embodiments, an optical coherence tomography-based ophthalmic testing method comprises obtaining, using an optical coherence tomography device, an anterior optical coherence tomography scan of a anterior region of an eye of a subject, and a posterior optical coherence tomography scan of a posterior region of the eye, and an intermediate optical coherence tomography scan of a region in between the anterior region and posterior region of the eye; using a processor to analyze the anterior, posterior, and intermediate optical coherence tomography scans or to the generate an optical coherence tomography-based image based on the optical coherence tomography scans; and outputting on an output device a report based on the analysis or the optical coherence tomography-based image.

In various embodiments, an optical coherence tomography-based ophthalmic testing method for conducting a best fixating retina verification comprises identifying, using an optical coherence tomography device, a region for a best fixating retina detection; generating, using the optical coherence tomography device, a scan of the region; using a processor to analyze the optical coherence tomography scan to determine the presence of a fovea; and outputting on an output device an output based on the analysis.

In various embodiments, an optical coherence tomography-based ophthalmic testing method for conducting a best fixating retina search comprises generating, using an optical coherence tomography device, a three-dimensional optical coherence tomography scan of a region; using a processor to analyze the three-dimensional optical coherence tomography scan to determine the location of a best fixating retina; and outputting on an output device an output based on the analysis.

In various embodiments, an optical coherence tomography-based biomicroscopy method comprises performing, using an optical coherence tomography device, optical coherence tomography scans; using a processor to obtain a first set of optical coherence tomography data from a first optical coherence tomography scan and a set of second optical coherence tomography data from said first optical coherence tomography scan or from a second optical coherence tomography scan, further using said processor to logically operate on the first set of optical coherence tomography data with the second set of optical coherence tomography data to produce a resultant optical coherence tomography scan with less ghost imagery than said first optical coherence tomography scan; and outputting on an output device an output based on the resultant scan.

In an embodiment, a chronic eye disease optical coherence tomography measuring and monitoring system comprises an optical coherence tomography measurement device for measuring at least one ophthalmic characteristic of at least one eye of a user. The optical coherence tomography measurement can be configured to enable the user to self-administer the measuring by using the optical coherence tomography measurement device. The optical coherence tomography measuring and monitoring system also comprises a processor configured to compare the measured optical coherence tomography characteristic with at least one previously measured optical coherence tomography characteristic of the user stored in a storage medium. The processor can further be configured to determine a difference between the measured optical coherence tomography characteristic and the previously measured optical coherence tomography characteristic. The processor can also be configured to determine that an increased probability exists for required treatment if the difference satisfies the at least one criterion. The optical coherence tomography measuring and monitoring system further comprises an output device for generating an output to the user, the processor further configured to generate an output on the output device based on the difference.

In an embodiment, a method for self-administering an optical coherence tomography test to monitor an ophthalmic condition comprises receiving information related to the ophthalmic condition, obtaining optical coherence tomography measurements of at least one user eye using an optical coherence tomography instrument, determining an ophthalmic output based on results of the optical coherence tomography scanning, the output being related to a state of the ophthalmic condition, and outputting the ophthalmic condition to at least one of the user, a healthcare provider and an agent of the healthcare provider.

In an embodiment, an optical coherence tomography system comprises an input device configured to receive information related to an ophthalmic condition, an eyepiece for receiving at least one eye of a user, a light source that outputs light that is directed through the eyepiece into the user's eye, an interferometer configured to produce optical interference using light reflected from the user's eye, an optical detector disposed so as to detect said optical interference, electronics coupled to the detector and configured to analyze optical coherence tomography measurements obtained using said interferometer and determine an ophthalmic output related to a state of the ophthalmic condition, and an output device electrically coupled to the electronics, the output device configured to output the ophthalmic output.

In an embodiment, a self-administered optical coherence tomography system for glaucoma detection comprises an optical coherence tomography measurement device configured to obtain a first set of optical coherence tomography data for a first region of an eye of a user and a second set of optical coherence tomography data for a second region of the eye. The first and second regions of the eyes can be at different anterior-posterior depths. The optical coherence tomography measurement device can also be configured to enable the user to self-administer the scanning by using the device. The self-administered optical coherence tomography system for glaucoma detection also comprises a processor configured to determine a first boundary position using the first set of optical coherence tomography data and to determine a second boundary position using the second set of optical coherence tomography data. The processor can further be configured to determine an ophthalmic distance based on the first boundary position and the second boundary position and to compare the ophthalmic distance with a threshold value to screen for glaucoma in the eye. The self-administered optical coherence tomography system for glaucoma detection further comprises an output device configured to generate an output on the output device based on the comparison.

In an embodiment, a glaucoma detection method for providing a self-administered optical coherence tomography test of a user's eye comprises obtaining optical coherence tomography measurements of an anterior segment at least one user eye using an optical coherence tomography instrument, determining an ophthalmic output based on results of the optical coherence tomography scanning, the output being related to a state of glaucoma, and outputting the ophthalmic output to at least one of the user, a healthcare provider and an agent of the healthcare provider.

In various embodiments, an optical coherence tomography instrument for detecting the causes of amblyopia comprises an eyepiece for receiving both eyes of a subject; a light source that outputs light that is directed through the eyepiece into the subject's eyes; an interferometer configured to produce optical interference using light reflected from the subject's eyes; an optical detector disposed so as to detect said optical interference in the subject's eyes; a processing module coupled to the detector and configured to perform an analysis to automatically detect the causes of amblyopia based on optical coherence tomography measurements obtained using said interferometer; and an output device electrically coupled to the processing module, said output device configured to output results of the amblyopia analysis to the subject through the output device.

In various embodiments, an optical coherence tomography instrument for detecting strabismus comprises an eyepiece for receiving both eyes of a subject; a light source that outputs light that is directed through the eyepiece into the subject's eyes; an interferometer configured to produce optical interference using light reflected from the subject's eyes; an optical detector disposed so as to detect said optical interference in the subject's eyes; a processing module coupled to the detector and configured to perform an analysis to automatically detect strabismus based on optical coherence tomography measurements obtained using said interferometer; and an output device electrically coupled to the processing module, said output device configured to output results of the strabismus analysis to the subject through the output device.

In various embodiments, an optical coherence tomography instrument for detecting refractive error disorders comprises an eyepiece for receiving both eyes of a subject; a light source that outputs light that is directed through the eyepiece into the subject's eyes; an interferometer configured to produce optical interference using light reflected from the subject's eyes; an optical detector disposed so as to detect said optical interference in the subject's eyes; a processing module coupled to the detector and configured to perform an analysis to automatically detect refractive error disorders based on optical coherence tomography measurements obtained using said interferometer; and an output device electrically coupled to the processing module, said output device configured to output results of the refractive error disorders analysis to the subject through the output device.

In various embodiments, an optical coherence tomography instrument for detecting eye occlusion comprises an eyepiece for receiving both eyes of a subject; a light source that outputs light that is directed through the eyepiece into the subject's eyes; an interferometer configured to produce optical interference using light reflected from the subject's eyes; an optical detector disposed so as to detect said optical interference in the subject's eyes; a processing module coupled to the detector and configured to perform an analysis to automatically detect eye occlusion based on optical coherence tomography measurements obtained using said interferometer; and an output device electrically coupled to the processing module, said output device configured to output results of the eye occlusion analysis to the subject through the output device.

In various embodiments, an interpupillary distance measurement device comprises an ocular eyepiece comprising at least two openings, the openings configured for placement on eyes of a subject; and a support structure having a measurement guide, the support structure connected to the ocular eyepiece, the support configured to be adjustable for allowing the two openings to be slidable with respect to each other and to measure the interpupillary distance of the subject, the measurement guide configured to change in dimension based on the measured interpupillary distance; wherein the measurement guide is configured to be connected to an OCT instrument to be adjusted to the measured interpupillary distance of the subject.

In various embodiments, an optical coherence tomography instrument for measuring dioptric power of eyes of a subject, the instrument comprises an eyepiece for receiving both eyes of a subject; a light source that outputs light that is directed through the eyepiece into the eyes of the subject; an interferometer configured to produce optical interference using light reflected from the eyes of the subject; an optical detector disposed so as to detect said optical interference in the eyes of the subject; a processing module coupled to the detector and configured to perform an analysis to automatically measure dioptric power based on optical coherence tomography measurements obtained using said interferometer; an output device electrically coupled to the processing module, said output device configured to output results of the dioptric power analysis to the subject through the output device; and an auto-focus system for automatically determining refractive errors for each eye of the subject, wherein the processing module is configured to perform the refractive error analysis based on optical coherence tomography measurements and focus measurements obtained using the bilateral auto-focus system.

In various embodiments, a computer-implemented method for detecting the causes of amblyopia, the computer-implemented method comprises receiving the eyes of a subject in an eyepiece; outputting light from a light source that is directed through the eyepiece into the subject's eyes; producing optical interference using an interferometer and the light reflected from the subject's eyes; detecting said optical interference in the subject's eyes using an optical detector; performing an analysis, using a processing module coupled to the detector, to automatically detect the causes of amblyopia based on optical coherence tomography measurements obtained using said interferometer; and generating an output through an output device electrically coupled to the processing module, the output comprising the results of the amblyopia analysis.

In various embodiments, an optical coherence tomography instrument for estimating visual acuity of a subject, the optical coherence tomography instrument comprises an eyepiece for receiving both eyes of a subject; a light source that outputs light that is directed through the eyepiece into the subject's eyes; an interferometer configured to produce optical interference using light reflected from the subject's eyes; an optical detector disposed so as to detect said optical interference in the subject's eyes; a processing module coupled to the detector and configured to perform an analysis to automatically estimate visual acuity based on data measurements obtained using said light source; and an output device electrically coupled to the processing module, said output device configured to output results of the visual acuity analysis to the subject through the output device.

In various embodiments, the optical tomography instrument of claim 51, further comprises a fixation marker control module configured to change the fixation mark shown to the eyes of the subject; the processing control module further configured to generate a plurality of B-scans based on optical coherence tomography measurements obtained at different times and changes in the fixation mark, wherein the processing control module is further configured to automatically detect changes in the plurality of B-scans; wherein the processing control module is further configured to output through the output device that a visual acuity disorder has been detected if the detected change in the plurality of B-scans is greater than a threshold value.

In various embodiments, an optical coherence tomography instrument for estimating optic nerve head volume to monitor glaucoma in a subject, the optical coherence tomography instrument comprises an eyepiece for receiving both eyes of a subject; a light source that outputs light that is directed through the eyepiece into the subject's eyes; an interferometer configured to produce optical interference using light reflected from the subject's eyes; an optical detector disposed so as to detect said optical interference in the subject's eyes; a processing module coupled to the detector and configured to perform an analysis to automatically estimate optic nerve head volume in both eyes based on optical coherence tomography measurements obtained using said interferometer; and an output device electrically coupled to the processing module, said output device configured to output results of the optic nerve head volume analysis to the subject through the output device.

In various embodiments, an optical coherence tomography instrument for estimating the angular misalignment between two eyes for determining prism lens prescriptions in a subject, the optical coherence tomography instrument comprises an eyepiece for receiving both eyes of a subject; a light source that outputs light that is directed through the eyepiece into the subject's eyes; an interferometer configured to produce optical interference using light reflected from the subject's eyes; an optical detector disposed so as to detect said optical interference in the subject's eyes; a processing module coupled to the detector and configured to perform an analysis to automatically estimate the angular misalignment between two eyes based on optical coherence tomography measurements obtained using said interferometer; and an output device electrically coupled to the processing module, said output device configured to output results of the angular misalignment analysis report through the output device.

For purposes of this summary, certain aspects, advantages, and novel features of the invention are described herein. It is to be understood that not necessarily all such aspects, advantages, and features may be employed and/or achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

BRIEF DESCRIPTION OF THE DRAWINGS

The foregoing and other features, aspects and advantages of the present invention are described in detail below with reference to the drawings of various embodiments, which are intended to illustrate and not to limit the invention. The drawings comprise the following figures in which:

FIGS. 6A-6C are schematic diagrams illustrating the use of optical coherence tomography to scan retinal tissue to generate A-scans and B-scans.

FIGS. 7A-7F are schematic diagrams illustrating embodiments for adjusting and/or calibrating interpupillary distance.

FIGS. 11A-11B illustrate possible embodiments of output reports generated by the optical coherence tomography device.

FIG. 15 is an illustration of RPE detection and RPE polynomial fit curvature, and the difference there between.

FIG. 23 is high-level flow diagram illustrating an example process for using an OCT system to detect causes of amblyopia such as strabismus, anisometropia, isoametropia, visual occlusion, and the like.

FIG. 25 comprises example illustrations of OCT system-generated images of retinas, and the images can be used to detect causes of amblyopia, or strabismus, anisometropia, isoametropia, visual occlusion, and the like.

FIGS. 30A-30F illustrate various embodiments of OCT devices of an OCT-based ophthalmic testing center system.

FIGS. 32A and 32B illustrate an embodiment of performing refractive error correction on a myopic eye.

FIGS. 35A, 35B, 35C, 36, and 37 illustrate various embodiments of performing eye tracking functions using the OCT-based ophthalmic testing center system as described herein.

FIG. 42 illustrates various embodiments of visual acuity tests conducted using the OCT-based ophthalmic testing center system as described herein.

DETAILED DESCRIPTION OF THE PREFERRED EMBODIMENT

Figure 1:
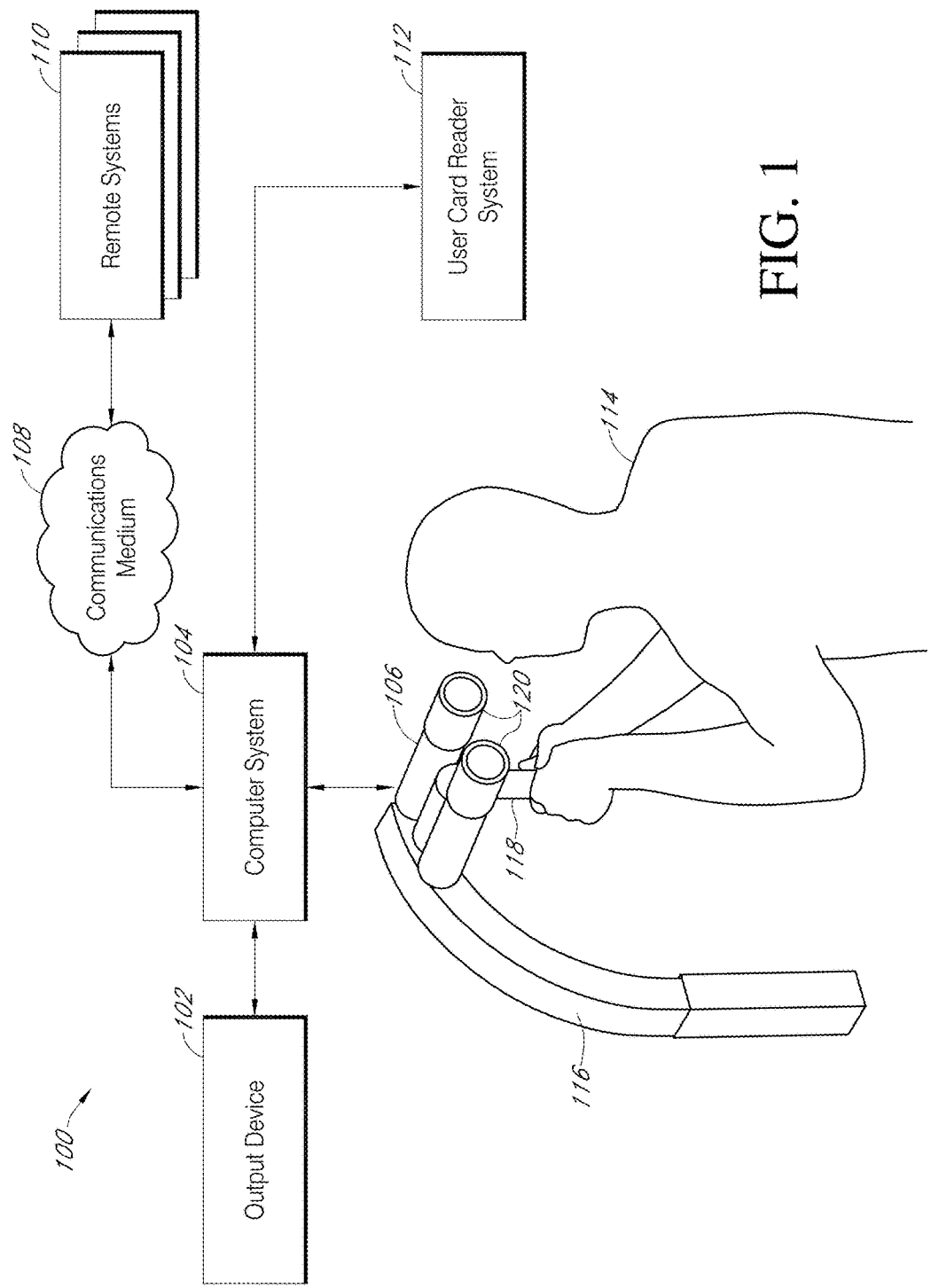
FIG. 1 is a schematic diagram of one embodiment of the optical coherence tomography system described herein.

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may comprise several novel features, no single one of which is solely responsible for its desirable attributes or which is essential to practicing the inventions herein described. The embodiments described herein make OCT screening more accessible to users thereby allowing for earlier detection and/or treatment of various diseases, ailments, or conditions, for example, maculopathy, glaucoma, or the like.

The terms "optical coherence tomography" and "OCT" generally refer to an interferometric technique for imaging samples, in some cases, with micrometer lateral resolution. This non-invasive optical tomographic imaging technique is used in ophthalmology to provide cross-sectional images of the eye, and more particularly the posterior of the eye, though it can also be used to image other samples or tissues in areas of the user's body.

Generally, OCT employs an interferometer. Light from a light source (for example, a broadband light source, swept source, or tunable laser) is split (for example, by a beam splitter) and travels along a sample arm (generally comprising the sample) and a reference arm (generally comprising a mirror). Alternatively, the light from the light source can travel down fiber optics, microfiber, and/or any other medium capable of transmitting light. A portion of the light from the sample arm is reflected by the sample. Light is also reflected from a mirror in the reference arm. (Light from the test arm and the reference arm is recombined, for example by the beam splitter.) When the distance travelled by light in the sample arm is within a coherence length of the distance travelled by light in the reference arm, optical interference occurs, which affects the intensity of the recombined light. The intensity of the combined reflected light varies depending on the sample properties. Thus, variations for the intensity of the reflectance measured are indications of the physical features of the sample being tested.

In time-domain OCT, the length of the reference arm can be varied (for example, by moving one or more reference mirrors). The reflectance observed as the reference arm distance changes indicates sample properties at different depths of the sample. (In some embodiments, the length of the sample arm is varied instead of or in addition to the variation of the reference arm length.) In frequency-domain OCT, the distance of the reference arm can be fixed, and the reflectance can then be measured at different frequencies. For example, the frequency of light emitted from a light source can be scanned across a range of frequencies or a dispersive element, such as a grating, and a detector array may be used to separate and detect different wavelengths. Fourier analysis can convert the frequency-dependent reflectance properties to distance-dependent reflectance properties, thereby indicating sample properties at different sample depths. In certain embodiments, OCT can show additional information or data other than nonmydriatic color fundus imaging.

The term "A-scan" describes the light reflectivity associated with different sample depths. The term "B-scan" as used herein refers to the use of cross-sectional views of tissues formed by assembly of a plurality of A-scans. In the case of ophthalmology, light reflected by eye tissues is converted into electrical signals and can be used to provide data regarding the structure of tissue in the eye and to display a cross-sectional view of the eye. In the case of ophthalmology, A-scans and B-scans can be used, for example, for differentiating normal and abnormal eye tissue or for measuring thicknesses of tissue layers in the eyes. The term "B-scan" as used herein may also be used generally to represent a set of B-scans instead of a single B-scan.

In ophthalmic instances, an A-scan can generally include data from the precorneal region to the choroid. In some instances, a B-scan can include cross-sectional data from a medial border to a lateral border of the eye and from the precorneal region to the choroid. In some instances, a B-scan can include cross-sectional data from a superior border to an inferior border of the eye and from the precorneal region to the choroid. A 3D-OCT can be formed by combining a plurality of B-scans.

As used herein the terms "user" or "patient" or "subject" may be used interchangeably, and the foregoing terms comprise without limitation human beings, whether or not under the care of a physician, and other mammals.

The terms "eye scan," "scanning the eye," or "scan the eyes," as used herein, are broad interchangeable terms that generally refer to the measurement of any part, substantially all, or all of the eye, including but not limited to the pre-cornea, the cornea, the retina, the eye lens, the iris, the vitreous body, the anterior chamber, the anterior chamber angle, the optic nerve, or any other tissue or nerve related to the eye.

The terms "risk assessment" and "diagnosis," may be used in the specification interchangeably although the terms have different meanings. The term "risk assessment" generally refers to a probability, number, score, grade, estimate, etc. of the likelihood of the existence of one or more illnesses, diseases, ailments, or the like. The term "diagnosis" generally refers to a determination by examination and/or tests the nature and circumstances of an illness, ailment, or diseased condition.

Various methods, systems, and devices may be used to generate and utilize optical coherence tomography image data to perform precision measurements on ocular tissue for the detection of disease features and findings, and generating a risk assessment and/or diagnosis based on data obtained by optical coherence tomography imaging techniques. These methods, systems and devices may employ, in some embodiments, a statistical analysis of the detected disease features obtained by optical coherence tomography imaging techniques. Such methods, systems, and devices can be used to screen for diseases.

With reference to FIG. 1, there is illustrated a block diagram depicting one embodiment of the optical coherence tomography system. In one embodiment, computer system 104 is electrically coupled to an output device 102, a communications medium 108, and a user card reader system 112. The communications medium 108 can enable the computer system 104 to communicate with other remote systems 110. The computer system 104 may be electrically coupled to main body 106, which the user 114 positions near or onto the user's eyes. In the illustrated example, the main body 106 is a binocular system (for example, has two oculars or optical paths for the eyes providing one view for one eye and another view for another eye, or the like) configured to scan two eyes without repositioning the oculars with respect to the head of the patient, thereby reducing the time to scan a patient. In some embodiments, the eyes are scanned simultaneously using a scanner (for example, galvanometer), which provides interlaces of measurements from both eyes. Other embodiments are possible as well, for example, the binocular system or a two ocular system having two respective optical paths to the two eyes can be configured to scan the eyes in series, meaning one eye first, and then the second eye. In some embodiments, serial scanning of the eyes comprises scanning a first portion of the first eye, a first portion of the second eye, a second portion of the first eye, and so on. Alternatively, the main body 106 can comprise a monocular system or one ocular system or optical path to the eye for performing eye scans.

Referring to FIG. 1, the user 114 can engage handle 118 and position (for example, up, down, or sideways) the main body 106 that is at least partially supported and connected to a zero gravity arm 116, and accordingly the system 100 has no chin rest. In some embodiments, this configuration can introduce positioning error due to movement of the mandible. When the main body 106 is in such a position, the distance between the outermost lens (the lens closest to the user) and the user's eye can range between 10 mm and 30 mm, or 5 mm and 25 mm, or 5 mm and 10 mm. The close proximity of the lens system to the user's eyes increases compactness of the system, reduces position variability when the patient places his eyes (for example, orbital rims) against the main body 106, and increases the viewing angle of the OCT apparatus when imaging through an undilated pupil.

Accordingly, the main body 106 can also comprise eyecups 120 (for example, disposable eyecups) that are configured to contact the user's eye socket to substantially block out ambient light and/or to at least partially support the main body 106 on the eye socket of the user 114. The eyecups 120 have central openings (for example, apertures) to allow passage of light from the light source in the instrument to the eyes. The eyecups 120 can be constructed of paper, cardboard, plastic, silicon, metal, latex, or a combination thereof. The eyecups 120 can be tubular, conical, or cup-shaped flexible or semi-rigid structures with openings on either end. Other materials, shapes and designs are possible. In some embodiments, the eyecups 120 are constructed of latex that conforms around eyepiece portions of the main body 106. The eyecups 120 are detachable from the main body 106 after the eye scan has been completed, and new eyecups 120 can be attached for a new user to ensure hygiene and/or to protect against the spread of disease. The eyecups 120 can be clear, translucent or opaque, although opaque eyecups offer the advantage of blocking ambient light for measurement in lit environments.

The main body 106 may comprise one or more eyepieces, an interferometer, one or more target displays, a detector and/or an alignment system. The optical coherence tomography system may comprise a time domain optical coherence tomography system, a spectral, or frequency, domain optical coherence tomography system and/or a swept-source optical coherence tomography system. Accordingly, in some embodiments, the main body 106 comprises a spectrometer, (for example, a grating) and a detector array. The main body 106 may, in some embodiments, comprise a signal processing component (for example, electronics) for performing, for example, Fourier transforms. Other types of optical coherence tomography systems may be employed.

Figure 2:
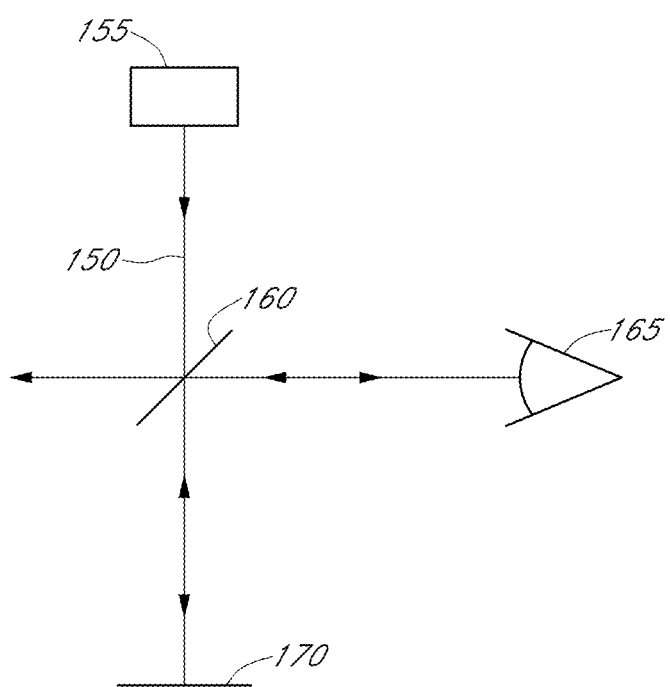
FIG. 2 is a schematic diagram of one embodiment of an interferometer arranged to perform measurements of an eye.

FIG. 2 shows a diagram of an example optical coherence tomography system. Light 150 is output from a light source 155. The light source 155 may comprise a broadband light source, such as a superluminescent diode, a microelectromechanical system or a white light source. Light emitted from the light source 155 may vary in frequency as a function of time. The light 150 may comprise collimated light. In one embodiment, light 150 from the light source 155 is collimated with a collimating lens. In another embodiment, two light sources can be used for each optical path in the binocular system 106. In yet another embodiment, the light is split at beam splitter 160. Beam splitters, as described herein, may comprise, without limitation, a polarization-based beam splitter, a temporally-based beam splitter, a 50/50 beam splitter and/or other devices and configurations. A portion of the light travels along a sample arm, directed towards a sample, such as an eye 165 of a user 114. Another portion of the light 150 travels along a reference arm, directed towards a reference mirror 170. The light reflected by the sample and the reference mirror 170 are combined at the beam splitter 160 and sensed either by a one-dimensional photodetector or a two-dimensional detector array, such as a charge-coupled device (CCD) or complementary metal-oxide-semiconductor (CMOS). A two-dimensional array may be included in a full field OCT instrument, which may gather information more quickly than a version that uses a one dimensional photodetector array instead. In time-domain OCT, the length of the reference arm (which may be determined in part by the position of the reference mirror 170) may be varying in time.

Whether interference between the light reflected by the sample and the light reflected by the reference mirror/s occurs will depend on the length of the reference arm (as compared to the length of the test arm) and the frequency of the light emitted by the light source. High contrast light interference occurs between light travelling similar optical distances (for example, differences less than a coherence length). The coherence length is determined by the bandwidth of the light source. Broadband light sources correspond to smaller coherence lengths.

In time-domain OCT, when the relative length of the reference and sample arms varies over time, the intensity of the output light may be analyzed as a function of time. The light signal detected results from light rays scattered from the sample that interfere constructively with light reflected by the reference mirror/s. Increased interference occurs, however, when the lengths of the sample and reference arms are approximately similar (for example, within about one coherence length in some cases). The light from the reference arm, therefore, will interfere with light reflected from a narrow range of depths within the sample. As the reference (or sample) arms are translated, this narrow range of depths can be moved through the thickness of the sample while the intensity of reflected light is monitored to obtain information about the sample. Samples that scatter light will scatter light back that interferes with the reference arm and thereby produce an interference signal. Using a light source having a short coherence length can provide increased to high resolution (for example, 0.1-10 microns), as the shorter coherence length yields a smaller range of depths that is probed at a single instant in time.

In various embodiments of frequency-domain optical coherence tomography, the reference and sample arms are fixed. Light from a broadband light source comprising a plurality of wavelengths is reflected from the sample and interfered with light reflected by the reference mirror/s. The optical spectrum of the reflected signal can be obtained. For example, the light may be input to a spectrometer or a spectrograph comprising, for example, a grating and a detector array, that detects the intensity of light at different frequencies.

Fourier analysis performed, for example, by a processor may convert data corresponding to a plurality of frequencies to that corresponding to a plurality of positions within the sample. Thus, data from a plurality of sample depths can be simultaneously collected without the need for scanning of the reference arm (or sample) arms. Additional details related to frequency domain optical coherence tomography are described in Vakhtin et al., (Vakhtin A B, Kane D J, Wood W R and Peterson K A. "Common-path interferometer for frequency-domain optical coherence tomography," Applied Optics. 42(34), 6953-6958 (2003)).

Other methods of performing optical coherence tomography are possible. For example, in some embodiment of frequency domain optical coherence tomography, the frequency of light emitted from a light source varies in time. Thus, differences in light intensity as a function of time relate to different light frequencies. When a spectrally time-varying light source is used, a detector may detect light intensity as a function of time to obtain optical spectrum of the interference signal. The Fourier transform of the optical spectrum may be employed as described above. A wide variety of other techniques are also possible.

Figure 3A:
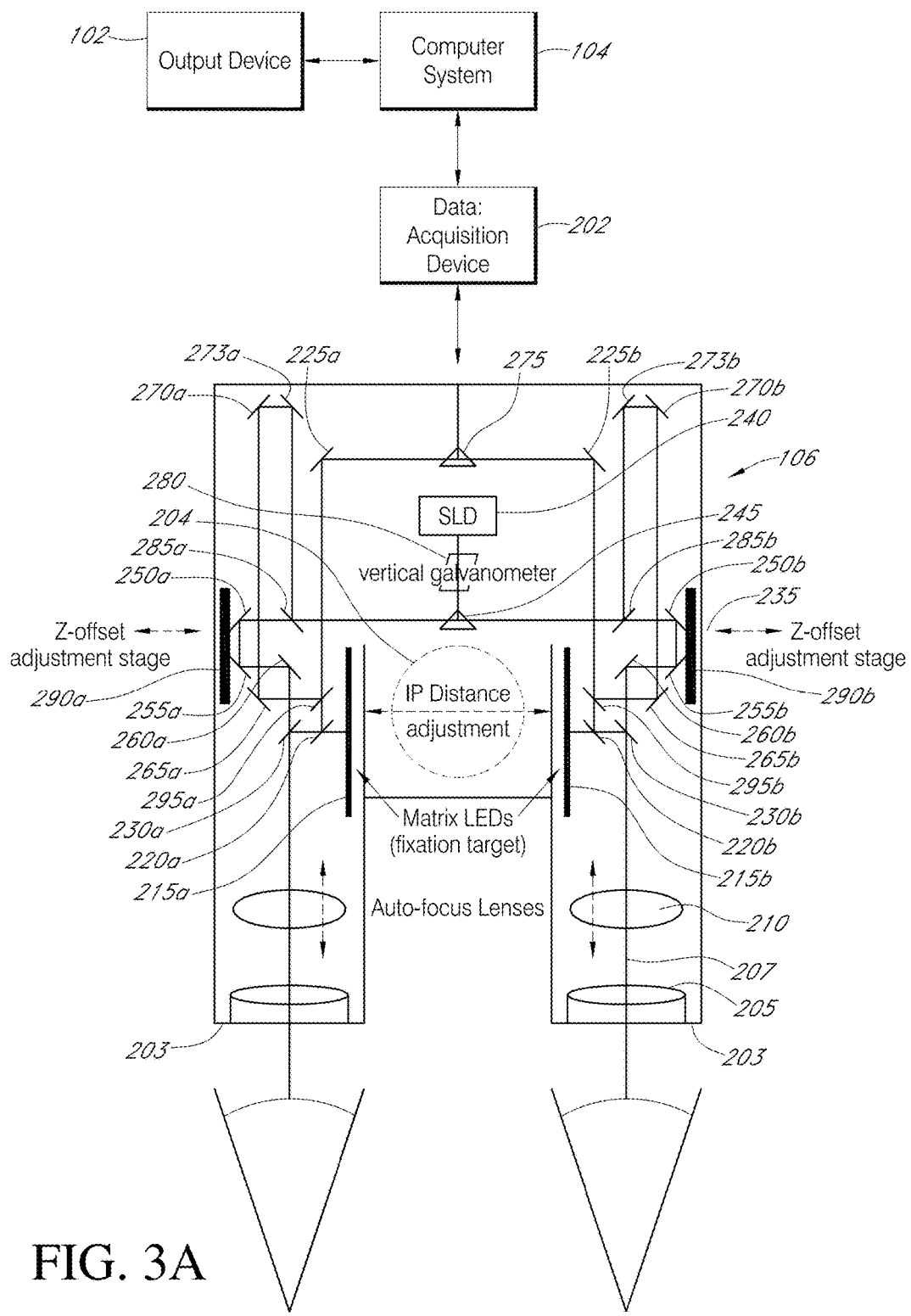
FIG. 3A is a schematic diagram of one embodiment of an OCT system comprising a main body configured to conveniently interfere with a person's eyes, the main body being in communication with various systems as described herein.

FIG. 3A shows one configuration of main body 106 comprising an optical coherence tomography system and an alignment system. Other optical coherence tomography systems and/or alignment systems may be included in place of or in addition to the systems shown in FIG. 3A. As shown, the main body 106 can include two eyepieces 203, each eyepiece configured to receive an eye from a user 114. In various embodiments, the main body 106 includes only one eyepiece 203.

FIG. 3A shows one representative embodiment of an optical coherence tomography system. Light from a light source 240 may propagate along a path that is modulated, for example, vertically and/or horizontally by one or more beam deflectors 280. (Alternatively, the light from the light source can travel down and/or be modulated by fiber optics, microfiber, and/or any other medium capable of transmitting/modulating light.) A galvanometer may be used for this purpose. The galvanometer 280 can control the horizontal and/or vertical location of a light beam from the light source 240, thereby allowing a plurality of A-scans (and thus one or more B-scan and/or a 3D-OCT) to be formed.

The light from the light source 240 is split at beam splitter 245. In some embodiments, beam splitter 245 is replaced by a high frequency switch that uses, for example, a galvanometer, that directs about 100% of the light towards mirror 250a for about ½ of a cycle and then directs about 100% of the light towards mirror 250b for the remainder of the cycle. The light source 240 may include a broadband light source, such as a superluminescent light-emitting diode or a microelectromechanical tunable laser source. Light split at the beam splitter 245 is then split again at beam splitter 285a or 285b to form a reference arm and a sample arm. A first portion of the light split at beam splitter 285a or 285b is reflected by reference mirrors 273a or 273b, reference mirrors 270a or 270b, and reference mirrors 265a or 265b. A second portion of the light split at beam splitter 285a or 285b is reflected by mirror 250a or 250b, by mirror 255a or 255b and by mirror 260a or 260b. Mirrors 255a or 255b and mirrors 250a and 250b are connected to a Z-offset adjustment stage 290b. By moving the position of the adjustment stage 290a or 290b, a different portion of the eye can be imaged. Thus, the adjustment stage 290a or 290b can adjust the difference between the optical length from the light source 240 to a portion of the sample and the optical length from the light source 240 and the reference mirror 270a or 270b and/or reference mirror 273a or 273b. This difference can be made small, for example, less than a coherence length, thereby promoting optical interference to occur. In some embodiments, the positions of one or more reference mirrors (for example, reference mirror 270a or 270b and reference mirror 273a or 273b) are movable in addition to or instead of the adjustment stage being movable. Thus, the length of the reference arm and/or of the sample arm may be adjustable. The position of the adjustment stages 290a and/or 290b may be based on the signals from the device, as described in more detail below.

The light reflected by mirror 260a or 260b is combined with light from display 215a or 215b at beam splitter 230a or 230b. The displays 215a and 215b may comprise one or more light sources, such as in an emissive display like an array of matrix LEDs. Other types of displays, such as LCD, FFD or FLCOS displays, can be used. The display can display targets of varying shapes and configurations, including a bar and/or one or more dots. It can also be configured to display images or movies. A portion of the optical path from the light source 240 to the eye may be coaxial with a portion of the path from the displays 215a and 215b to the eye. These portions may extend though the eyepiece. Accordingly, a light beam from the light source 240 is coaxial with a light beam from the displays 215a and 215b such that the eyes can be positioned and aligned with respect to the eyepieces using the displays. A lens may be placed in the light path between display 215a and element 220a (or 215b and 220b) to enable manipulation of the vergence of light emitted from the display wherein the target appears at a large distance (for example, infinity). In many configurations, collimated light may be desirable. In others, divergent light simulating a near target may be desirable. In some embodiments, therefore, one or more lenses are interposed in the light path between elements 260a and 230a or 260b and 230b to produce the same vergence effect on the light from light source 240. Mirrors, prisms, or other optical elements may be used, in certain embodiments, to provide increased optical path for insertion of the one or more lenses. In certain embodiments, the one or more lenses can be Stokes' lenses. The display may be used for a variety of tests, such as functional tests where controlled eye fixation is used. Additional discussion of such tests is provided below.

Figure 3B:
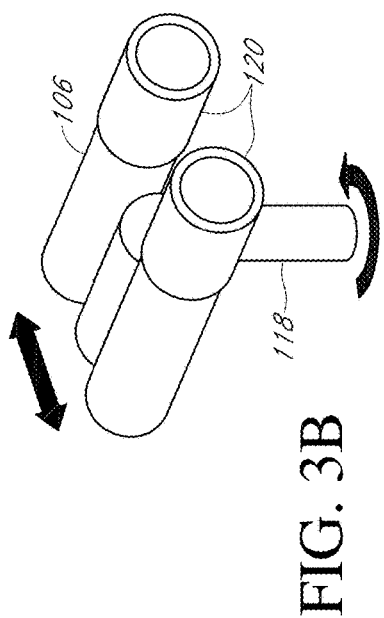
FIG. 3B is a perspective view schematically illustrating an embodiment of the main body shown in FIG. 3A.

As described in greater detail below, for example, the user 114 may use images from the displays in order to adjust interpupillary distance. In various embodiments, for example, proper alignment of two images presented by the displays may indicate that the interpupillary distance is appropriately adjusted. Thus, one or more adjustment controls 235 may be used to adjust the distance between the display targets 215a and 215b and/or between the eyepieces 203. The adjustment controls 235 may be provided on the sides of the main body 106 or elsewhere. In certain embodiments, the adjustment control 204 may comprise a handle on the main body 106, as shown in FIG. 3B. In this embodiment, rotation of the adjustment control 204 may increase or decrease the interpupillary distance. In various embodiments, the adjustment control 204 may be controlled electronically by processors within the main body 106 based on the detected position of the pupils, the iris in one eye or both eyes, or lens region in at least one eye, by using, for example, edge detection algorithms, from B-scans or C-scans of the anterior chamber. In certain embodiments, the interpupillary distance can be adjusted by control 204 until the pupils are substantially centered in both B-scans or C-scans, thereby indicating optimal optical axis alignment. In certain embodiments, the interpupillary distance can be adjusted in two axes (horizontal and vertical). Additional discussion of electronic interpupillary distance adjustment is provided below in the section on pupillometry.

The combined light (that is reflected by mirror 260a or 260b and that comes from display 215a or 215b) is focused by adjustable powered optics (for example, lens) 210 possibly in conjunction with optical element 205. The adjustable optics 210 may comprise a zoom lens or lens system that may have, for example, a focal length and/or power that is adjustable. The adjustable optics 210 may comprise or be part of an auto-focus system or may be manually adjusted. The adjustable optics 210 may provide optical correction for those in need of such correction (for example, a user whose glasses are removed during testing). The position of the powered optics 210 may be based on the signals obtained from the device, as described in more detail below. The focused light then travels through eyepiece windows or lens 205, positioned at a proximal end of the eyepiece 203, towards the eye of a user 114. In the case where a lens 205 is included, this lens 205 may contribute to focusing of the light into the eye.

This light directed into the eye may be scattered by tissue or features therein. A portion of this scattered light may be directed back into the eyepiece. Lens 205 may thus receive light 207 reflected from the user's eye, which travels through the powered optics 210, reflects off of the beam splitter 230a or 230b towards beam splitter 220a or 220b, which reflects the light towards mirrors 295a and 295b. At 295a or 295b, light reflected by the sample interferes with light in the reference arm (path between beam splitter 285a or 285b and beam splitter 295a or 295b that includes mirrors 273a or 273b and 270a or 270b). (Accordingly, the sample arm includes the optical path between beam splitter 285a or 285b and beam splitter 295a or 295b that includes mirrors 250a or 250b and 255a or 255b and the sample or eye.) The light is then reflected by mirror 225a or 225b towards switch 275. In some embodiments, the switch 275 comprises a switchable deflector that switches optical paths to the first or second eye to collect data from the respective eye to be sent to the data acquisition device 202. The switch may comprise a low-frequency switch, such that all data to be collected from one eye is obtained before the data is collected from the other eye. Alternatively, the switch may comprise a high-frequency switch, which may interlace data collected from each eye.

The instrument may be configured differently. For example, a common reference path may be used for each eye. In some embodiments, the reference arm includes one or more movable mirrors to adjust the optical path length difference between the reference and sample arms. Components may be added, removed, or repositioned in various embodiments. Other techniques, may be used.

Although not shown, for example, polarizers and polarizing beams splitters may be used to control the propagation of light through the optical path in the optical system. Other variations are possible. Other designs may be used.

In some embodiments, an A-scan may be formed in the time domain. In these instances, the Z-offset adjustment stage and corresponding mirror 250a or 250b and mirror 255a or 255b may change positions in time. Alternatively, reference mirrors 270a and 270b and reference mirrors 273a and 273b or other mirrors in the reference or sample arms may be translated. The combined light associated with various mirror positions may be analyzed to determine characteristics of an eye as a function of depth. In various embodiments, an A-scan may be formed in the spectral domain. In these instances, the frequencies of the combined light may be analyzed to determine characteristics of an eye as a function of depth. Additionally, one or more galvanometers 280 can control the horizontal and/or vertical location of the A-scan. Thus, a plurality of A-scans can be obtained to form a B-scan and/or a 3D-OCT scan.

Light output from the structure 275 can be input into a data acquisition device 202, which may comprise, for example, a spectrometer, a photodetector, or a light meter. A grating may be in the main body 106. The data acquisition device 202 is coupled to a computer system 104, which may present output based on scans to the user 114. The output device may include a monitor screen, in which output results are displayed. The output device may include a printer, which prints output results. The output device may be configured to store data on a portable medium, such as a compact disc or USB drive, or a custom portable data storage device.

In some embodiments, the computer system 104 analyzes data received by the data acquisition device 202 in order to determine whether one or more of the adjustment stages 290a and/or 290b and/or one or more movable components and/or the powered optics 210 should be adjusted. In one instance, an A-scan is analyzed to determine a position (for example, a coarse position) of the retina such that data on the retina may be obtained by the instrument. In some embodiments, each A-scan comprises a plurality of light intensity values, each associated with a different depth into the sample. The A-scan may be obtained, in some embodiments, by translating the Z adjustment stage 290a or 290b. Likewise, the A-scan comprises values of reflected signal obtained at different locations of the Z adjustment stage. The retina reflects more light than other parts of the eye, and thus, it is possible to determine a position of the adjustment stage 290a or 290b that effectively images the retina by assessing what depths provide an increase in reflected intensity. In some embodiments, the Z adjustment stage may be translated and the intensity values may be monitored. An extended peak in intensity for a number of Z adjustment stage positions may correspond to the retina. A variety of different approaches and values may be monitored to determine the location of the retina. For example, multiple A-scans may be obtained at different depths and the integrated intensity of each scan may be obtained and compared to determine which depth provided a peak integrated intensity. In certain embodiments, intensity values within an A-scan can be compared to other values within the A-scan and/or to a threshold. The intensity value corresponding to the preferred location may be greater than a preset or relative threshold and/or may be different from the rest of the intensity values, (for example, by more than a specified number of standard deviations). A wide variety of approaches may be employed.

After the positions of the adjustment stages 290a and 290b have been determined, subsequent image analysis may be performed to account for vibration or movement of the user's head, eyes or retinas relative to the light source 240. A feedback system such as a closed loop feedback system may be employed in effort to provide a more stabilized signal in the presence of such motion. The optical coherence tomography signal may be monitored and feedback provided to, for example, one or more translation stages to compensate for such vibration or movement. In one embodiment, the positions of tissue features identified from non-interferometric light reflected from the subject's eye are tracked to determine the movement of the subject's eye. This movement can then be compensated for by modifying the galvanometer movements to correct for underlying eye movements. In some embodiments, subsequent image analysis may be based on initial image and/or detect changes in image characteristics. For example, the image analysis may determine that the brightest pixel within an A-scan has moved 3 pixels from a previous scan. The adjustment stage 290a or 290b may thus be moved based on this analysis. Other approaches may be used.

In some instances, optical coherence tomography signals are used to adjust the powered optics 210 to provide for increased or improved focus, for example, when a patient needs refractive correction. Many users/patients, for example, may wear glasses and may be tested while not wearing any glasses. The powered optics 210 may be adjusted based on reflected signal to determine what added correction enhances signal quality or is otherwise an improvement. Accordingly, in some embodiments, a plurality of A-scans is analyzed in order to determine a position for the powered optics 210. In some instances, a plurality of A-scans is analyzed in order to determine a position for the powered optics 210. In some embodiments, this determination occurs after the position of the adjustment stage 290a or 290b has been determined. One or more A-scans, one or more B-scans or a 3D-OCT may be obtained for each of a plurality of positions of the powered optics 210. These scans may be analyzed to assess, for example, image quality. The position of the powered optics 210 may be chosen based on these image quality measures.

The image quality measure may include a noise measure. The noise measure may be estimated based on the distribution of different intensity levels of reflected light within the scans. For example, lower signals may be associated with noise. Conversely, the highest signals may be associated with noise. A noise measure may be compared to a saturation measure as in signal to noise ratios or variants thereof. The lowest reflectivity measured (referred to as a low measure or low value) may also be considered. In some embodiments, the positions of the adjustment stages 290a and/or 290b and/or the powered optics 210 is determined based upon a signal-to-noise measure, a signal strength measure, a noise measure, a saturation measure, and a low measure. Different combinations of these parameters may also be used. Values obtained by integrating parameters over a number of positions or scans, etc., may also be used. Other parameters as well as other image quality assessments may also be used.

In one embodiment, a noise value is estimated to be a reflected light value for which approximately 75% of the measured reflected light is below and approximately 25% of the measured reflected light is above. The saturation value is estimated to be a reflected light value for which approximately 99% of the measured reflected light is below and approximately 1% of the measured reflected light is above. A middle value is defined as the mean value of the noise value and the saturation value. An intensity ratio is defined as the difference between the saturation value and the low value divided by the low value multiplied by 100. A tissue signal ratio is defined as the number of reflected light values between the middle value and the saturation value divided by the number of reflected light values between the noise value and the saturation value. A quality value is defined as the intensity ratio multiplied by the tissue signal ratio. Additional details are described, for example, in Stein D M, Ishikawa H, Hariprasad R, Wollstein G, Noecker R J, Fujimoto J G, Schuman J S. A new quality assessment parameter for optical coherence tomography. Br. J. Ophthalmol. 2006; 90; 186-190. A variety of other approaches may be used to obtain a figure of merit to use to measure performance and adjust the instrument accordingly.

In the case of adjusting the adjustable power optics, 210, in some embodiments, a plurality of positions are tested. For example, the powered optics may be continuously moved in defined increments towards the eyes for each scan or set of scans. Alternatively, the plurality of positions may depend on previously determined image quality measures. For example, if a first movement of the powered optics 210 towards the eye improved an image quality measure but a subsequent second movement towards the eye decreased an image quality measure, the third movement may be away from the eye. Accordingly, optical power settings may be obtained that improve and/or maintains an improved signal. This optical power setting may correspond to optical correction and increase focus of the light beam in the eye, for example, on the retina, in some embodiments.

As described above, various embodiments employ an arrangement wherein a pair of oculars is employed. Accordingly, such adjustments, may be applied to each of the eyes as a user may have eyes of different size and the retina may located at different depths and thus a pair of z adjust stages may be used in some embodiments. Similarly, a user may have different prescription optical correction for the different eyes. A variety of arrangements may be employed to accommodate such needs. For example, measurements and/or adjustments may be performed and completed on one eye and subsequently performed and completed the other eye. Alternatively, the measurements and/or adjustments may be performed simultaneously or interlaced. A wide variety of other variations are possible.

Figure 4:
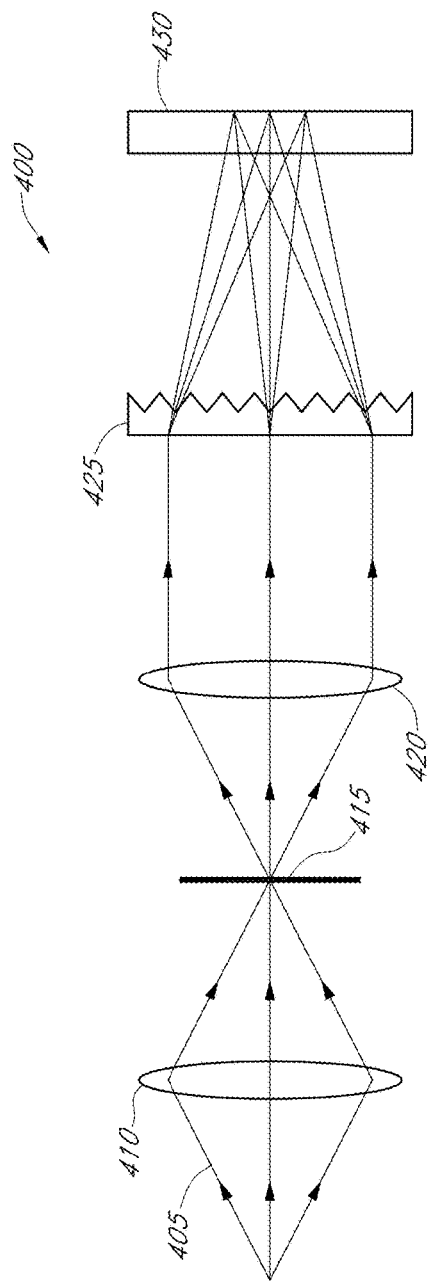
FIG. 4 is schematic diagram of one embodiment of a spectrometer used to analyze data from an interferometer used for OCT.

FIG. 4 shows a diagram of a spectrometer 400 that can be used as a data acquisition device 202 for a frequency domain OCT system. Light 405 input into the spectrometer 400 is collected by collecting lens 410. The collected light then projects through a slit 415, after which it is collimated by the collimating lens 420. The collimated light is separated into various spectral components by a grating 425. The grating 425 may have optical power to focus the spectral distribution onto an image plane. Notably, other separation components, such as a prism may be used to separate the light. The separated light is then directed onto a detector array by focusing lens 430, such that spectral components of each frequency from various light rays are measured.

A wide variety of OCT designs are possible. For example, frequency can be varied with time. The reference and sample arms can overlap. In some embodiments, a reference arm is distinct from a sample arm, while in various embodiments, the reference arm and sample arm are shared. See, for example, Vakhtin A B, Kane D J, Wood W R and Peterson K A. "Common-path interferometer for frequency-domain optical coherence tomography," Applied Optics. 42(34), 6953-6958 (2003). The OCT arrangements should not be limited to those described herein. Other variations are possible.

Figure 5:
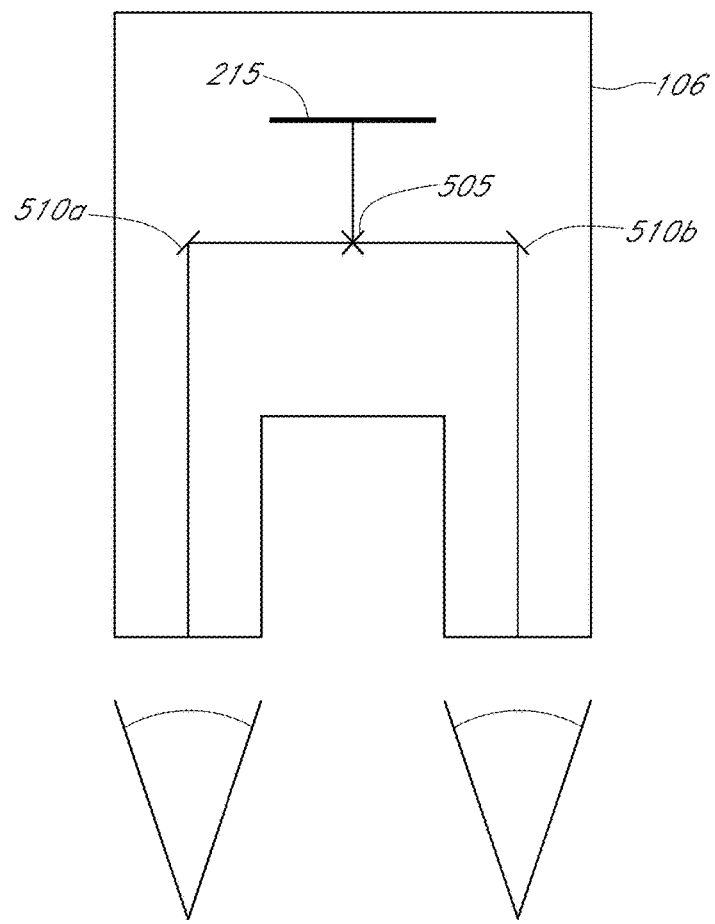
FIG. 5 is a schematic diagram of the main body of an OCT system comprising a single display for presenting a display target to a patient/subject.

In some embodiments, as shown in FIG. 5, the main body 106 includes only a single display target 215. Light from the display target 215 is split at an x-prism 505. Notably, other optical devices that split the source light into a plurality of light rays may be used. This split light is reflected at mirror 510a or 510b and directed towards the user 114.

The user may be directed to fixate on a display target 215 while one or more galvanometers 280 move light from the light source 240 to image an area of tissue. In some embodiments, the display targets 215 are moved within the user's field of vision while an area of tissue is imaged. For example, in FIG. 6A, a display target 215 may be moved horizontally (for example, in the medial-lateral direction), such that a patient is directed to look from left to right or from right to left. Meanwhile, a vertical scanner (for example, galvanometer) allows the vertical location (for example, in the superior-inferior) of the sample scanning to change in time. FIG. 6 shows an eye, which is directed to move in the horizontal direction 605. Due to the vertical scanner, the scanned trajectory 610 covers a large portion of the eye 600. Scanning in the vertical and horizontal directions can produce a 3D-OCT scan. In some embodiments, continuous and/or regularly patterned A-scans are combined to form a full scan for example, B-scan or 3D-OCT scan. In various embodiments, discrete and/or random A-scans are combined to form the full scan. Systems configured such that users 114 are directed to move their eyes throughout a scan may include fewer scanners than comparable systems configured such that users 114 keep their eyes fixated at a stationary target. For example, instead of a system comprising both a vertical and a horizontal scanner, the user 114 may move his eyes in the horizontal direction, thereby eliminating the need for a horizontal scanner.

In various embodiments, two scanners (for example, a vertical and a horizontal scanner) can be used. The design, capabilities and/or specifications for these scanners need not be the same. For example, one of the scanners may be faster and/or higher resolution than the other. Specifically, a vertical scanner may be used that scans more rapidly than a horizontal scanner, or vice versa. Scanners such as galvanometers having different speeds may be used in some example embodiments to scan continuously in the vertical direction and only occasionally increment along the horizontal (or vice versa). In some embodiments, for example, one of the scanners may be ½ to 1/500 as fast as the other scanner although values outside this range are possible. Similarly, in some embodiments, the 3D-OCT image may not contain as many pixels in one direction (for example horizontal) as the other direction (for example, vertical). In some embodiments, for example, the 3D-OCT image may be 600×512 although other sizes are possible. Likewise, one scanner or galvanometer may have a reduced resolution compared to the other scanner. In instances wherein the specifications for one scanner include slower scan rates or less resolution than the other scanner, possibly a less expensive scanner or galvanometer may be used. Accordingly, the two scanners or galvanometers need not be the same type or grade. A relatively high performance (higher cost) and a relatively lower performance (lower cost) scanner may be used. Use of a lower performance/cost scanner or galvanometer instead of two scanners or galvanometers of equal quality and cost may reduce the overall cost of the instrument. Other variations are also possible. Some embodiments disclosed herein refer to one or more galvanometers. In some embodiments, a different kind of scanner may be used in place of the galvanometer.

FIG. 6B shows an example of an A scan. The A scan comprises the signal strength (indicated by the brightness) as a function of depth for one horizontal and vertical position. Thus, an A-scan comprises a plurality of intensity values corresponding to different anterior-posterior positions. A plurality of A scans form a B scan. FIG. 6C shows a B-scan, in which the largest portion of the bright signal corresponds to retinal tissue and the elevated region under the retina corresponds to diseased tissue within the eye.

With reference to FIG. 7A, there is illustrated an enlarged view depicting an embodiment of the main body 106 that is configured with a handle 118 for adjusting the eyepieces to conform to the user's interpupillary distance. In the illustrative embodiment, the main body 106 comprises a left eyepiece 712 and a right eyepiece 714 wherein each is connected to the other by interpupillary distance adjustment device 718. The interpupillary distance adjustment device 718 is coupled to the handle 118, wherein the handle 118 is configured to allow the user to engage the handle 118 to adjust the distance between the left and right eyepieces 712, 714 to match or substantially conform to the interpupillary distance between the eyes of the user.

Referring to FIG. 7A, the user can rotate, turn, or twist the handle 118 to adjust the distance between the left and right eyepieces 712, 714 so as to match or substantially conform to the interpupillary distance between the eyes of the user. Alternatively, the handle 118 can be configured to move side to side to allow the user to adjust the distance between the left and right eyepieces 712, 714. Additionally, the handle 118 can be configured to move forward and backward to allow the user to adjust the distance between the left and right eyepieces 712, 714. In the alternative, the handle 118 can be configured to move up and down to allow the user to adjust the distance between the left and right eyepieces 712, 714. In another embodiment, the distance between the left and right eyepieces 712, 714 can be adjusted and/or controlled by a motor activated by the user. Alternatively, the motor can be configured to be controlled by computer system 104 to semi-automatically position the left and right eyepieces 712, 714 to match the interpupillary distance between the eyes of the user. In these instances, eye tracking devices may be included with a system described herein. In various embodiments, a combination of the foregoing are utilized to adjust the distance between the left and right eyepieces 712, 714 to match or substantially conform to the user's interpupillary distance.

A user 114 may adjust interpupillary distance based on the user's viewing of one or more fixation targets on one or more displays 215. For example, the displays 215 and the fixation targets may be configured such that the user views two aligned images, which may form a single, complete image when the interpupillary distance is appropriate for the user 114. The user 114 may adjust (for example, rotate) an adjustment control 204 to change the interpupillary distance based on the fixation target images, as shown in FIG. 7A. FIGS. 7B-7F illustrate one embodiment of fixation targets as seen by the viewer under a plurality of conditions; however, other fixation targets are possible, including but not limited to a box configuration. FIG. 7B shows a U-shaped fixation target 715a on the display 215a for the left eye. FIG. 7C shows an upside-down U-shaped fixation target 715b on the display 215b for the right eye.

When the interpupillary distance is appropriately adjusted, the bottom and top images 715a and 715b are aligned, as shown in FIG. 7D to form a complete H-shaped fixation target 715. When the interpupillary distance is too narrow, the fixation target 715a on the display 215a for the left eye appear shifted to the right and the fixation target on the display 215b for the right eye appear shifted to the left and the user sees the image shown in FIG. 7E. Conversely, when the interpupillary distance is too wide, the fixation target 715a on the display 215a for the left eye appear shifted to the left and the fixation target on the display 215b for the right eye appear shifted to the right and the user sees the image shown in FIG. 7F. Thus, the interpupillary distance may be adjusted based on these images.

In particular, in FIG. 7D, the alignment image 715 is in the shape of an "H." Thus, when the interpupillary distance is properly adjusted, the fixation targets on the left and right displays overlap to form an "H". Other alignment images 715 may be provided.

In another embodiment, B-scans or C-scans through the iris plane in each eye can demonstrate the location of the pupil, or light entrance to the back of the eye. Image analysis routines, such as edge detection, could be applied to these B-scan or C-scan images to detect the borders of the pupil in each eye. The computer system 104 can be configured to automatically adjust the interpupillary distance to center these pupillary borders in the center of the B-scan or C-scan on each side.

Figure 8:
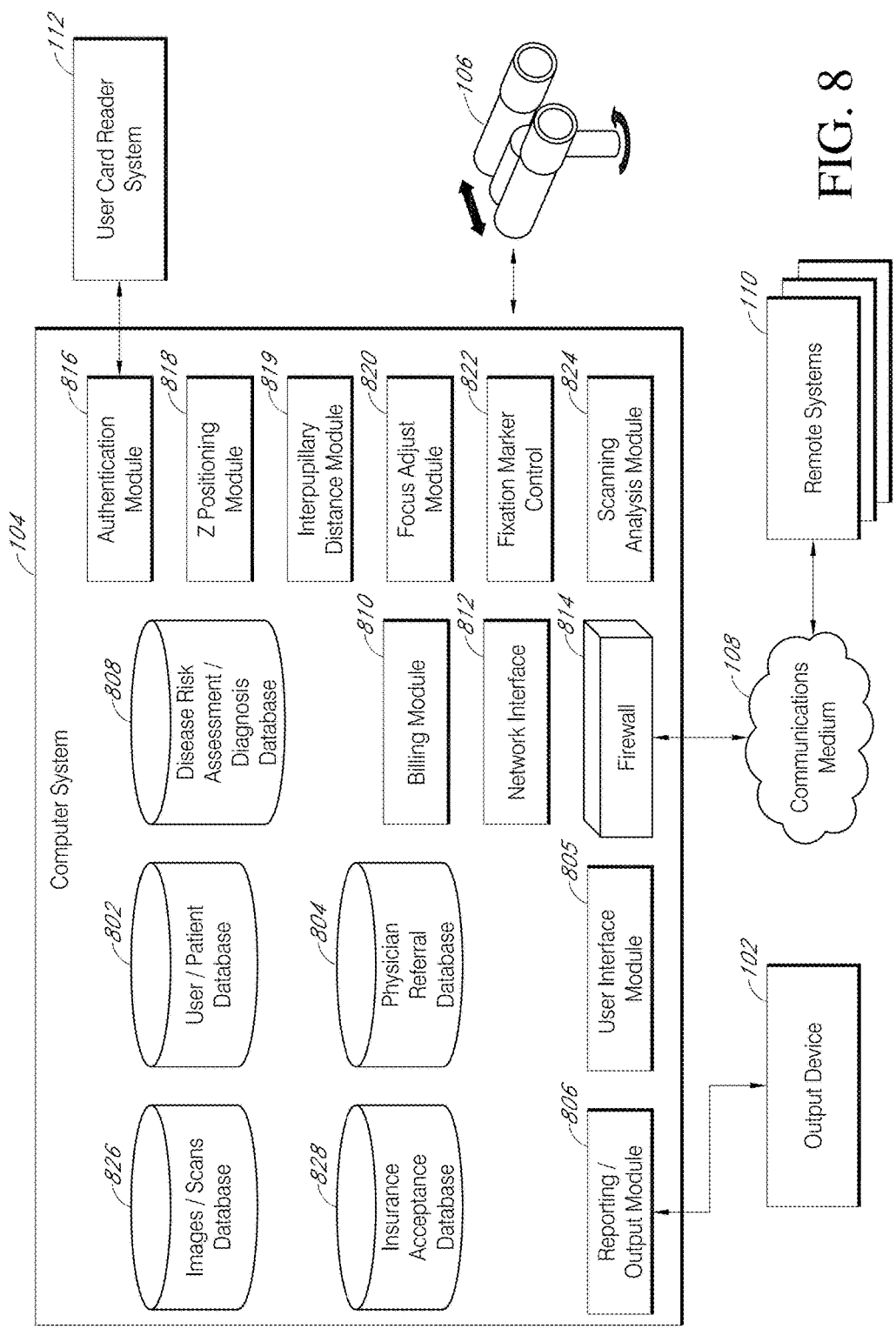
FIG. 8 is a block diagram schematically illustrating one embodiment of the computer system of the optical coherence tomography system described herein.

With reference to FIG. 8, there is illustrated an embodiment of the computer system 104. In the illustrated embodiment, the computer system 104 can comprise a scan control and analysis module 824 configured to control the scanning operations performed by the main body 106. The computer system 104 can also comprise a fixation marker control system 822 configured to display a fixation marker visible by the user from main body 106. In certain embodiments, the fixation marker is displayed as an "X," a dot, a box, or the like. The fixation marker can be configured to move horizontally, vertically, diagonally, circularly, or a combination thereof. The fixation marker can be repositioned quickly to relocate the beam location on the retina as the eye repositions itself. The computer system 104 can also comprise a focus adjust module 820 for automatically adjusting the focusing lenses in the main body 106 as further discussed herein. The computer system 104 can also comprise a Z positioning module 818 for automatically adjusting the Z offset as herein discussed.

Referring to FIG. 8, the computer system 104 comprises in the illustrative embodiment a disease risk assessment/diagnosis module 808 for storing and accessing information, data, and algorithms for determining, assessing the risk or likelihood of disease, and/or generating a diagnosis based on the data and/or measurements obtained from scanning the eyes of the user. In one embodiment, the scan control and analysis module 824 is configured to compare the data received from the main body 106 to the data stored in the disease risk assessment/diagnosis module 808 in order to generate a risk assessment and/or diagnosis of disease in the eyes of the user as further illustrated. The computer system 104 can also comprise an image/scans database configured to store images and/or scans generated by the main body 106 for a plurality of users, and to store a unique identifier associated with each image and/or scan. In certain embodiments, the scan control and analysis module 824 uses historical images and/or scans of a specific user to compare with current images and/or scans of the same user to detect changes in the eyes of the user. In certain embodiments, the scan control and analysis module 824 uses the detected changes to help generate a risk assessment and/or diagnosis of disease in the eyes of the user.

In the illustrative embodiment shown in FIG. 8, the computer system 104 can comprise a user/patient database 802 for storing and accessing patient information, for example, user name, date of birth, mailing address, residence address, office address, unique identifier, age, affiliated doctor, telephone number, email address, social security number, ethnicity, gender, dietary history and related information, lifestyle and/or exercise history information, use of corrective lens, family health history, medical and/or ophthalmic history, prior procedures, or other similar user information. The computer system 104 can also comprise a database of biometric markers, such as the retinal vessel pattern or other measurements made from eye tissues. In certain embodiments, the database of biometric markers can be used to determine or verify the identity of a user for authentication, for follow-up comparisons, and/or for other like purposes. The computer system 104 can also comprise a physician referral database for storing and accessing physician information, for example, physician name, physician training and/or expertise/specialty, physician office address, physician telephone number and/or email address, physician scheduling availability, physician rating or quality, physician office hours, or other physician information.

In reference to FIG. 8, the computer system 104 can also comprise a user interface module 805 (which can comprise without limitation commonly available input/output (I/O) devices and interfaces as described herein) configured to communicate, instruct, and/or interact with the user through audible verbal commands, a voice and/or speech recognition interface, a key pad, toggles, a joystick handle, switches, buttons, a visual display, touch screen display, etc. or a combination thereof. In certain embodiments, the user interface module 805 is configured to instruct and/or guide the user in utilizing and/or positioning the main body 106 of the optical coherence tomography system 100. The computer system 104 can also comprise a reporting/output module 806 configured to generate, output, display, and/or print a report (for example, FIGS. 10A and 10B) comprising the risk assessment and/or diagnosis generated by the disease risk assessment/diagnosis module 808. In various embodiments, the report comprises at least one recommended physician to contact regarding the risk assessment.

Referring to FIG. 8, the computer system 104 can also comprise an authentication module 816 for interfacing with user card reader system 112, wherein a user can insert a user identification card into the user card reader system 112. In certain embodiments, the authentication module 816 is configured to authenticate the user by reading the data from the identification card and compare and/or store the information with the data stored in the user/patient database 802. In certain embodiments, the authentication module 816 is configured to read or obtain the user's insurance information from the user's identification card through the user card reader system 112. The authentication module 816 can be configured to compare the user's insurance information with the data stored in the insurance acceptance database 828 to determine whether the user's insurance is accepted or whether the user's insurance company will pay for scanning the user's eyes. In various embodiments, the authentication module communicates with the billing module 810 to send a message and/or invoice to the user's insurance company and/or device manufacturer to request payment for performing a scan of the patient's eyes. The card can activate one or more functions of the machine allowing the user, for example, to have a test performed or receive output from the machine. In various embodiments, the billing module 810 is configured to communicate with the user interface module 805 to request payment from the user to pay for all or some (for example, co-pay) of the cost for performing the scan. In certain embodiments, the billing module 810 is configured to communicate with the user card reader system 112 to obtain card information from the user's credit card, debit card, gift card, or draw down credit stored on the user's identification card. Alternatively, the billing module 810 is configured to receive payment from the user by communicating and/or controlling an interface device for receiving paper money, coins, tokens, or the like. Alternatively, the billing module 810 is configured to receive payment from the user by communicating with the user's mobile device through Bluetooth® or other communications protocols/channels in order to obtain credit card information, billing address, or to charge the user's mobile network service account (for example, the cellular carrier network).

With reference to FIG. 8, the user card may be used by insurers to track which users have used the system. In one embodiment, the system can print (on the face of the card) or store (in a chip or magnetic stripe) the scan results, risk assessment, and/or report directly onto or into the card that the patient inserts into the system (wherein the card is returned to the user). The system can be configured to store multiple scan results, risk assessments, and/or reports, and/or clear prior scan results, risk assessments, and/or reports before storing new information on the magnetic stripe. In certain embodiments, the calculation of the risk assessment is performed by the system (for example, scanning analysis module 824). In certain embodiments, the calculated risk assessment is transmitted a centralized server system (for example, remote systems 110) in another location that provides the results via a web page to physicians, users, patients, or the like. The centralized server system (for example, remote system 110) allows the user, patients, or doctors to enter their card code to see the results which are saved in the centralized database.

In the example embodiment of FIG. 8, the computer system 104 can comprise a network interface 812 and a firewall 814 for communicating with other remote systems 110 through a communications medium 108. Other remote systems 110 can comprise without limitation a system for checking the status/accuracy of the optical coherence tomography system 100; a system for updating the disease risk assessment/diagnosis database 808, the insurance acceptance database 828, the physician referral database 804, and/or the scan control and analysis module 824. In certain embodiments, the computer system 104 can be configured to communicate with a remote system 110 to conduct a primary and/or secondary risk assessment based on the data from scanning the user's eyes with the main body 106.

Referring to FIG. 8, the remote system 110 can be configured to remotely perform (on an immediate, delayed, and/or batch basis) a risk assessment and/or diagnosis and transmit through a network or communications medium the risk assessment, diagnosis, and/or report to the computer system 104 for output to the user using output device 102. In certain embodiments, the output device 102 is configured to display the risk assessment, diagnosis, and/or report as a webpage that can be printed, emailed, transmitted, and/or saved by the computer system 104. The remote system 110 can also be configured to transmit through a network or communications medium the risk assessment, diagnosis, and/or report to the user's (or doctor) cellular phone, computer, email account, fax, or the like.

Figure 9:
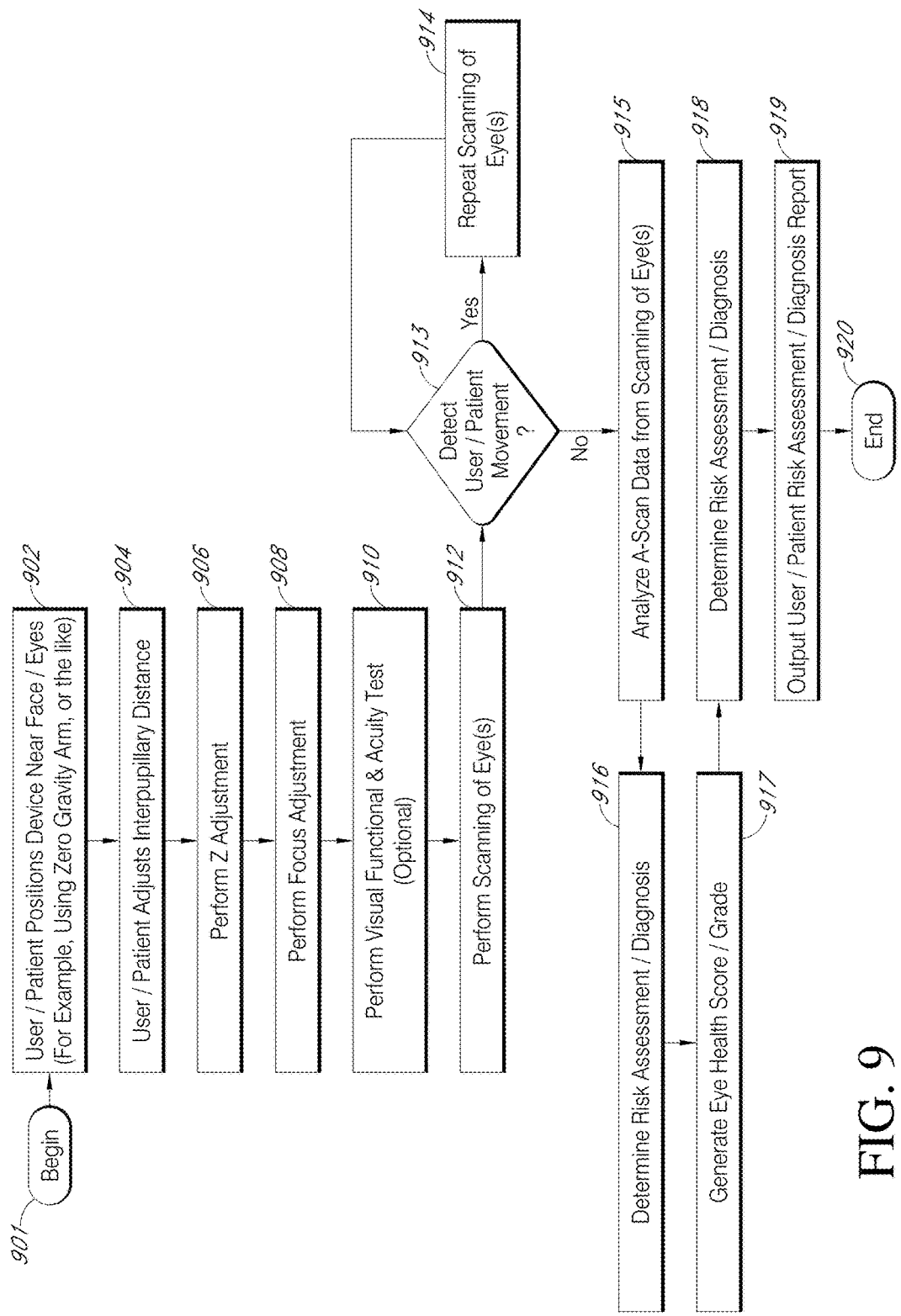
FIG. 9 is illustrates a process flow diagram of one embodiment of performing precision measurements on retinal tissue for the detection of pathognomonic disease features.

With reference to FIG. 9, there is shown an illustrated method of using the optical coherence tomography system 100 to self-administer an OCT scan of the user's eyes and obtain a risk assessment or diagnosis of various diseases and ailments. The process begins at block 901 wherein the user approaches the optical coherence tomography system 100 and activates the system, by for example pushing a button or typing in a activation code or anonymous identification number. In various embodiments, the user interface module 805 instructs users at block 901 to first insert an identification card or anonymous coded screening card in user card reader system 112 to activate the system. The system can also be activated at block 901 when users insert their user identification card in user card reader system 112. Other means of activating the system are possible as well as, including without limitation, a motion sensor, a weight sensor, a radio frequency identification (RFID) device, or other actuator to detect the presence of the user. Alternatively, the optical tomography system 100 can be activated when the billing module 810 detects that the user has inserted paper money, coins, tokens, or the like into an interface device configured to receive such payment. Alternatively, the billing module 810 can also be configured to activate the optical tomography system 100 when the billing module 810 communicates with a user's mobile device in order to obtain the user's credit card information, billing address, or the like, or to charge the user's mobile network service account (for example, the cellular carrier network)

In referring to FIG. 9 at block 902, the user interface module 805 is configured to direct the user to attach disposable eyecups onto the main body 106, and then position the main body 106 with the disposable eyecups near the eyes of the user and/or support the disposable eyecups against the user's eye socket. The user interface module 805 instructs the user to engage handle 118 to adjust the distance between the left and right eyepieces 612, 614 to match or substantially conform to the interpupillary distance of the user as described with respect to FIGS. 6A-6F. After the main body 106 and the interpupillary distance has been appropriately calibrated and/or adjusted by the user, the user inputs into or indicates to the user interface module 805 to begin the scan. The scan control and analysis module 824 substantially restricts movement or locks the position of the zero gravity arm and/or the distance between the left and right tubes 612, 614 to begin the scan.

Referring to FIG. 9, the Z module 818 automatically adjusts the z-offset in the main body 106 at block 906 such that the OCT measurement will be obtained, for example, from tissue in the retina. The Z module 818 may identify and/or estimate a position of part of the sample (for example, part of an eye of a user 114) and adjust the location of one or more optical components based on the position. One of ordinary skill in the art will appreciate the multitude of ways to perform such an adjustment. For example, the Z module 818 may comprise a motor, such as a piezoelectric motor, to translate the reference mirror/s longitudinally such that the optical path length from the beam splitter to the retina is about equal to (within a coherence length of) the optical path length in the reference arm. This movement may enable light from the reference arm to interfere with light reflected by a desired portion of the sample (for example, the retina). At block 908, the illustrative method performs a focus adjustment using the focus adjustment module 820. Those of ordinary skill in the art will also appreciate the different techniques for performing such auto-focus calibration. Block 910 illustrates an optional test performed by the computer system 104 to determine the visual function and acuity of the user's eye. In certain embodiments, the visual acuity test works with or is combined with the fixation marker control system 722, and can test both eyes simultaneously or one eye at time. For example, the fixation marker will initially appear small and then gradually increase in size until the user indicates through the user interface module 705 that the fixation marker is visible. Based on the size at which the user can clearly see the fixation marker, fixation marker control system 722 can estimate or determine or assess the visual acuity of the user's eyes (for example, 20/20, 20/40, or the like). In some embodiments, visual acuity can be estimated by measuring or evaluating the stability of fixation using cross-correlations of neighboring B-scans or changes in fundus reflectivity due to eye movements measured with a scanning laser light source. Generally, when acuity is decreased, an eye may move more often and in greater amplitudes. For example, one way to detect greater eye movements and/or eye movements having greater amplitudes is to cross-correlate B-scans that are supposed to be next to each other. When B-scans are next to each other, the cross-correlation will generally be high since the data does not generally change significantly. However, when the eye has moved a significant distance, the cross-correlation will be lower since there will generally be more change in the features. In some embodiments, the system can be configured to detect eye movements by imaging the retina with scanning laser illumination and comparing adjacent images in time for mutual information or to determine movement of retinal features, such as retinal vessels, the optic nerve, SIFT features, or other information-based features.

With reference to FIG. 9 at Block 912, the user interface module 805 instructs the user to follow the movement of the fixation marker that is visible to the user from the main body 106. In one embodiment, the fixation marker control 822 is configured to display a fixation marker that moves horizontally. In some embodiments, the horizontal movement of the fixation marker allows the scan control and analysis module 824 to scan the eye vertically as the eye moves horizontally, thus possibly obtaining a two-dimensional, volume, or raster scan of the eye tissue at issue. Alternatively, the scan control and analysis module 824 and/or the fixation marker control may cause the fixation marker or the beam to jump or move around to obtain measurements at different lateral locations on the eye.

During the scanning of the eye, the scan control and analysis module 824 could be configured to detect at block 913 whether there has been a shift in the position of the main body 106 relative to the user. In one embodiment, the scan control and analysis module 824 can detect (in real-time, substantially real-time, or with a delay) whether a shift has occurred based on what the values the module 824 expects to receive during the scanning process. For example, as the scan control and analysis module 824 scans the retina, the module 824 expects to detect a change in signal as the scanning process approaches the optic nerve (for example, based on the location of the fixation target and/or state of the scanner(s)). Alternatively, the expected values or the expected change in values can also be determined or generated using a nomogram. If the system does not detect an expected signal change consistent with a detection of the optic nerve and/or receives no signal change, then the module 824 can be configured to interpret such data as the user is not tracking properly. Other features, for example, the fovea, or the like, can be used to determine whether the expected signal is observed. If improper tracking occurs enough (based on, for example, a threshold), the system 100 may request that the user fixate again (using fixation marker control 822) for another scan. If the foregoing shift detection process does not occur in real-time or substantially real-time, then the system can be configured to complete the scan, perform data analysis, and during the analysis the system can be configured to detect whether a shift occurred during the scan. If a substantial shift is detected, then the user may be instructed (through visual, audible, or verbal instructions using the user interface module 805) to sit forward again so another scan can be performed. If the system detects a shift 2 or 3 or more times, the system can be configured to refer the user to a general eye doctor.

At the end of a scan, the scan control and analysis module 824 can be configured to produce a confidence value that indicates how likely the nomograms will be to apply to this patient. For example, if the patient had borderline fixation, the confidence value might be lower than a patient whose fixation appeared to be good.

In the real-time embodiment, the system can be configured to perform rapid cross-correlations between adjacent A-scans or B-scans to make sure the eye is moving somewhat. In some embodiments, the foregoing can be advantageous for ANSI laser safety standards so as to avoid having users stare at the same location with laser energy bombarding the user's retina. Accordingly, in some embodiments, the system is configured with a laser time-out feature if the system detects no eye moment (for example, cross-correlations above a certain threshold). In some embodiments, to expedite this process and provide real time analysis in frequency domain OCT, signal data may be analyzed prior to performing an FFT. Other technologies can be used to determine that the user has some eye movement.

If no fixation problem has been detected, the scan control and analysis module 824 completes the scan of the user's eyes, stores the image and/or scan data in the images/scans database 826, and analyzes the A-scan data at block 915 to generate/determine a risk assessment and/or diagnosis at block 916 by accessing the data and/or algorithms stored in the disease risk assessment/diagnosis database 808. In some embodiments, groups of A-scans, partial or full B scans, or partial or full 3D-OCT data can be analyzed.

As used herein the term "nomogram" generally refers to predictive tools, algorithms, and/or data sets. Nomograms in general can provide predictions for a user based on the comparison of characteristics of the user with the nomogram. The nomograms are derived, generated, calculated, or computed from a number, for example, hundreds, thousands, or millions of users/patients who exhibited the same condition (normal or diseased). In some embodiments described herein, nomograms compare the risk of having a disease based on physical characteristics. Accordingly, in some cases, nomograms can provide individualized predictions that are relative to risk groupings of patient populations who share similar disease characteristics. In some embodiments, nomograms can be used to provide the risk estimation or risk assessment on a 0-100% scale. Alternatively, nomograms used herein can provide an expected value, for example, at a certain position in the eye there is an expected eye thickness value of 100 microns.

Generally, nomograms have been developed and validated in large patient populations and are highly generalizable, and therefore, nomograms can provide the objective, evidence-based, individualized risk estimation or assessment. Accordingly, nomograms can be used as described herein to empower patients and allow them to better understand their disease. Further, nomograms as used herein can assist physicians with clinical decision-making and to provide consistent, standardized and reliable predictions.

Figure 10A:
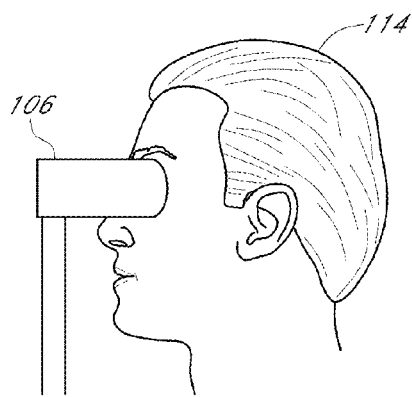
FIGS. 10A-10D illustrate possible embodiments of disposing the main body of an optical coherence tomography device with respect to a user.
Figure 10B:
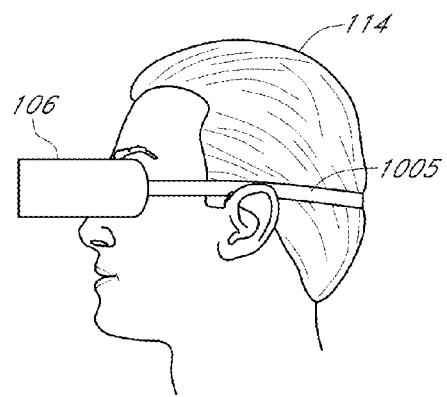

In the illustrative method shown in FIG. 9 at block 917, an eye health assessment or eye health grade report, as illustrated in FIGS. 10A and 10B, is generated for the user by accessing the disease risk assessment/diagnosis database 808. At block 918, the physician referral database 804 is accessed to generate a recommendation of when the user should visit a physician (for example, within one to two weeks). The physician referral database 804 is also accessed to generate, compile a listing of physicians suitable for treating the patient. Suitability for treatment could be determined by a physician-defined subspecialty area or areas, such as retina, cornea, glaucoma, or the like. In another embodiment, suitability for treatment could be determined additionally or completely by the severity of a given diagnosis. For example, some physicians may feel comfortable treating mild diabetic retinopathy while others would permit referrals for severe forms of retinopathy, such as proliferative retinopathy. The physician referral list can be randomly generated or selected based on referral fee payments paid by physicians, insurance companies, or based on location of the physician relative to the user's present location or office/home address, or based on the type of detected disease, or based on the severity of the detected disease, based on the location or proximity of the system relative the location of the physician, or based on a combination thereof. At block 919, the report is displayed to the user by using reporting/output module 806 and output device 102. In certain embodiments, the report data is stored in the user/patient database 802 for future analysis or comparative analysis with future scans.

In some embodiments, the main body 106 is not supported by the user 114. For example, the main body 106 may be supported by a free-standing structure, as shown in FIG. 10A. The user 114 may look into the eyepiece(s). The user 114 may be seated on a seating apparatus, which may include a height-adjusting mechanism. The main body 106 may supported by a height-adjustable support.

Figure 10C:
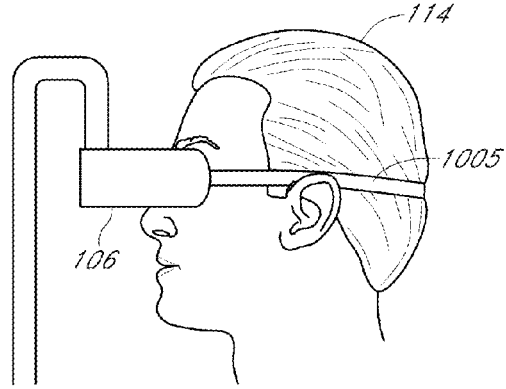

In some embodiments, such as those shown in FIGS. 10B-10C, a strap 1005 is connected to the main body 106. The strap may function to fully or partly support the main body 106, as shown in FIG. 10B. The strap 905 may be excluded in some embodiments. The main body 106 may be hand held by the user. In some embodiments, the main body 106 may be supported on eyewear frames. In some embodiments, all of the optics are contained within the main body 106 that is directly or indirectly supported by the user 114. For example, the main body 106 in FIG. 10B may include an optical coherence tomography system, an alignment system, and a data acquisition device. The data acquisition device may wirelessly transmit data to a network or computer system or may use a cable to transfer control signals. FIG. 10C is similar to that of FIG. 1 and is supported by a separate support structure (for example, an zero gravity arm). In some embodiments, a strap, belt, or other fastener assists in the alignment of the main body 106 with one or both eyes of the user 114.

Figure 10D:
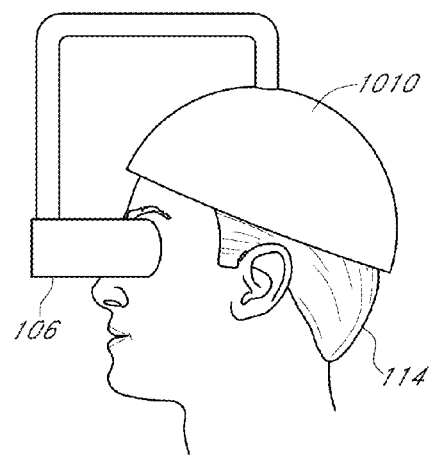

In some embodiments, as shown in FIG. 10D, the user wears an object 1010 connected to the eyepiece. The wearable object 1010 may include a head-mounted object, a hat or an object to be positioned on a user's head. As described above, in some embodiments, the main body 106 is supported on an eyewear frame worn by the user like glasses. The wearable object 1010 may fully or partly support the main body 106 and/or may assist in aligning the main body 106 with one or both eyes of the user 114.

Figure 11B:
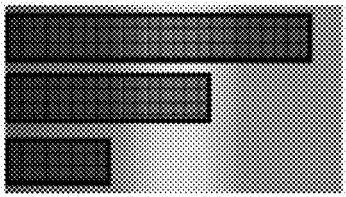

Referring to FIGS. 11A and 11B, there are illustrated two example embodiments of the eye health grades and the eye health assessment reports. With reference to FIG. 11A, the eye health grades report can comprise without limitation a numeric and/or letter grade for each eye of the user for various eye health categories, including but not limited to macular health, optic nerve health, eye clarity, or the like. The eye health grades report can also comprise at least one recommendation to see or consult a physician within a certain period of time, and can provide at least one possible physician to contact. Data for generating the recommendation information and the list of referral physicians are stored in the physician referral database 804. In reference to FIG. 11B, the eye health assessment report can comprise a graphical representation for each eye of the user for various eye health categories. The report can be presented to the user on an electronic display, printed on paper, printed onto a card that the user inserted into the machine, electronically stored on the user's identification card, emailed to the user, or a combination thereof.

Figure 12:
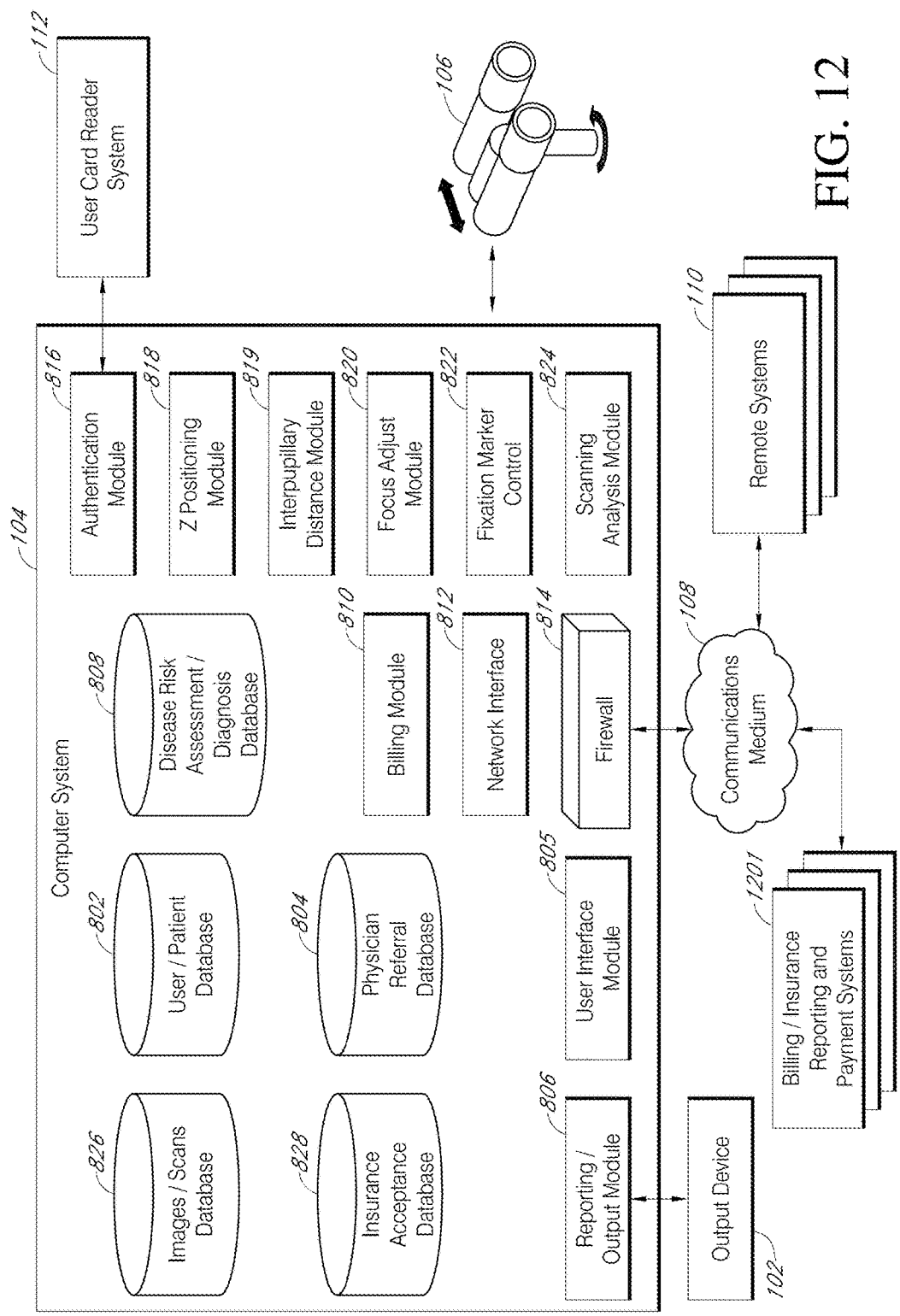
FIG. 12 is a block diagram schematically illustrating another embodiment of the computer system for an optical coherence tomography system described herein.

With reference to FIG. 12, there is illustrated another embodiment of the computer system 104 connected to remote system 110 and billing/insurance reporting and payment systems 1201. The billing module 810 can be configured to communicate with billing/insurance reporting payment systems 1201 through communications medium 108 in order to request or process an insurance claim for conducting a scan of the user's eyes. Based on communications with billing/insurance reporting and payment system 1201, the billing module 810 can also be configured to determine the amount payable or covered by the user's insurance company and/or calculate or determine the co-pay amount to be charge the consumer. In certain embodiments, the user can interact with the user interface module 805 to schedule an appointment with the one of the recommended physicians and/or schedule a reminder to be sent to the user to consult with a physician. The computer system 104 or a remote system 110 can be configured to send the user the reminder via email, text message, regular mail, automated telephone message, or the like.

Computing System

Figure 13:
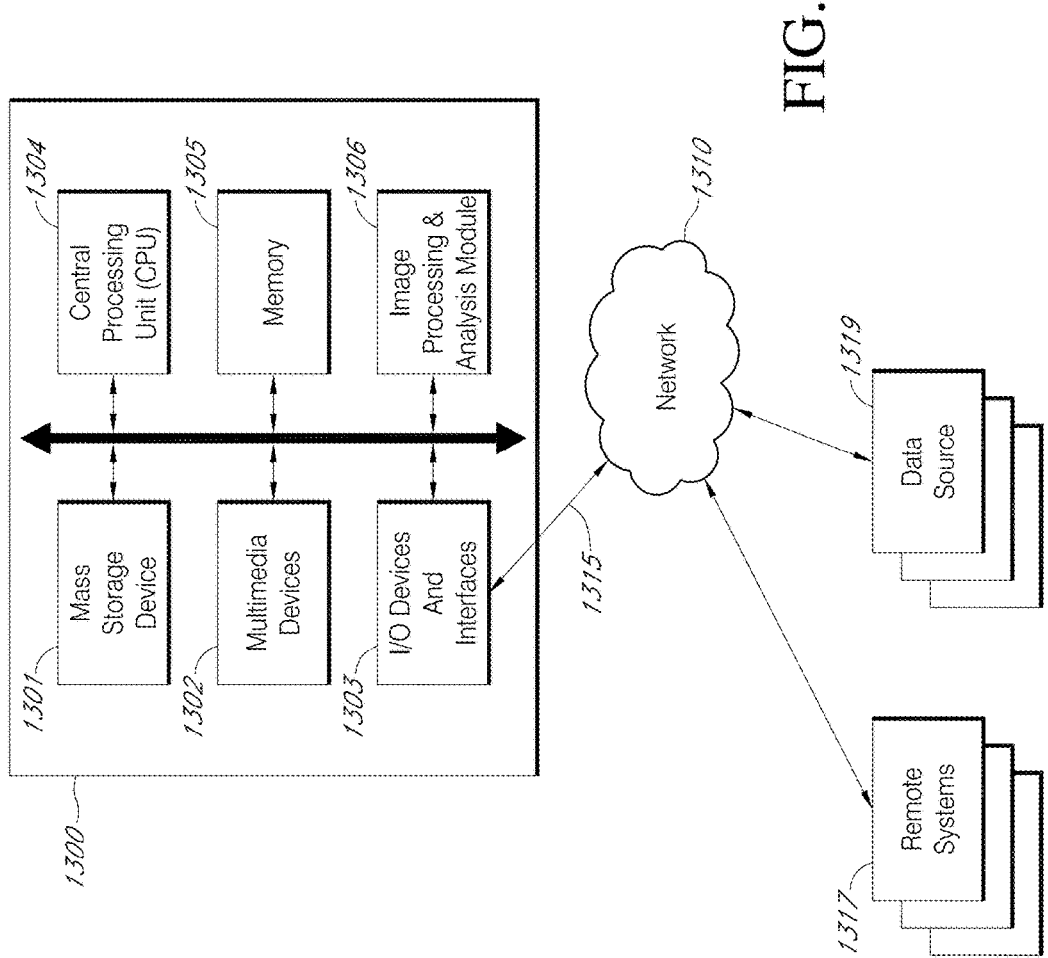
FIG. 13 is a block diagram schematically illustrating components in one embodiment of the computer system for an optical coherence tomography system described herein.

In some embodiments, the systems, computer clients and/or servers described above take the form of a computing system 1300 shown in FIG. 13, which is a block diagram of one embodiment of a computing system (which can be a fixed system or mobile device) that is in communication with one or more computing systems 1310 and/or one or more data sources 1315 via one or more networks 1310. The computing system 1300 may be used to implement one or more of the systems and methods described herein. In addition, in one embodiment, the computing system 1300 may be configured to process image files. While FIG. 13 illustrates one embodiment of a computing system 1300, it is recognized that the functionality provided for in the components and modules of computing system 1300 may be combined into fewer components and modules or further separated into additional components and modules.

Client/Server Module

In one embodiment, the system 1300 comprises an image processing and analysis module 1306 that carries out the functions, methods, and/or processes described herein. The image processing and analysis module 1306 may be executed on the computing system 1300 by a central processing unit 1304 discussed further below.

Computing System Components

In one embodiment, the processes, systems, and methods illustrated above may be embodied in part or in whole in software that is running on a computing device. The functionality provided for in the components and modules of the computing device may comprise one or more components and/or modules. For example, the computing device may comprise multiple central processing units (CPUs) and a mass storage device, such as may be implemented in an array of servers.

In general, the word "module," as used herein, refers to logic embodied in hardware or firmware, or to a collection of software instructions, possibly having entry and exit points, written in a programming language, such as, for example, Java, C or C++, or the like. A software module may be compiled and linked into an executable program, installed in a dynamic link library, or may be written in an interpreted programming language such as, for example, BASIC, Perl, Lua, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

In one embodiment, the computing system 1300 also comprises a mainframe computer suitable for controlling and/or communicating with large databases, performing high volume transaction processing, and generating reports from large databases. The computing system 1300 also comprises a central processing unit ("CPU") 1304, which may comprise a microprocessor. The computing system 1300 further comprises a memory 1305, such as random access memory ("RAM") for temporary storage of information and/or a read only memory ("ROM") for permanent storage of information, and a mass storage device 1301, such as a hard drive, diskette, or optical media storage device. Typically, the modules of the computing system 1300 are connected to the computer using a standards based bus system. In different embodiments, the standards based bus system could be Peripheral Component Interconnect (PCI), Microchannel, SCSI, Industrial Standard Architecture (ISA) and Extended ISA (EISA) architectures, for example.

The example computing system 1300 comprises one or more commonly available input/output (I/O) devices and interfaces 1303, such as a keyboard, mouse, touchpad, and printer. In one embodiment, the I/O devices and interfaces 1303 comprise one or more display devices, such as a monitor, that allows the visual presentation of data to a user. More particularly, a display device provides for the presentation of GUIs, application software data, and multimedia presentations, for example. In the embodiment of FIG. 13, the I/O devices and interfaces 1303 also provide a communications interface to various external devices. The computing system 1300 may also comprise one or more multimedia devices 1302, such as speakers, video cards, graphics accelerators, and microphones, for example.

Computing System Device/Operating System

The computing system 1300 may run on a variety of computing devices, such as, for example, a server, a Windows server, a Structure Query Language server, a Unix server, a personal computer, a mainframe computer, a laptop computer, a cell phone, a personal digital assistant, a kiosk, an audio player, and so forth. The computing system 1300 is generally controlled and coordinated by operating system software, such as z/OS, Windows 95, Windows 98, Windows NT, Windows 2000, Windows XP, Windows Vista, Linux, BSD, SunOS, Solaris, or other compatible operating systems. In Macintosh systems, the operating system may be any available operating system, such as MAC OS X. In various embodiments, the computing system 1300 may be controlled by a proprietary operating system. Conventional operating systems control and schedule computer processes for execution, perform memory management, provide file system, networking, and I/O services, and provide a user interface, such as a graphical user interface ("GUI"), among other things.

Network

In the embodiment of FIG. 13, the computing system 1300 is coupled to a network 1310, such as a modem system using POTS/PSTN (plain old telephone service/public switched telephone network), ISDN, FDDI, LAN, WAN, or the Internet, for example, via a wired, wireless, or combination of wired and wireless, communication link 1315. The network 1310 communicates (for example, constantly, intermittently, periodically) with various computing devices and/or other electronic devices via wired or wireless communication links. In the example embodiment of FIG. 13, the network 1310 is communicating with one or more computing systems 1317 and/or one or more data sources 1319.

Access to the image processing and analysis module 1306 of the computer system 1300 by remote computing systems 1317 and/or by data sources 1319 may be through a web-enabled user access point such as the computing systems' 1317 or data source's 1319 personal computer, cellular phone, laptop, or other device capable of connecting to the network 1310. Such a device may have a browser module implemented as a module that uses text, graphics, audio, video, and other media to present data and to allow interaction with data via the network 1310.

The browser module or other output module may be implemented as a combination of an all points addressable display such as a cathode-ray tube (CRT), a liquid crystal display (LCD), a plasma display, or other types and/or combinations of displays. In addition, the browser module or other output module may be implemented to communicate with input devices 1303 and may also comprise software with the appropriate interfaces which allow a user to access data through the use of stylized screen elements such as, for example, menus, windows, dialog boxes, toolbars, and controls (for example, radio buttons, check boxes, sliding scales, and so forth). Furthermore, the browser module or other output module may communicate with a set of input and output devices to receive signals from the user.

The input device(s) may comprise a keyboard, roller ball, pen and stylus, mouse, trackball, voice and/or speech recognition system, or pre-designated switches or buttons. The output device(s) may comprise a speaker, a display screen, a printer, or a voice synthesizer. In addition a touch screen may act as a hybrid input/output device. In another embodiment, a user may interact with the system more directly such as through a system terminal connected to the score generator without communications over the Internet, a WAN, or LAN, or similar network.

In some embodiments, the system 1300 may comprise a physical or logical connection established between a remote microprocessor and a mainframe host computer for the express purpose of uploading, downloading, or viewing interactive data and databases on-line in real time. The remote microprocessor may be operated by an entity operating the computer system 1300, including the client server systems or the main server system, and/or may be operated by one or more of the data sources 1319 and/or one or more of the computing systems. In some embodiments, terminal emulation software may be used on the microprocessor for participating in the micro-mainframe link.

In some embodiments, computing systems 1317 that are internal to an entity operating the computer system 1300 may access the image processing and analysis module 1306 internally as an application or process run by the CPU 1304.

User Access Point

In one embodiment, a user access point comprises a personal computer, a laptop computer, a cellular phone, a GPS system, a Blackberry® device, a portable computing device, a server, a computer workstation, a local area network of individual computers, an interactive kiosk, a personal digital assistant, an interactive wireless communications device, a handheld computer, an embedded computing device, or the like.

Other Systems

In addition to the systems that are illustrated in FIG. 13, the network 1310 may communicate with other data sources or other computing devices. The computing system 1300 may also comprise one or more internal and/or external data sources. In some embodiments, one or more of the data repositories and the data sources may be implemented using a relational database, such as DB2, Sybase, Oracle, CodeBase and Microsoft® SQL Server as well as other types of databases such as, for example, a flat file database, an entity-relationship database, and object-oriented database, and/or a record-based database.

Figure 14A:
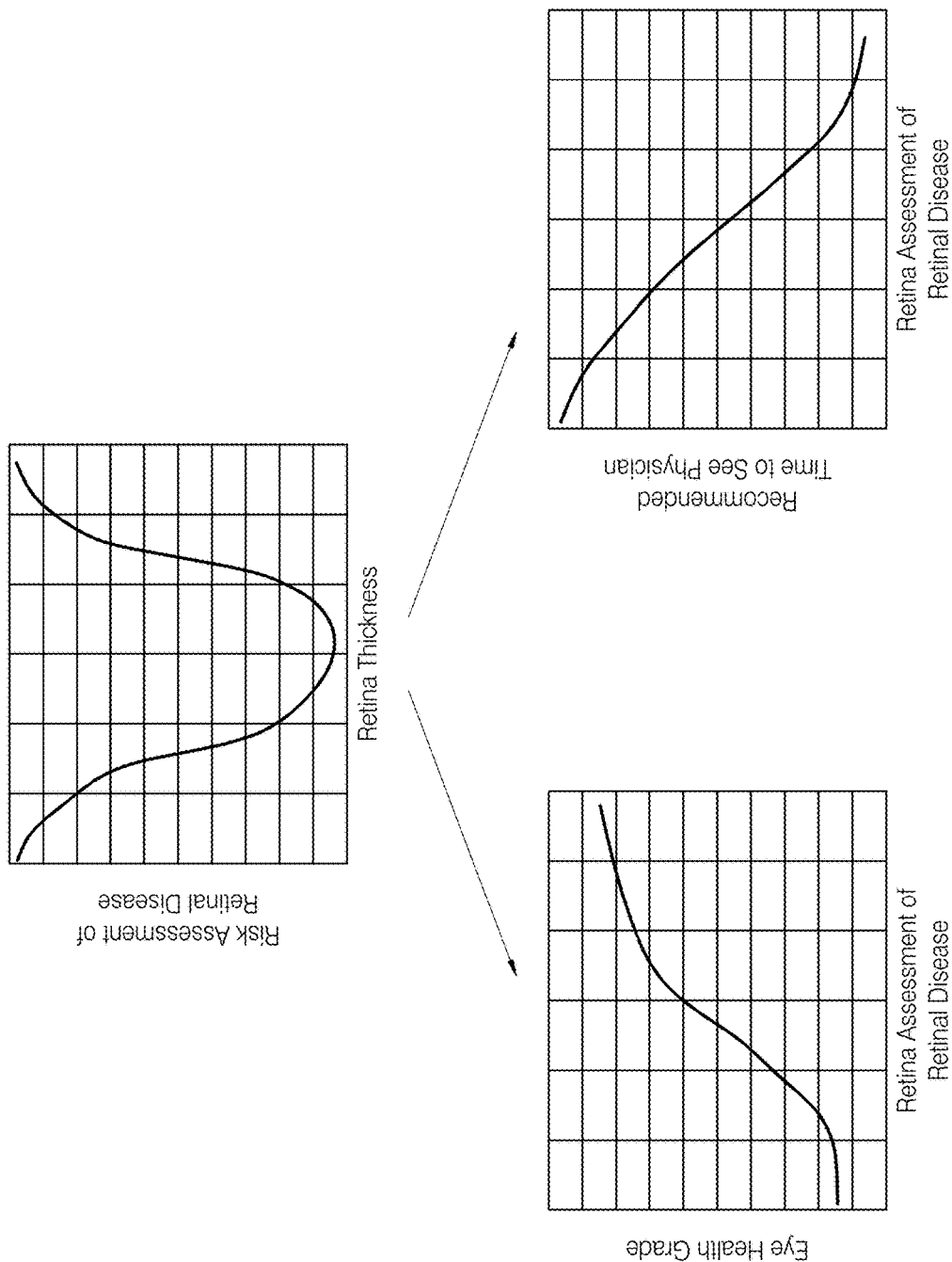
FIG. 14A is a diagram schematically illustrating one embodiment for determining a risk assessment.

With reference to FIG. 14A, there is illustrated an example method for determining or generating a risk assessment of a disease, such as an eye disease, thereby allowing the generation of a health grade and recommended time to see a physician. The example shown in FIG. 14A is for retinal disease, however, the process and method illustrated can be used for other diseases or eye diseases. For example, by focusing the optical coherence tomography system at different antero-posterior locations using the power optics 210, A-scan, B-scan, or 3D-OCT scan data can be collected for any of the structures of the eye that lie along the central axis, such as, for example, the pre-cornea, cornea, anterior chamber, iris, crystalline lens, intraocular lens implant, vitreous body, retina, retinal pigment epithelium, choriocapillaris, choroid, optic nerve, or lamina cribrosa. In this example, the scan control and analysis module 824 is configured to determine the thickness of the retina based on the A-scan data derived from the main body 106. This data may include but is not limited to A-scan data from different A-scans. The scan control and analysis module 824 can also be configured to access data and algorithms in the disease risk assessment/diagnosis database 808 to calculate the risk assessment of retinal disease based on the measured thickness of the retina as illustrated by the function curve in FIG. 14A. The reporting/output module 806 can be configured to normalize the calculated risk assessment value into an eye health letter or numerical grade or score. The reporting/output module 806 can also be configured to access data and algorithms in the physician referral database 804 to calculate a recommended time to see a physician based on the calculated risk assessment value.

Figure 14B:
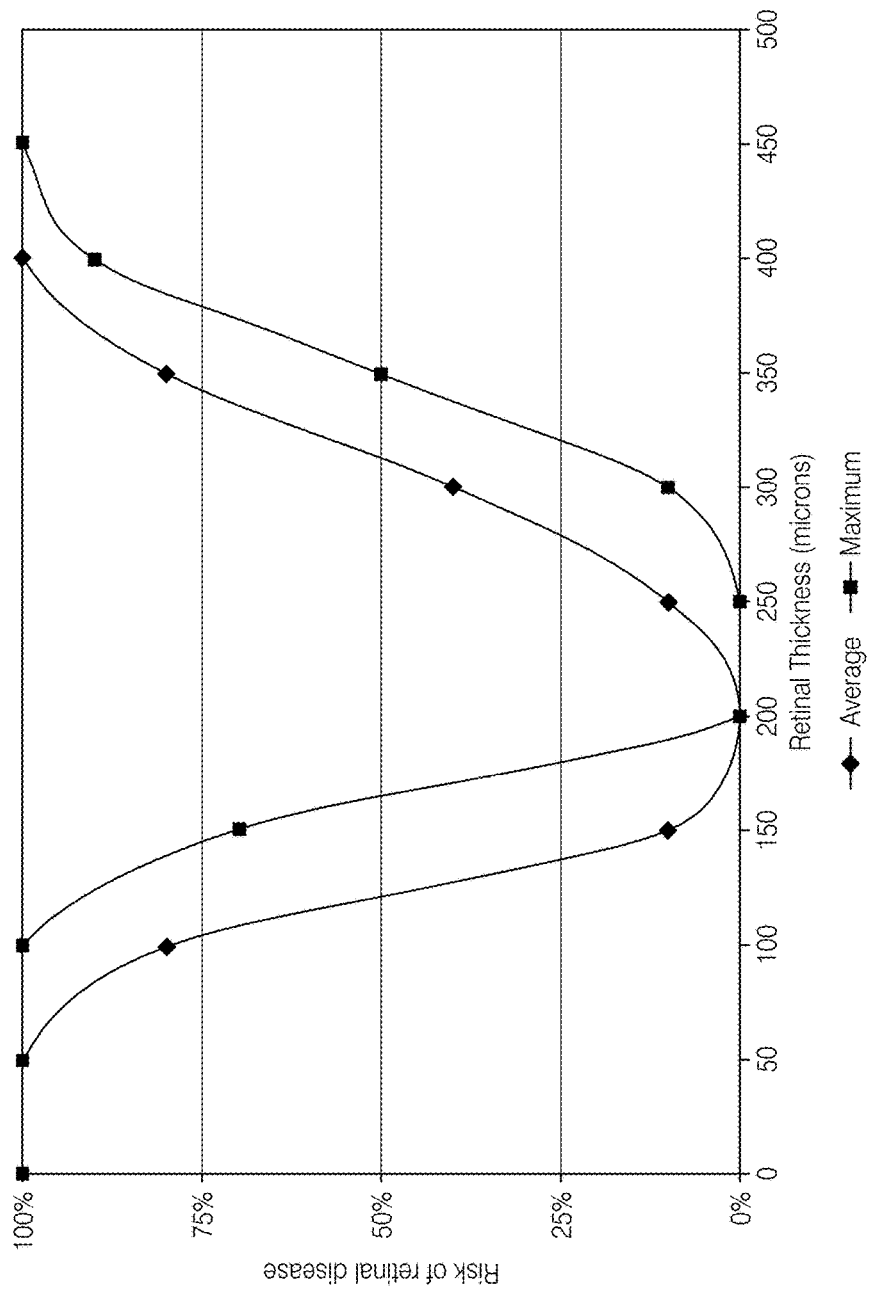
FIG. 14B is a schematic illustration of a plot of risk of retinal disease versus retinal thickness for determining a risk assessment in another embodiment.

With reference to FIG. 14B, there is illustrated another example method or process for determining or generating a risk assessment of disease by comparing the scan data to the disease risk assessment/diagnosis database 808 comprising, for example, minimum and maximum thickness data and algorithms, and such minimum and maximum thickness data and algorithms that can be based on or are in the form of nomograms. In certain embodiments, the system is configured to generate scan data for portions of the eye scanned to determine thickness of the retina at any one point, and compare such data to histograms and/or nomograms (for example, nomograms that show expected thickness at said location likelihood of or disease for a given thickness) to derive a risk assessment. The system can also be configured to generate an average thickness for the entire retina that is scanned, and compare such data to histograms and/or nomograms to derive a risk assessment.

The term "histogram" as used herein generally refers to an algorithm, curve, or data or other representation of a frequency distribution for a particular variable, for example, retinal thickness. In some cases, the variable is divided into ranges, interval classes, and/or points on a graph (along the X-axis) for which the frequency of occurrence is represented by a rectangular column or location of points; the height of the column and/or point along the Y-axis is proportional to or otherwise indicative of the frequency of observations within the range or interval. "Histograms," as referred to herein, can comprise measured data obtained, for example, from scanning the eyes of a user, or can comprise data obtained from a population of people. Histograms of the former case can be analyzed to determine the mean, minimum, or maximum values, and analyze changes in slope or detect shapes or curvatures of the histogram curve. Histograms of the latter case can be used to determine the frequency of observation of a measured value in a surveyed sample.

In the instance where an average thickness value is derived from the scan data, there are some conditions/diseases that may be indicated by thickening of the retina in a localized area. Accordingly, such a condition may not significantly affect the average thickness value (for example, if a substantial portion of the retina is of normal thickness). Therefore, the maximum thickness value may be needed to detect this abnormal thickening in the retina. In some embodiments, this maximum thickness value may be due to a segmentation error. Accordingly, a more stable way of determining the maximum value may also be to use the value corresponding to 95% (or any value between 75% and 99%) maximal thickness. The foregoing can also be applied to minimum retinal thickness or any other value, measurement, and/or detectable condition in the eye. For example, with minimum retinal thickness, if the user has a macular hole, there will only be a small area of zero thickness, and possibly not enough to significantly reduce the average thickness, but definitely an abnormality that may be detected.

In various embodiments, the system may be configured to create histograms of measured thickness and/or measured intensity values and/or slopes or derivatives of intensity values and/or variables to identify abnormalities. For example, changes or substantial changes in slope (calculated as the derivative of adjacent intensity values) may indicate hyporeflective or hyperreflective structures that may not affect mean or average intensity values, but may be indicative of disease or conditions. For example, the system can determine if the distribution of retinal thicknesses across the measured portion of the retina matches that of the normal population. Deviation from such a "normal" histogram would result in lower health grades/higher risk assessments.

In various embodiments, the methods or processes described herein can be used to determine or generate a risk assessment of maculopathy based, for example, on abnormal thickening of the retina or fovea, the presence of hyperreflective (bright or high intensity) or hyporeflective (dark or low intensity) structures in the outer half of the retina, the presence of hyporeflective (dark) structures in the inner half of the retina, the presence of irregularities in the contour of the retinal pigment epithelium that depart from the normal curvature of the eye, or of the presence of hypertransmission of light through the retinal pigment epithelium when compared to a database of normal values stored in the disease risk assessment/diagnosis database 708.

As described above, there are several ways to detect or generate a risk assessment for several diseases or conditions. In certain embodiments, scan data is compared to data found in normal people to identify similarities or differences from a nomogram and/or histogram. In various embodiments, scan data is compared to data found in people with diseases to identify similarities or differences from nomograms and/or histograms. The pathognomonic disease features could be indicated by similarity to nomograms, for example, images, histograms, or other data, etc. from diseased patients.

In one embodiment, "normal" data (for example, histograms) are created for retinal thickness in each region of the retina (optic nerve, fovea, temporal retina) and compare to measured, detected, scanned, or encountered values to these "normal" data (for example, histograms) to determine relative risks of retinal disease or other diseases. The same can be performed for nerve fiber layer (NFL) thickness to detect glaucoma. In various embodiments, the detection or generation of a risk assessment for glaucoma is performed or generated by analyzing collinear A-scan data to see if curvilinear thinning indicates the presence of glaucoma because glaucoma tends to thin the NFL in curvilinear bundles. The NFL radiates out from the optic nerve in a curvilinear fashion like iron filings around a magnet. Measuring and analyzing a sequence of A-scan data that follow such a curvilinear path may be useful to identify such thinning that is characteristic of glaucoma. The analysis could be centered on and/or around the optic nerve or centered on and/or around the fovea or elsewhere. In another embodiment, the detection and/or generation of a risk assessment for glaucoma is performed or generated by analyzing the inner surface of the optic nerve to determine the optic disc cup volume.

The system can also be configured to detect and/or generate a risk assessment for optical clarity wherein the system integrates A-scan data in the Z direction and compares some or all the A-scan data to a nomogram value or values, or, for example, a histogram. In general, darker A-scans will probably indicate the presence of media opacities, for example, cataracts, that decrease optical clarity (therefore, increase the subject's risk of having an optical clarity problem, for example, cataracts). In various embodiments, OCT data, either in the form of A-scans, B-scans or 3D-OCT scans, can be collected of the cornea, anterior chamber, iris, and lens to directly detect abnormalities, such as, for example, cataracts or corneal scars, that may interfere with optical clarity. Nomograms of intensity values normally encountered in these structures could be used for determination of abnormal intensity values. Alternatively, a database of features encountered with specific diseases can be referenced to determine if features consistent with that disease are present.

Figure 15:
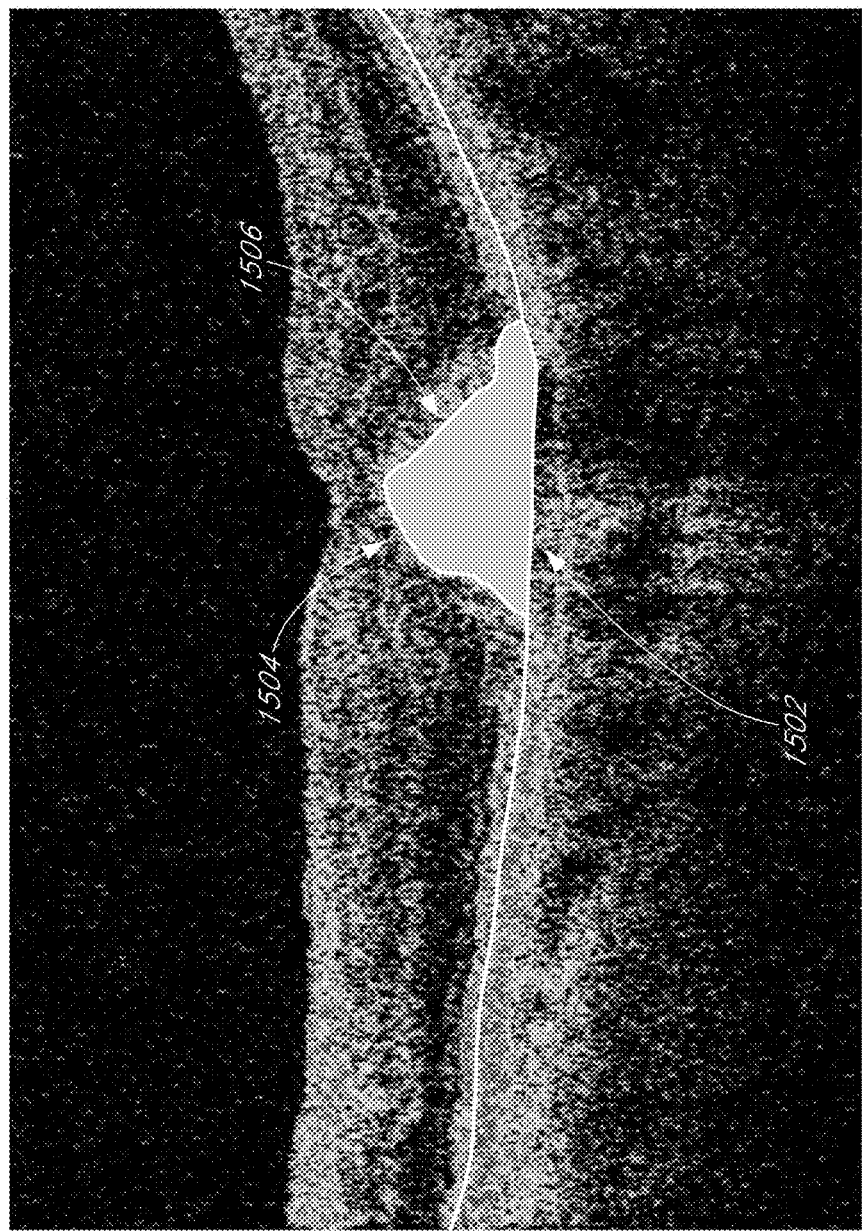

The system can also be configured to detect or generate risk assessments for retinal pigment epithelium (RPE) features that depart from the normal curvature of the eye (drusen, retinal pigment epithelial detachments). Such RPE features can be detected by fitting the detected RPE layer to a polynomial curve that mimics the expected curvature for the eye, and using a computer algorithm to analyze, compare, or examine the difference between these curves. For example with respect to FIG. 15, the system can be configured to subtract the polynomial curve that mimics the expected curvature of the RPE layer 1502 from the detected RPE layer curve 1504, and analyze and/or compare the resulting difference/value 1506 with the values (for example, in a histogram or nomogram) from normal and/or diseased eyes to generate a diagnosis or risk assessment. The foregoing method and process is similar to a measure of tortuosity in that a bumpy RPE detection will generally have more deviations from a polynomial curve than smooth RPE detections, which are common in young, healthy people.

Such RPE detection can also be used to detect increased transmission through the RPE which is essentially synonymous with RPE degeneration or atrophy. In certain embodiments, the system is configured to analyze the tissue layer beyond or beneath the RPE layer. Using imaging segmentation techniques, the RPE layer can be segmented. In certain embodiments, the system is configured to add up all of the intensity values beneath the RPE detection. When atrophy is present, there are generally many high values beneath the RPE line, which makes the integral value high and would increase the patient's risk of having a serious macular condition, such as geographic atrophy.

Figure 16:
FIG. 16 is an illustration of retinal tissue segmented into inner and outer retinal tissue regions.

With reference to FIG. 16, the system can also be used to detect or generate risk factors for abnormal intensities within the retina. In certain embodiments, the system is configured to divide the retina into an inner 1602 and outer 1604 half based on the midpoint between the internal limiting membrane (ILM) detection 1606 and the RPE detection lines 1608. In some instances, a blur filter (for example, a Gaussian blur, radial blur, or the like) is applied to the retinal tissue to remove speckle noise and/or other noise. For each the inner and outer retina regions, a first derivative of the intensity values (with respect to position, for example, d/dx, d/dy, or the like) can be calculated to determine the slope of the curve to differentiate the areas where there are large changes from dark to bright or vice versa across lateral dimensions of the tissue. For example, intensities or derivatives within the retina can be compared to, for example, normal histograms, wherein inner retinal hypointensity can be an indicator of cystoid macular edema; or wherein outer retinal hypointensity can be an indicator of cystoid macular edema, subretinal fluid, or diffuse macular edema; or wherein outer retinal hyperintensity can be an indication of diabetes (which may be the cause of diabetic retinopathy, or damage to the retina due to, for example, complications of diabetes mellitus), or age-related macular degeneration.

Data from normal patients can used to compile histograms of intensity and/or slope (derivative) data to indicate expected values for normal people. Data from people with various diseases can also be placed into histograms of intensity and/or derivative (slope) values to indicate expected values for those people with diseases. In certain embodiments, a relative risk will then be developed for each entry on the histogram such that this risk can be applied to unknown cases. For example, in some instances, people with 10% of their outer retinal intensity values equal to 0 have an 85% chance of having a retinal problem. Accordingly, such users may receive a health grade of 15. In another example, people with any inner retinal points less than 10 have a 100% chance of disease, and therefore such users may receive a health grade of 5.

Alternatively, as discussed herein, the foregoing method or process can also be used to determine or generate a risk assessment of glaucoma based on patterns of thinning of the macular and/or peripapillary nerve fiber layer or enlarged cupping of the optic nerve head as compared to a database of normal and abnormal values stored in the disease risk assessment/diagnosis database 708. Similarly, to detect or develop a risk assessment for uveitis, a histogram of expected intensity values above the inner retinal surface (in the vitreous), for example, can be used. The presence of large, bright specks (for example, high intensity areas) in the vitreous cavity would indicate possible uveitis and would likely indicate a need for referral. The foregoing method and process can also be used to determine or generate a risk of eye disease based on the intensity levels of the image signal as compared to a database of normal and abnormal values stored in the disease risk assessment/diagnosis database 708.

In various embodiments, the foregoing method and process can also be used to determine or generate a risk assessment of uveitis based on hyperreflective features in the anterior chamber or vitreous cavity as compared to normal and abnormal hyperreflective features stored in the disease risk assessment/diagnosis database 708. The foregoing method can also be used to detect so-called 'tobacco dust,' pigment clumps, or granules posterior to the lens that can indicate the presence of a peripheral retinal tear allowing liberation of retinal pigment epithelial pigment. The foregoing method and process can also be used to determine or generate a risk assessment of anterior eye disease based on detection of pathognomonic disease features, such as cystoid retinal degeneration, outer retinal edema, subretinal fluid, subretinal tissue, macular holes, drusen, retinal pigment epithelial detachments, and/or retinal pigment epithelial atrophy, wherein the detected features are compared with such pathognomonic disease features stored in the disease risk assessment/diagnosis database 708. In certain embodiments, the system is configured to perform template matching wherein the system detects, compares, and/or matches characteristics from A-scans generated from scanning a user, also known as unknown A-scans, with a database of patterns known to be associated with disease features, such as subretinal fluid, or the like.

With reference to FIGS. 1, 8 and 9, the optical coherence tomography system 100 is configured to allow the user to self-administer an OCT scan of the user's eyes without dilation of the eyes, and obtain a risk assessment or diagnosis of various diseases and ailments without the engaging or involving a doctor and/or technician to align the user's eyes with the system, administer the OCT scan and/or interpret the data from the scan to generate or determine a risk assessment or diagnosis. In one embodiment, the optical coherence tomography system 100 can perform a screening in less than two minutes, between 2-3 minutes, or 2-5 minutes. In certain embodiments, the use of the binocular system allows the user to self-align the optical coherence tomography system 100. The optical coherence system 100 with a binocular system is faster since it scans both eyes without repositioning and can allow the optical coherence tomography system 100 to scan a person's bad eye because the person's bad eye will follow the person's good eye as the latter tracks the fixation marker. Accordingly, the optical coherence tomography system 100 reduces the expense of conducting an OCT scan, thereby making OCT scanning more accessible to more people and/or users, and saving millions of people from losing their eye sight due to eye diseases or ailments that are preventable through earlier detection. In one embodiment, the optical coherence tomography system 100 is configured to have a small-foot print and/or to be portable, such that the optical coherence tomography system 100 can be installed or placed in drug stores, retail malls or stores, medical imaging facilities, grocery stores, libraries, and/or mobile vehicles, buses, or vans, a general practitioner's or other doctor's office, such that the optical coherence tomography system 100 can be used by people who do not have access to a doctor. In another embodiment, the optical coherence tomography system 100 is configured to be a hand-held device, and/or can be powered by an external power source and/or bidirectional communications with a computer system, such as, for example, a desktop computer, laptop computer, and/or other computer system.

Additional features may be added to the optical coherence tomography system 100. In some instances, the additional features may enhance performance of the system 100.

Figures 17A, 17B, 17C:
FIGS. 17A-C show B-scans obtained when the OCT system is positioned too far anterior, at a position that provides increased field of view, or too far posterior with respect to the eye.

FIGS. 17A-C show B-scans obtained when the OCT system is positioned too far anterior, at a position that provides increased field of view, or too far posterior with respect to the eye. As shown, when the OCT system is too far anterior or too far posterior with respect to the eye the field of view (here the size or width of the B-scan) is reduced.

Figure 18A:
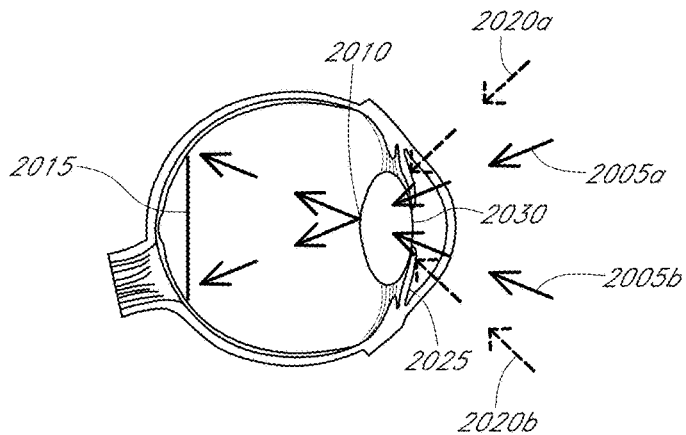
FIGS. 18A-C show light beam trajectories when the OCT system is positioned too far anterior, at a position that provides increased field of view, or too far posterior wherein the intersection of the trajectories is behind the pupil, at a pupil plane or in front of the pupil.
Figure 18B:
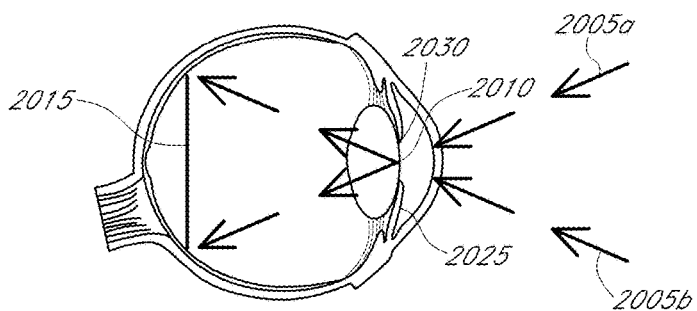
Figure 18C:
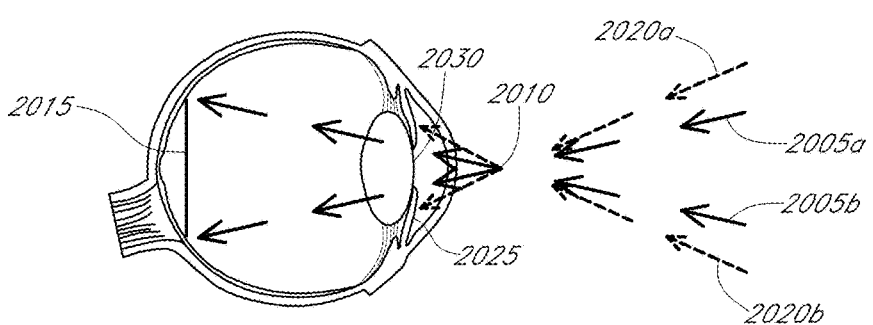

FIGS. 18A-C further show how a field of view of the system 100 can be affected by the location of the OCT system with respect to the eye. FIGS. 18A-C each show two probe beams 2005*a* and 2005*b* emitted from an optical coherence tomography system along different trajectories, as shown, by, for example, rotating a galvanometer 280 to probe different portions of the retina. For example, rotation of the galvanometer 280 may cause light to be emitted along different trajectories as described above. The trajectories may intersect with each other at rotation point 2010. Movement, for example, rotation, of the galvanometer 280, may cause the trajectory of the probe beam 2005 to rotate about the rotation point 2010. Typically, a plurality of beams 2005 will be emitted by the system, such that the eye tissue can be sufficiently imaged. Thus, in some embodiments, numerous other beams are emitted between beams 2005*a* and 2005*b*. The beams are shown to intersect with each other at a rotation point or common point 2010. In some embodiments, the location of this point may coincide with a focus of the beams. Each of the beams 2005a and 2005b and the beams therebetween (not shown) can cause structures of the eye to reflect light, such that A-scan data can be beams associated with each beam. FIGS. 18A-C show a region 2015 that can be imaged by the plurality of beams. Thus, the emitted light may sweep across a swath of points of the retina. The position of the rotation point 2010 may influence the lateral dimension (for example, length or width) of this region 2015. The region 2015 may be described as a field of view and may be correlated with the amount of data within a B-scan or set of A-scans that is above a threshold intensity.

In FIG. 18A, the rotation point 2010 is located behind/posterior to the pupil 2030. Light beams 2020a and 2020b incident at high incident angles will therefore be unable to enter the eye, as they will be blocked by the iris 2025. The angle of incidence and therefore the region 2015 of the eye that can be imaged are limited in this situation.

In FIG. 18B, the rotation point 2010 is located at a pupil plane at the pupil 2030 (for example, in the plane of the pupil). Because the light beams intersect at the rotation point 2010, no incident light will be blocked by the iris 2025. Therefore, the region 2015 of the eye that can be imaged is not limited to obstruction by the iris as shown. A larger field of view is thereby provided.

In FIG. 18C, the rotation point 2010 is located in front of/anterior to the pupil 2030. As in FIG. 18A, light beams 2020a and 2020b incident at high incident angles will therefore be unable to enter the eye, as the will be blocked by the iris 2025. The angle of incidence and therefore the region 2015 of the eye that can be imaged are limited in this situation. Accordingly, the regions 2015 probed in FIGS. 18A and 18C are shown reduced in comparison to the region 2015 probed in FIG. 18B.

Referring again to FIGS. 17A-C, examples of how B-scans can be affected by the position of one or more movable components are shown. When the rotation point 2010 is too far anterior (FIG. 17A) or too far posterior (FIG. 17C), less tissue is imaged than if the rotation point 2010 is positioned at a more optimal position (FIG. 17B). In each case, light from the center of the eye is reflected back towards the OCT system. However, when the rotation point 2010 is at a non-optimal location, light from the more extreme positions of the eye is not reflected back towards the OCT system. It is theorized that this light is instead scattered by the iris before it ever enters the eye, as illustrated in FIGS. 18A-C. By analyzing the resultant B-scans obtained for different positions of one or more movable components, it may thus be possible to determine a position that improves the field of view and thus the imaging capabilities of the OCT system. A risk assessment or diagnosis may then (for example, automatically) be performed by the OCT system using an improved field of view, the improved field of view being obtained when the movable components are in a first position, and the improved field of view being larger than a field of view obtained from when the movable components are in a different second position.

Figure 19:
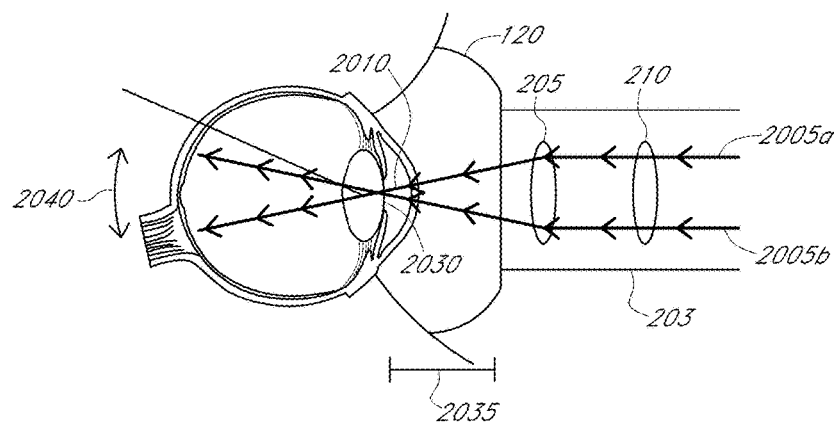
FIG. 19 shows one embodiment of a suitable working distance between an optical coherence tomography system and a retina of a subject/patient.

Accordingly, it can be advantageous in some embodiments to position the intersection/rotation point 2010 at a specific location of the eye to, for example, improve the field of view and/or to reduce obstruction of incident light by the iris 2025. The location may comprise, for example, a position in or near the pupil of the user eye, a location in a plane of the iris of the user eye, a location within the lens of the user eye, or a location posterior to the pupil of the user eye. Other locations are possible. Additionally, certain embodiments may not include a well-defined intersection/rotation point 2010 at all. In some embodiments, OCT system 100 is configured to adjust an anterior-posterior distance of the OCT system with respect to the eye or a working distance of the OCT system. FIG. 19 shows at least one movable optical component (for example, lens 205) of the optical coherence tomography system 100. The position of the at least one movable optical component can at least partly determine the position of the rotation point 2010 and the working distance of the OCT system. In certain embodiments, for example, the working distance may at least partly determine the position of the rotation point 2010. The working distance 2035 may be measured, for example, as the distance between the outermost lens or window of the eyepiece and the rotation point 2010 or a position of the eyecup 120 and the rotation point 2010. (Other reference locations on the OCT system 100 can be used.) Thus, increasing the working distance can move the rotation point 2010 further anterior. In some embodiments, the OCT system may be moved with respect to the eye. As changing either the position of the at least one movable component, the working distance of the OCT system 100, or of the OCT system itself can change the position of the rotation point 2010 with respect to the eye, these changes may affect an angular field of view of the retina 3010, for reasons described above in relation to FIGS. 18A-C.

As described above, it may be desirable to position the intersection point or rotation point 2010, or another region of the emitted probe beam in order to reduce such blocking. In one instance, a field of view (a size of a set of A-scans, a B-scan or a region of the eye that can be imaged) is monitored as the galvanometer 280 is rotated. A moveable or adjustable optical component, such as one or more of the lens 205, adjustable optics 210, eyecup 120, and the eyepiece 203, may be moved to adjust a working distance, the location of the eyepiece 203 and/or OCT system 100 (in whole or part) with respect to the eye, which may at least partly control the field of view. The adjustment may change a rotation point to, for example, position the rotation point in or near the plane of the pupil. The adjustment may allow more light (for example, a wider range of probe beam trajectories) to enter the eye from the system than would otherwise occur, thereby increasing a field of view. For example, the adjustment may increase the number of probe beam orientations that can enter the eye across a B-scan by reducing the light blocked by one or more structures of the eye (for example, the iris).

Translation stages and other actuators or movement devices may be employed to position the eye or the optics of the OCT system in the anterior-posterior direction or otherwise adjusted to provide movement in a longitudinal direction along the optical axis of the OCT instrument. Thus, the position (for example, longitudinally along the optical axis of the OCT instrument) of the movable component may determine the anterior-posterior position of the rotation point.

In certain embodiments, a translation stage such as a stage configured to move laterally (for example horizontally) may be included. Such a translation stage or actuator may determine the horizontal position of the rotation point. For example, if the stage was positioned too far medial or lateral, the iris may block a portion of the light from entering the eye that would be used to form a medial or lateral portion of, for example, a B-scan. In some instances, the iris may block a medial portion of the scan if the stage is too far medial, while in others, it may block a lateral portion. Accordingly, the field of view (for example, B-scans) for the left and right eye can be compared. If one is smaller than the other, the translation stage for the eye with the smaller field of view can be adjusted to increase the field of view of that eye.

Accordingly, in some instances, a B-scan or other OCT measurement may be analyzed or a plurality of scans or measurements are compared to determine whether a lateral (for example, horizontal) movement of the stage or actuator is advantageous. The stage or actuator may be adjusted for example after a user-conducted interpupillary distance alignment process using for example a fixation target, such as that described above. Additional alignment may be performed subsequent to adjustment of the stage or actuator which may affect interpupillary distance. Moreover, movement of the stage or actuator may affect the position of the rotation point or the portion of the sample being imaged and additional modifications of the positions of the system components may be made to account for this effect. In various embodiments, movement of the stage may move one or more of the components of the OCT system. For example, in certain embodiments, the stage may support lens 205, adjustable optics 210, beam splitter 230 and/or mirror 260. One such stage may be included for each of the eyes. In some embodiments, the components supported by the stage are those such that stage movement does not affect the angle at which the beam is output from the device. In some instances, one or more movements or adjustments (for example, of a horizontal stage) may be asymmetric across the two eyes, such that a movement associated with one eye is unparalleled or is different than a movement associated with the other eye.

In order to determine an appropriate adjustment, the one or more of the movable or adjustable optical components may be positioned (for example, systematically) in a plurality of positions, and data (for example, optical coherence data) may be obtained at these positions. The one or more movable/adjustable optical components may then be adjusted to be positioned at a desired position, the desired position being based on a comparison the optical coherence data obtained at each of the positions. The image data, for example, B-scan, may be obtained at the desired position.

In one instance, one or more sets of A-scans or one or more B-scans are analyzed to determine a position of one or more movable/adjustable components. Each of the B-scans or the sets of A-scans can be associated with a distinct position/setting of the one or more movable/adjustable components. A property of the scans (for example, an image quality measure or signal intensity value) may be compared across the B-scans or sets of A-scans in order to, for example, determine a preferred position or setting of the one or more movable/adjustable components. In one instance, the sum total of the integrated intensities across the B-scans or sets of A-scans are compared. In another instance, the intensities (for example sum total of integrated intensities) at a particular point or location within the A-scans comprising a B-scan or set of A-scans is used in the comparison. For example, a variable may be defined as the sum of the intensity at the approximate location of the retina across all A-scans within a B-scan or set of A-scans. This variable may then be compared across sets of A-scans or B-scans. A resultant position/setting of the one or more movable/adjustable components may be defined as the position/setting with a set of A-scans or a B-scan having a value for the variable that is above a threshold or is maximum (for example, greatest total intensity). Other values may be measured, calculated or considered and other approaches may be used to determine the desired position/setting and thereby increase the field of view.

In some instances, a plurality (for example, a predetermined number) of B-scans or sets of A-scans are obtained and a preferred position/setting of the one or more movable/adjustable components is determined as a position/setting associated with one of the B-scans or sets of A-scans. In another instance, the data is used to predict a preferred position/setting that may or may not be a position/setting associated with the collected data. For example, extrapolation or interpolation may be employed. In some instances, the B-scan or A-scan set data is dynamically collected. For example, if a shift of the one or more movable components along an axis from a first position to a second position caused a preferable change in a variable, then subsequent movements may avoid drastic changes in the opposite direction. In another example, the one or more movable components may repeatedly be adjusted until a variable crosses a threshold. Other approaches and methods may be used.

It may be desirable to position or set the one or more movable or adjustable components such that a rotation point of the probe beams emitted from the optical coherence tomography system are at or close to the pupil plane. If the probe beams are rotated around a position not at the pupil plane but instead shifted longitudinally towards the retina, then some of the light emitted from the optical coherence tomography system may be blocked by, for example, the iris before reaching the focal point. If the probe beam is rotated around a position not at the pupil but instead shifted towards the cornea, then some of the light emitted from the optical coherence tomography system may be blocked by, for example, the iris after reaching the focal point but before reaching other ocular structures such as the retina. By rotating light beams emitted by the OCT system around a point at the pupil, ocular structures, such as the iris, which surround the pupil might not block input light. Thus, rotating the probe beams at the pupil may increase or maximize the amount of tissue that may be imaged by the instrument.

In some instances, a position of the retina is determined for a plurality of B-scans or sets of A-scans, each associated with a different position or setting of the one or more movable or adjustable components. The position of the retina may then be used to predict the position of the pupil, and the movable/adjustable components may be positioned/set such that a rotation point is at or near the predicted pupil position. In some instances, a position of a structure of the eye, such as the cornea, iris, retina, vitreous, anterior chamber, or tear film interface, or from another anatomical feature, such as the orbital rim, nasal bridge, cheekbone (maxilla), frontal bone, eyelid or skin surface, is determined and the movable/adjustable components are positioned/set based on the determined location. The determined location may be used to predict a location of another structure, such as that of the pupil.

In some instances, a desired position or setting of the one or more movable or adjustable components is not based on optical coherence tomography data obtained for a specific patient. For example, the position or setting may be selected based on normative data which may comprise, for example, a normative position or setting that is determined based on population-based measurements or data. For example, for each of a plurality of patients, field of view measurements may be made for each of a plurality of positions or settings of the one or more movable/adjustable components. In a first instance, a preferred position or setting is determined for each patient. A normative position/setting may be, for example, a mean, median, or mode of the preferred positions/setting across patients. In a second instance, the measurements are compared to a threshold for all patients. The normative position or setting may then be determined as a position or setting for which, for example, the measurements exceeded this threshold across the most patients. In some embodiments, the movable or adjustable components are fixed at a normative position or setting. The movable/adjustable component may be fixed in the same system or in different systems at the position or setting determined based on normative data. This position/setting may be used as the selected position/setting or may be used as a starting point for measuring different fields of view for different positions/settings as described above to determine the position/setting having an increased field of view.

In some embodiments, the normative position/setting is not determined based on optical coherence tomography data but is instead based on anatomical data otherwise obtained. For example, the normative position may be determined based on an average distance between a pupil and a retina, an average anterior-posterior distance between an eye socket and a pupil, an average anterior-posterior distance between the cornea and the pupil, or an average anterior-posterior distance between a chin and a pupil. The normative position/setting may be separately determined for different patient groups. For example, the normative position/setting may be based on a person's age, gender or race.

In some instances, the position/setting of the one or more movable/adjustable components may be based at least partly on sensor data. For example, a sensor may detect a position of the patient or a patient feature (for example, an eye, a cornea, a pupil, an iris, a lens, a chin, an eye socket), and this position may be used to determine the position or setting of the eyepiece 203 or OCT system 100. In one instance, the detected position is used to predict the position of the pupil, which is used to determine the position of the one or more movable components.

Accordingly, in some embodiments, an optical coherence tomography system (for example, that of FIG. 1 or 3) comprises a sensor or tracker. The sensor or tracker may determine a position of the user, one or two eyes of the user, and/or one or more structures (for example, a retina, pupil, cornea, or lens) of the user's eye. In some embodiments, the sensor or tracker is positioned on or attached to main body 106, zero gravity arm 116, or even eyecup 120. In some embodiments, the sensor or tracker is a device separate from the main body 106. In some embodiments, the sensor or tracker is attached to or comprised within the system shown in FIG. 3.

In one instance, the sensor emits light or ultrasound from a light source and detects light reflected back. The light may be reflected back from a structure of the user's eye, such as the cornea, iris, pupil, retina, vitreous, anterior chamber, or tear film interface, or from another anatomical feature, such as the orbital rim, nasal bridge, cheekbone (maxilla), frontal bone, eyelid or skin surface. The sensor may determine the position of the structure based on the time difference between the time the light (for example, a pulse) was emitted and the time the light was detected. In other instances, other types of sensors or trackers may be used. For example, an optical coherence tomography instrument may determine the position of an eye structure based on interference or reflectance results.

In some embodiments, the position/setting of the one or more movable/adjustable components is based on a combination of approaches. For example, the position/setting may be determined based on non-optical coherence tomography sensor data and optical coherence tomography data. The position/setting may be determined based on field-of-view data and sensor data and/or a determined normative position. The position may be determined based on sensor data and a determined normative position. In certain embodiments, at least one of normative data or sensor data may be used to assist in determining a starting point for multiple OCT measurements that are subsequently employed to determine a position or setting which provides a further increased field of view.

Other approaches are possible. In some embodiments, for example, an optical coherence tomography system 100 comprises a chin rest. In such instances, the system 100 may be configured to automatically adjust or to allow for manual adjustment between the main body (and/or the eyepiece) and the patient's eyes. The adjustment may be fine, on the order of about 0.5, 1, 2, 3, 4, 5, 10, 20, 30 or 50 millimeters. The adjustment may comprise any adjustment described herein, such as an adjustment of one or more moveable optical components to, for example, improve a field of view of the system 100. In one instance, the distance between the main body and/or an optical component of in the main body and the patient's eye is systematically adjusted from a first distance to a second distance. The chin rest may move in certain embodiments although in various embodiments the chin rest may be fixed. The distance may be based at least partly on normative values, such as an average offset (for example, in the anterior-posterior direction) between a chin and a pupil or an average distance between a pupil and an eyecup. In some instances, the distance is determined based at least partly on a sensor reading. For example, a sensor may detect a position of the user's eye, pupil or iris. The sensor may comprise an optical tomography instrument or may comprise another optical or ultrasonic instrument. For example, as described above, the sensor may emit a light and determine the time elapsed between the emission and that at which reflected light (for example, a pulse) is received. The sensor may comprise a weight sensor to sense, for example, a location of the patient's chin. A sensor may detect a position or weight of the user's chin. In certain embodiments the chin rest may move or the main body and/or eyepiece of the OCT system may move with respect to the chin rest and the field of view monitored as described above to determine a suitable location of the eye. Other variations are possible.

In some embodiments, a position/setting of one or more moveable/adjustable optical components can be manually adjusted by the patient. The patient may be instructed, for example, to adjust the position/setting based on one or more images seen by the patient. For example, the patient may be instructed to adjust the position until two or more images (for example, working distance images) are aligned. Alignment may correspond to an appropriate distance of the eye to the OCT instrument. Other designs are also possible.

In some embodiments, the system 100 may be configured to screen for one or more ophthalmic conditions. In other embodiments, the system 100 may be configured to monitor one or more conditions. In some instances, a patient suffers from a condition that requires regular monitoring. For example, the condition may worsen, which may warrant different treatments or the condition may improve, which may warrant termination of a treatment or follow-up. However, frequent regular appointments with a health care provider can be expensive and inconvenient. The inconvenience and busy schedules of the health care provider and patient may reduce the frequency of appointments to an undesirably low level, such that a health care provider is unlikely to detect changes at their earliest stage. By having the patient use the optical coherence tomography system 100 to self administer testing and monitor the condition, more frequent, cheaper, faster and/or more convenient monitoring may be possible.

In certain embodiments, the system 100 can be configured to enforce standards of care determined by a physician. For example, the system 100 can be configured to be programmed to perform ophthalmic diagnostic tests and other testing according to a standard of care schedule prescribed by a physician. In certain embodiments, the system 100 can be programmed to operate only after a specified time interval has elapsed since the last diagnostic test. Alternatively, the system 100 can be configured to notify the patient via an alarm, email, or other reminder mechanism when it is time to perform another diagnostic test.

As described in greater detail below, the system 100 may be notified of a particular condition. For example, a physician may (for example, indirectly) indicate that a patient is suffering from or at risk of suffering from a condition. The system 100 may be configured to determine whether the condition is improving or worsening based on optical coherence tomography measurements obtained by the system. The system may inform a health care provider (for example, an optometrist or physician) and/or a patient (for example, after each scan or only after scans yielding specific results) of a monitoring result obtained by the system. The results may indicate whether it is advisable to see the health care provider. For example, the results may indicate a condition is worsening (such that, for example, the health care provider may wish to consider alternative treatment strategies) or that the condition is improving (such that, for example, the health care provider may wish to consider terminating a treatment).

Figure 20:
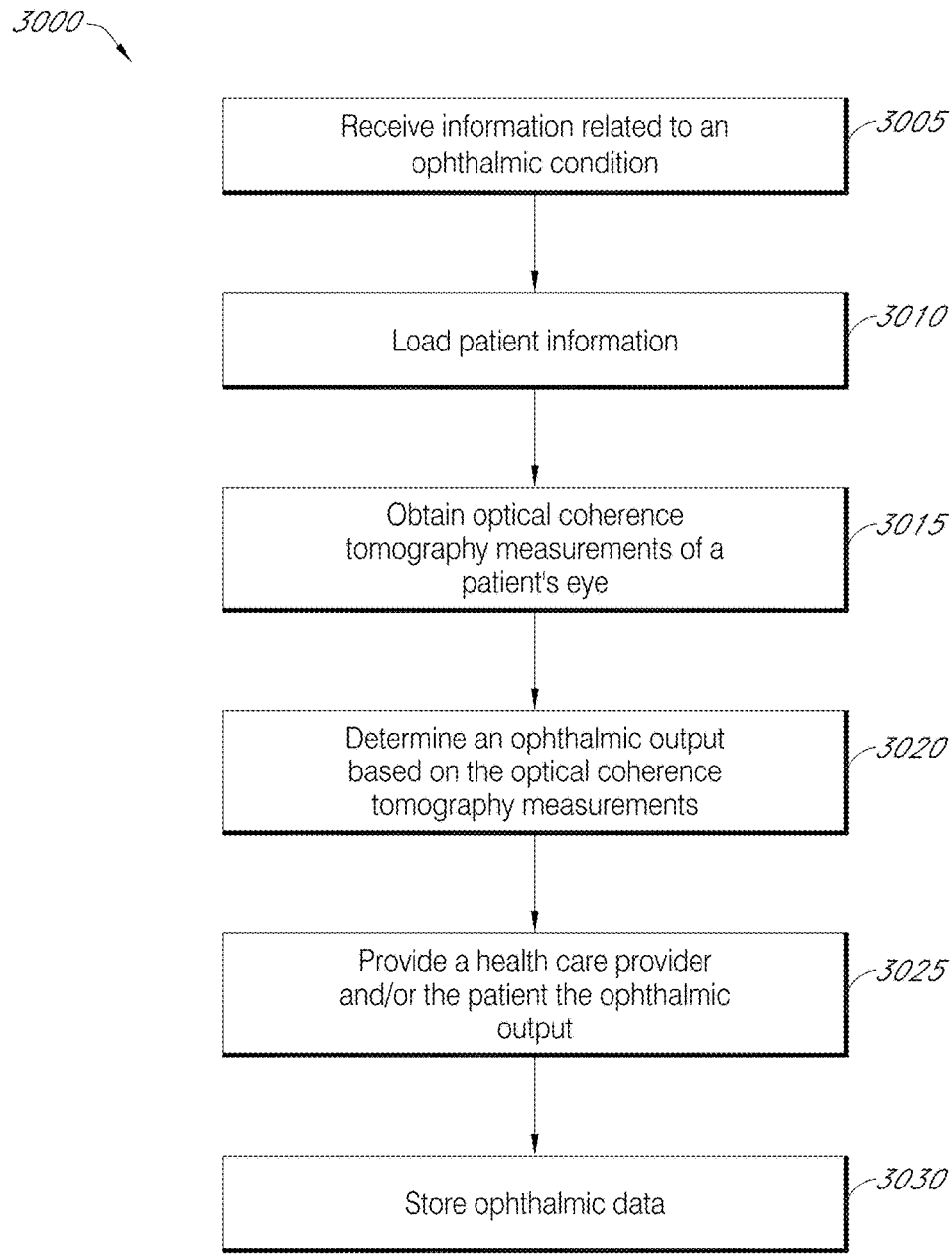
FIG. 20 shows a process for monitoring an ophthalmic condition using an optical coherence tomography system.
Figure 21:
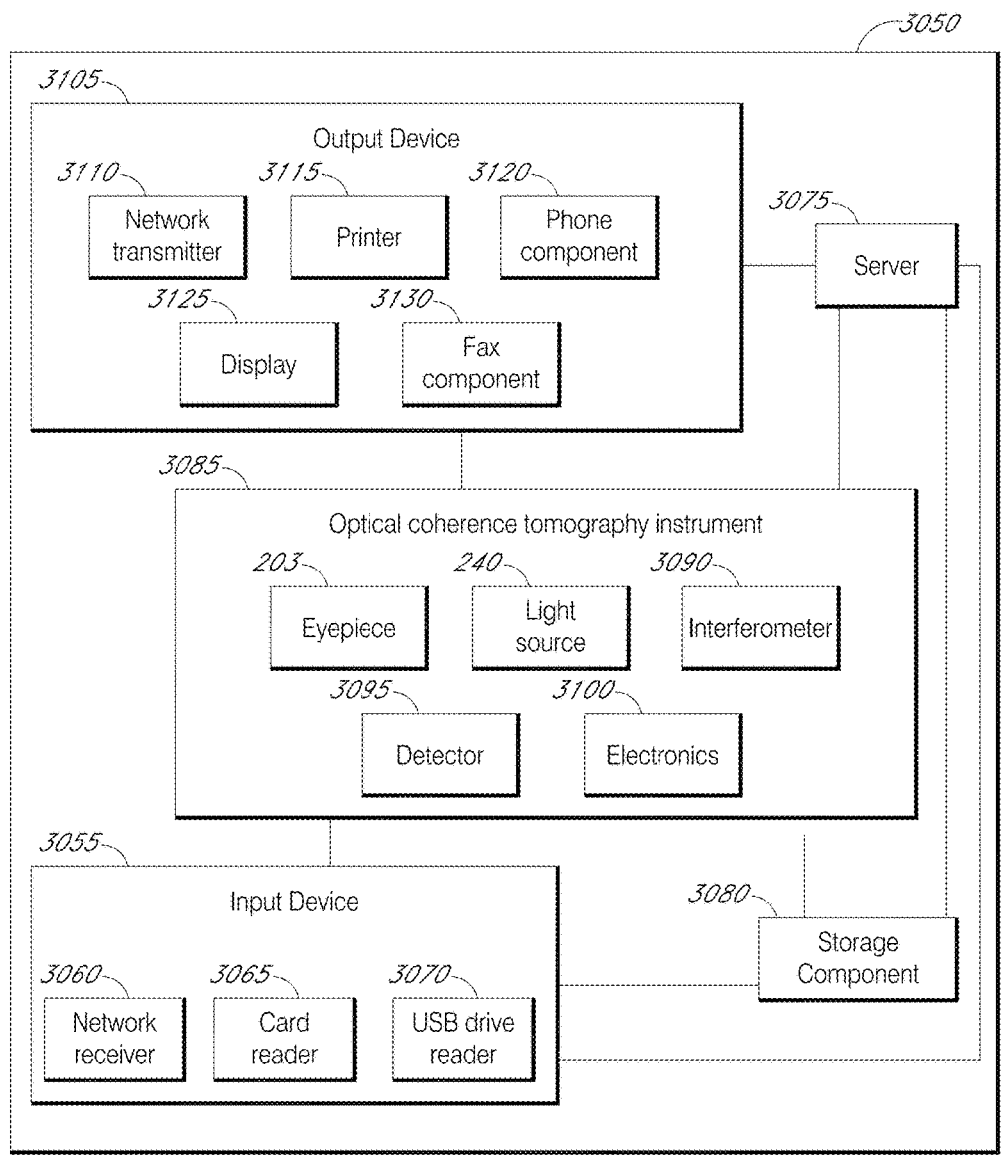
FIG. 21 is a block diagram of one embodiment of an OCT system comprising an input device and an output device that can be used to monitor an ophthalmic condition.

FIG. 20 shows a process 3000 for using an optical coherence tomography system for monitoring an ophthalmic condition, and FIG. 21 shows a block diagram of an optical coherence tomography system 3050. Lines between components of the system 3050 show connections between the components. In some embodiments, one or more of the connections are not present in the system 3050, and in some embodiments, additional connections are present. The connections may be a direct physical connection, a virtual connection, a physical network connection (for example, using a telephone line) and/or a wireless network connection. Other connection types are also possible. In some instances, the system 3050 includes additional components not shown in FIG. 21, and in some instances, the system 3050 does not include one or more components shown in FIG. 21. Similarly, in some instances, process 3000 does not include one or more steps shown in FIG. 20 and/or contains additional steps. The process steps may also be rearranged.

At step 3005 of process 3000, information related to an ophthalmic condition may be received. Information may be received by reading a data storage device, such as a card with a magnetic strip, a smart card or a USB device. Information may be electronically received, wirelessly received, and/or received over a network (for example, over an Internet network).

Information may be received by an input device 3055 of the system 3050. The input device 3055 may comprise, for example, a receiver 3060 (for example, a wireless receiver). The receiver 3060 may be connected to a local or remote network, such as the Internet. While in some embodiments, the receiver 3060 receives signals from a wireless device, in others it does not. For example, the receiver 3060 may be configured to receive a telephone line. The input device 3055 may comprise a card reader 3065. The input device 3055 may comprise a USB drive reader 3070. In some instances, the input device receives (for example, via the receiver 3060) information from a server 3075. For example, a physician may send information to the server 3075. The server may store information and may then transmit the information to the input device when a user is ready for a scan. For example, the user may enter an identification code or may use a device comprising an identifier, and the server 3075 may then send information corresponding to the user to the input device 3055. Although one server is referred to above, one or more servers or computers, for example, in a network, may be used. In some instances, disease monitoring activities occur substantially on one computer system that holds all scan data from previous visits locally so that comparisons to previous visits can be accomplished without communicating data across a network.

The information may identify a condition or disease. For example, the information may indicate that a patient is suffering from a particular condition (for example, age-related macular degeneration, macular edema, diabetic retinopathy or glaucoma). The information may indicate a past severity of a condition, such as the severity of the condition at a previous appointment. The information may indicate a threshold indication for the condition. For example, the information may indicate that the patient and/or a health care provider (for example, a physician or optometrist) should be notified if the condition worsens by a specified amount as predicted by specific measures. Thus, the system 3050 may not need to screen for diseases but instead may monitor progression of specific conditions. (However, in some embodiments, the system 3050 both monitors at least one condition and screens for one or more other conditions.) In some instances, process 3000 does not include a step 3005.

At step 3010, patient information is loaded. The patient information may comprise a history related to the ophthalmic condition. For example, the patient information may comprise optical coherence tomography measurements or output related to such measurements from previous scans. The patient information may include health care provider information (for example, a name, address, e-mail and/or phone number of the patient's physician). In some instances, the health care provider information and/or a patient identifier is received (for example, with the information received at step 3005). The identifier may include, for example, an identification number or the patient's name. The information may be loaded from a storage component 3080 (for example, of a local or remote computer). For example, the information may be loaded from a local memory or may be wirelessly received from a server 3075, which may have the information stored on a storage component 3080. In some instances, the information is loaded from a data storage device, such as a smart card or a credit card, which may be provided by a patient. Thus, the input device 3055 may receive the patient information. In some instances, process 3000 does not include a step 3010.

In one embodiment, the patient inserts a card into a card reader. The card is encoded with a card number or code. The card number or code is transmitted to a remote location such as a server. The server can provide information regarding condition, patient information, health care provider information, etc.

Though only a single storage component 3080 is shown in FIG. 21, a plurality of storage components may be present. For example, some storage components 3080 may be physical connected to the OCT instrument 3085, one or more storage components 3080 may be physically connected to the server 3075 and one or more storage components 3080 may be physically connected to the input device 3055. In some instances, both a removable and a non-removable storage component 3080 are connected to the OCT instrument 3085. Other arrangements are also possible.

At step 3015, optical coherence tomography measurements are obtained. These measurements may be any such measurements described herein. The measurements may be obtained by an optical coherence tomography instrument 3085. The optical coherence tomography instrument 3085 may include components described herein, such as those associated with system 100. For example, the instrument 3085 may include an eyepiece 203, a light source 240, an interferometer 3090, a detector 3095 and/or electronics 3100. The eyepiece 203 can be configured to receive at least one of the user's eyes. The light source 240 can be configured to output light that is directed through the eyepiece 203 into the user's eye. The interferometer 3090 can be configured to produce optical interference using light reflected from the user's eye. The detector 3095 can be disposed so as to detect said optical interference. The electronics 3100 can be coupled to the detector 3095 and can be configured to analyze optical coherence tomography measurements obtained using said interferometer 3090 as described herein and/or can be configured to determine an ophthalmic output related to a state of the ophthalmic condition as described in greater detail below. The optical coherence tomography instrument 3085 may, for example, obtain A-scan, B-scan or 3D-OCT data. In some instances, the type of optical coherence tomography measurements obtained depend on the information regarding the optical condition, for example, received at step 3005. For example, if a patient is suffering from narrow-angle glaucoma, the optical coherence tomography instrument 3085 may measure the depth of the anterior chamber and forego more extensive imaging of the eye. Alternatively, this anterior chamber depth measurement may occur immediately prior to scanning of the posterior structures in the eye.

As described in greater detail above, in certain embodiments, a Z-offset adjustment stage 290 is adjusted prior to an optical coherence tomography screening or test, thereby changing the portion of the eye that is imaged. In some instances, one or more components of the optical coherence tomography instrument 3085 (for example, the Z-offset adjustment stage 290) are moved until a posterior structure (for example, the retina) is being imaged. During this antero-posterior movement, optical coherence tomography data could be continuously acquired to produce a 3D-OCT having a total axial depth covering some or all of the antero-posterior depth of a normal eye such as 16 millimeters, 22 millimeters, or 30 millimeters of distance. The components may be initially positioned to image a more anterior structure and may then be gradually adjusted until the posterior structure is being imaged. In some instances, the instrument 3085 may therefore first scan an anterior structure and subsequently scan a posterior structure. For example, the anterior structure may be imaged during a process of locating the posterior structure. In some instances, the posterior structure is imaged before (for example, immediately before) the anterior structure.

At step 3020, an ophthalmic output is determined based on the optical coherence tomography measurements. In some instances, the electronics 3100 of the optical coherence tomography instrument 3085 determine the ophthalmic output. Notably, while—in this instance—the electronics 3100 are shown to be within the optical coherence tomography instrument 3085, in some embodiments the electronics are on a remote device. For example, data from a scan may be sent to the server 3075 and electronics of the server may analyze the data and determine the ophthalmic output. In some embodiments, the electronics can be both in the optical coherence tomography instrument 3085 and at in a remote device.

The type of output may depend on the information received in step 3005. The output may be quantitative or qualitative. For example, the output may include, among other things, the presence of structures such as an epiretinal membrane, macular hole, cystoid macular edema, hard exudates, neovascularization, IRMA, cotton wool spots, microaneurysms, intraretinal hemorrhages, subretinal fluid, subretinal tissue, subretinal hemorrhage, retinal pigment epithelial detachment, drusen or RPE atrophy. It may also include measurements such as the anterior chamber depth or foveal thickness. It may include aggregated measurements collected from many OCT A-scans such as the macular volume, nerve fiber layer volume, optic disc cup volume, subretinal fluid volume, drusen volume, drusen area, and geographic atrophy area. These measurements may be based on the entire area scanned or be subsampled from a subset of scanned points. The output could include a count of structures, such as drusen or microaneurysms, or a density measure for structures either based on their area compared to the total area scanned or based on their volume in relation to the total volume of tissue scanned. It could also be based on reflection intensities from the OCT A-scan data itself. For example, measurements of media clarity may rely on OCT signal intensities while measurements of hard exudates may rely on the distribution of intensity values for bright objects in the inner and outer retina.

The output may be based at least partly on patient information loaded in step 3010. For example, the output may compare the measurements obtained at step 3015 to previously obtained measurements. Such a comparison may include an alignment process, such as an alignment of retina maps obtained across a plurality of scans. The comparisons may be comparisons of aggregate values (for example, areas, volumes, sums or values integrated over a region such as the retina, nerve fiber layer or optic cup or parts thereof) or point-by-point comparisons of values for example of thicknesses or structure classifications (for example, drusen or cystoid space) across a plurality of locations in the eye. Thus, changes in sizes such as widths, areas, volumes or thicknesses may be recognized, as well as the occurrence of new structures. The previously obtained measurements may be stored on the storage component 3080, which may be comprised within the OCT instrument 3085 and/or the server 3075. The stored measurements may be associated with a date and/or time that the measurements were obtained or a code (such as a code associated with a card input by the user) indicating, for example, a scan number. Thus, in determining the output, the most recent scan or another reference scan may be identified and data from this scan may be loaded (or transmitted from the server 3075) for a comparison. The comparison may then be performed (for example, by electronics 3100). In some instances, a computer comprises the electronics 3100. Thus, the computer may be configured to perform a step described in embodiments herein to be performed by the electronics 3100. For example, the computer may compare two or more scans, may compare a measurement to a threshold, may calculate a percent change in a measurement, etc. The computer may be contained within the OCT instrument 3085. In some embodiments, the computer is connected to the OCT instrument 3085. In some embodiments, the computer is connected to the server 3075. In some embodiments the server comprises the computer or at least part thereof. A computer-readable medium may also include instructions for performing steps described herein.

Accordingly, the system may comprise software configured to determine the ophthalmic output and/or to compare measurements to other OCT measurements (for example, measurements previously obtained from the patient or benchmark measurements). This software may be at a remote location such as a server. Raw image data or extracted numerical data may be transferred to the remote location such as the server and calculations and/or comparisons performed at that remote location. In some embodiments, data corresponding to prior tests need not be sent to the OCT system, for example, in the case where the comparison is made at the remote location, for example, the server. In some embodiments, analysis is performed both at the OCT instrument and at a remote location such as the server. Accordingly, suitable software may be included in at both the OCT instrument and the remote location.

The output may include a probability, such as the probability that a condition is worsening or improving. The output may include a confidence measure. As another example, the output may indicate that an ophthalmic condition is worsening, improving or staying substantially the same. The output may comprise an appointment request. For example, if it is determined that a particular change has occurred or that a threshold has been crossed based on OCT data, output comprising an appointment request may be sent to a health care provider. The output may also comprise an indication of a recommendation for a referral or an appointment.

At step 3025, a health care provider and/or the patient are provided the ophthalmic output. The ophthalmic output may be output by an output device 3105, such as a transmitter 3110 (for example, a wireless network transmitter, an electronic transmitter), a printer 3115, a phone component 3120, a display 3125 and/or a fax component 3130. The ophthalmic output may be stored on a storage component 3080 (for example, a removable storage component), such as a compact disc or a USB key. In some instances, the storage component 3080 can be sent (directly or indirectly, such as via the user) to a health care provider. The notification may comprise an output of a quantitative or qualitative ophthalmic output variable. In some instances, the notification to one or both of the health care provider and the patient only occurs if it is probable that the condition is worsening, if it is probable that the condition is improving and/or if the ophthalmic output variable crosses a threshold. In some instances, the ophthalmic output itself indicates that a variable related to the OCT screening crossed the threshold. The threshold may be predefined (for example, included in the information received in step 3005 or a set threshold associated with a specific ophthalmic condition). For example, for a user suffering from wet age-related macular degeneration, the ophthalmic output variable may comprise a central retinal thickness, and a threshold may be set as a previously determined thickness plus 100 microns. The threshold and comparison with the threshold may be made at a remote location such as at a server. If the threshold is exceeded, the health care provider may wish to consider re-treating, for example, with an anti-VEGF treatment. In another example, the ophthalmic output variable itself is an indication as to whether the threshold was crossed.

The patient may be notified of the ophthalmic output by displaying the output on, for example, a display 3125 such as a screen. The output may also be printed by a printer 3115. The output may be printed on paper or on a surface of a data storage device. For example, the patient may initially input a card into the system. The system may read the card to identify information related to an ophthalmic condition or the patient. The system may then print the ophthalmic output on the surface of the card. In some instances, the patient is instructed to return the card to a health care provide, for example, optometrist, ophthalmologist, such that he/she can read the printed results and/or verify that the process was completed. Date and time information may also be printed along with the output. In some instances, only the date and time information is printed.

The health care provider may be provided ophthalmic output by any appropriate process. In some embodiments, the output transmitted to the health care provider does not include the patient's name. Instead, the transmission may include a patient identifier such as the code from the card provided to the patient by the healthcare provider. Thus, the patient's privacy may be respected in the instance that a third party was to receive the transmission instead of the health care provider. The output may be electronically sent to the health care provider (for example, by email). In one instance, the system 3050 electronically transmits (for example, via a transmitter) the output to the health care provider. The output may be printed via a printer 3115 and mailed to the health care provider. In one instance, the output is faxed to the health care provider. The output may be faxed (for example, via a fax component 3130) to a health care provider. In one instance, the output is audibly sent to the health care provider. For example, the system may comprise an automated telephone component 3120, such that results are relayed via a telephone call to the health care provider. In another example, the system may display, print or send the results to a person who calls the health care provider. In some embodiments, the output is directly sent (for example, via an output device 3105) to the health care provider from an instrument 3085. In other embodiments, the instrument 3085 transmits the output to a server 3075 which then transmits (for example, via an output device 3105) the output to the health care provider. In still other embodiments, data is sent from the instrument 3085 to the server 3075, the output is determined and the output is then transmitted (for example, via an output device 3105) to the health care provider. The server may, for example, transmit the output to the health care provider using a network. For example, the output may be provided on a (for example, password-protected) Internet site. The health care provider may check the site regularly and/or may be sent a message (for example, a telephonic or email message) to check the site. In some instances, the system 3050 comprises the capability of outputting the output in a number of manners, such as those described herein, and a health care provider indicates a preferred method of receiving the output. The output is then transmitted to the health care provider via this preferred method.

Accordingly, in various embodiments, the output comprises a number of types of outputs. For example, the output may comprise an appointment request, a summary report, a single B-scan image, multiple B-scan images or selected B-scan images representing the disease detected by the instrument, all of which are to be output to a health care provider, and a confirmation of the scan and a different summary report, all of which are to be output to the user.

At step 3030, the ophthalmic data is stored. The data may be stored at a storage component 3080. The storage component 3080 may be associated with an OCT instrument 3085 and/or with a remote location, such as the server 3075. In some instances, the ophthalmic data comprises raw optical coherence tomography data. In some instances, the ophthalmic data comprises summary data, such as an ophthalmic output disclosed herein. The stored data may be associated with the patient (for example, by using a patient identifier).

The system 3050 described herein may enable users to monitor ophthalmic conditions with fewer visits to a health care provider. Patients suffering from conditions such as age-related macular degeneration, diabetic retinopathy, retinal vaso-occlusive disease, macular edema, macular holes, central serous chorioretinopathy, epiretinal membranes, schisis cavities associated with optic disc pits, retinal inflammatory diseases, cataracts, and/or glaucoma, may especially benefit from use of the system 3050. Patients suffering from dry age-related macular degeneration are often advised to use an Amsler grid. The Amsler grid resembles a checkboard, but an individual suffering from age-related degeneration may find that, while focusing at a dot, straight lines appear wavy and that some of the lines are missing. Thus, by comparing the appearance of the grid across a time period, the patient may be able to estimate whether his disease is progressing or improving. However, this test is highly subjective. Use (especially frequent use) of the system 3050 could provide a substitute objective measure of a disease state and a health care provider may determine a specific result that may lead to a recommendation to see the health care provider again.

Patients suffering from wet age-related macular degeneration may receive frequent, repeated anti-VEGF treatments. The number and/or frequency of the treatments may be customized based upon the anatomical state of the patient's eye/s to reduce the total number of visits required within a given time period. For example, re-treatment may be indicated if the central retinal thickness as measured by OCT increases by at least 100 microns, if new or increased cystoid edema is detected, if subretinal fluid is present, or if pigment epithelial detachments increase substantially in size. By monitoring the disease with an OCT system 3050 described herein, the patient can frequently and conveniently monitor disease characteristics without inconvenient and expensive visits to their eyecare provider and then schedule an appointment with a health care provider if it is probable that a new treatment is required or if other dangerous conditions develop.

Treatment of conditions such as macular edema and glaucoma is aided by frequent monitoring of the condition. The OCT systems described herein can monitor the condition, which may thereby allow more frequent monitoring and/or reduce inconvenience to the patient and/or health care provider. With regards to glaucoma, the system could provide more quantitative interval data points for optic nerve and nerve fiber layer assessments.

In some embodiments, one or more data storage devices such as cards (for example, card with magnetic tape, smart card, USB device) are provided. Data may be transferred to the device(s) via standard data transferring techniques, such as by using a computer or a magnetic strip encoder and by data transfer and storage devices yet to be developed. The data storage devices may be configured to store information related to an ophthalmic condition, a patient and/or a health care provider. In one instance, the devices are configured to receive information from a health care provider or an agent of the health care provider. The information to be received from the health care provider may include patient identification information, such as the patient's name or a patient identifier (for example, number). The information may indicate an ophthalmic condition of which the patient is suffering from or is at risk of suffering from. The information may indicate a particular ophthalmic measurement of interest (for example, an anterior chamber depth, macular volume, optic disc cup volume, nerve fiber layer volume) or a concerning feature (for example subretinal fluid, macular hole, retinal neovascularization, cystoid spaces, pigment epithelial detachment) The information may indicate a current ophthalmic measurement and/or a threshold of the measurement. The threshold may be absolute or relative. The information may include information related to the health care provider, such as his name, business, profession, association, address, email, fax number and/or telephone number. The information may include information about the scan timing. For example, the information may indicate that the patient is to receive a scan within a time period or is to receive a specific number of scans. In some instances, a system will compare the time period on the device to the current time and only perform an OCT scan and/or only accept the device if the current time is within the time period. The information may indicate a scan type (for example, full or partial) or a scan characteristic (for example, a resolution or area to be imaged).

In some instances, the data storage device is configured to be used multiple times. For example, the patient may be advised to receive scans according to a particular schedule (for example, weekly for ten weeks, or every 2 weeks until a scan result is achieved) and the patient may use the same card for each scan visit. In some instances, software or a component (for example, an electronics component or a fraud protection component) is used to determine if the same subject is using the card multiple times to prevent fraudulent use of the card by multiple people. In this case, patterns unique to individuals, such as their retinal vessel pattern, may be compared between visits to ensure that the same person is being scanned each time. Other biometric measurements may be developed or implemented for this purpose as well. In some instances, the system is configured to require the data storage device (for example, card) be used within a time period indicated on the data storage device before scanning the patient's eye/s. In some instances, the data storage device (for example, card) is configured to be used only once. The system may be configured to accept the data storage device and not return it (confiscate it), thereby disabling the patient from using it again. Alternatively, the system may alter a part of the data storage device (for example, a software component, data on magnetic tape) such that the system either does not accept the data storage device after a single use or does not perform another scan after the data storage device is inserted after a single use. Multiple cards can be issued for a patient who is to receive scans according to a particular schedule (for example, weekly for ten weeks, or every 2 weeks until a scan result is achieved) and the patient may use, for example, one card for each scan visit. (Note that in some embodiments, multiple scans may be provided in one sitting, for example, to investigate multiple regions of the eye.)

As referred to above, the data storage device (for example, card) may comprise a writable surface. Thus, the system may print a result on the data storage device. The result may include a confirmation result, which can confirm (for example, to the health care provider) that the scan was performed. The confirmation result may include a date and/or a time. The result may include an ophthalmic output or other result of the scan.

In narrow-angle or angle-closure glaucoma, a block or obstruction of drainage canals can lead to a chronic or rapid increase in eye pressure. Such a block can occur when the iris pushes against the lens of the eye, and the iris and lens may even stick together. Narrow-angle glaucoma is highly prevalent in areas such as China and India. Thus, it may be advantageous to identify whether a patient is at risk of developing this condition. The depth of the anterior chamber may be associated with the occurrence of narrow-angle glaucoma in that patients suffering from narrow-angle glaucoma generally have shorter anterior chamber depths than control subjects. See, for example, Lavanya et al. Screening for narrow angles in the Singapore population: evaluation of new noncontact screening methods. Ophthalmology. 2008 May 15, which is hereby incorporated by reference in its entirety. This depth can be calculated as the distance between the posterior corneal surface and the anterior lens capsule. Alternative anterior borders for the anterior chamber depth might be the anterior corneal surface or within the corneal stroma. Alternative posterior borders for the anterior chamber depth may be the lens body. A corneal thickness (for example, a central corneal thickness) may also be indicative of whether a patient is suffering from or is at risk of suffering from glaucoma (for example, open angle glaucoma). The central corneal thickness can be measured as the distance between the anterior and posterior corneal surfaces at the center of the cornea.

Thus, a system disclosed herein (for example system 100, 3050) may be used to screen for glaucoma, such as narrow-angle glaucoma and open-angle glaucoma. The self-administered OCT test may be performed on patients that have or have not been diagnosed with glaucoma. The system 100, 3050 may indicate that the patient is suffering from a glaucoma condition, that the patient is at risk of suffering from a glaucoma condition, or may provide an indication of a severity or progression of the condition.

The system 100, 3050 may, for example, measure the anterior chamber depth or corneal thickness of a user and compare the depth to a threshold depth or thickness to determine whether the user is suffering from or is at risk of suffering from a glaucoma condition. If the depth or thickness is beyond a threshold, an output indicating as such may be output to the user and/or a health care provider. The output may indicate the measured depth or thickness, may indicate that the measured data is within a particular range, may indicate that the measured data is beyond a threshold, and/or may indicate a probability that the user is suffering from a glaucoma condition or optic nerve disorder. Other outputs may be provided. Notably, in some instances "beyond a threshold" includes being greater than the threshold, while in other conditions it includes being less than the threshold. For example, in the instance of narrow-angle glaucoma, smaller anterior chamber depths are associated with the condition, so beyond the threshold can mean that the measured depth is less than the threshold. A threshold may include an anterior chamber depth of about 3.5 mm, 3.3 mm, 3.1 mm, 3.0 mm, 2.9 mm, 2.8 mm, 2.7 mm, 2.6 mm, 2.5 mm, 2.4 mm, 2.3 mm, 2.2 mm, 2.1 mm, 2.0 mm, 1.5 mm or 1.0 mm. Notably, the threshold value may balance sensitivity and specificity, such that some thresholds are more likely to detect all occurrences of a disease but also more likely to include false positives, while other thresholds are likely to miss more actual occurrences of the disease but also will be associated with fewer false positives. The output may indicate a probability that the patient is suffering from a disease based on how far a measurement is beyond a threshold or which threshold of a plurality of thresholds the measurement is beyond. In various embodiments, however, a risk assessment is provided.

An OCT measurement may indicate a risk of suffering from a condition. In some instances, a relationship (for example, a monotonic relationship) may be established between the measurement and a probability of having the condition. This relationship may be established based on empirical data. Thus, the measurement may be converted into the probability or risk of suffering from the disease. In some instances a relationship may be established between the measurement and the probability of later having the condition. Thus, preventative measures may be taken in order to reduce this probability. In some instances, a number of measurement ranges are established, each range being associated with a (present or future) probability of having the condition.

In various embodiments, the system 100, 3050 may measure the anterior chamber depth or a corneal thickness of a user, for example, and compare the depth to a previously measured depth or thickness to determine whether the condition is improving or worsening. The previously measured data may be loaded from a storage component. The output may indicate that the condition is improving, worsening or substantially the same. The output may quantify a change in a condition-related measurement. The output may indicate whether the change is beyond a threshold amount.

In some instances, the anterior segment of the eye is imaged by appropriate positioning of the Z-offset adjustment stage 290. In some instances, the quality of the scan at least partly determines which anatomical structures are used for the boundaries defining the anterior chamber distance. The posterior corneal surface and the anterior lens surface may be used as the anterior and posterior boundaries, respectively, when the quality is high, whereas the corneal stroma may be substituted as the anterior boundary and/or the lens body may be substituted as the posterior boundary when the quality is low.

In some instances, an A-scan may be used to determine a thickness or depth. However, the depth or thickness may depend on a radial location of the scan. Therefore, a B-scan or set of A-scans may be obtained and a first thickness or depth may be determined for each A-scan. The thickness or depth with the largest value or at a certain distance from the central axis of the eye may be determined to be a useful thickness or depth to be used in comparisons or as output.

OCT systems may position a Z-offset adjustment stage 290, thereby adjusting the portion of the eye being imaged, and adjustable optics 210 may then focus the beam such that a particular small region can be clearly imaged. For some OCT applications, it is desirable to obtain scans through small regions (for example, through an axial distance of about 2.2 mm) of the eye. Instruments designed specifically for smaller regions may be able to image the regions with higher resolution. However, limiting the range of the scan to such a short depths may prevent capture of an entire region of interest. For example, an A-scan through a depth or longitudinal distance of 2.2 mm may be too small to include both an anterior and posterior boundary of the anterior chamber in the A-scan. In one instance, larger A-scans (for example, over distances in the Z direction of about 3 or of about 4 mm) may be obtained, such that both the anterior and posterior boundaries of the region may be imaged. In some instances, the system is configured such that all scans extend over the longer range of depths. In some instances, the system is configured such that all scans of a particular region (for example, the anterior segment) extend over a larger range of depths but that all scans of other regions extend over shorter ranges, thereby allowing higher resolution imaging at the other regions. In some instances, the system is configured such that scans of a particular region (for example, the anterior segment) may extend over a longer or a shorter (for example, depending on a setting or particular test) range of depths. In some instances, both larger and short length A-scans of a region are obtained.

In another instance, a plurality of scans is obtained, each of the scans performed at a different depth. For example, a first scan may adjust at least one optical component to image an anterior boundary of a region, while a second scan may adjust the at least one component to image at a posterior boundary. For example, the Z-offset adjustment stage 290 and the adjustable optics 210 may be positioned such that the posterior corneal surface is imaged and an A-scan may be obtained. The Z-offset adjustment stage 290 and the adjustable optics 210 may then be positioned such that the anterior lens surface is imaged and another A-scan may be obtained. The distance between these anatomical features may be determined based on the combination of the different positions of the features within the A-scans and the different positions of the Z-offset adjustment stage.

In some instances, a plurality of A-scans is obtained thereby imaging selected portions or possibly a substantial portion of the width or the entire width of the anterior chamber. In these instances, the peripheral chamber depth, angle geometry and/or angle structures may be determined. These measurements may be used to determine that the patient is suffering from a condition (for example, narrow-angle glaucoma), that the patient is at risk of suffering from a condition, or may provide an indication of a severity or progression of a condition.

Other variations are possible. For example, since central corneal thickness may also have some predictive value (and can be calculated by measuring the distance between the anterior and posterior corneal surfaces), this measure might also be used for screening for open angle glaucoma.

Another method of monitoring glaucoma may be to estimate the optic nerve head volume by subtracting the volume of the optic disc cup (generally, the depression in the middle of the optic nerve) from the volume of optic nerve tissue bounded by the vitreous (on the anterior side), the lamina cribrosa or bottom of the optic disc cup (on the posterior side), and the circumferential retinal pigment epithelium (RPE) and Bruchs membrane termination that bounds the optic nerve on all or substantially all sides. Generally, as glaucoma progresses, the optic nerve volume may decrease as the nerve fibers die or atrophy, and/or the optic disc cup may increase relative to the area covered by the optic nerve fibers in the optic nerve head. Therefore, the OCT system described herein can be configured to estimate the amount of remaining optic nerve tissue by subtracting the optic disc cup volume from the known bounded optic nerve tissue volume. The optic disc cup volume can be measured by first detecting the posterior border of the optic disc cup with image analysis routines, such as edge detection, that delineate the transition from vitreous to optic nerve tissue. The anterior optic disc cup boundary is an imaginary plane cutting through vitreous tissue or aqueous and spanning the peaks of the optic nerve tissue much like a plate placed on a bowl. It can be approximated by detecting the highest point of optic nerve tissue (transition from vitreous to optic nerve tissue) for 360 degrees around the optic nerve circumference with image analysis routines such as edge detection. In another embodiment, the circumferential termination of Bruchs membrane can be used to delineate the circumference of the optic nerve. The position of the transition from vitreous to optic nerve tissue at this circumference could be used as an alternate anterior optic disc cup boundary plane. Alternatively, the system can be configured to compare measurements of optic nerve head volume, and/or other optic nerve, retinal nerve fiber layer and/or retinal thickness measurements, between the eyes of a subject (and/or at different periods of time) to estimate the risk of glaucoma.

Figure 22:
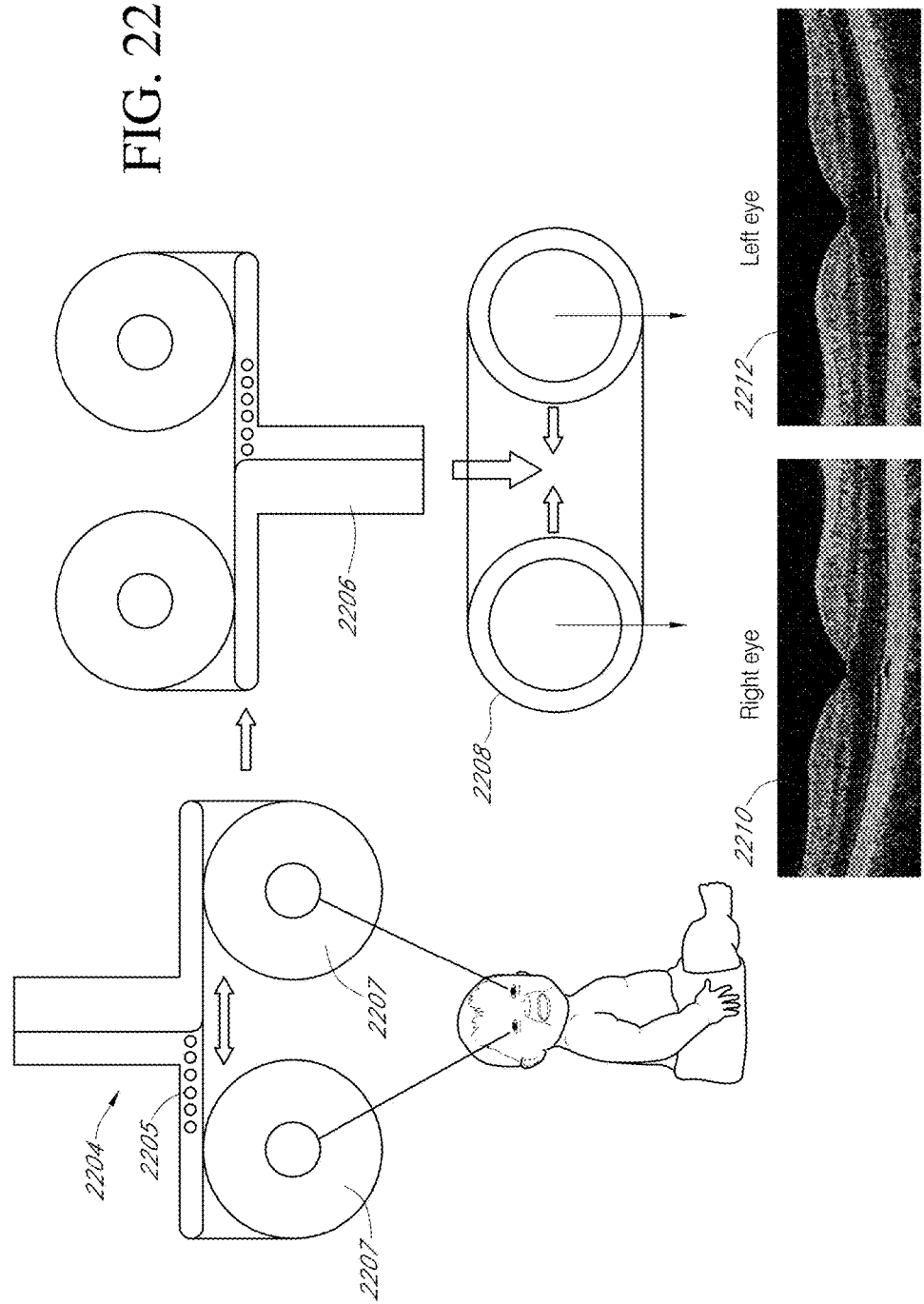
FIG. 22 is high-level flow diagram illustrating an example of using an interpupillary distance measurement device, for example on an uncooperative or pediatric subject, to determine the appropriate interpupillary distance for a binocular OCT system.

With reference to FIG. 22, there is illustrated an OCT system 2208 for detecting the major causes of amblyopia: strabismus, anisometropia, isoametropia, and visual occlusion. In general, amblyopia can occur when the best-corrected visual acuity in one or both eyes is reduced but the decreased vision cannot be attributed to abnormalities in the structure of the eye or the posterior visual pathway. For example, a normal eye and an eye with one of the above-mentioned predisposing conditions (for example, strabismus, anisometropia, isoametropia, and visual occlusion, and the like) can project two images to the brain, and there can likely be discrepancies between the two images and/or both images can be substantially unfocused. In response to the two images, a child's brain can likely adapt because the brains of children are more neuroplastic, and in some situations, the brain will respond by suppressing the image from one of the eyes. Such a response from the brain can interfere and/or interrupt the brain's normal development, resulting in amblyopia. Accordingly, amblyopia is generally a disorder of the visual system that can be characterized by poor and/or indistinct vision in an eye that is otherwise physically normal. Generally, amblyopia can be caused by strabismus, anisometropia or isoametropia, and/or occlusion of one or both eyes. Strabismus is a condition in which the eyes are misaligned (horizontal, vertical, torsional, or any combination of the foregoing). Anisometropia is a condition in which the eyes have unequal refractive power or optical power or dioptric power. Dioptric power can be generally defined as the combined power of the cornea and eye lens, and more specifically, it is the inverse of focal length. In general, dioptric power can be expressed in three-component form of sphere, cylinder, and axis. Isoametropia is a condition in which both eyes have substantially equal refractive power (or refractive errors within a threshold range) but have abnormal refractive errors. Occlusion is a condition in which light is blocked from reaching the retina, and such blockage can be caused by the ocular media becoming opaque, for example, with cataracts or corneal scarring. Detection of amblyopia in early childhood can increase the chances of successful treatment. Failure to detect amblyopia until young adulthood usually results in irreversible vision loss. Accordingly, there is a need for an OCT system for detecting causes of amblyopia in children so early treatments can be implemented. Detection of these predisposing disorders in adults is also important since they may be acquired during adulthood and may reflect underlying neurologic or other systemic diseases.

In reference to FIG. 22, there is illustrated a high-level flow diagram depicting an example of using an interpupillary distance measurement device 2204 on a patient/subject (for example, an infant or an adult) to determine the approximate and appropriate interpupillary distance for the binoculars without subjective participation of the subject (such as, a child or uncooperative adult). The interpupillary distance measurement device 2204 and/or the OCT system 2208 can be used on children 2202 and/or adults and/or other mammals (also referred to herein as subjects and/or patients). In various embodiments, the interpupillary distance measurement device 2204 can be a separate device held up to the eyes and face of a subject. The interpupillary distance measurement device 2204 can be reusable, disposable, and/ or a one-time use device. The interpupillary distance measurement device 2204 can be separate from or attached to the OCT system 2208.

With reference to FIG. 22, the interpupillary distance measurement device 2204 can be configured to attach to the subject's/patient's 2202 face and/or be positioned over the subject's/patient's eyes. The interpupillary distance measurement device 2204 can comprise openings 2207, which can be configured to go over and/or be aligned with the eyes of the subject. In various embodiments, the openings 2207 can be smaller or larger depending on the size of the eyes or other features of the eyes (for example, iris, pupil, or the like). In various embodiments, interpupillary distance can be better estimated when the openings 2207 are sized to substantially match the eye (or iris, pupil, or the like) size of the subject. The interpupillary distance measurement device 2204 can be used by the subject/patient or a user assisting the subject/patient. In various embodiments, the interpupillary distance measurement device 2204 can be configured to comprise a row of holes/openings 2205 to be used as a horizontal adjustment mechanism and/or locking mechanism for the device having two pieces that slide with respect to each other depending on the interpupillary distance. The interpupillary distance measurement device 2204 can be manufactured from plastic, metal, cardboard, or other similar materials, and can be reusable and/or disposable. As the two pieces slide with respect to each other, the pieces can be snapped and/or locked into place along the row of holes/openings 2205. The interpupillary distance measurement device 2204 can also comprise flanges 2206 or other measurement guide, which can be configured to change in dimension or width based on the measured interpupillary distance. In various embodiments, the dimensions or width of the flange or other measurement guide can be used as width guides that can be positioned between the barrels of the binoculars on the OCT instrument. By closing the pair of oculars of the OCT system 2208 on the flanges 2206, or horizontally shifting the binoculars of the OCT system 2208 to conform to the size of the flanges 2206, the binoculars of the OCT system 2208 can be adjusted to conform to the interpupillary distance estimated using the interpupillary distance measurement device 2204. In various embodiments, the interpupillary distance measurement device 2204 can be fitted to the subject's/patient's eyes by horizontally sliding the interpupillary distance measurement device 2204 to fit over the eyes of the subject/patient 2202 or using preplaced holes in the device. Alternatively, the interpupillary distance measurement device 2204 can be connected (for example, electronically through a wire and/or wireless connection, and/or mechanically) to the OCT instrument to transfer the measured interpupillary distance to the OCT instrument.

As illustrated in FIG. 22, the interpupillary distance measurement device 2204 (which can help align the OCT imaging system with the optical axes of the two eyes, or match up the OCT imaging system with the pupils, irises, or the like) can generally be configured to determine the subject's interpupillary distance with minimal cooperation from the subject. The OCT system 2208 can then be adjusted to conform to the fitted interpupillary distance measurement device 2206. Alternatively, the fixation targets, such as simple or other shapes/objects (for example, houses, balls, animals, or the like) or movies may be projected into the eyes of the subject/patient to facilitate self-adjustment by the subject/patient. In another embodiment, manual adjustment of the interpupillary distance can be replaced with automated methods based on pupil tracking. In various embodiments, fast pairs of horizontal and vertical retinal B-scans could be used to center the system on the optical axis of the subject. When the system is correctly centered, the maximum lateral extent of both horizontal and vertical B-scans can be visualized. Decentration of the scanning light source beam in any direction can be detected as premature contact with the pupillary border (iris tissue) in one direction leading to truncation of the B-scan signal in that lateral direction. With the OCT system 2208 properly fitted and/or correlated to the user's eyes, the OCT system 2208 can obtain OCT measurements, as described herein, to produce OCT images 2210, 2212. The OCT system 2208 can be configured to analyze the OCT images 2210, 2212 to perform risk assessments, generate diagnoses, and/or detect the causes of amblyopia and/or adult strabismus, anisometropia, visual occlusion, and the like.

Figure 23:
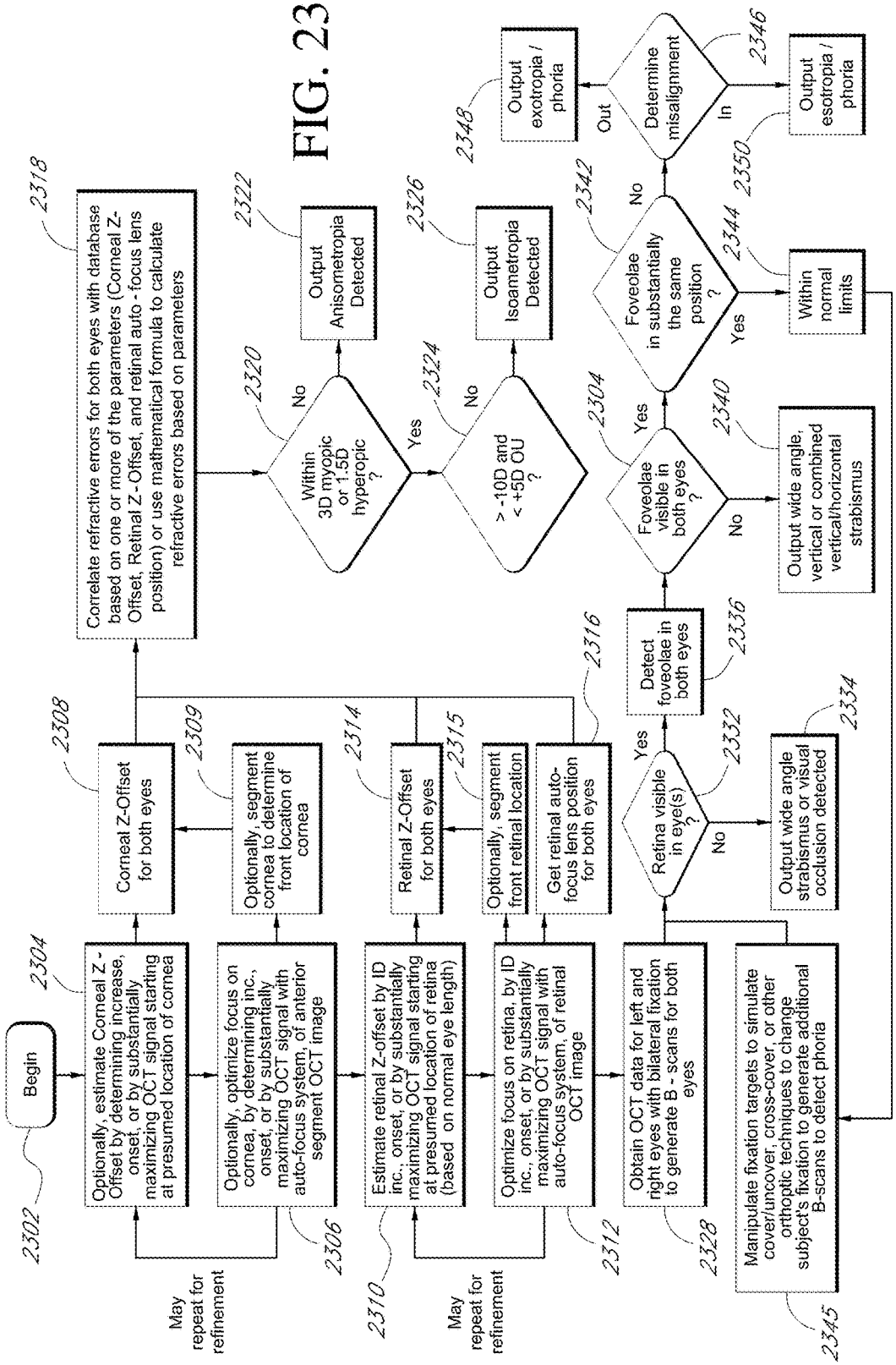

In reference to FIG. 23, there is illustrated a high-level process flow diagram depicting an example process for using an OCT system to detect the causes of amblyopia and/or adult strabismus, anisometropia, visual occlusion, or the like. As indicated, the process flow can begin at block 2302 where at block 2304 the computer system 104 can be configured to optionally obtain the OCT data (sequentially or simultaneously) for the left and/or the right eye(s) and use the OCT data to estimate at block 2304 the approximate axial (z) position of the anterior segment and/or the corneal Z-offset by determining an increase or an initial onset of OCT signal, or by substantially maximizing OCT signal strength. The corneal Z-offset can be the location of the cornea with respect to the OCT instrument. The corneal Z-offset in combination with the retinal Z-offset can be used to determine the axial length of the eye. In various embodiments, the computer system 104 can be configured to use corneal Z-offset in combination with other parameters to determine and/or calculate the refractive error of the eyes. In various embodiments, the computer system 104 starts at a presumed location of the cornea based on the position of the binocular eyecups, and adjusts the Z-offset stage within the main body 106 to determine which Z-offset position produces the substantially strongest OCT signal strength (or increased or elevated OCT signal strength). This substantially strongest OCT signal strength correlates with a Z-offset position that places the cornea and anterior segment of the eye within the imaging portion of the OCT system. In various embodiments, the approximate corneal Z-offset for both eyes is stored and/or outputted at block 2308.

In FIG. 23, at block 2306, the computer system 104 can be configured to optionally refine the estimated corneal Z-offset and/or generate a more accurate corneal Z-offset by using an auto-focus system (as described herein) to focus on the anterior segment of the OCT image, thereby allowing for more accurate corneal Z-offset measurements. Alternatively, the computer system 104 at block 2309 can be configured to optionally segment the cornea (outline the anterior and posterior boundaries of the corneal tissue) using imaging techniques, such as, for example, edge detection methodologies or the like, to determine the substantially front location of the cornea. In various embodiments, the front location or substantially front location of the cornea will generally produce and/or result in an OCT signal with substantially maximum signal strength. In determining the location that produces the substantially maximum OCT signal, the computer system 104 can determine the corneal Z-offset, which can be outputted and/or stored at block 2308.

In reference to FIG. 23, the computer system 104 can be configured to obtain the OCT data (sequentially or simultaneously) for the left and/or the right eye(s) and/or foveolae, and use the OCT data to estimate at block 2310 a retinal Z-offset by determining the location of the average maximum OCT signal in all A-scans of a B-scan or by substantially maximizing OCT signal strength. The retinal Z-offset can be the location of the retina with respect to the OCT instrument. The retinal Z-offset can be used in combination with other parameters to determine and/or calculate the refractive error of the eyes. In various embodiments, the computer system 104 starts at a presumed location of the retina, and adjusts the Z-offset stage within the main body 106 to determine which Z-offset position produces the substantially strongest OCT signal strength, or increased or elevated OCT signal strength. This substantially strongest OCT signal strength (or increased or elevated OCT signal strength) correlates with a Z-offset position that places the retina of the eye within the imaging portion of the OCT system. In various embodiments, the estimated retinal Z-offset for both eyes is stored and/or outputted at block 2314.

In FIG. 23, at block 2312, the computer system 104 can be configured to optionally refine the estimated retinal Z-offset and/or generate a more accurate retinal Z-offset by using an auto-focus system (as described herein) to focus on the posterior segment of the OCT image, thereby allowing for more accurate retinal Z-offset measurements. Alternatively, the computer system 104 at block 2315 can be configured to optionally segment the retina using imaging techniques, such as edge detection methodologies, to determine the anterior or posterior border of the retina. In various embodiments, the front, center or back of the retina will generally produce and/or result in an OCT signal with substantially maximum signal strength, or increased or elevated OCT signal strength. In determining the location that produces the substantially maximum OCT signal (or increased or elevated OCT signal strength), the computer system 104 can determine the retinal Z-offset, which can be outputted and/or stored at block 2314. In determining the auto-focus lens position that produces the most focused image of the retina, the computer system 104 can be configured to store and/or output the position of the auto-focus lens for both eyes at block 2316. The auto-focus lens position that produces the most focused retinal image and therefore the substantially strongest OCT signal strength (or increased or elevated OCT signal strength) can be used in combination with other parameters to determine and/or calculate the refractive error of the eyes.

With reference to FIG. 23, the computer system 104 can be configured to analyze the corneal Z-offset and the retinal Z-offset to determine whether the axial length of the eye is greater or less than a threshold value. In various embodiments, the threshold value is determined by clinical studies and/or observations, for example, if the axial length of the eye is greater than 25 mm then the subject/patient is at a higher risk for various eye diseases or abnormalities. In various embodiments, refractive error can be determined by the OCT system. For example, the position of the auto-focus lens system can be adjusted so that the probe beam and/or the fixation target is focused on the retina. The position of the auto-focus lens system (see, for example, block 2316) can then be used to determine the vergence of light exiting the main body lens system. Using the distance to the cornea from block 2308, the vergence of the light as it hits the cornea can also be calculated. Since the OCT instrument is optimally focused on the retina, this means that the vergence of light entering the cornea is essentially counteracted completely to focus on the retina. This vergence of light entering the cornea is therefore a very close approximation to the spherical equivalent refractive error in the eye. In another embodiment, lenses to correct astigmatic errors, such as Stokes' lenses, could be introduced into the instrument's light path. In various embodiments, the Stokes' lenses can be in the non-collimated light path. In certain embodiments, the Stokes' lenses can be in the autofocus lens system in the oculars. The positions/orientation of these lenses that produces a substantially increased, peaked, or most the focused retinal image could be determined, for example, after determination of the general spherical error correction as described previously.

With reference to FIG. 23, at block 2318, the computer system 104 can be configured to analyze the OCT data to determine the dioptric power and/or the refractive error of the left and/or right eyes. In various embodiments, the computer system 104 can be configured to determine the dioptric power and/or the refractive error of each eye by correlating measured OCT data parameters to a database and/or lookup table. In various embodiments, the database and/or lookup table can be generated based on clinical studies and/or observations, wherein data parameters, such as corneal Z-offset, retinal Z-offset, and auto-focus lens position, are correlated to observed refractive errors. Using the database and/or the lookup table, the computer system 104 can be configured to correlate/lookup the retinal Z-offset value of an eye (block 2314) and the position of the auto-focus lens for the eye (block 2316) (both as independent variables) to determine and/or derive a refractive error for the eye. In various embodiments, the computer system 104 can be configured to correlate/lookup the corneal Z-offset value of an eye (block 2308), the retinal Z-offset value of the eye (block 2314), and the position of the auto-focus lens for the eye (block 2316) (as independent variables) to determine and/or derive a refractive error for the eye. Other combinations of variables can be possible.

In reference to FIG. 23, the computer system 104 can be configured to analyze the refractive error and/or dioptric power (or the difference between refractive errors) to detect causes of amblyopia, such as, for example, anisometropia, isoametropia, and/or the like. In various embodiments, the computer system 104 can be configured to determine whether the refractive error and/or the dioptric power (or the difference between refractive errors) is above and/or below a threshold value, or within a threshold range. For example, at block 2320, the computer system 104 can be configured to determine the difference between the refractive errors for the left and right eyes, and determine whether the difference is within 3 diopters in the myopic range, or within 1.5 diopters in the hyperopic range. In various embodiments, the computer system 104 can be configured to determine whether the difference between the refractive errors for the left and right eyes is within a 1-5 diopters in the myopic range, or within 1-3 diopters in the hyperopic range. If the difference between the refractive errors for the left and right eyes is not within the threshold range (for example, 3 diopters myopic, or within 1.5 diopters hyperopic), then the computer system 104 can be configured to output at block 2322 that anisometropia has been detected.

With reference to FIG. 23, the computer system 104 can be configured to perform another threshold analysis, if the difference between the refractive errors for the left and right eyes is within the threshold range (for example, 3 diopters myopic, or within 1.5 diopters hyperopic). For example, if the difference between the refractive errors for the left and right eyes is within the threshold range (for example, 3 diopters myopic, or within 1.5 diopters hyperopic), then at block 2324 the computer system can be configured to determine whether the refractive errors for both eyes (also known as OU or Oculus Utro) is greater than −10 diopters in the myopic range and less than +5 diopters in the hyperopic range. If the refractive errors for both eyes are not between −10 diopters and +5 diopters, then the computer system 104 can be configured to output at block 2326 that isoametropia has been detected. If the refractive errors for both eyes are between −10 diopters and +5 diopters, then the computer system 104 can be configured to output that neither anisometropia nor isoametropia has been detected, or in various embodiments, the computer system 104 can be configured to output nothing and/or perform other analyses.

In FIG. 23, at block 2328, the computer system 104 can be configured to perform other analyses. For example, the computer system 104 can be configured to obtain OCT data for the left and right eyes while two fixation targets are presented to the subject/patient to generate B-scans for both eyes. Since these fixation targets are near to the subject's eye, various techniques could be used to simulate bilateral distance fixation including lateral displacement of the fixation targets with respect to each other. Additionally, in some embodiments, collimation of the light between display 215*a* and mirror 230*a* or 215*b* and 230*b* can be used to simulate the target at a large distance (for example, infinity). Optics such as a computer-controlled lens system or collimator, for example, between display 215*a* and mirror 230*a* or 215*b* and 230*b* can be employed to produce the collimation, if the distance from the display 215*a*, 215*b* is not already sufficiently large. Similarly, near targets could be simulated by diverging the light between 215*a* and 230*a* or 215*b* and 230*b* to simulate targets at reading distance (typically 14 inches) or computer distance (typically 30 inches). This could be accomplished with a computer-controlled lens system inserted into the light path, for example, between display 215*a* and mirror 230*a* or 215*b* and 230*b*. Different target distances could also be simulated. Measurements of refractive error as the distance to the fixation targets is changed could be used to estimate the accommodative amplitude. For example, if no refractive error is found to exist when the fixation target is at infinity (collimated light), then measurement of the appearance of a small amount of refractive error when the fixation targets are at 20 cm would imply that the eye has an accommodative amplitude of 5D. Measurement of the full range of accommodative amplitude of an eye could be advantageous for determining the true refractive error in an eye that is accommodating on a near fixation target. Other techniques could be used to relax accommodation during the process of measuring refractive error, especially in children, including adding additional plus lenses, such as +2.0D, +3.0D or +2.5D, into the light path to 'fog' the fixation target or removing the fixation target from view prior to autorefraction to determine the range of refractive errors in a user's eye.

At block 2332, the computer system 104 can be configured to determine whether the retina is visible. In various embodiments, the computer system can be configured to review the histogram of the B-scan images, and if the pixel distribution in the histogram is below a threshold value, than the computer system 104 can be configured to determine that the retina is not visible. In another embodiment, the OCT signal strength can be used to determine if the retina is visible within the OCT imaging area. For example, if the signal-to-noise ratio of the OCT B-scan falls below a pre-determined and/or dynamically determined threshold value, such as, for example, 10, 20, or 30 (which can be unitless threshold values because each is a ratio of signals in similar units), for existence of the retina within the image, the computer system 104 can be configured to determine that the retina is not visible. One skilled in the art will appreciate that there are other ways to determine whether the retina is visible. If the retina is not visible, then the computer system 104 can be configured to output at block 2334 that wide angle strabismus and/or visual occlusion may have been detected. If the retina is detected, then the computer system 104 can be configured to detect the foveolae in both eyes at block 2336.

As illustrated in FIG. 23, the computer system 104 at block 2336 can be configured to analyze the OCT data to determine the location of the foveal depressions in the eyes. The fovea can be located in several ways. For example, the inner retina can be detected using edge detection methods and fit to a polynomial curve. The substantially maximal foveal depression could be detected as the substantially maximal edge-detected deviation downward from this polynomial curve. In various embodiments, the degree of confidence in foveal detection can be measured as the deviation from the polynomial curve. Alternatively, since the outer nuclear layer comprises nearly 100% of the retina thickness in the foveola, the fovea can be detected by looking for the area with nearly 100% outer nuclear layer composition to the retina. Other ways in which the fovea can be detected are to look for focally increased thickness of the photoreceptor outer segments, substantially maximal separation of thick nerve fiber layer and location of a bright foveal reflex at the vitreoretinal interface. Still other approaches are possible. If the computer system 104 cannot locate the foveolae at block 2338, then the computer system 104 can be configured to output at block 2340 that the wide angle vertical or a combination of vertical and horizontal strabismus has been detected. If the computer system 104 can locate the foveal depressions at block 2338, then the computer system 104 can be configured to determine at block 2342 whether the foveolae are in substantially the same position.

With reference to FIG. 23, the computer system can be configured to determine at block 2346 the type and/or degree of misalignment in the foveolae, if the foveolae are not in substantially the same position. If the eye deviation is outward (as determined, for example, by analyzing whether the location of the fovea is located within a threshold range), then the computer system 104 can be configured to output at block 2348 that exotropia has been detected. If the eye deviation is inward (as determined, for example, by analyzing whether the location of the fovea is located within a threshold range), then the computer system 104 can be configured to output at block 2350 that esotropia has been detected. If the locations of the foveal depressions are substantially the same, for example within a pre-determined threshold distance, then the computer system 104 can be configured to output at block 2344 that the eyes are within normal limits.

Figure 27:
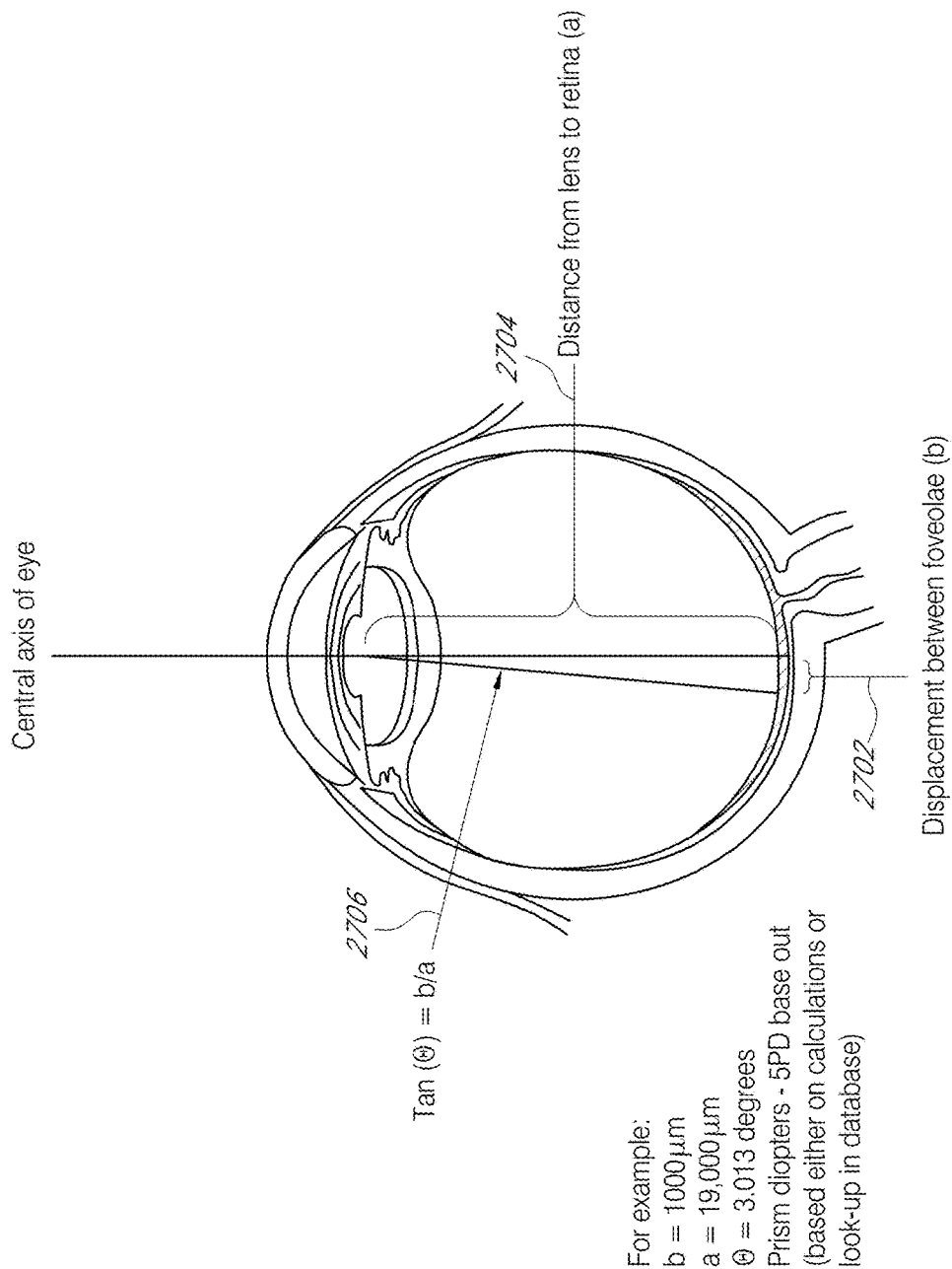
FIG. 27 is a high-level eye anatomy diagram, illustrating an embodiment for estimating angular misalignment between two eyes.

With reference to FIG. 27, the computer system 104 can also be configured to use optical coherence tomography measurement data and/or other data to estimate the angular misalignment, such as, for example, horizontal misalignment, vertical misalignment, or combinations thereof, between the two eyes to guide prism measurements for glasses prescriptions. For example, if one foveola in a first eye is found to be centered in a first B-scan while the other foveola in a second eye as observed in a second B-scan is found to be displaced by a distance 2702 of 1000 microns, this forms the short leg of the right triangle describing the angular difference between the two eyes. The long leg of the right triangle describing the angular difference between the two eyes can be determined with an axial measurement, such as, for example, the distance 2704 between the cornea and retina or the lens and the retina as described herein. By using the Pythagorean theorum, the angular displacement between the two eyes can be estimated from the arc tangent of the ratio of these two distances. This value could be translated into prism diopters required to center the foveola in the second eye as detected in the second B-scan. Alternatively, instead of calculating the explicit angular difference, the foveolae distance 2702 and/or the cornea-retina distance, and/or the lens-retina distance, and/or the iris-retina distance, and/or the axial length of the eye, and/or other distance measurements, could be looked up in a database comprising known deviations/measurement and prism lens prescriptions (for example, a database generated based on clinical data and/or studies) to determine the prism measurements that correspond to these measurements. The process of estimating angular misalignment can be used for determining or analyzing tropias (for example, manifest misalignments of the eyes) and/or phorias (for example, latent misalignments of the eyes that can be elicited by breaking and/or disrupting fixation) as both are described herein.

As illustrated in FIG. 23, the computer system 104 can be configured at block 2344 to perform additional testing on the eyes. For example, the computer system 104 can be configured to perform an additional test to detect phoria at block 2345 if the eyes are found to be substantially aligned. Generally, phoria is a latent deviation in the eye, and such latent deviation in the eyes can occur when fusion is broken. In subjects/patients with phoria, the natural resting position of the eye muscle system is not generally straight (ortho). Accordingly, when the subject/patient is visually active (for example, awake and/or alert), then the power of fusion keeps the eyes straight but if fusion is broken by dissimilar visual targets, then the eyes can generally move to their natural resting positions (for example, eso, exo, or hyper). To detect phoria, the computer system 104 can be configured to project and hide various images in or shown to the eyes of the subject, thereby simulating cover/uncover, cross-over, and/or other commonly-used orthoptic techniques to disrupt or augment fixation. For example, at block 2345, the computer system 104 can be configured to manipulate the fixation targets to simulate cover/uncover, cross-cover, or other orthoptic techniques to change fixation to generate additional B-scans to detect phoria. The computer system 104 can be configured to analyze the additional B-scan images by processing the image as discussed above in connection with blocks 2332 to 2350 (for example, to identify misalignment in visual axis based on location on the location of the foveolae, etc.).

Figure 24:
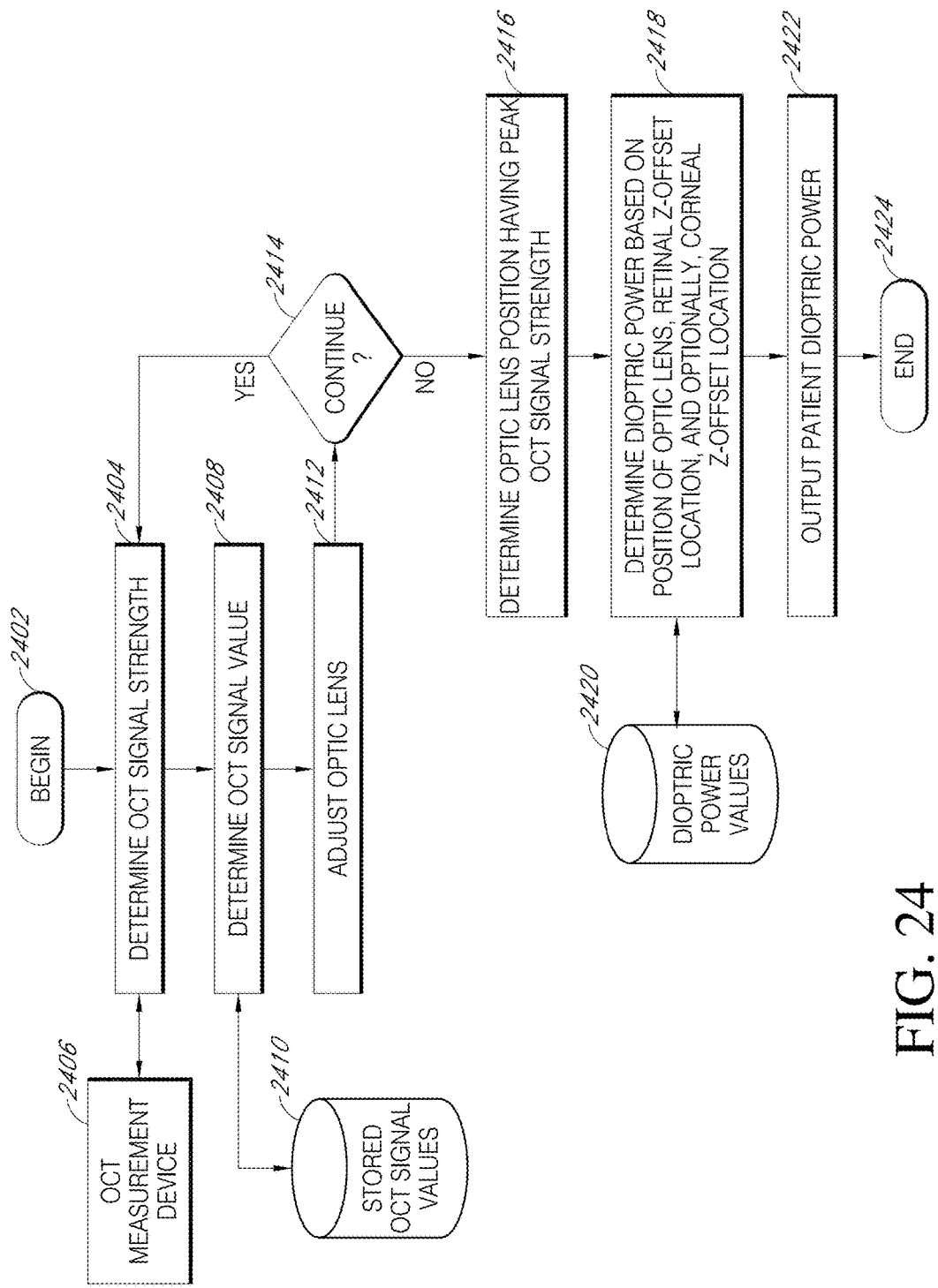
FIG. 24 is a high-level flow diagram illustrating an example process for using an OCT system to estimate the corrected or uncorrected refractive error of an eye in diopters.

In FIG. 24, there is illustrated a high-level flow diagram of an example process for using an OCT system to determine dioptric power based on the OCT signal detected. In various embodiments, the process illustrated in FIG. 24 is the process employed to perform the actions in blocks 2312 and 2318 of FIG. 23. As indicated, the process flow can begin at block 2402 where at block 2404 the computer system 104 can be configured to obtain the OCT data for the left and/or the right eye(s) from the OCT measurement device 2406 to determine the OCT signal strength at the corresponding optic lens location (for example, adjustable optics 210 in FIG. 3A and the like). At block 2408, the computer system can be configured to store the OCT signal strength and the corresponding optic lens location in the OCT signal values memory 2410. At block 2412, the computer system 104 can be configured to adjust the location of the optic lens in the OCT measurement device 2406 that affects the convergence or divergence or focus of the laser beam into the subject's eyes. At block 2414, the computer system 104 can be configured to determine whether the optic lens can be adjusted to a different position. If the lens can be adjusted to a different position, then the computer system 104 can be configured repeat the process at blocks 2404, 2408, and 2412. If the lens cannot be adjusted to a different position, then at block 2416 the computer system 104 can be configured to determine the optic lens position providing the peak OCT signal strength by analyzing the OCT signal values stored in the OCT signal values memory 2410. One skilled in the art will recognize there are other ways to configure the computer system 104 to determine the optic lens position providing the peak OCT signal strength, such as identifying a optic lens position producing a signal strength that is higher than the signal strength produced by the two adjacent optic lens positions. At block 2418, the computer system 104 can be configured to determine dioptric power based on the position of optic lens, retinal Z-offset location, and optionally, the corneal Z-offset location. At block 2422, the computer system 104 can be configured to output the dioptric power of the subject's/patient's eyes.

Figure 25:
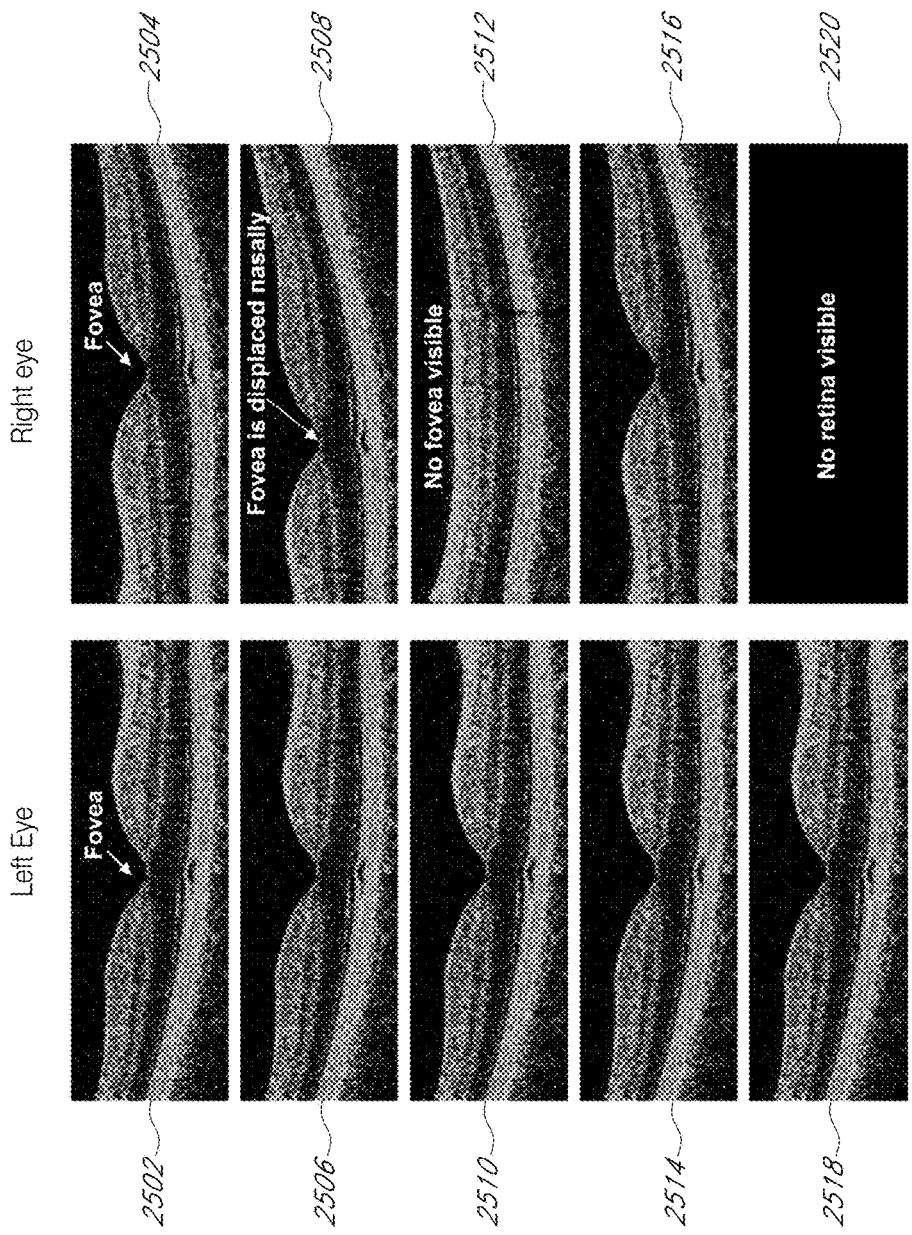

With reference to FIG. 25, there are example illustrations of OCT system-generated images of retinas. Elements 2502 and 2504 represent examples of OCT system-generated images illustrating normal binocular fixation as exhibited by the two central foveolae positioned substantially in the same position, thereby indicating no strabismus or misalignment of the eyes. In this example, the OCT system can be configured to measure the focus of each eye, and has determined that the dioptric power of each eye is substantially the same. The OCT system can be configured to output that the causes of amblyopia (or strabismus, anisometropia, and visual occlusion) have not been detected in this example. Elements 2506 and 2508 represent examples of OCT system-generated images illustrating strabismus or misalignment of the eyes, and in this case, there is horizontal deviation. As illustrated in element 2508, the fovea is displaced nasally, therefore the foveolae are not substantially in the same position. In this example, the OCT system can be configured to output that strabismus has been detected, and specifically, exotropia (deviation of the eyes outward, as opposed to esotropia, which is inward deviation of the eyes).

In reference to FIG. 25, elements 2510 and 2512 represent examples of OCT system-generated images illustrating strabismus, wherein the fovea is visible in the oculus sinister (also known as OS, meaning left eye) but the fovea is not visible in the oculus dexter (also known as OD, meaning right eye). Here the strabismus could be caused by many combinations of deviations such as a vertical and/or horizontal deviation. In this example, the OCT system can be configured to output that strabismus of an unknown type has been detected. Elements 2514 and 2516 represent examples of OCT system-generated images illustrating anisometropia wherein both foveolae are visible but each eye has a different or substantially different dioptric power or focus. Here, the OCT can be configured to determine the focus, optical power, refractive power, or dioptric power, for example, the OS dioptric power can be −1.5 whereas the OD dioptric power can be −7.0. In this example, the OCT system can be configured to output that no strabismus has been detected but that anisometropia is present based on the process described above in blocks 2318-2326. Elements 2518 and 2520 represent examples of OCT system-generated images illustrating visual occlusion from obstruction or wide-angle strabismus, wherein the fovea is visible in the oculus sinister (also known as OS, meaning left eye) but the retina is not visible in the oculus dexter (also known as OD, meaning right eye). In this example, the OCT system can be configured to output that there could be an occlusion of the right eye (for example, cataract) or there could be large angle deviation in the right eye.

Figure 26:
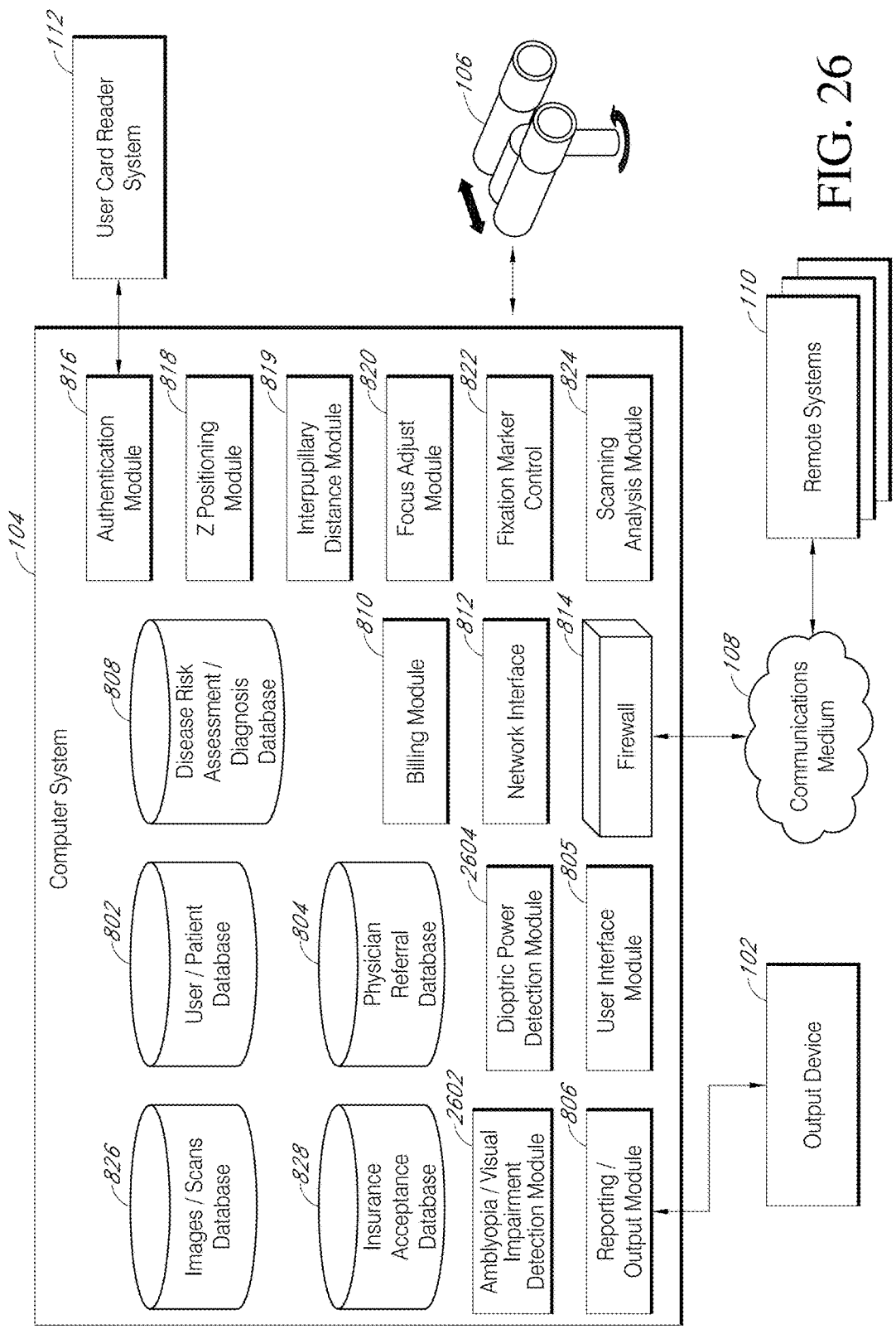
FIG. 26 is a high-level block diagram schematically illustrating components in one embodiment of the computer system for the optical coherence tomography systems described herein.

In reference to FIG. 26, there is illustrated a high-level block diagram schematically depicting components in one embodiment of the computer system for the optical coherence tomography systems described herein. As described above in connection with FIG. 13, the methods, systems, and devices described herein can be implemented using the computing system 1300 illustrated in FIG. 13. The module 2602 for detecting the causes of amblyopia, such as, for example, strabismus, anisometropia, and visual occlusion, (the AVI detection module 2602) can be connected to or in communication with any of the devices, components, controls, modules, interfaces, and/or databases in or connected to the computer system 104. For example, the AVI detection module 2602 can be configured to connect to or communicate with the main body device 106 to obtain OCT data measured from the subject's/patient's eye. In various embodiments, the AVI detection module 2602 can be configured to connect to or communicate with the authentication module 816 to determine the subject/patient identification and/or associate an evaluation output with a subject/patient.

In connection with FIG. 26, the AVI detection module 2602 can also be configured to connect to or communicate with the focus adjust module 820 to obtain the dioptric power of the subject's/patient's eye(s). Alternatively, the AVI detection module 2602 can be configured to obtain the dioptric power of the subject's/patient's eye(s) by connecting to or communicating with the dioptric power detection module 2604, which can be configured to communicate with or connect to the focus adjust module 820. In various embodiments, the AVI detection module 2602 can also be configured to connect to or communicate with the scanning analysis module 824 to obtain OCT data/information measured from the subject's/patient's eye(s) using the main body 106. The AVI detection module 2602 and/or the dioptric power detection module 2604 can be configured to connect to or communicate with the reporting/output module 806 in order to output an evaluation data and/or report and/or dioptric power measurements of the subject's eyes on the output device 102. In various embodiments, the AVI detection module 2602 can be configured to connect to or communicate with the network interface 812 and/or the firewall 814 in order to output, send, and/or communicate over communications medium 108 an evaluation data and/or report to the billing/insurance reporting and payment systems 1201 and/or the remote systems 110. The AVI detection module 2602 can be configured to connect to or communicate with the user interface module 805 to output an evaluation data and/or report to the user/patient.

With reference to FIG. 26, the AVI detection module 2602 can be configured to connect to or communicate with the images/scans database 826, and/or the user/patient database 802, and/or the disease risk assessment/diagnosis database 808. In various embodiments, the AVI detection module 2602 can be configured to connect to or communicate with the images/scans database 826 and/or the user/patient database 802 to determine and/or obtain prior or previous evaluation data and/or report(s). The AVI detection module 2602 can be configured to compare and/or analyze the prior/previous evaluation data/report(s) with the current evaluation data/report to determine/detect any changes and/or trends in a subject's/patient's condition. In various embodiments, the AVI detection module 2602 can be configured to output to the user a report comparing current data with prior/previous data. If the difference between the current and prior/previous data exceeds a threshold level, such as 0.25D, 0.5D, 0.75D or 1.0D, and/or is outside a threshold range such as 1.0D then the AVI detection module 2602 can be configured to output/recommend to the user/patient that the patient consult with a doctor, and can output physician referrals near the patient. In various embodiments, the threshold level and/or threshold range data can be stored in the disease risk assessment/diagnosis database 808. In various embodiments, the AVI detection module 2602 can be configured to output/recommend to the user/patient that the patient consult with a doctor, and can output physician referrals near the patient, based on comparing and/or analyzing threshold data values (for example, derived from clinical observations and/or studies) with the current evaluation data/report to determine/detect any differences and/or changes and/or trends in a subject's/patient's eyes. The foregoing can occur when the patient has no historical and/or prior/previous amblyopia evaluation data/report(s). In various embodiments, the AVI detection module 2602 can be configured to output/recommend to the user/patient that the patient consult with a doctor, and can output physician referrals near the patient, based on comparing and/or analyzing the subject's current corrective lenses (such data can be provided by the subject or stored in a database and/or the user's identification card and/or measured by the OCT instrument) with the current evaluation data/report to determine/detect any differences and/or changes and/or trends in a subject's/patient's eyes.

Ophthalmic Testing Center

Generally, the OCT-based ophthalmic testing center system described herein can be configured to perform a multitude of functional and/or structural ophthalmic testing procedures, including, but not limited to: corneal topography, corneal pachymetry, autorefraction, biomicroscopy, visual acuity testing, photostress recovery time testing, color vision assessments, gonioscopy, central vision distortion testing, reading speed assessments, contrast sensitivity testing, fixation stability testing, static perimetry, kinetic perimetry, confrontation visual fields, stereoacuity testing, suppression testing, ocular alignment testing, extraocular motility testing, exophthalmometry, pupillometry, and optical coherence tomography imaging. Distillation of the multitude of ophthalmic functions into a single instrument can allow for cost-savings and for improved clinical efficiency.

In various embodiments, the OCT-based ophthalmic testing center system can be configured such that practitioners and/or physicians can order ophthalmic tests a la carte to be performed. In various embodiments, the user, subject, and/or patient can order and/or perform the ophthalmic tests. In various embodiments, the OCT-based ophthalmic testing center system can be configured to order ophthalmic tests to be performed on a user, subject, and/or patient. For example, a glaucoma specialist can choose to order visual acuity testing, extraocular motility testing, corneal pachymetry, gonioscopy, biomicroscopy, pupillometry, and perimetry tests for new patient visits. In various embodiments, the OCT-based ophthalmic testing center system can be configured to administer a computerized medical history questionnaire, wherein the OCT-based ophthalmic testing center system can be configured to ask the subject, user, and/or patent a series of general questions and then follow-up with additional questions using logical branches to expand on the patient's responses.

In various embodiments, the OCT-based ophthalmic testing center system can comprise software, hardware, and/or logic configured to enable the OCT-based ophthalmic testing center system to conduct and/or dynamically conduct ophthalmic tests on users, subjects, and/or patients in response to historical data, user input/response data, other test data, and/or the like, or to test subjects, users, and patients in an intelligent matter. If, for example, the OCT-based ophthalmic testing center system detects an abnormal condition during a particular test, the OCT-based ophthalmic testing center system can be configured to automatically follow up with other ophthalmic tests that can provide useful information for making a diagnosis, differential diagnosis, screening, risk assessment, and/or other outputs. In various embodiments, the OCT-based ophthalmic testing center system can be configured to automatically perform ophthalmic tests based on a patient's personal and/or family medical history and/or other data stored in a database associated with the OCT-based ophthalmic testing center system.

Figure 28:
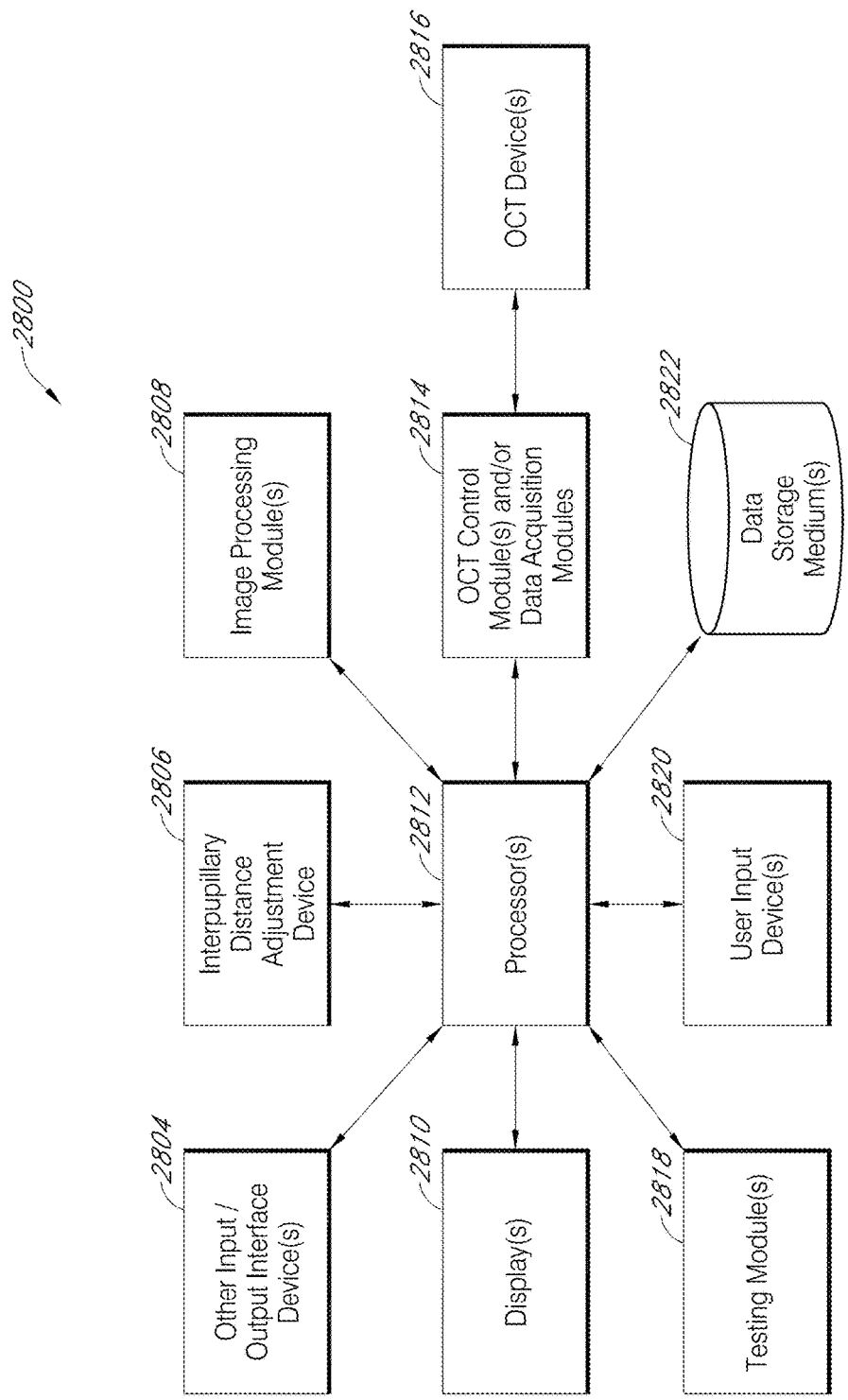
FIG. 28 is a block diagram schematically illustrating one embodiment of an optical coherence tomography-based ophthalmic testing center system described herein.

FIG. 28 illustrates various embodiments of an OCT-based ophthalmic testing center system 2800. The OCT-based ophthalmic testing center system 2800 comprises a processing unit and/or processor 2812, one or more display devices 2810, and OCT devices 2816. In various embodiments, the OCT-based ophthalmic testing center 2800 further comprises other input/output interface devices 2804, an interpupillary distance adjustment device 2806, image processing modules 2808, OCT control modules and/or OCT data acquisition modules 2814, testing modules 2818, user input devices 2820, and/or data storage mediums 2822. In certain embodiments, the processor or processing unit 2812 comprises a general or a special purpose microprocessor and/or digital signal processors, and/or the like. The processing unit 2812 can comprise an application-specific integrated circuit (ASIC).

In reference to FIG. 28, the display 2810 can be a liquid crystal display (LCD) and/or other display device (for example, as disclosed herein) configured to present images, dots, stimuli, or the like to a user, subject, and/or patient. The display 2810 can be located externally or internally to a main body, or housing, of the OCT-based ophthalmic testing center system 2800. For example, the display devices 2810 can comprise display screens located within ocular eyepieces of the OCT-based ophthalmic testing center system 2800. The display devices 2810 may comprise one or more light sources, for example, in an emissive display like an array of matrix LEDs. Other types of displays, for example, LCD, FFD or FLCOS displays can be used. The display devices 2810 can display targets of varying shapes and configurations, including a cross, a bar, alphanumeric characters, and/or one or more dots. The display devices 2810 can also be configured to display images (stationary or in motion) or movies.

With reference to FIG. 28, the OCT devices 2816 can comprise any of the components and/or features of the OCT systems described herein (for example, the various embodiments illustrated in FIGS. 1, 3A, 5, 8, 12, 21, and/or 26). In various embodiments, the OCT devices 2816 can comprise, as described herein, an eyepiece for receiving one or both eyes of a user, a light source that outputs light that is directed through the eyepiece into the user's eyes, and an interferometer configured to produce optical interference using light reflected from the user's eyes, and an optical detector disposed so as to detect optical interference in the user's eyes. In various embodiments, the OCT devices 2816 can comprise a time domain optical coherence tomography system, a frequency domain optical coherence tomography system and/or a swept-source optical coherence tomography system. In various embodiments, the OCT devices 2816 can comprise a Z-offset adjustment stage and/or optics as described herein.

In various embodiments, the OCT-based ophthalmic testing center system 2800 can be configured to perform manual and/or electronic interpupillary distance adjustment using the interpupillary distance adjustment device 2806, as described in more detail herein. The processing unit 2812 can communicate with memory to retrieve and/or store data and/or program instructions for software and/or hardware. The memory can include random access memory ("RAM") for temporary storage of information, a read only memory ("ROM") for permanent storage of information, and a mass storage device, such as a hard drive, diskette, or optical media storage device. In certain embodiments, the processing unit 2812 is coupled to a network, such as a LAN, WAN, or the Internet, for example, via a wired, wireless, or combination of wired and wireless, communication link as described herein. The network communicates with various computing devices and/or other remote electronic devices via wired or wireless communication links.

In various embodiments, the processing unit 2812 is located within the OCT device 2816 itself. In other embodiments, the processing unit 2812 is housed within a computing device and/or computer system that is electrically coupled to and/or in communication with the OCT device 2816. In certain embodiments, the processing unit 2812 is connected to the OCT device 2816 via a wired or wireless network connection or other communications medium. The processing unit 2812 can be configured to communicate with other remote processing or computing devices via the wired or wireless network connection or other communications medium. The remote processing or computing devices can include display devices (for example, a display and/or a monitor), output devices (for example, a printer or the like), a communications device (for example, a cell phone, PDA, or the like), and/or storage devices (for example, a storage database).

The user input devices 2820 can include tactile input devices, for example buttons, keyboards or switches, and/or audio input devices, for example, a microphone. In various embodiments, the tactile and/or audio input devices can be located on or within the main body of the OCT-based ophthalmic testing center system 2800, and/or can be connected to or in communication with the OCT-based ophthalmic testing center system 2800. In various embodiments, in which eye tracking is desirable, OCT image data can also be used as a functional input by the OCT-based ophthalmic testing center system 2800. In various embodiments in which the OCT-based ophthalmic testing center is operated or controlled by someone other than the testing subject, an external input device such as a keyboard, mouse, microphone or touch-screen display device, can be used to control testing, algorithms, processes, protocols and outputs within the OCT-based ophthalmic testing center.

In various embodiments, the processing unit 2812 receives user input (for example, button presses, verbal responses) through the user input devices 2820. In various embodiments, the processing unit 2812 controls and transmits output (for example, audio instructions, textual instructions, light flashes, images, animated content) to the display devices 2810 and/or other output interface devices 2804. In various embodiments, the OCT-based ophthalmic testing center system 2800 can be configured to enforce standards of care determined by a physician. For example, the OCT-based ophthalmic testing center system 2800 can be configured to be programmed to perform ophthalmic tests according to a standard of care schedule prescribed by a physician. In certain embodiments, the OCT-based ophthalmic testing center system 2800 can be programmed to operate only after a specified time interval has elapsed since the last ophthalmic test. Alternatively, the OCT-based ophthalmic testing center system 2800 can be configured to notify the patient via an alarm, email, or other reminder mechanism when it is time to perform another ophthalmic test. In various embodiments, the OCT-based ophthalmic testing center system 2800 comprises a binocular system (two optical paths). In various embodiments, the OCT-based ophthalmic testing center system 2800 comprises a monocular system (one optical path). The binocular system advantageously can perform diagnostic functions that are either not possible or more difficult to accomplish using a monocular system. The OCT-based ophthalmic testing center system 2800 can be configured to be fully automated and self-administered by a patient user, as opposed to a technician, photographer or physician. In certain embodiments, patients can take OCT-based ophthalmic testing center system 2800 to their homes and transmit electronic images of their self-administered examination to their physician via a communications network for an evaluation, risk assessment and/or diagnosis.

In certain embodiments, the OCT-based ophthalmic testing center system 2800 can be configured to output the results of and/or data from the various ophthalmic tests to one or more output interface devices 2804 in physical or remote communication with the OCT-based ophthalmic testing center system 2800. The output interface device 2804 may include a monitor screen/display, in which output results are displayed. The output interface device 2804 may include a printer, which prints output results. In certain embodiments, the OCT-based ophthalmic testing center system 2800 comprises a speaker or headphone jack for providing verbal instructions and feedback to the user during testing. The output interface devices 2804 may be configured to store data on a portable medium, for example, a compact disc or USB drive or magnetic card reader, or a portable data storage device. In various embodiments, the OCT-based ophthalmic testing center system 2800 can be configured to transmit output, such as a risk assessment, screening, diagnosis, differential diagnosis, and/or report of data, through a network or communications medium. Remote output interface devices can include, for example, a server, a laptop computer, a cell phone, a smartphone, a personal digital assistant, a kiosk, or an audio player. For example, the results of self-administered ophthalmic tests can be outputted directly to a user, ancillary clinic staff, an ordering physician and/or a clinical trials organization in a hardcopy (for example, printed card or paper) or electronic format (for example, on a display, via email, text messaged, or in a magnetic strip); stored in local memory on a USB drive or on an attached computer; transmitted to a central database; or transmitted directly to the ordering or related physician. In various embodiments, the OCT-based ophthalmic testing center system 2800 comprises a user interface module configured to operate in conjunction with input and output devices to allow interaction with a user, as described in detail above. In another embodiment in which the OCT-based ophthalmic testing center system 2800 is operated or controlled by someone other than the testing subject, output devices, such as display devices or remote devices as described above, can be used to provide information during testing that can enable a person other than the testing subject to control the tests, algorithms, processes, protocols and outputs during and after a testing session.

Figure 29:
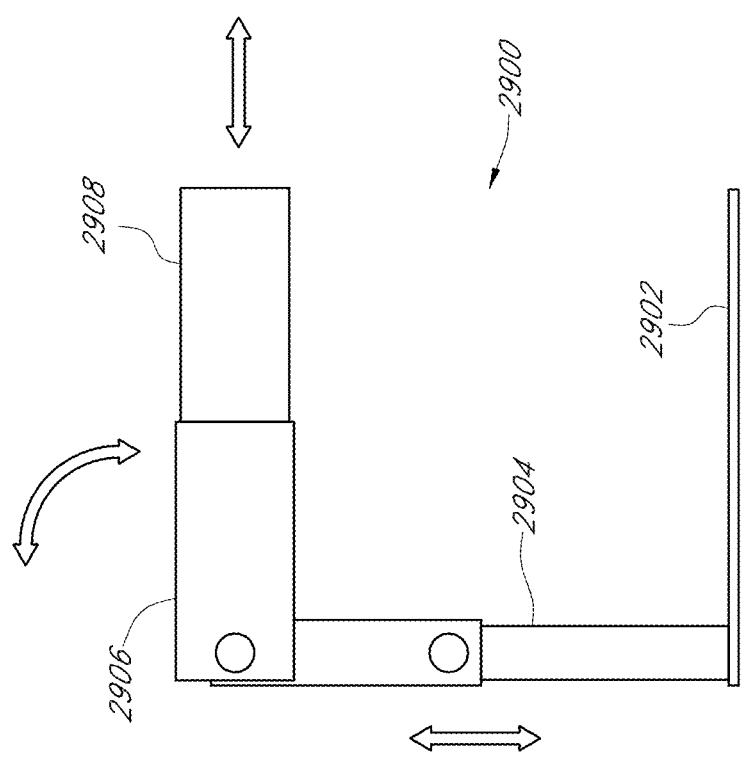
FIG. 29 is a diagram illustrating a generic freestanding embodiment of an OCT device.

In various embodiments, the OCT-based ophthalmic testing center system 2800 comprises a tabletop device as illustrated, for example, in FIG. 29. For example, the tabletop device can comprise a free-standing structure similar to a microscope. In various embodiments, the OCT-based ophthalmic testing center system 2800 can comprise a device to be worn by the user like glasses (with earstems supporting the device on top of each ear), like goggles (with a strap that extends around the back of the head), or like a hat (with a support extending over the top of the head). Other designs and alternatives of structures to interface with the user's eyes are possible without departing from the spirit and/or scope of the disclosure.

FIG. 29 illustrates a diagram of one embodiment of a free-standing tabletop device 2900. The tabletop device 2900 includes a base 2902, a support 2904, a holder 2906, and one or more oculars 2908. As illustrated, the base 2902 can be configured to rest on a substantially level surface. The support 2904 can be configured to extend substantially vertically from the base 2902. In certain embodiments, the support 2904 can be configured to be height-adjustable. The holder 2906 is configured to retain the oculars 2908. The holder 2906 can be configured to be rotated with respect to the longitudinal axis of the support to allow for a comfortable viewing angle. The holder 2906 can include a locking mechanism configured to fix the rotation of the holder 2906 once the holder 2906 has been rotated to the desired position. The holder 2906 can be configured to slidably retain the oculars 2908. For example, the oculars 2908 can be configured to slide in and out of the holder 2906. The holder 2906 and/or the oculars 2908 can include suitable mechanisms for locking the oculars 2908 with respect to the holder 2906 after proper adjustment. For example, the locking mechanisms can include a détente, a clamp or the like.

Figure 30B:
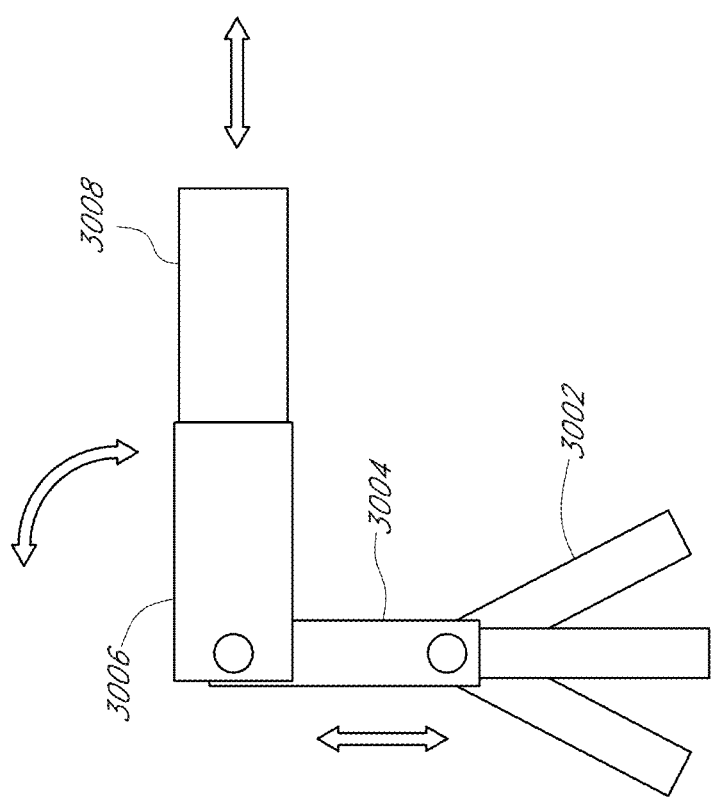
Figure 30C:
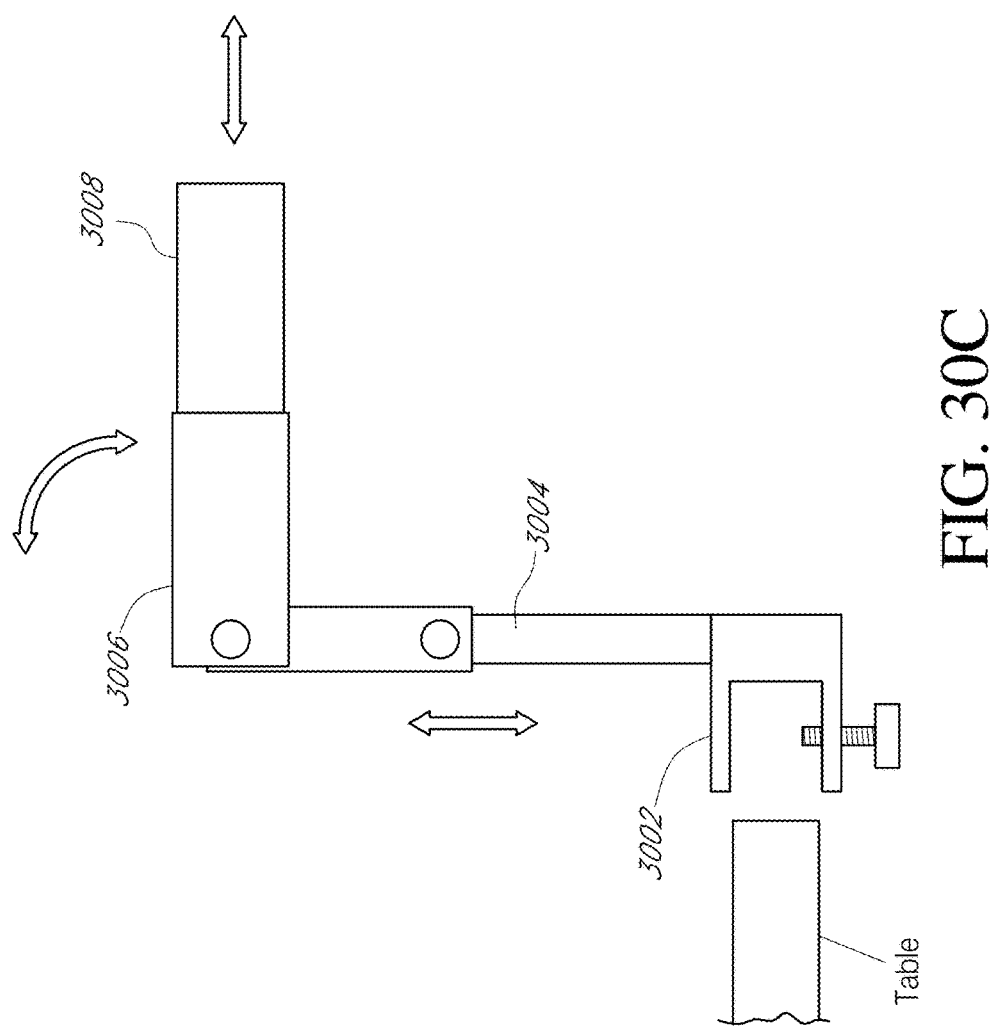
Figure 30D:
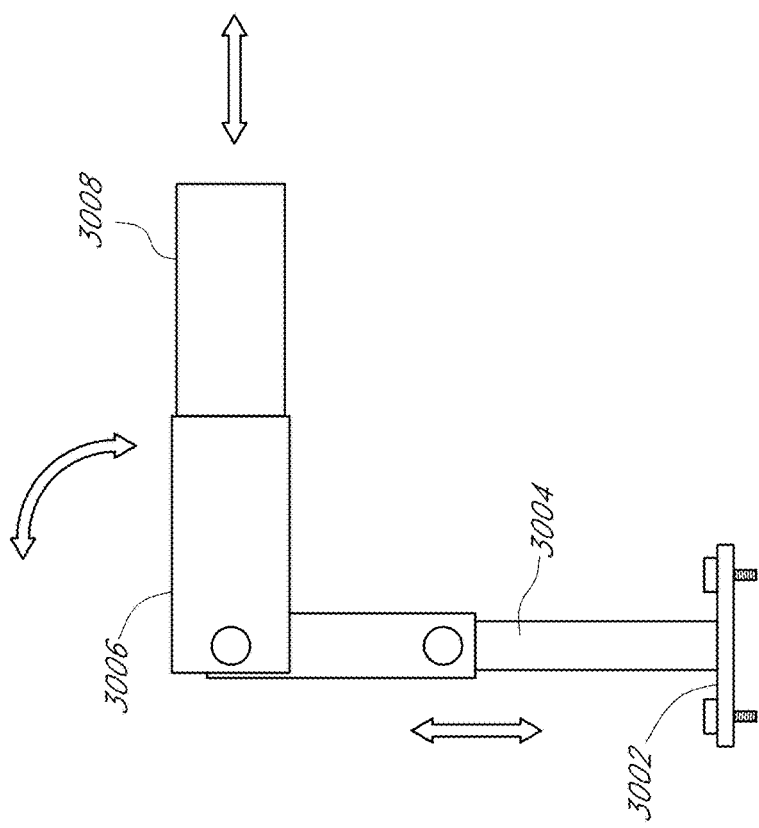
Figure 30E:
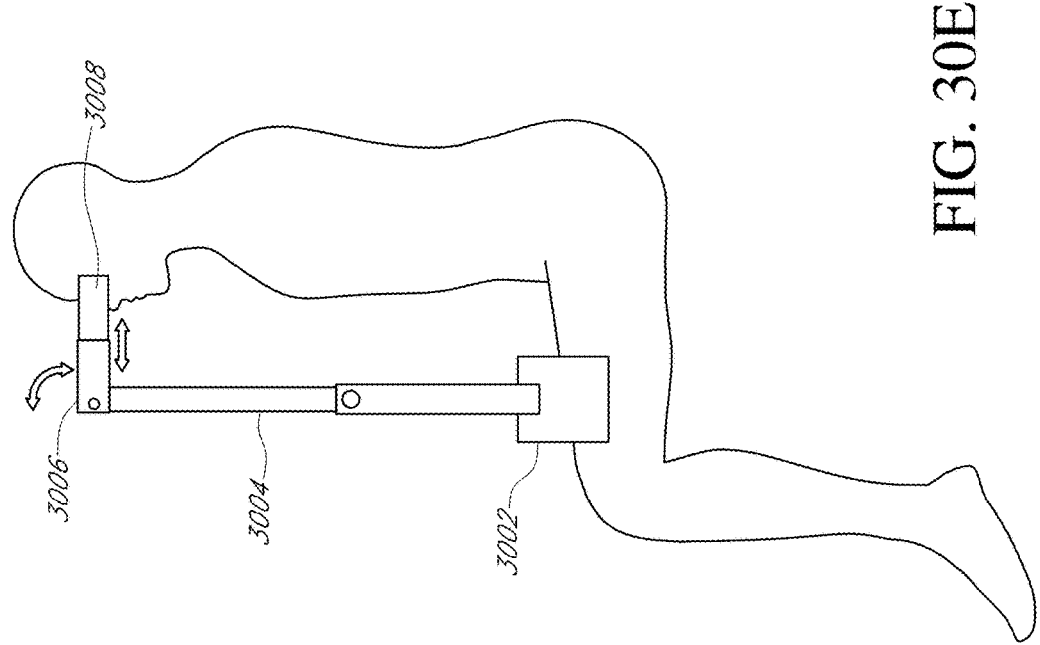

FIGS. 30A-30E illustrate various alternative embodiments of base designs. In certain embodiments, the base 3002 comprises a flat base formed of a solid and/or heavy material configured to prevent the OCT device from tipping over (as illustrated, for example, in FIG. 30A). In various embodiments, the base 3002 comprises a tripod mechanism (as illustrated, for example, in FIG. 30B). In various embodiments, the base 3002 comprises a clamp-on or screw-mounted base configured to secure the OCT device to a tabletop or other substantially level surface (as illustrated in FIGS. 30C and 30D, respectively). In yet other embodiments, the base 3002 comprises an ergonomic lap support (as illustrated in FIG. 30E). It should be appreciated that other base designs are possible without departing from the spirit and/or scope of the disclosure.

In various alternative embodiments, the oculars 2908 comprise one ocular or two oculars. In various embodiments, the ocular interface of the oculars 2908, which is the portion of the OCT device that contacts the user's eyes, comprises an integrated, one-piece design (as illustrated by the ocular interface 3008 of the handheld device in FIG. 30F) as opposed to a dual-barrel design. The corresponding disposable hygienic barrier can also comprise a one-piece design to conform with the ocular and/or forehead interface. In certain embodiments, the oculars 2908 comprise an auto-focus lens system guided by software modules or routines that automatically adjust for refractive errors to provide clearer OCT images.

Figure 30F:
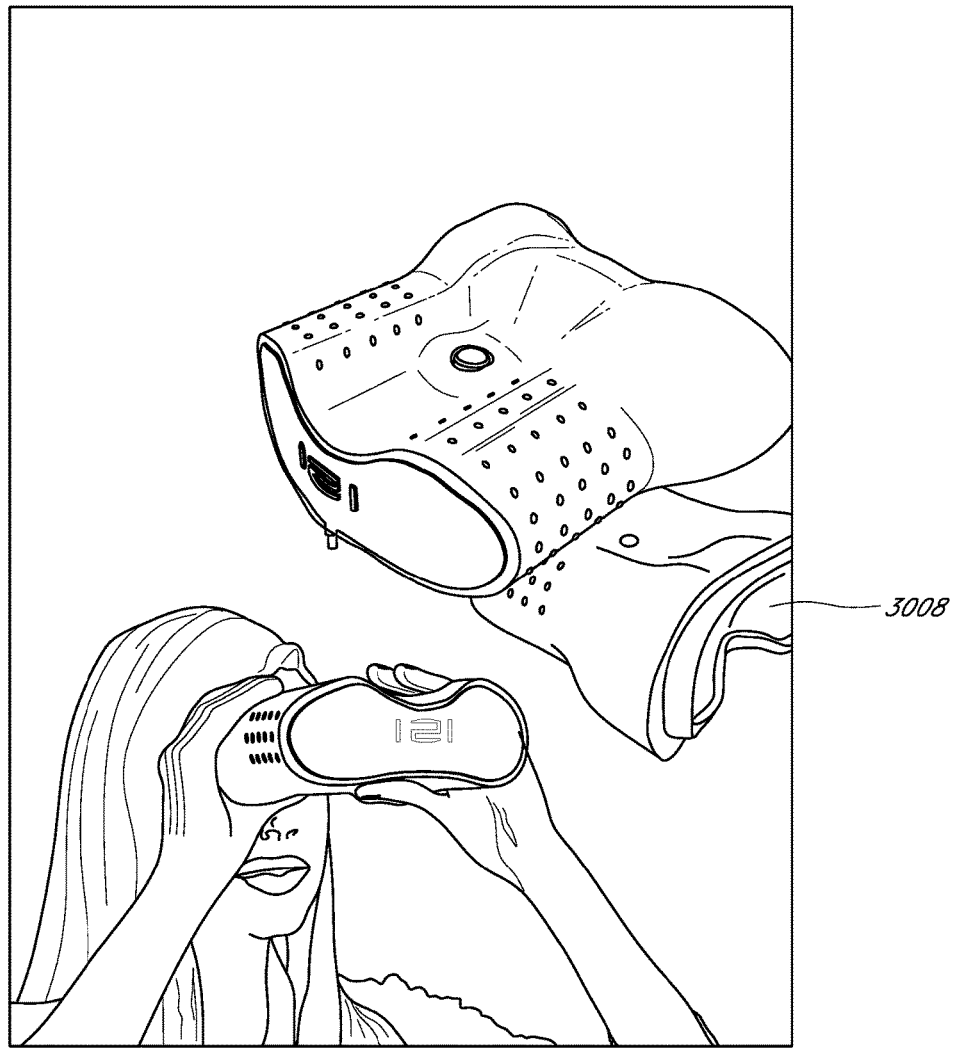

In certain embodiments, the OCT-based ophthalmic testing center system 2800 comprises a handheld device to be supported by the user (similar to a pair of binoculars or a telescope) as illustrated, for example, in FIG. 30F. In certain embodiments, the internal interpupillary distance adjustment device 2806 of the OCT-based ophthalmic testing center system 2800 can comprise an internal interpupillary distance adjustment device that can be controlled using an electric motor that can be adjusted, for example, by centering B-scans through the pupils, as described herein. In various embodiments, the internal interpupillary distance adjustment device 2806 can be mechanically controlled and/or adjusted using an interpupillary distance adjustment device as described herein. In various embodiments, interpupillary adjustments can be conducted in two axes, horizontal and vertical. In various embodiments, the handheld device can be configured to connect to a hygienic barrier that can either be a one-piece or two ocular pieces as described herein.

As discussed herein, in various embodiments, the OCT-based ophthalmic testing center system can be configured to detect, measure a wide variety of other conditions and/or characteristics of the eye, including but not limited to the location of the fovea and/or other fixation targets/structures in the eye, extraocular motility, response of the pupils to stimuli, depth of the eye, visual acuity, contrast sensitivity, peripheral vision, topographies, thicknesses, distances, angles, distortions perceived by the eye, reading speed, stereoacuity, degrees of foveal suppression, and refractive errors. The OCT-based ophthalmic testing center system can be configured to perform a variety of ophthalmic tests (for example, via execution of the testing modules 2818) including but not limited to refractive error testing, gaze detection, for example, through iris plane analysis and/or pupillary analysis, foveal/fixation verification, foveal/fixation location, biomicroscopy, extraocular motility testing, pupillometry testing, exophthalmometry testing, visual acuity testing, contrast sensitivity testing, fixation stability testing, perimetry testing (confrontation and/or kinetic and/or static), corneal topography testing, corneal pachymetry testing, visual gonioscopy testing, color vision testing, distortion testing, reading speed testing, stereoacuity testing, foveal suppression testing, and any other ophthalmic testing.

Refractive Error Correction

In addition to improving the image produced by the OCT system, the autofocus system can also provide an output corresponding to refractive error correction for the eye. Determining the refractive error of the eye using the OCT signal has been described above. Accordingly, the OCT-based ophthalmic testing center system can output refractive error, for example, sphere and astigmatism, or may output that one or more conditions, such as anisometropia or largely unequal refractive errors that can lead to amblyopia, has been detected.

As described above, in various embodiments, the Z-offset used to identify the distance to the cornea and/or the retina can be employed in conjunction with the auto-focus to arrive at an appropriate value of spherical power correction for the patient or user.

Figure 31:
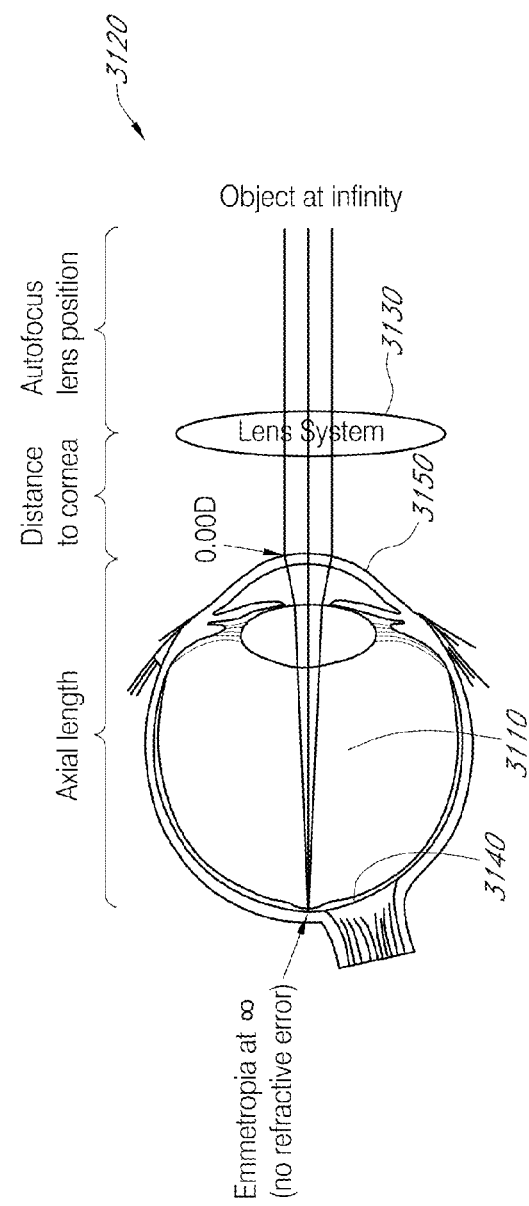
FIG. 31 illustrates an embodiment of performing refractive error correction on an emmetropic eye.

FIG. 31 shows an example of an emmetropic eye 3110. The object is at infinity. In various embodiments, the probe beam and the object are both substantially collimated. FIG. 31 shows a lens system 3130, which may include the autofocus optics, set to provide a collimated beam incident on the eye 3110. Because the eye 3110 is emmetropic, the collimated beam is focused on the retina 3140. As described above, the OCT signal can be monitored (while adjusting the Z-offset) to set the OCT instrument 3120 to probe the retina 3140 (for example, by identifying a peak in the scan of the OCT signal, which is increased for the reflective tissue of the retina 3140). Additionally, the auto-focus can be adjusted to demonstrate that the OCT signal is peaked when the auto-focus is configured to provide a collimated beam. Since the lens system 3130 is adjusted to provide a collimated beam, and the beam is determined to be focused on the retina 3140, the eye 3110 is identified as emmetropic. In another embodiment, lenses to correct for astigmatic error can be inserted into the lens system 3130 and adjusted to increase or maximize the OCT signal from the retina 3140 in the same manner as auto-focus.

Another framework for determining the refractive correction, which is 0 D in this case, is to consider the vergence of the beam upon entry into the eye 3110. As described above, when the beam of light is focused on the retina 3140, the vergence of the light entering the cornea 3150 is essentially counteracted to focus on the retina 3140. This vergence of light entering the cornea 3150 is therefore a very close approximation to the spherical equivalent refractive error in the eye 3110. Accordingly, if the lens system 3130 is adjusted so that the probe beam (and/or the fixation target) is focused on the retina 3140, vergence of light entering the cornea 3150 can be determined to obtain an estimate of the refractive correction of the eye 3110. In the example shown in FIG. 32B, the lens system 3230 is adjusted so that the beam is collimated. The vergence of the light entering the cornea 3250 is 0 D (regardless of the distance to the cornea 3250). Accordingly, the refractive error is 0 D.

FIGS. 32A and 32B show an example of a myopic eye 3210. In this example, the object is generally at infinity. In FIG. 32A, the lens system 3230 is set such that the beam incident on the cornea 3250 is collimated. However, because the eye 3210 is myopic, the beam comes to a focus prior to reaching the retina 3240.

FIG. 32B shows the lens system 3230, which may include the autofocus optics, adjusted to focus the beam (target and probe beam) on the retina 3240. As described above, the OCT signal can be monitored (while adjusting Z offset) to set the OCT instrument 3220 to probe the retina 3240 (for example, by identifying a peak in the scan of the OCT signal, which is increased for the reflective tissue of the retina 3240). Additionally, the auto-focus can be adjusted such that the OCT signal is peaked, wherein presumably the OCT instrument 3220 is optimally focused on the retina 3240. In another embodiment, lenses to correct for astigmatic error can be inserted into the lens system 3230 and adjusted to substantially increase, identify a peak in, or substantially maximize the OCT signal from the retina 3240 in the same manner as auto-focus.

With the auto-focus set such that the OCT instrument 3220 is focused on the retina 3240, the auto-focus setting can be used to determine the refractive error in the eye 3210 causing the eye 3210 to be myopic.

For example, the position of the auto-focus lens system 3230 can be used to determine the vergence of light exiting the lens system 3230. Additionally, the distance to the cornea 3250 can be obtained using a separate measurement, for example, the Z-offset to the cornea or refined anterior corneal boundary as discussed previously. The distance to the cornea 3250 can be employed to determine the vergence of the light as it hits the cornea 3250.

As described above, when the OCT instrument 3220 is optimally focused on the retina 3240, the vergence of light entering the cornea 3250 is essentially counteracted to focus on the retina 3240. This vergence of light entering the cornea 3250 is therefore a very close approximation to the spherical equivalent refractive error in the eye 3210. Accordingly, if the lens system 3230 is adjusted so that the probe beam (and/or the fixation target) is focused on the retina 3240, the vergence of light entering the cornea 3250 can be determined to obtain an estimate of the refractive correction of the eye 3210. In the example shown in FIG. 32B, the vergence of the beam upon entry into the eye 3210, determined based on the vergence of light exiting the lens system 3230 and the distance of the lens system 3230 to the cornea 3250, is −4.0 D. Accordingly, the refractive error of the eye 3210 can be estimated to be about −4.0 D.

Figure 33A:
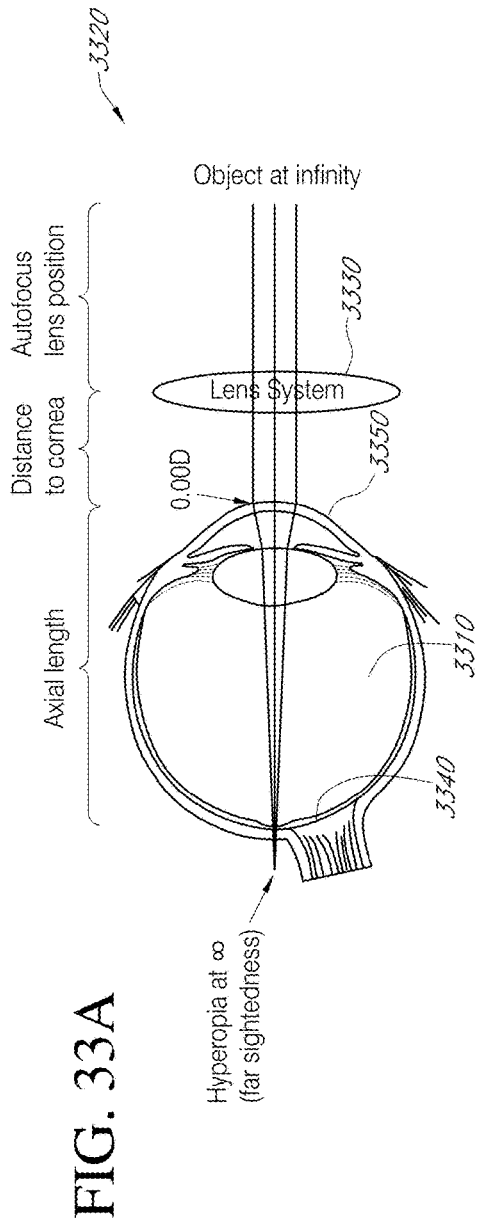
FIGS. 33A and 33B illustrate an embodiment of performing refractive error correction on a hyperopic eye.
Figure 33B:
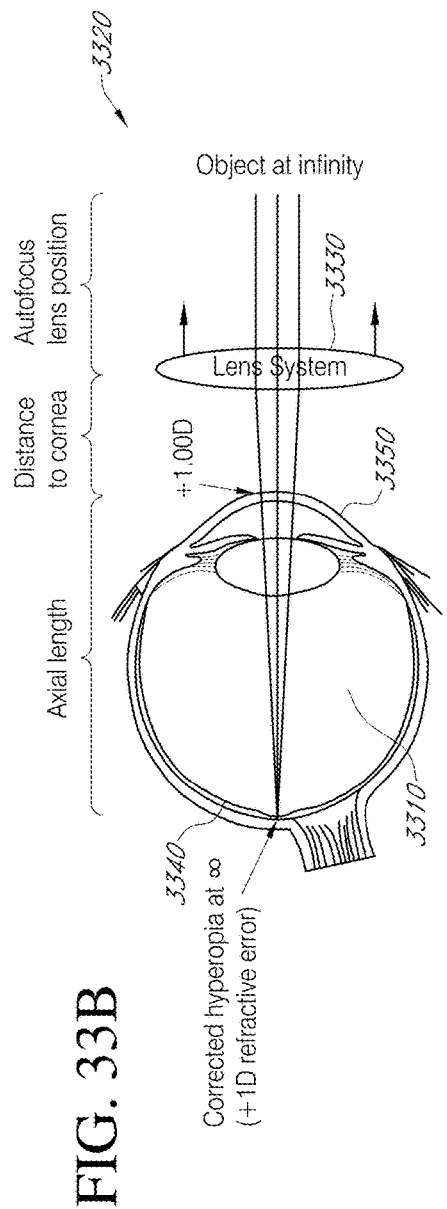

FIGS. 33A and 33B show an example of a hyperopic eye 3310. In this example, the object is generally at infinity. In FIG. 33A, the lens system 3330 is set such that the beam incident on the cornea 3350 is collimated. However, because the eye 3310 is hyperopic, the beam comes to a focus beyond the retina 3340.

FIG. 33B shows the lens system 3330, which may include the auto-focus optics and/or optics to correct for astigmatic error, adjusted to focus the beam (target and probe beam) on the retina 3340. As described above, the OCT signal can be monitored (while adjusting the z-offset) to set the OCT instrument 3320 to probe the retina 3340 (for example, by identifying a peak in the scan the OCT signal, which is increased for the reflective tissue of the retina 3340). Additionally, the auto-focus can be adjusted such that the OCT signal is peaked, wherein presumably the OCT instrument 3320 is optimally focused on the retina 3340. In another embodiment, lenses to correct for astigmatic error can be inserted into the lens system 3330 and adjusted to substantially increase, identify a peak in, or substantially maximize the OCT signal from the retina 3340 in the same manner as auto-focus.

With the auto-focus set such that the OCT instrument 3320 is focused on the retina 3340, the auto-focus setting can be used to determine the refractive error in the eye 3310 causing the eye 3310 to be hyperopic.

For example, the position of the auto-focus lens system 3330 can be used to determine the vergence of light exiting the lens system 3330. Additionally, the distance to the cornea 3350 can be obtained using in a separate measurement, for example, the Z-offset to the cornea or refined anterior corneal boundary as discussed previously. The distance to the cornea 3350 can be employed to determine the vergence of the light as it hits the cornea 3350.

As described above, when the OCT instrument 3320 is optimally focused on the retina 3340, the vergence of light entering the cornea 3350 is essentially counteracted to focus on the retina 3340. This vergence of light entering the cornea 3350 is therefore a very close approximation to the spherical equivalent refractive error in the eye 3310. Accordingly, if the lens system 3330 is adjusted so that the probe beam (and/or the fixation target) is focused on the retina 3340, the vergence of light entering the cornea 3350 can be determined to obtain an estimate of the refractive correction of the eye 3310. In the example shown in FIG. 33B, the vergence at the eye 3310, determined based on the vergence of beam exiting the lens system 3330 and the distance of the lens system 3330 to the cornea 3350, is +1.0 D. Accordingly, the refractive error can be estimated to be about +1.0 D.

The object need not be set at infinity. In certain embodiments, for example, measurements of refractive error as the distance to the fixation targets is changed can be used to estimate the accommodative amplitude. For example, if no refractive error is found to exist when the fixation target is at infinity (collimated light), while refractive error is measured when the fixation targets are closer to the eye 3310, the eye 3310 may be accommodative.

Figure 34A:
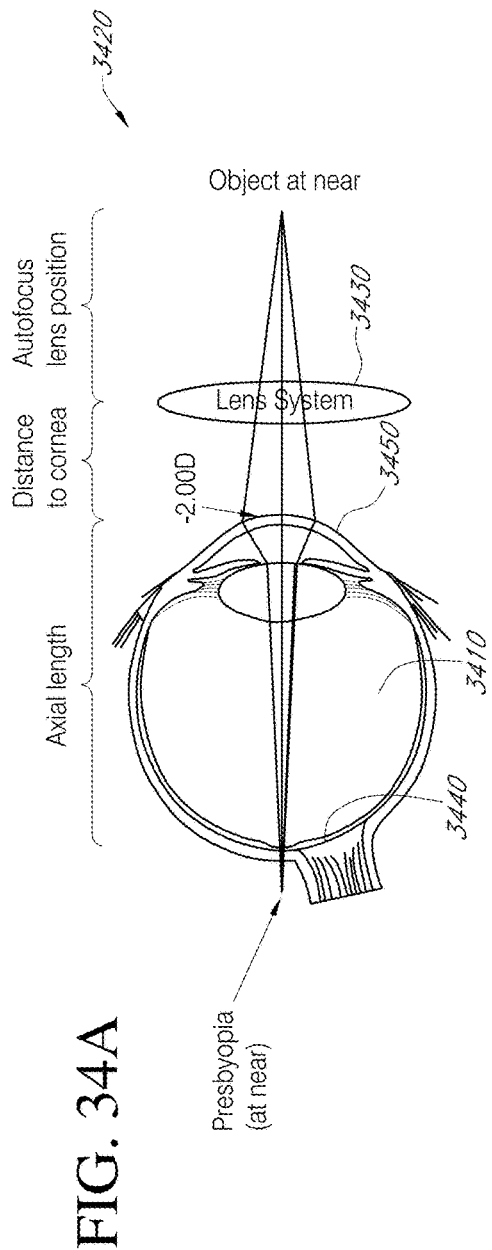
FIGS. 34A and 34B illustrate an embodiment of performing refractive error correction on a presbyopic eye.
Figure 34B:
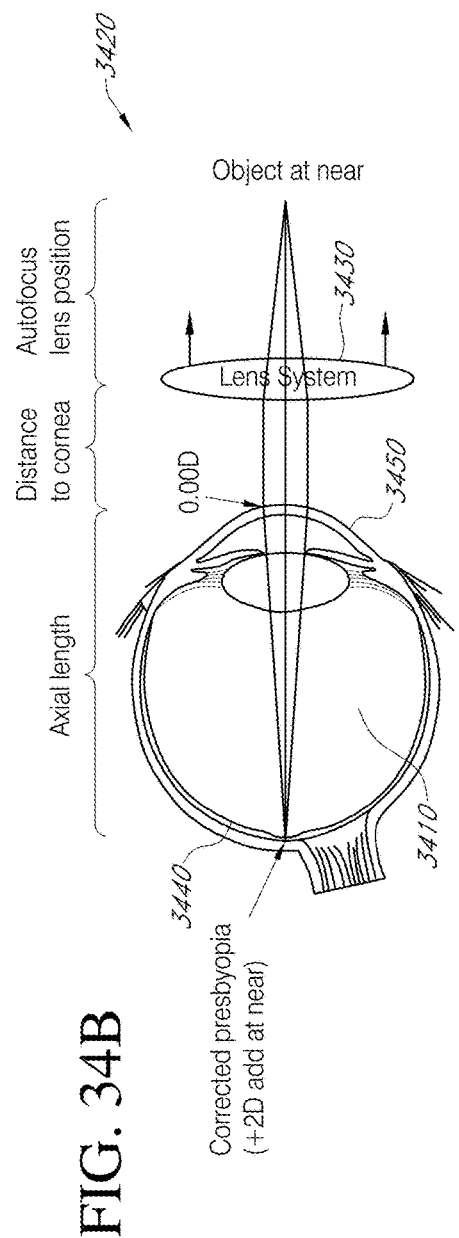

FIGS. 34A and 34B show an example of an eye 3410 with presbyopia. In this example, the object is generally near. As described above, optics may be included between the fixation target display and the eye 3410 to diverge the beam and simulate a target that is near. In some embodiments, the target distance is set to be at 3414 inches (typical reading distance) or possibly 3430 inches (typical computer viewing distance), although other values are possible. Accordingly, in FIG. 34A, the lens system 3430 is adjusted such that target that is near. However, because the eye 3410 exhibits presbyopia, the beam comes to a focus beyond the retina 3440.

FIG. 34B shows the lens system 3430, which may include the auto-focus optics and/or optics to correct for astigmatic error, adjusted to focus the beam on the retina 3440. As described above, the OCT signal can be monitored (while adjusting the z-offset) to set the OCT instrument 3420 to probe the retina 3440 (for example, by identifying a peak in the scan the OCT signal, which is increased for the reflective tissue of the retina 3440). Additionally, the auto-focus can be adjusted such that the OCT signal is peaked, wherein presumably the OCT instrument 3420 is optimally focused on the retina 3440. The adjustment of the autofocus optics that produces a focused beam on the retina 3440 provides an estimate of the add power used to correct the presbyopia for a near fixation target at the distance specified above, and thus the refractive error of the eye 3410.

Variations in the methodology for measuring refractive error as well as the system design are possible.

Eye Tracking

In certain embodiments, the OCT-based ophthalmic testing center system can be configured to perform automatic eye tracking or fixation monitoring during the various structural and functional ophthalmic tests. In various embodiments, the OCT-based ophthalmic testing center system can be configured to perform eye tracking based on OCT imaging modalities, non-OCT imaging modalities, or a combination of both. In general, OCT images contain information about unique eye structures, for example, the pupil, anterior segment, fovea, retinal vessels or optic nerve, and high speed OCT scans can be used to track the movement of the pupil, anterior segment, fovea, retinal vessels and/or other fundus structures to be used as an objective functional input when no verbal or manual input is desired. The functional input can be used to provide confidence to a physician that the data and/or results of the ophthalmic tests are accurate and reliable. In certain embodiments, eye tracking is performed in real-time during testing. Real-time eye tracking can provide automatic, objective feedback to the OCT-based ophthalmic testing center system and allow the test to be modified in real-time. For example, if the ophthalmic testing center system determines that a subject is not gazing in the right direction during testing, the subject can be given instructions to conform to the testing protocol. In various embodiments, eye tracking is performed after testing during a post-processing phase. Post-processing eye tracking can be used to quantify data/results and/or remove unreliable data/ results. In certain embodiments, the OCT-based ophthalmic testing center system can be configured to rerun an ophthalmic test based on the results of a post-processing eye tracking analysis. As described in further detail below, eye tracking can be performed during various ophthalmic tests using OCT data to assist in determining the function of the eye.

With reference to FIG. 35A and FIG. 35B, the ophthalmic testing center can be configured to perform eye tracking or fixation monitoring during various ophthalmic tests by performing iris plane analyses, pupillary analyses, or anterior chamber analyses. For example, iris plane analysis is the process of determining the planar configuration, direction, tilt and/or slope of the iris tissue 3504A. When an eye changes it fixation and/or gaze to look in a new direction, the slope of the iris plane 3504A containing the pupil changes in a similar manner to a satellite dish pointing in a new direction. In various embodiments, the tilt or slope of the iris plane 3504A can be determined by performing optical coherence tomography A-scans, B-scans and/or 3D-OCT scans 3502A of the anterior chamber and/or iris, and can include the angle, the cornea and/or the lens, as discussed below in the gonioscopy test. Generally the plane of the iris 3504A may not be regular or perpendicular to the central axis of the eye. To account for this, in various embodiments, the starting plane of an iris 3504A is determined during foveal fixation in an eye prior to gaze tracking. In various embodiments, the changes in the tilt or slope of the iris plane can be determined as differences from this starting plane. In various embodiments, errors in iris detection can be handled by fitting all detected iris plane locations to a linear regression formula to approximate a straight plane through the iris 3504A. This can have the effect of accounting for and/or ignoring outlying errors that do not fit with the other detected points. Other methodologies for determining the plane of the iris are possible, for example, RANSAC (Random Sample Consensus). The foregoing is similarly applicable to pupillary analyses, and/or anterior chamber analyses.

In reference to FIG. 35A and FIG. 35B, in various embodiments, A-scans 3502A are collected more toward the periphery of the iris and/or cornea because generally little iris tissue exists in the pupil region. This can also allow for easier change detection because the differences at the extreme distances from the center of the eye due to changes in gaze direction will generally be larger than differences in the central of the eye; however, the OCT-based ophthalmic testing center can be configured to detect change by collecting A-scans toward the center of the eye. In various embodiments, A-scans are more evenly distributed across the anterior segment. Other data collection configurations are possible. OCT A-scans acquired from the anterior segment are analyzed by a processor, which can use image analysis routines, for example, edge detection, to identify the interface between the anterior chamber fluid and the iris tissue. This boundary can constitute the iris plane. As discussed previously, a plane fit to these data points with linear regression can be compared to a similar plane fit captured as a reference scan. In various embodiments, anterior chamber analysis can be used to augment these measurements and/or provide additional information on gaze direction.

With reference to FIG. 35A and FIG. 35B, in various embodiments, A-scans are collected in a radial line pattern centered on the optical axis of the instrument ocular. Individual A-scans can be analyzed with an attached processor using image processing algorithms, for example, edge detection, to determine the anterior border of the iris tissue, if present. In each radial line B-scan, a central block of A-scans not containing iris tissue can represent the pupil. Using the foregoing, the pupil margin can be detected for all radial line scans, and/or the border delineated for 360 degrees, and/or the roundness 3502B of the pupil analyzed to determine the direction of gaze.

The ophthalmic testing center system can be configured to perform eye tracking or fixation monitoring during various ophthalmic tests by performing foveal verification, or foveal detection, and/or foveal location. Foveal verification is the process of verifying that the fovea or "best fixating retina" is present in an expected location. In other words, foveal verification can be used to double-check that a test subject is looking where they are expected to look. Foveal verification can be performed during functional tests that instruct the subject to follow fixation targets on a display screen to ensure that the subject complies with the instructions, such as perimetry tests, extraocular motility tests, and visual acuity tests. In certain embodiments, if the subject has been instructed to look at a fixation target, the expected location of the fovea would be at a location on the retina corresponding to the opposite end of an optical projection axis extending from the fixation target back to the retina. For example, if the subject is supposed to be gazing at a fixation target in the upper right corner of a display screen, then the expected foveal location would be at a lower left region of the retina. In certain embodiments, the ophthalmic testing center system can determine the optical axial length of the eye to aid in foveal verification.

Figure 35C:
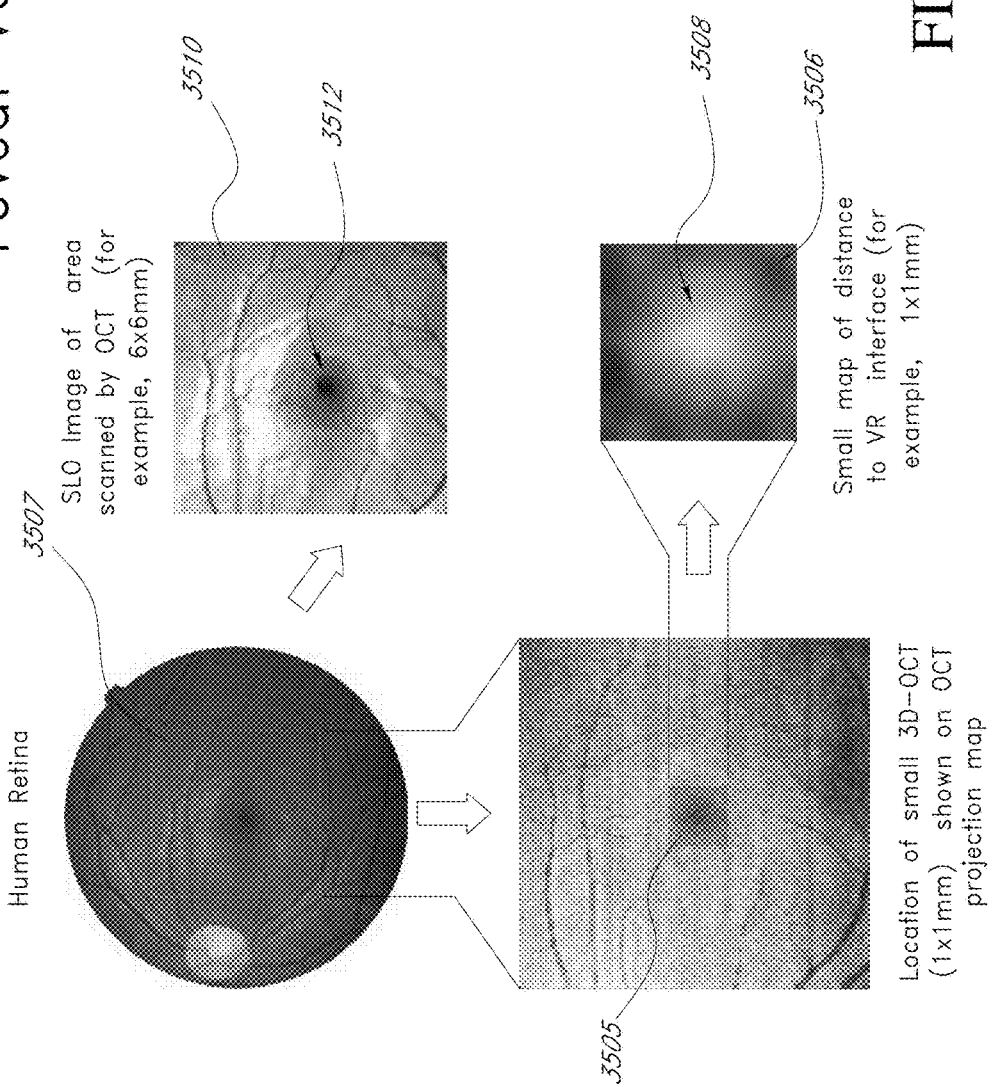

With reference to FIG. 35C, in certain embodiments, the OCT-based ophthalmic testing center system can be configured to acquire a small 3D-OCT scan 3505 (for example, 100×100 A-scans or 50×50 A-scans), of a small area (for example, 1×1 mm) around the expected location of a fovea on a retina 3507. The acquisition of the small 3D-OCT scan could occur repeatedly at high speeds, for example, at least every second, every 100 milliseconds, every 25 milliseconds, every 10 milliseconds, or any other number of seconds, or only a single time. In certain embodiments, the OCT-based ophthalmic testing center system can be configured to detect the interface between the vitreous and retina/nerve fiber layer (the "VR interface") for each of the A-scans in the small 3D-OCT dataset using edge detection routines. The OCT-based ophthalmic testing center system can then be configured to form a 2D map 3506 of scalar values of the distance to, or depth of, the VR interface for each of the A-scans. In certain embodiments, the fovea or optic nerve, if present, can be detected from this map as the most extreme (either largest or smallest) value in the set. With reference to FIG. 35C, the fovea can be identified as the brightest area 3508 of the 2D map 3506.

In another example, the inner retina can be detected using edge detection methods and fit to a polynomial curve. The substantially maximal foveal depression can be detected as the substantially maximal edge-detected deviation downward from this polynomial curve. In various embodiments, the degree of confidence in foveal detection can be measured as the deviation from the polynomial curve. Alternatively, since the outer nuclear layer comprises nearly 100% of the retina thickness in the foveola, the fovea can be detected by looking for the area with nearly 100% outer nuclear layer composition to the retina. Other ways in which the fovea can be detected are to look for focally increased thickness of the photoreceptor outer segments, substantially maximal separation of thick nerve fiber layer and location of a bright foveal reflex at the vitreoretinal interface.

In another embodiment, the OCT-based ophthalmic testing center system can be configured to detect the interface between retina and the retinal pigment epithelium (the "RR" interface) for each of the A-scans in the small 3D-OCT dataset using edge detection routines. The presence of breaks or discontinuities in this "RR" interface can be used to indicate the presence of retinal vessels which are substantially absent from the fovea. Therefore, an absence of "RR" discontinuities can be used as a positive indicator of foveal presence. Conversely, presence of "RR" discontinuities can be used as an indicator that the fovea is absent from the imaged region. In still another embodiment, the OCT-based ophthalmic testing center system can be configured to form a 2D map of scalar values of the difference between the VR and RR interfaces, also known as the retinal thickness, for each of the A-scans.

In various embodiments, the 2D map of scalar values can be converted to a slope, or first derivative, map that can be registered to other 2D slope maps with registration routines, such as Scale Invariant Feature Transform ("SIFT") or cross-correlation. The slope maps and registration routines can advantageously be used to indicate the point of maximum or preferred retinal fixation for eyes that don't have normal foveal depressions. For example, the slope map and registration routines can be used for subjects having a protrusion from retinal thickening instead of a normal foveal depression. In certain embodiments, the OCT-based ophthalmic testing center system can be configured to acquire a small reference image of the expected foveal location at a point of preferred fixation during testing. For example, the point of preferred fixation can occur during visual acuity testing when the subject is instructed to look straight ahead. The reference image can be used as the "best fixating retina" for subsequent fixation monitoring. In certain embodiments, the reference image can be stored by the OCT-based ophthalmic testing center system for subsequent comparison and reference.

In certain embodiments, the OCT-based ophthalmic testing center system can be configured to perform foveal verification using non-OCT modalities. For example, the OCT-based ophthalmic testing center system can be configured to acquire fundus images using infrared or scanning laser ophthalmoscopy ("SLO") imaging. An exemplary SLO image 3510 of a 6×6 mm retinal area is illustrated in FIG. 35C. The fovea can be identified as present in the non-OCT images by the point/region of maximal fundus pigmentation 3512. Alternatively, the fundus images can be registered to previous non-OCT images, such as a reference image obtained during preferred fixation, to use for comparison by sum of squared differences or SIFT registration.

Figure 36:
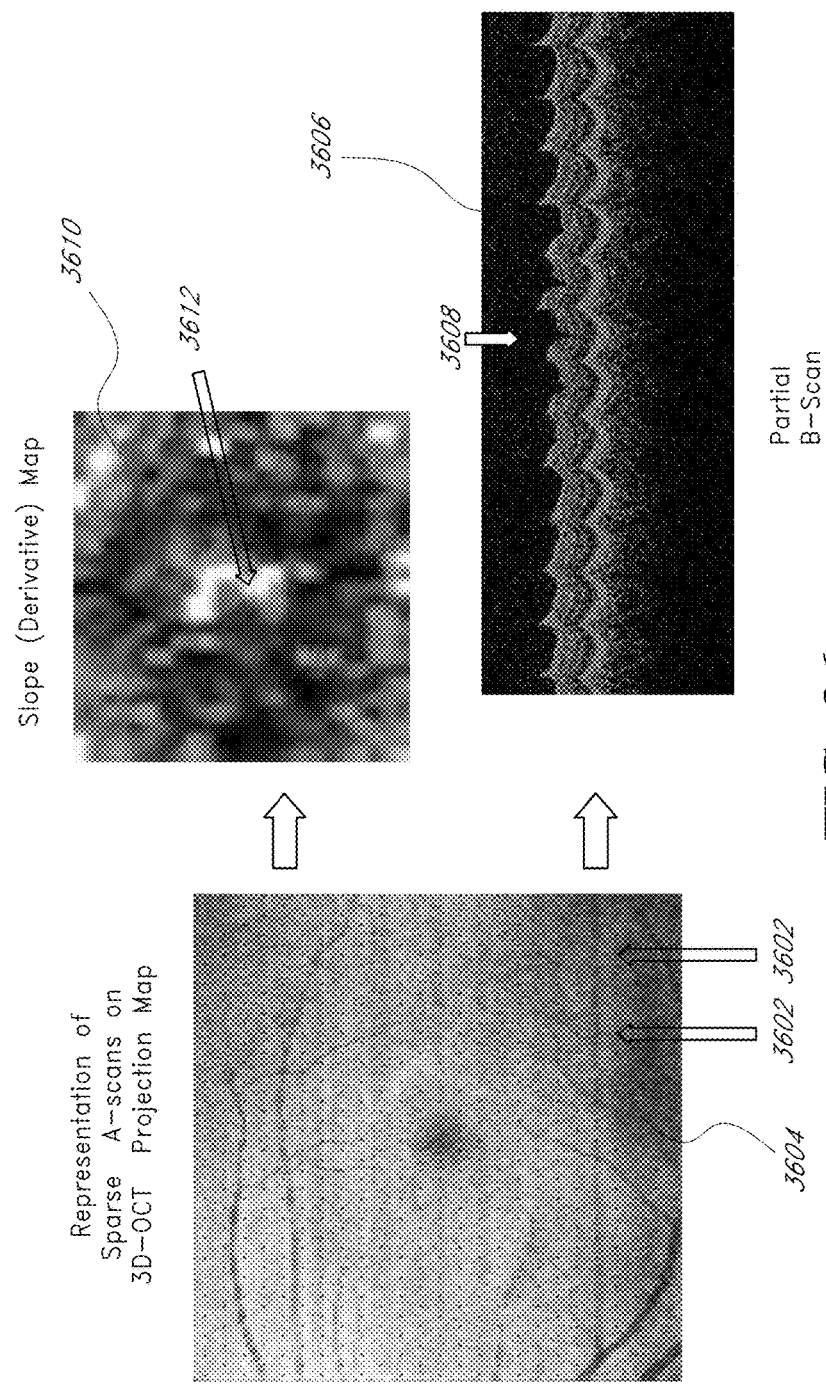

With reference to FIG. 36, foveal location can be performed by the OCT-based ophthalmic testing center system when no prior information is known about the foveal location and/or when foveal verification testing fails. For example, foveal location can be performed during extraocular motility testing to determine a quantifiable measurement of a deficiency in extraocular movement when the fovea is not found to be directed at the fixation target. In conducting foveal location, the OCT-based ophthalmic testing center system can be configured to acquire a set of A-scans (such as hundreds or thousands) in a sparse pattern (such at least as every 50 microns, every 100 microns, or every 200 microns) across a two-dimensional fundus field at high speeds (such as every 10-20 ms). With reference to FIG. 36, each of the small circles 3602 on the illustrated fundus image 3604 represents an individual A-scan. In certain embodiments, the fundus field 3604 can comprise a field in the range of 3×3 mm to 15×15 mm. For example, the set of A-scans can comprise 625 or 2400 individual A-scans across a 6×6 mm field. The OCT-based ophthalmic testing center system can be configured to compile the sparsely-placed individual A-scans into a long B-scan of the fundus field. FIG. 36 illustrates a portion of a B-scan 3606 generated from the set of A-scans (represented by circles 3602). In certain embodiments, a foveal depression can be identified as the region having the lowest profile on the B-scan (identified by arrow 3608 on the partial B-scan 3606). In another embodiment, the section of a similar long B-scan identifying the "best fixating retina," as described previously, could be matched or registered to this long B-scan to identify the location of the best fixating retina in the current long B-scan.

In various embodiments, as described above in connection with foveal verification, the OCT-based ophthalmic testing center system can be configured to identify a foveal location by performing edge detection of the VR interface for each of the A-scans in the sparse 3D-OCT dataset or by creating a slope (derivative) map 3610. The area of the VR interface having the greatest slope (corresponding to the lightest area on the slope map 3610) indicates the location of the fovea.

Figure 37:
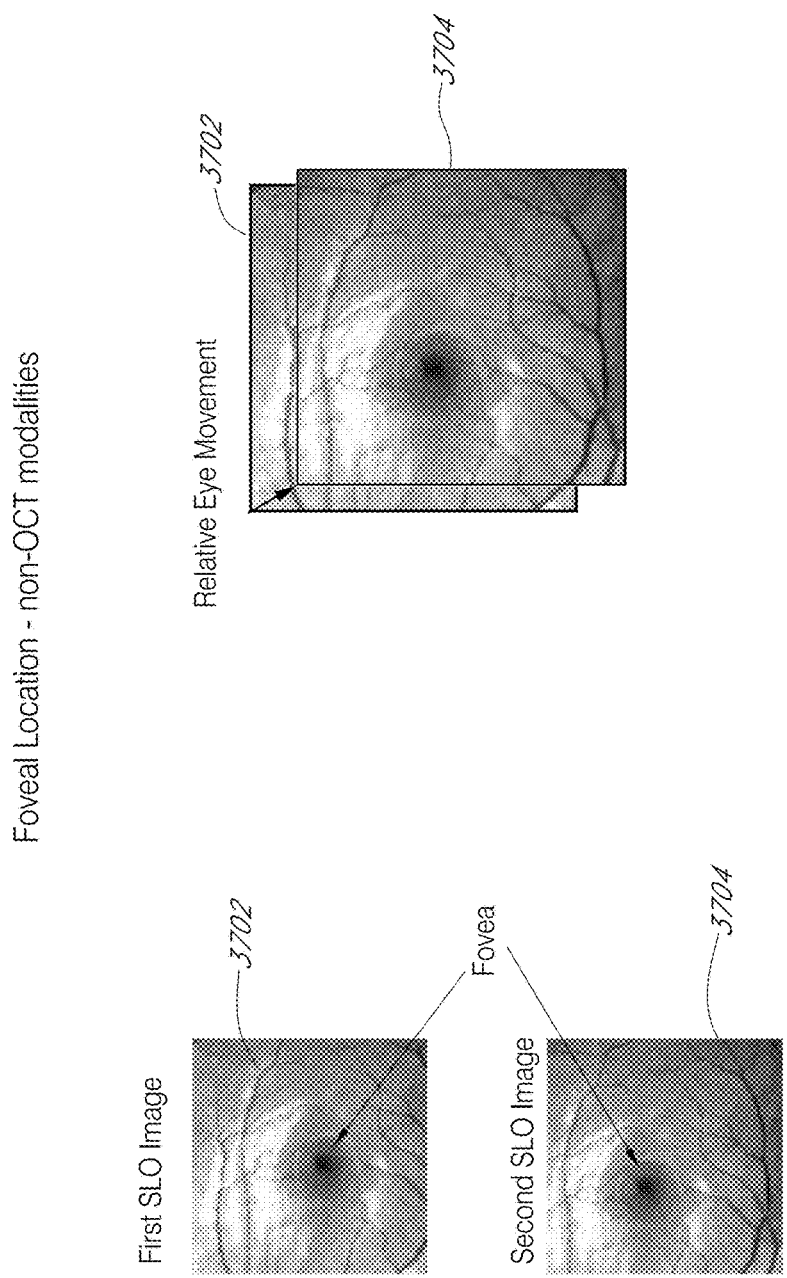

With reference to FIG. 37, as described above, in certain embodiments, the OCT-based ophthalmic testing center system can be configured to use non-OCT imaging modalities to track the fovea and retina. For example, non-OCT imaging modalities such as infrared or SLO imaging can acquire fundus images without pupillary dilation. In certain embodiments, the information from the fundus images can be used as a functional input to the OCT-based ophthalmic testing center system. In certain embodiments, (for example, where the fovea is normal and disease free) the foveal location can be detected as the point/region of maximal fundus pigmentation (identified as the darkest areas in the first SLO image 3702 and the second SLO image 3704 and pointed to by arrows). In various embodiments, (for example, where the fovea is not well-defined), the OCT-based ophthalmic testing center system can be configured to analyze the relative eye movement between the first SLO image 3702 and the second SLO image 3704 in order to track the foveae. For example, the second SLO image 3704 can be registered to the first SLO image 3702, or each of the first and second SLO images 3702, 3704 can be registered to a reference image obtained during a point of preferred fixation during testing using cross-correlation, sum of squared differences or SIFT registration.

OCT Biomicroscopy

Figure 38:
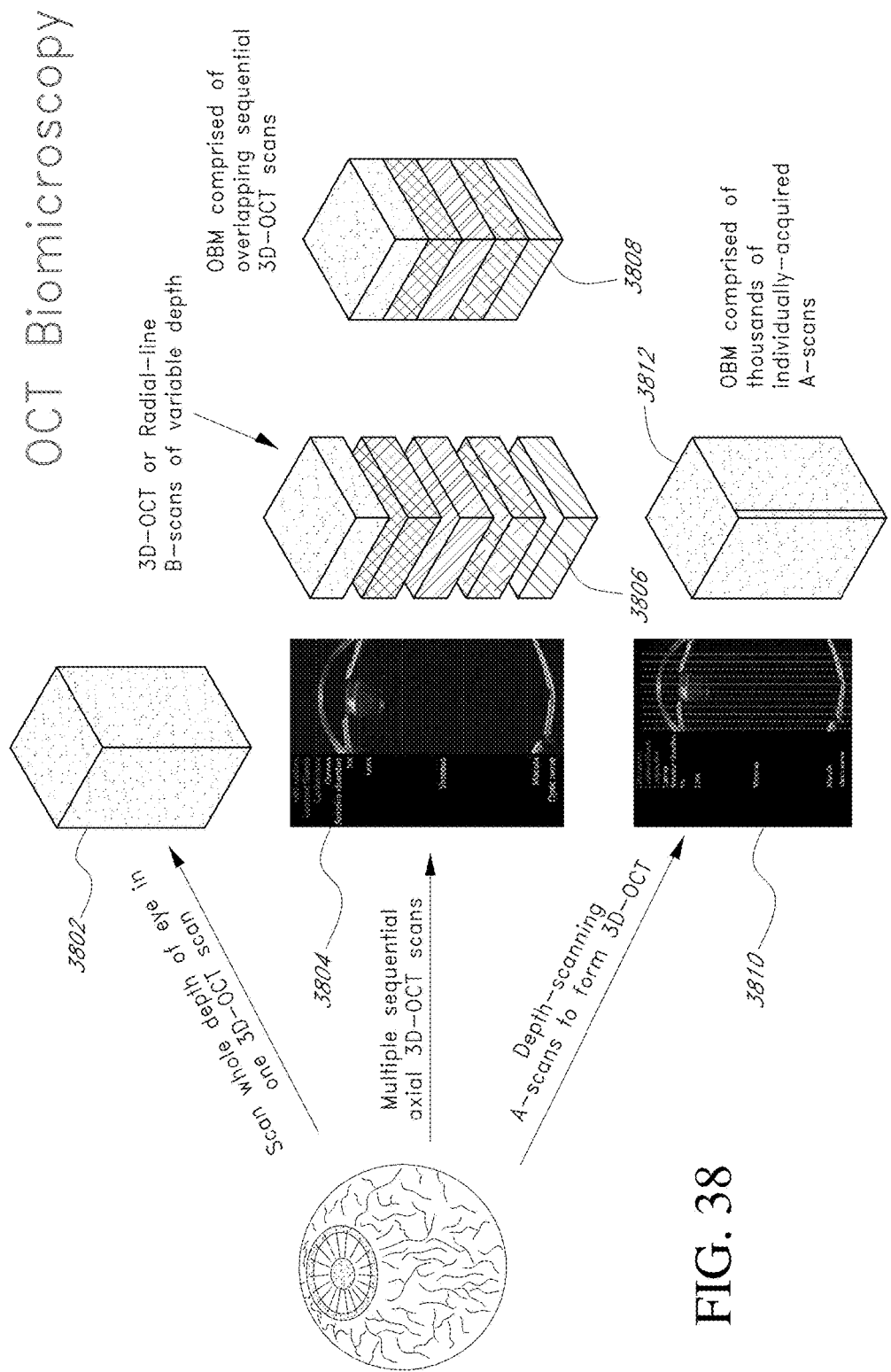
FIG. 38 illustrates various embodiments of performing OCT biomicroscopy tests using the OCT-based ophthalmic testing center system as described herein.

With reference to FIG. 38, optical coherence tomography ("OCT") instruments provide magnified, cross-sectional views of transparent tissues in the eye. In general, OCT biomicroscopy ("OBM") comprises scanning and imaging of the transparent tissues of the eye in order to provide a structural analysis. OBM scans advantageously provide objective, documented, reproducible, standardized, and quantifiable results. In certain embodiments, the OCT-based ophthalmic testing center system can be configured to generate OBM images of various regions of the eye. For example, the OCT-based ophthalmic testing center system can be configured to generate OBM images of all or substantially all of the eye tissues along the central axis (for example, optical axis) of the eye from the pre-cornea to the choroid. In various embodiments, the OCT-based ophthalmic testing center system can be configured to image the front of the eye (for example, the pre-cornea, the cornea, the anterior chamber, the anterior chamber angle, and the iris) and the back of the eye (for example, the retina, choroid, and the optic nerve) at the same time. In certain embodiments, the OCT-based ophthalmic testing center system can be configured to scan at least the entire central axis of the eye from front to back. The scan of the central axis of the eye can include imaging the panaxial tissues of the eye. In certain embodiments, the OCT-based ophthalmic testing center system can be configured to scan the eye, including tissues from the front to the back, in either a side-to-side pattern, in a top-to-bottom pattern, or in a front to back pattern. In certain embodiments, OBM is advantageously more objective, documented, detailed, consistent and quantitative than slit lamp biomicroscopy.

OBM can be performed on children or adults. For example, OBM can be performed on children to detect anterior chamber inflammation and/or cystoid macular edema associated with Juvenile Rheumatoid Arthritis. As another example, OBM can be performed on adults to detect narrow angle glaucoma by assessing their angle geometry and anterior chamber depth, as well as optic disc cupping due to optic nerve damage from the glaucoma. In various embodiments, the OCT-based testing center system can be configured to conduct OBM in either a self-operated or self-administered fashion, or in an assisted fashion with someone other than the subject either partially or completely administering the test. The OBM test can be performed on both eyes simultaneously or first on one eye and then on the other eye.

The OCT-based ophthalmic testing center system can be configured to perform OBM scans on an anterior region of the eye (for example, using 3D raster scans or radially oriented B-scans) to detect and quantify ophthalmic conditions in the cornea, anterior chamber and angle, such as keratic precipitates, anterior chamber cell or flare, or iris neovascularization (with the aid of Doppler OCT). OBM scans of the crystalline lens can enable more objective assessments of cataract progression (for example, by monitoring the lens thickness and curvature or by comparing lens opacity and reflectivity between scans). OBM scans can also be used to quantify axial length measurements and monitor posterior capsular opacification and post-operative intraocular lens position.

In certain embodiments, OBM scans can be used to image the entire vitreous cavity, thereby enabling more objective and automated quantification of vitreous pathology, such as vitritis and vitreous hemorrhage. OBM scans of the entire axial vitreous cavity can also aid in detecting peripheral lesions, posterior vitreous detachments, vitreoretinal interface disorders and/or the like. OBM scans of the posterior retinal region can be used to detect subretinal fluid, drusen, retinal pigment epithelial detachments, and/or geographic atrophy. OBM scans of the choroid region can advantageously aid in the diagnosis and monitoring of central serous choroidopathy and age-related macular degeneration.

In certain embodiments, the OCT-based ophthalmic testing center system can comprise display devices configured to present stationary fixation targets to the user, such as dots, crosses, circles or images. In various embodiments, the OCT-based ophthalmic testing center system can be configured to present animated or transient targets, such as movies, to the user. In certain embodiments, the OCT-based ophthalmic testing center system can be configured to instruct the user (visually and/or audibly) to look straight ahead at the fixation targets throughout the examination. In various embodiments, OBM, as a structural analysis, does not employ eye tracking modalities. Tissues included in the OBM scans could include, but would not be limited to, the eyelids and lid margins, precorneal structures (including the tear film and contact lenses), the conjunctiva, the cornea, angle structures, the anterior chamber, the iris, the lens and capsule, the vitreous, the retina, the retinal pigment epithelium, the optic nerve, the choroid and the sclera.

Imaging from the front to the back of the eye can be accomplished in several ways. With continued reference to FIG. 38, in certain embodiments, the OCT-based ophthalmic testing center system can be configured to scan the entire depth of the eye (e.g., at least 30 mm, 35 mm or 40 mm) in a single A-scan, B-scan and/or 3D-OCT scan 3802 using an instrument having a suitable light source and sufficient depth of field or focus. In various embodiments, the B-scans and/or the 3D-OCT scans comprise A-scans that are generated by using the OCT-based ophthalmic testing center system that scans the entire depth or substantially the entire depth of the eye in a single scan. For example, in various embodiments, a "scout" scan, similar to high-speed, substantially full-body scans performed prior to computed tomography or magnetic resonance imaging of the human body, can be acquired by combining a first B-scan (or set of laterally displaced B-scans) with the Fourier domain zero delay position set anteriorly with a second B-scan (or set of lateral displaced B-scans) with the Fourier domain zero delay position set posteriorly using a mathematical operator, such as a logical OR operator, to generate a single result OCT image. (In some embodiments, the first B-scan and the second B-scan are derived from data obtained using a single OCT scan extending from an anterior region to a posterior region of the eye but are processed using different Fourier domain zero delay positions.) This image can have high sensitivity anteriorly and high sensitivity posteriorly to enable measurements, such as the axial length, from the anterior cornea to the posterior retina, of an eye. In various embodiments, the position of the anterior corneal surface can be estimated using normative data or detected using OCT imaging of the cornea as described previously. The initial B-scan depth can be set at a predefined value, such as 35 mm, that is longer than most human eyes. A procedure can then be used to shorten this anticipated length progressively by increments, such as 2 mm, until the posterior border of the retina is visualized. The distance between the anterior corneal surface and the posterior retinal surface can be used as the axial length of the eye and subdivided into sections for progressive B-scan imaging of panaxial tissues as described below. In various embodiments, the OCT-based ophthalmic testing center system can be configured to generate A-scans, B-scans, and/or 3-D scans using scanning that are not scout scans but that comprise a single scan of the entire or substantially entire depth of the eye. Eyes vary in depth depending on the subject, but may range, e.g., from at least 18 mm, 20 mm, 30 mm, 35 mm or 40 mm but may have other depths. Measurements may be performed on these scans and/or images or information may otherwise be extracted from these scans to perform various ophthalmic tests (e.g., functional and/or structural) disclosed herein.

In certain embodiments, the OCT-based ophthalmic testing center system comprises a variable focus system with a wide range of focus depth, such that the focal point is capable of simultaneously focusing, for example, on the retina and the cornea.

In various embodiments, raster (3D) scans or radial line B-scans of variable depth (for example, 2 mm, 4 mm or 5 mm thick, or larger or smaller), can be captured sequentially from the front to the back of the eye using a programmatic approach. For example, a plurality 3D-OCT scans (formed by rastering laterally in orthogonal x and y directions) having a thickness of 2 mm can be arranged or stacked longitudinally along an axis of the eye, one 3D-OCT scan in front of another so as to form a larger 3D-OCT scan having a depth greater than 2 mm thick, e.g., at least 4, 6, 8, 10, 12, 14, 16, 18, 20, 22, 24, 26, 28, 30, 32, 34, 36, 38, 40 mm. The axis may be parallel to the optical axis of the eye in certain embodiments. The plurality of 3D-OCT scans arranged one in front of the other may produce a resultant 3D-OCT scan that extends from an anterior structure of the eye, e.g., cornea, to a posterior structure of the eye, such as the retina, and may include an intermediate structure such as the vitreous. Smaller 3D-OCT scans may extend from an anterior structure (e.g., cornea) to an intermediate structure (e.g.

vitreous) or from an intermediate structure to a posterior structure (e.g., retina). Similarly, a plurality of B-scans that have a thickness of 2 mm can be arranged or stacked longitudinally along an axis of the eye, one B-scan in front of another, so as to form a larger B-scan having a depth greater than 2 mm thick, e.g., at least 4, 6, 8, 10, 12, 14, 16, 18, 20, 22, 24, 26, 28, 30, 32, 34, 36, 38, 40 mm. The scans arranged one in front of the other may or may not overlap each other and may or may not be spaced apart by gaps. The location of the scan along the longitudinal axis may be controlled by the Z-offset. Translating the Z-offset mirror, for example, varies the depth within the eye which is imaged. Accordingly, to obtain a plurality of scans at different depths, the Z-offset can be suitably adjusted for each scan. The focus may similarly be adjusted to increase image quality, especially if the depth of focus of the focusing optics is small.

FIG. 38 illustrates a simulated OBM image 3804 generated by stacking multiple 3D-OCT scans sequentially along an axis of the eye and a virtual representation of an OBM image 3806 illustrating the variable depth scans. In some embodiments, the OCT-based ophthalmic testing center system can be configured to montage the multiple sequential axial 3D scans or B-scans together either with or without axial overlap. FIG. 38 also illustrates a demonstrative virtual representation of an OBM image with axial overlap 3808. The longitinal array of scans together produce an aggregate scan that spans a larger longitudinal distance along the axis, e.g. optical axis of the eye.

As described above, a plurality of 3D OCT scans or B-scans can be obtained at different depths into the eye so as to produce an aggregate OCT scan that extends over the longitudinal thickness of the eye. For example, ten to twenty OCT scans 2 mm thick can be used to produce an OCT scan 20-40 mm thick. Controlling the depths at which the different scans are obtained, and consequently any overlap or spacing between adjacent scans, affects the overall longitudinal thickness of the resultant scan. Similarly, the thickness of each of the plurality of scans affects the overall longitudinal thickness of the resultant scan. Accordingly, to include pre-corneal tissue as well as scleral tissue in a scan, formed by a plurality of longitudinally displaced scans, will involve less scans if the scans are thicker and more scans if the scans are thinner. The thickness of the each of the scans arranged or montaged to form the larger scan need not be the same.

In various embodiments, the OCT-based ophthalmic testing center system can be configured to programmatically capture sequential 3D scans or B-scans in such as way as to reduce, minimize, or remove the mirror image artifact around the zero delay point that exists with Fourier domain OCT. As is well known, a ghost image may be introduced as a result of the folding of scan data about the zero delay point in Fourier domain OCT. This ghost image may be an inverted image of nearby tissue. In the case where OCT scanning extends through the anterior chamber, the vitreous chamber, and the posterior chamber, ghost images of the anterior or posterior chamber may be superimposed on the image of the vitreous chamber. These ghost images may be inverted images of, for example, the iris or retina, or other structure features.

Various techniques may be used to reduce the effect of the mirror image artifact resulting from folding of scan data about the zero delay point in Fourier domain OCT. Phase-shifting the signal using electro-optic modulators, acousto-optic frequency modulators, piezo transducers, as well as employing small beam offsets at the fast-scanning mirrors are possible. See, for example:

Zhang J, Jung W, Nelson J S, Chen, Z. Full range polarization-sensitive Fourier domain optical coherence tomography. Optics Express. November 2004. 12(24):6033-6039.

Bachmann A. Leitgeb R A, Lasser T. Heterodyne Fourier domain optical coherence tomography for full range probing with high axial resolution. Optics Express. February 2006. 14(4):1487-1496.

Bu P, Wang Z, Sasaki O. Full-range parallel Fourier domain optical coherence tomography using sinusoidal phase-modulating interferometry. J. Opt A: Pure Appl. Opt. 9(2007) 422-426.

Vakhtin A B, Peterson K A, Kane D J. Demonstration of complex-conjugate-resolved harmonic Fourier-domain optical coherence tomography imaging of biological samples. Applied Optics. June 2007. 46(18):3870-3877.

Yasuno Y, Makita S, Endo T, Aoki G, Sumumura H, Itoh M, Yatagai T. One-shot-phase-shifting Fourier domain optical coherence tomography by reference wavefront tilting. Optics Express. 2004. 12(25):6184-6191.

Additionally, image processing techniques can be employed. In various embodiments, for example, two images of the same tissue can be combined using an AND logical operator to preserve or reinforce the real tissue signal while removing, or at least attenuating the ghost image. The two images may, for example, correspond to two scans of the same tissue captured with different zero delay points. One scan may be completed with a zero delay point on the top of the scan and another scan may be completed with the zero delay point on the bottom of the scan. A different ghost image will accompany each of the two scans since, in the first case, the ghost image would be comprised of reflected tissue from above the scanning area while in the second case, the ghost image would be comprised of reflected tissue from below the scanning area. Likewise, by ANDing the two scans together, the ghost image can be attenuated while the recurrent tissue features in the two images will be reinforced. Although in this case the two images may comprise scans having zero delay points on opposite sides (for example, top and bottom) of the B-scan image, in various embodiments, the scans of the same tissue can be otherwise perturbed so as to change the ghost images, while substantially maintaining the imaged tissue features. As described above, applying a logical AND process on these scans can cause the different ghosting images to be attenuated, minimized or removed in contrast to the recurrent tissue features in the two scans, which will be reinforced or otherwise remain. In some embodiments, these processes may be performed in an interactive fashion to progressively remove ghost image artifacts.

Additionally, in various embodiments, the ghost image could be attenuated, minimized or removed by arithmetically subtracting a mirrored image similar to the ghost image. If, for example, the ghost image is an image of the cornea, an image of the cornea can be obtained from a separate scan and used to subtract out the ghost image. In certain embodiments, for example, data of neighboring scans can be used. For example, B-scan images that are more anterior can be mirrored around their lower border and can be subtracted from subsequent images that are posterior. Alternatively, B-scan images that are more posterior can be mirrored about their upper border and subtracted from images that are anterior. Additionally, prior B-scan images can be subtracted from previous B-scan images or vice-versa. Although there may be differences between the ghost image and the mirrored image, for example, there may be differences in intensity and shifting of the eyes due to movement of the eyes, mirroring and subtracting may substantially reduce the ghost image while not consistently affecting the real tissue image.

Also, in certain embodiments, the ghost image can be addressed by using overlapping scans. A large overlap segment may comprise, for example, 25% or 50% of the B-scan depth. In example of this embodiment, the z-offset position of subsequent B-scans can be shifted posteriorly by an amount less than the current B-scan depth. For example, for a B-scan that has a depth of 2 mm, a subsequent B-scan that could also have a depth of 2 mm would overlap by 50% if the z-offset position was changed only by 1 mm. The overlap may be, for example, at least 20%, 30%, 40%, 50%, although other values are possible. In various embodiments the amount of overlap is known. Logical AND operations can be performed on sequential scans shifted by this known offset amount. As described above, the logical AND process can reinforce data that is common between the two scans (real image) versus mirror ghost images, which will be different in the two scans. A logical AND process may, for example, be used. However, a wide variety of variations are possible.

In certain embodiments, light sources, optical configurations, and/or processing capable of providing deep penetration, can be used to enable deeper scans and thus, coverage of the eye in fewer scan sequences. In certain embodiments, the sequential axial scans can be programmatically controlled so that changes in the focus of the device are coordinated with changes in the z-offset position between sets of B-scans oriented along the longitudinal axis of the eye. For example, the OCT-based ophthalmic testing center system can be configured to begin to capture OCT scans of the anterior segment at the approximate distance expected (based, e.g., on the location of the ocular cups) when the ocular cups of the OCT-based ophthalmic testing center system are placed against the user's eye sockets and then z-offsets and autofocus can be performed for each successive scan as discussed previously. One example of an automated process for generating an OBM image based on multiple sequential scans of variable depth can be performed by the OCT-based ophthalmic testing center system as follows. In one embodiment, a first axial 3D or radial-line B scan can be performed with a particular preset depth, such as 3 mm. Based on the preset thickness of this first B-scan set, the OCT-based ophthalmic testing center system can be configured to move the z-offset posteriorly by a certain distance in preparation for the next sequential axial scan. If the focal depth of the variable focus lens system is not adequate to focus on the new posterior position, the OCT-based ophthalmic testing center can be configured to move the focal point of the variable focus lens system posteriorly by substantially the same amount as the z-offset. In certain embodiments, the z-offset distance can be configured such that the depth of the next sequential scan is less than the depth of the previous scan in order to induce overlap of scan data. In various embodiments, the z-offset distance can be configured such that the depth of the next sequential scan is equal to the depth of the previous scan. In still other embodiments, the z-offset distance can be configured such that the depth of the next sequential scan exceeds the depth of the first scan. The automated OBM imaging process can be continuously repeated until the retina and choroid are encountered, at which point a complete retina/choroidal/optic nerve scan can be completed, thereby concluding the imaging portion of the OBM test.

In certain embodiments, the aggregate scan (whether A-scan, B-scan, 3-D OCT scan) that is compiled does not extend from the cornea to the retina but may extend a different distance which may be a least 3 mm, 5 mm, 7 mm, 9 mm, 11 mm, 13 mm, 15 mm, 17 mm, 19 mm, 21 mm, 23 mm, 25 mm, 27 mm, 29 mm, 31 mm, 33 mm, 35 mm, 37 mm, 39 mm. In various embodiments, the OBM image of the entire depth of the eye can be comprised of multiple individually-acquired A-scans. In certain embodiments, the OBM image can be comprised of thousands of A-scans. In certain embodiments, each individual A-scan can be depth-scanned such that focus and z-offset are varied throughout acquisition of the individual A-scan. Raster or radial line compilations of these A-scans can enable 3D viewing of OBM images. FIG. 38 illustrates a simulated OBM image 3810 generated by multiple individually-acquired A scans and a virtual representation of an OBM image 3812 illustrating the compilation of individually-acquired A-scans. In various alternative embodiments, the depth of the A-scans can be configured to extend as far as the light source allows, to extend to some preset depth, or to continue until the retina or choroid is encountered. In certain embodiments, an average location for the retina and choroid can be used so that A-scans with ambiguous endpoints can benefit from data from adjacent A-scans. In various embodiments, a suitable light source, optics, and processing may be employed to capture the entire axial length of the eye in one A-scan, a depth that can exceed 35 mm, without substantially changing focus or z-offset. In certain embodiments, the A-scans generated can be combined in a raster or radial line pattern to form a 3D-OCT of the whole eye or at least a substantial portion of the whole eye. In some embodiments, A-scans generated can be used to plan the final depth and breakdown of sequential scans required to complete the sequential 3D-OCT capture pattern described above. The OBM image data can be used by physicians in many ways. In one embodiment, physicians can view the 3D scans of the eye as individual B-scans or in 3D mode. In another embodiment, the physicians can perform qualitative assessments of the features in the scans or view historical, or serial, sets of scans side-by-side to evaluate disease progression. In another embodiment, software modules or routines can be used to delineate various boundaries, such as the corneal boundaries, the pupillary boundaries, or the retinal boundaries, and provide measurements of these features based on the detected boundaries. In various alternative embodiments, the software modules or routines can be performed on the processing unit of the ophthalmic testing center system itself, on a processor of an attached computer, or on a remote computer that is connected to the ophthalmic testing center system via wired or wireless networking. The provided measurements can be compared with measurements from previous examinations, if available. In another embodiment, the OCT-based ophthalmic testing center system can be configured to use automated classifications algorithms to determine the identity of each pixel within the 3D dataset, such as identifying subretinal tissue, vitreous cells, or abnormal iris vessels, and extract quantitative measurements of these classified structures. Other measurements and analyses are possible without departing from the spirit and/or scope of the disclosure.

If processed in real-time, the OCT biomicroscopy data can be used to augment additional scans in the same session. For example, in certain embodiments, if the system is configured to perform radial line scans in the vitreous cavity but encounters many small bright signals during analysis, which can be indicative of bleeding or infection, the OCT-based ophthalmic testing center system can be configured to perform more dense scanning in this region to further elucidate the abnormalities. In various embodiments, the OCT-based ophthalmic testing center system can be configured to compare the OBM measurements to a normative database to determine patterns of deviation and/or generate risk assessments and/or clinical reports. In various embodiments, the OCT-based ophthalmic testing center system can be configured to analyze, compare, and/or add the OBM data to other data, such as the subject's ophthalmic history data that is stored on a subject's input card or retrieved from a historical database or other history-taking modules incorporated into the OCT-based ophthalmic testing center system. For example, the OCT-based ophthalmic testing center system can be configured to automatically perform periodic OBM scans on patients with chronic and/or potentially progressive conditions, such as corneal edema or keratoconus, or on patients with contact lenses to evaluate contact lens fit. In various embodiments, the OCT-based ophthalmic testing center system can be configured to automatically conduct and store an OBM image whenever another ophthalmic test is ordered and/or performed. The OCT-based ophthalmic testing center system can be configured to generate various statistics based on the OBM data, which may be combined with data from the normative database or historical data source.

With reference to FIG. 38, the OCT-based ophthalmic testing center system can be configured to output the results of and/or data from the OBM imaging and analysis. For example, the results can be outputted directly to the subject in a hardcopy (for example, printed card or paper) or electronic format (for example, on a display, via email, text messaged, or in a magnetic strip), stored locally on the device or on an attached computer, transmitted to a central database, or transmitted directly to the ordering or related physician.

In one embodiment, the OCT-based ophthalmic testing center system contains two independent OCT systems capable of capturing simultaneous OCT scans for each eye. In this embodiment, scanning protocols and measurements can be determined independently for each side. In another embodiment, the ophthalmic testing center system can be configured to stop moving from anterior to posterior when arriving at a structure of interest. For example, the ophthalmic testing center system can be directed to stop at the iris/pupillary plane as it moves from front-to-back. At this point, it may be configured to capture high speed bilateral B-scans (e.g., in 20 ms, 10 ms, 5 ms, 2 ms, 1 ms or less) to perform bilateral ophthalmic measurements, such as pupillometry (as discussed in further detail below). In another embodiment, the ophthalmic testing center system can stop scanning when it reaches the retina in order to perform measurements based on the location of both foveae (as discussed above in connection with strabismus and amblyopia).

Extraocular Motility Testing

Figure 39:
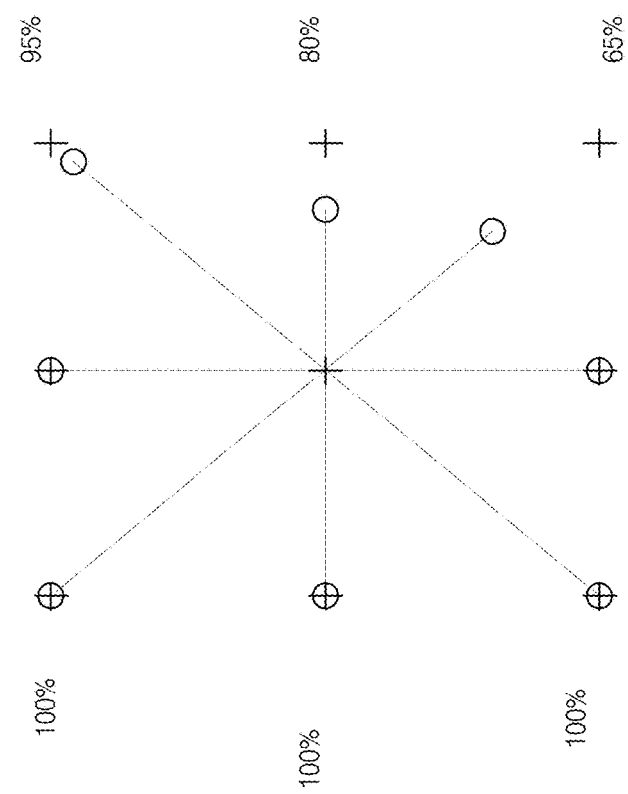
FIG. 39 illustrates an embodiment of an extraocular motility test conducted using the OCT-based ophthalmic testing center system as described herein.

With reference to FIG. 39, extraocular motility, or extraocular movement, is generally a measurement of the extent of movement of the eyes in various directions of gaze and can be used to detect a motility deficit. Extraocular motility testing can be performed on children and adults.

In reference to FIG. 39, an OCT-based ophthalmic testing center system could accomplish extraocular motility testing in either a self-operated or self-administered fashion, or in an assisted fashion where someone other than the subject either partially or completely administers the test. The extraocular motility test is a functional test that can employ eye tracking methodologies, for example, tracking the fovea using foveal verification and/or foveal location. The extraocular motility test can be performed on both eyes simultaneously (versions) or first on one eye and then on the other eye (ductions). In various embodiments, the OCT-based ophthalmic testing center system can be configured to display stationary fixation targets, such as dots, crosses, circles, or images in the ocular displays. The OCT-based ophthalmic testing center system can be configured to control the optical distance between the subject's eye and the fixation targets by adjusting the vergence of the light from the fixation display (for example, by collimation or divergence). For example, the optical distance could be set at 14 inches to simulate reading, 30 inches to simulate computer use, 20 feet to equate with conventional visual acuity measurements, infinity, or at any other distance.

In various embodiments of the testing phase, the fixation targets can be configured to move in one or both oculars to one of many predetermined positions, such as the nine cardinal positions of gaze. In certain embodiments, the fixation targets can be configured to momentarily dwell at each of the predetermined positions to enable measurement of motility along various axes of the eye. In certain embodiments, the OCT-based ophthalmic testing center system can be configured to instruct (visually and/or audibly) the subject to follow the fixation targets throughout the examination. The instruction can be auditory and/or visual in various embodiments.

The OCT-based ophthalmic testing center system can be configured to monitor the subject's gaze using OCT and/or non-OCT imaging modalities to ensure that the subject's gaze, either demonstrated by a foveal depression under the image of the fixation target on the retina or by appropriately changing locations for other retinal features, remains fixed on the moving or dwelling target. OCT imaging modalities can include, for example, foveal verification using small 3D-OCT scans centered on the image of the fixation target on the retina and/or foveal location using sparse 3D-OCT scans across the fundus. Non-OCT imaging modalities can include, for example, infrared ("IR") or scanning laser ophthalmoscopy ("SLO") imaging.

In certain embodiments, the OCT-based ophthalmic testing center system can be configured to first perform foveal verification. Detection of the foveal depression or "best fixating retina" at the expected location for a particular dwell point can indicate intact motility in the corresponding axis, whereas absence of a foveal depression can indicate a motility deficit. In certain embodiments, the OCT-based ophthalmic testing center system can be configured to continue on with the test without performing a foveal location if the presence of the fovea is detected for a particular dwell point. In the absence of a foveal or optic nerve depression within the expected region, the OCT-based ophthalmic testing center system can be configured to perform foveal location to quantify the motility deficit. As described above in connection with foveal verification and foveal location, the analysis to detect these features can comprise edge detection of the vitreoretinal ("VR") interface to detect the foveal depression, edge detection of the vitreoretinal interface and RPE to determine retinal thickness, edge detection of other retinal features, topographic or thickness slope calculations followed by 2D registration to previous maps, among other analyses.

In certain embodiments, if the subject's gaze departs from the fixation target, the OCT-based ophthalmic testing center system can be configured to remind the subject (for example, visually or audibly) to follow the fixation target. In various embodiments, the OCT-based ophthalmic testing center system can be configured to reject the current measurement and start the test or current measurement over.

In certain embodiments, measurements made with the extraocular motility test can include, but are not limited to, ratios of the actual distance traveled by the fovea in each axis over the expected distance to the dwell point in each axis, such as 75% or 110%; the actual angle traveled, such as 45 degrees; and/or the angular ratio (actual angle traveled over the expected angle traveled) for each axis, such as 75%. FIG. 39 graphically illustrates an example of extraocular motility test results for a subject with a motility deficit on the right side. The actual foveal locations (illustrated as circles) are aligned with the expected foveal locations (illustrated as crosses) for the left and central dwell points, indicating 100% motility. For the three dwell points on the right with deficient motility (less than 100%), the actual foveal locations do not align with the expected foveal locations. The dashed lines represent the various axes traveled by the fixation target during the testing phase. The percentages listed at the eight dwell points represent the ratios of the actual distance traveled by the fovea in each axis over the expected distance to the dwell point in each axis.

In certain embodiments, the extraocular motility data is presented separately for versions and ductions. In various embodiments, the OCT-based ophthalmic testing center system can be configured to employ logic to combine the extraocular motility measurements to deduce potential underlying cranial nerve palsies, such as third, fourth and sixth cranial nerve palsies. In certain embodiments, the OCT-based ophthalmic testing center system can be configured to combine the extraocular motility testing with the performance of strabismus evaluations (which are described in detail above). For example, the OCT-based ophthalmic testing center system can advantageously be configured to perform strabismus evaluations by analyzing the differences in foveal locations of the fellow eyes while the subject is gazing in different directions. This combination of extraocular motility testing with strabismus testing can advantageously aid in generating more information about the type of strabismus. Other measurements and analyses are possible without departing from the spirit and/or scope of the disclosure. If processed in real-time, the OCT-based ophthalmic testing center system can be configured to use the extraocular motility test data in conjunction with or to augment additional testing for the subject. In various embodiments, the OCT-based ophthalmic testing center system can be configured to compare the extraocular motility test data to a normative database to determine patterns of deviation and/or generate risk assessments and/or clinical reports. In various embodiments, the OCT-based ophthalmic testing center system can be configured to analyze, compare, and/or add the extraocular motility test data to other data, such as the subject's ophthalmic history data that is stored on a subject's input card or retrieved from a historical database or other history-taking modules incorporated into the OCT-based ophthalmic testing center system. The OCT-based ophthalmic testing center system can be configured to generate various statistics, based on the measured extraocular motility data, which may be combined with data from the normative database or historical data source.

With reference to FIG. 39, the OCT-based ophthalmic testing center system can be configured to output the results of and/or data from the extraocular motility test. For example, the results can be outputted directly to the subject in a hardcopy (for example, printed card or paper) or electronic format (for example, on a display, via email, text messaged, or in a magnetic strip), stored locally on the device or on an attached computer, transmitted to a central database, or transmitted directly to the ordering or related physician.

Pupillometry

Figure 40:
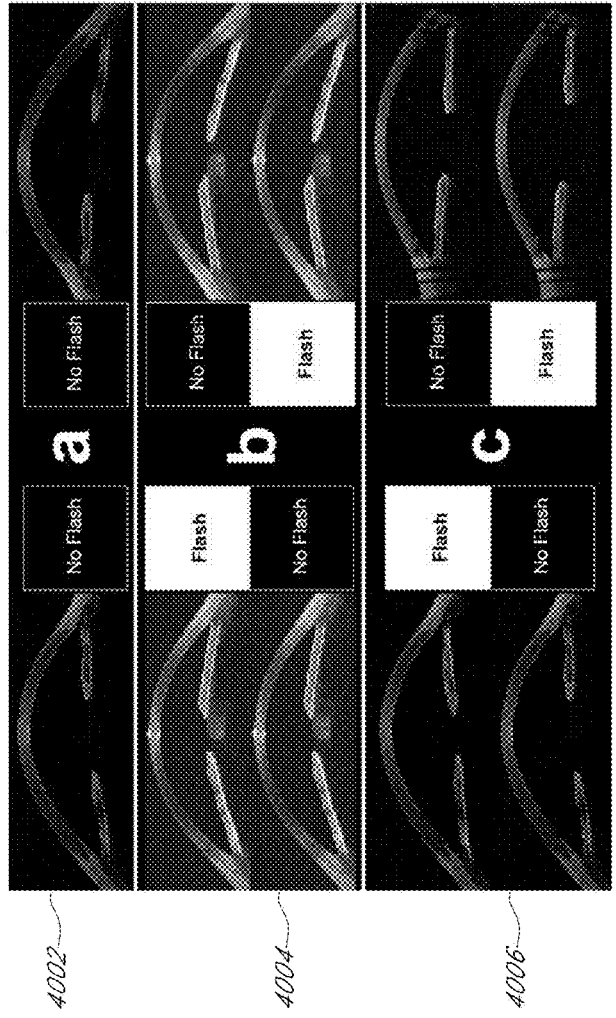
FIG. 40 illustrates an embodiment of a pupillometry test conducted using the OCT-based ophthalmic testing center system as described herein.

With reference to FIG. 40, pupillometry is generally a measurement of pupillary reactions, or pupillary responses. Pupillary reaction abnormalities can often signify serious disease, such as central nervous system disease. Pupillometry measurements can also be used to detect subtle optic nerve dysfunction in diseases such as early glaucoma. Pupillometry can be performed on children and adults. In general, there are two major types of pupillary responses (direct and consensual). The direct response occurs when a pupil constricts to a visual stimulus, such as a bright light, presented directly to that eye. The consensual response occurs when a pupil constricts in response to a visual stimulus presented to the fellow eye.

In reference to FIG. 40, an OCT-based ophthalmic testing center system could accomplish pupillometry in either a self-operated or self-administered fashion, or in an assisted fashion where someone other than the subject either partially or completely administers the test. In general, pupillometry is a structural test. In certain embodiments, the pupillometry test does not employ eye tracking methodologies; however, In various embodiments, eye tracking methodologies can be used, for example, tracking the fovea using foveal verification and/or foveal location. The pupillometry test is a binocular test and can be performed on both eyes simultaneously; however, in certain embodiments, the pupillometry test can be performed on one eye only or first on eye and then on the other. In various embodiments, the OCT-based ophthalmic testing center system can optionally display stationary fixation targets, such as dots, crosses or circles at the start of the pupillometry test. In embodiments where pupillary reactions to accommodation are to be tested, the OCT-based ophthalmic testing center system can be configured to control the optical distance between the subject's eye and the fixation targets by adjusting the vergence of the light from the fixation display (for example, by collimation or divergence) prior to acquiring B-scans through the iris planes. For example, the optical distance could be set at 14 inches to simulate reading, 30 inches to simulate computer use, 20 feet to equate with conventional visual acuity measurements, infinity, or at any other distance. In one embodiment of the testing phase, bright stimuli could be flashed at one or both eyes by filling the entire display screen on one or each side of the binocular visual interface with a bright color, such as white, or using an independent light source to provide a flash stimulus. In various embodiments, the OCT-based ophthalmic testing center system can be configured to instruct (visually and/or audibly) the subject to look straight ahead at fixation targets (if present). During various embodiments of the testing phase, the OCT-based ophthalmic testing center system device can be configured to capture bilateral simultaneous OCT B-scans through the iris/pupillary plane in both eyes at high speeds (for example, at least 10 per second, 50 per second or 100 per second) to detect pupillary responses to accommodation or visual stimuli, as described in more detail in the OCT biomicroscopy section above. In various embodiments, the OCT-based ophthalmic testing center system can be configured to analyze the resulting OCT images with image processing algorithms, such as edge detection routines, to generate measurements of various parameters of pupillary responses, such as size, latency, velocity, acceleration, and amplitude.

With reference to FIG. 40, OCT image 4002 illustrates normal mid-dilated pupils in dim light. OCT image 4004 illustrates a direct and consensual pupillary response in normal eyes. In general, the pupillary response in normal eyes should be substantially symmetric in all parameters (as illustrated by OCT image 4004). In eyes with diseases of the optic nerve or pupillary pathways, including glaucoma, the highly quantitative measurements of the OCT-based ophthalmic testing center system can be configured to detect asymmetries that may arise. For example, in certain embodiments, a relative afferent pupillary defect in a left eye can be detected if the flash stimulus in the right eye leads to both direct (right eye) and consensual (left eye) pupillary constriction, while a flash stimulus in the left eye leads to less constriction on both sides (as illustrated by OCT image 4006). Other measurements and analyses are possible without departing from the spirit and/or scope of the disclosure.

If processed in real-time, the OCT-based ophthalmic testing center system can be configured to use the pupillometry test data in conjunction with or to augment additional test stimuli presented to the subject. For example, if a test result is equivocal or close to the borderline of normal, a dimmer stimulus or a flicker stimulus can be presented to the user. In another example, if a pupillary defect is found to be present, the OCT-based ophthalmic testing center system can be configured to automatically perform perimetry or extraocular motility testing. In various embodiments, the OCT-based ophthalmic testing center system can be configured to compare the pupillometry test data to a normative database to determine patterns of deviation and/or to generate risk assessments and/or clinical reports. In various embodiments, the OCT-based ophthalmic testing center system can be configured to analyze, compare, and/or add the pupillometry test data, to other data, such as the subject's ophthalmic history data that is stored on the subject's input card or retrieved from a historical database or other history-taking modules incorporated into the OCT-based ophthalmic testing center system. In certain embodiments, the OCT-based ophthalmic testing center system can be configured to automatically perform a pupillometery test upon detection of increased optic disc cupping or a thinned retinal nerve fiber layer. The OCT-based ophthalmic testing center system can also be configured to generate various statistics, based on the pupillometry data, which may be combined with data from the normative database or historical data source.

With reference to FIG. 40, the OCT-based ophthalmic testing center system can be configured to output the results of and/or data from the pupillometry test. For example, the results can be outputted directly to the subject in a hardcopy (for example, printed card or paper) or electronic format (for example, on a display, via email, text messaged, or in a magnetic strip), stored locally on the device or on an attached computer, transmitted to a central database, or transmitted directly to the ordering or related physician.

In certain embodiments, the OCT-based ophthalmic testing center system can be configured to detect the pupil centers on each side to refine the interpupillary distance of the oculars to ensure that they remain centered on each eye's optical axis. In various embodiments, further refinement of the interpupillary distance can be guided by the image quality of the B-scans on each side. For example, if B-scans on either side were of low quality, the OCT-based ophthalmic testing center system can be configured to increase or decrease the interpupillary distance. If adjustment in one direction improves the average image quality of the two sides, the OCT-based ophthalmic testing center system can be configured to continue to pursue changes in that direction until the average image quality is optimized. In certain embodiments, interpupillary distance adjustment can be performed in the horizontal and vertical axes, instead of only the horizontal axis.

Exophthalmometry

Figure 41:
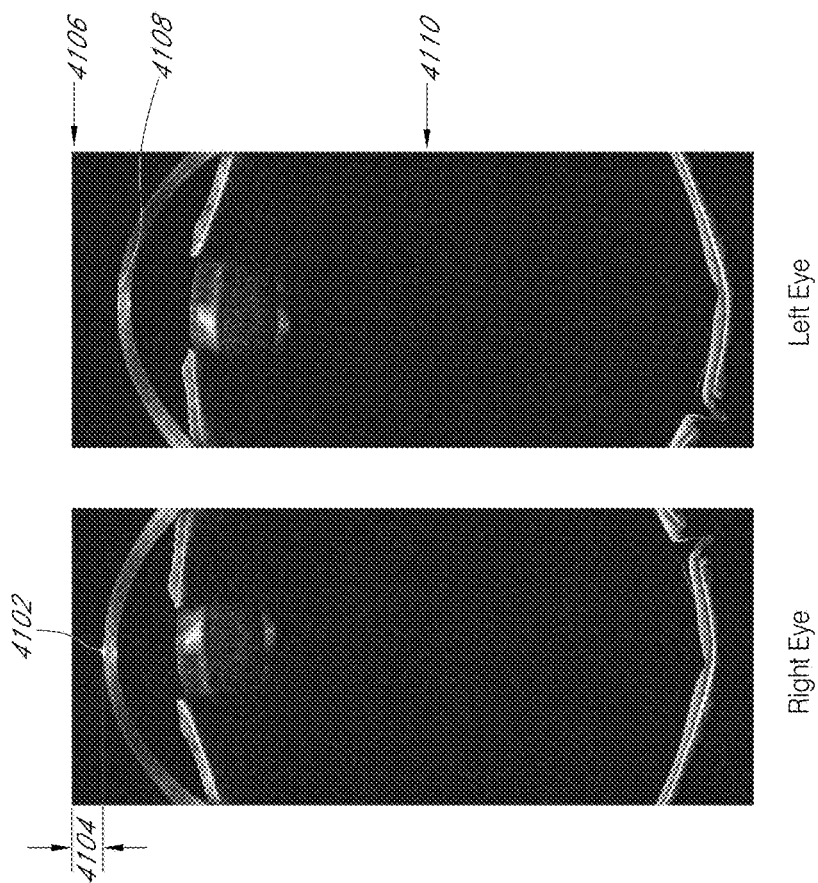
FIG. 41 illustrates an embodiment of an exophthalmometry test conducted using the OCT-based ophthalmic testing center system as described herein.

With reference to FIG. 41, exophthalmometry is generally a measurement of the extent of protrusion or bulging of the eyeballs from, or recession or sinking of the eyeballs into, the eye sockets. Protrusion of the eyes from the eye sockets can signify orbital diseases, such as thyroid eye disease. Recession of the eyes within the eye sockets may simply occur with age but may also be a condition that arises after trauma to the eyes and eye sockets. Exophthalmometry measurements are generally recorded in millimeters. Exophthalmometry testing can be performed on children and adults.

In reference to FIG. 41, the OCT-based ophthalmic testing center system can be configured to conduct exophthalmometry testing, which is generally a structural test that can employ OCT biomicroscopy. In certain embodiments, the OCT-based ophthalmic testing center system can be configured to conduct exophthalmometry testing in either a self-operated or self-administered fashion, or in an assisted fashion, in which someone other than the subject either partially or completely administers the test. The exophthalmometry test can be performed using either a binocular system or a monocular system. For example, the exophthalmometry test could be performed in both eyes simultaneously or first on one eye and then on the other eye. In certain embodiments, the OCT-based ophthalmic testing center system can comprise display devices configured to display stationary fixation targets, such as dots, crosses, circles, or other images during the test. The OCT-based ophthalmic testing center system can be configured to instruct (visually and/or audibly) the subject to look straight at the fixation targets throughout the examination. If larger than usual axial variations in corneal location are detected, the OCT-based ophthalmic testing center system can be configured to instruct (visually and/or audibly) the subject to stabilize the ocular cups on their orbital rims and repeat the test.

In certain embodiments, the OCT-based ophthalmic testing center system can be configured to capture high-speed bilateral B-scans that pass through the anterior segments of each eye, as described in more detail in the OCT bimicroscopy section above. The OCT-based ophthalmic testing center system can be configured to identify the anterior-most corneal interface, or apex of the cornea, 4102 by performing edge detection algorithms on the B-scans of the right and left eyes. For example, if radially-oriented B-scans are acquired, many of the scans may pass through the optical axis of the eye, which may coincide with the apex of the cornea. Alternatively, a 3D-OCT scan set can be obtained and the OCT-based ophthalmic testing center system can be configured to determine the apex of the cornea by comparing the anterior-most measurement from one or more scans in the 3D-OCT set.

Exophthalmometry measurements can be expressed as individual absolute measurements (in reference to the distal eye cup resting on the orbit) or as relative measurements (in reference to the other eye or in reference to a past examination). In general, absolute measurements reflect the distance to the front of the corneas from the orbital rim and relative measurements reflect the distance between the corneal apex of one eye and the corneal apex of the other eye. With reference to FIG. 41, in certain embodiments, an absolute exophthalmometry measurement can be obtained by subtracting the distance between the start of the anterior-most B-scan and the apex of the cornea (labeled as 4104)

from the z-offset value at the start of the B-scan set (labeled as 4106). Although various locations and distances have been illustrated on the left or right eye to reduce clutter, it should be appreciated that corresponding locations and distances (albeit not necessarily identical) exist with respect to the fellow eye. In various embodiments, an absolute exophthalmometry measurement can be obtained using the refined corneal boundary 4108 from segmentation of the 3D-OCT scan set, as described previously. Because the distance between the OCT instrument and the end of the eyecups (resting on the orbital rims) is also known, this distance can be subtracted from the absolute exophthalmometry measurements to calculate the distance between the front of the corneas and the orbital rims. FIG. 41 illustrates a potential anterior-posterior location of the orbital rim 4110 of the left eye. The relative exophthalmometry measurement can be calculated by subtracting the absolute exophthalmometry measurement for one eye from the absolute measurement for the fellow eye. For example, if one eye is 22 mm and the other eye is 19 mm, the relative exophthalmometry measurement is 3 mm.

In certain embodiments, the OCT-based ophthalmic detection center can be configured to record the interpupillary distance used to perform the exophthalmometry measurements. The interpupillary distance can then be used as a base measurement to provide consistency between successive tests. Other measurements and analyses can also be performed by the OCT-based ophthalmic detection center during exophthalmometry testing without departing from the spirit and/or scope of the invention. For example, exophthalmometry testing can be conducted while the subject is gazing in a direction other than straight ahead in order to measure exophthalmos due to extraocular muscle disorders.

In certain embodiments, the OCT-based ophthalmic testing center system can be configured to compare the exophthalmometry test data to a normative database to determine patterns of deviation and/or generate risk assessments and/or clinical reports. In various embodiments, the OCT-based ophthalmic testing center system can be configured to analyze, compare, and/or add the exophthalmometry test data to other data, such as the subject's ophthalmic history data that is stored on a subject's input card or retrieved from a historical database or other history-taking modules incorporated into the OCT-based ophthalmic testing center system. In certain embodiments, the OCT-based ophthalmic testing center system can be configured to automatically conduct an exophthalmometry test based on ophthalmic history. In various embodiments, if the patient has a family history of thyroid disease, or the patient complains of symptoms associated with thyroid disease, and such information is stored within the patient's ophthalmic history database, the OCT-based ophthalmic testing center system can be configured to automatically perform an exophthalmometry test. The OCT-based ophthalmic testing center system can be configured to generate various statistics based on the measured exophthalmometry test data, which may be combined with data from the normative database or historical data source.

With reference to FIG. 41, the OCT-based ophthalmic testing center system can be configured to output the results of and/or data from the exophthalmometry test. For example, the results can be outputted directly to the subject in a hardcopy (for example, printed card or paper) or electronic format (for example, on a display, via email, text messaged, or in a magnetic strip), stored locally on the device or on an attached computer, transmitted to a central database, or transmitted directly to the ordering or related physician.

Visual Acuity Testing

With reference to FIG. 42, in general, visual acuity testing measures a subject's acuteness or clarity of vision. In various embodiments, the OCT-based ophthalmic testing center system can be configured to conduct visual acuity testing, which is generally a functional test that can employ eye tracking methodologies, for example, tracking the foveae using foveal verification and/or foveal location. The eye tracking methodologies can also be used to determine the frequency, speed, and amplitude of foveal movements. In various embodiments, the eye tracking methodologies can be performed in real-time to modify test strategy.

In reference to FIG. 42, the OCT-based ophthalmic testing center system can be configured to conduct visual acuity testing in either a self-operated or self-administered fashion, or in an assisted fashion, in which someone other than the subject either partially or completely administers the test. The visual acuity testing can be performed on both eyes simultaneously or, first on one eye and then on the other eye. The OCT-based ophthalmic testing center system can be configured to control the optical distance between the subject's eye and the fixation targets by adjusting the vergence of the light from the fixation display (for example, by collimation or divergence). For example, the optical distance could be set at 14 inches to simulate reading, 30 inches to simulate computer use, 20 feet to equate with conventional visual acuity measurements, infinity, or at any other distance. As discussed previously, the OCT-based ophthalmic testing center system can be configured to correct for refractive error at the various optical distances.

The OCT-based ophthalmic testing center system can comprise display devices that can be configured to display alphanumeric symbols. With reference to FIG. 42, in various embodiments, the display devices of the OCT-based ophthalmic testing center system can be configured to display Snellen or ETDRS letters 4202 of varying size, contrast, spacing, font and color (with or without crowding bars for subjects with amblyopia). In another embodiment, the varying alphanumeric symbols can be displayed simultaneously (as illustrated in FIG. 42) or in serial fashion. In various embodiments the OCT-based ophthalmic testing center system can be configured to instruct (visually and/or audibly) the subject to read the alphanumeric symbols out loud (for example, via a speaker or headphone jack). The OCT-based ophthalmic testing center system can be configured to capture these verbalizations or voice responses using the OCT-based ophthalmic testing center system's microphone input device and process the verbalizations or voice responses using the OCT-based ophthalmic testing center system's processing unit and speech recognition software to determine letter recognition accuracy. If the subject's response is determined to be correct, the OCT-based ophthalmic testing center system can be configured to display another letter until the number of letters for that acuity level is satisfied. The OCT-based ophthalmic testing center system can be configured to then move on to smaller sets of letters until the user error reaches a predetermined threshold, such as 50% of the letters in a line. In various embodiments, the OCT-based ophthalmic testing center system can be configured to modify the test strategy in real-time based on a subject's performance in order to improve the quality and/or accuracy of the test. For example, the OCT-based ophthalmic testing center system can be configured to ask the user to repeat or retry incorrect letters. In various embodiments, the measurement of the subject's visual acuity that would be recorded and/or output by the OCT-based ophthalmic testing center system is the visual acuity corresponding to the last set of letters read that did not fail termination criteria.

In another embodiment, the OCT-based ophthalmic testing center system can be configured to display optokinetic targets, such as alternating light and dark lines 4204, 4206 that move laterally at a predetermined speed. This type of visual acuity testing advantageously provides a faster and more objective measure of visual acuity and does not require literacy or verbal feedback. The OCT-based ophthalmic testing center system can be configured to vary the size/frequency of the targets, the speed at which the targets move and the color/contrast of the targets to provide more detailed information about the acuity. The moving optokinetic targets can provide a stimulus that is configured to elicit responsive eye movements in subjects able to see that frequency of information.

In certain embodiments, OCT or non-OCT eye tracking modalities can be used to track fundus features, such as the fovea, to determine if the subject's eye is moving at the appropriate frequency and amplitude in response to the optokinetic stimulus. For example, the OCT-based ophthalmic testing center system can be configured to capture rapid small 3D-OCT scans, sparse 3D-OCT scans, or use non-OCT imaging, such as IR or SLO, to track the fovea or other fundus features, as described previously. In the absence of a foveal or optic nerve depression (for example, for subjects suffering from retinal disease), the relative slopes of the retinal surface can be used to indicate eye movement away from either the past fundus position or the position at the start of the test using mathematical registration algorithms. In certain embodiments, the OCT-based ophthalmic testing center system can be configured to determine the subject's visual acuity by calculating the minimum line width, maximum speed and/or the minimum color/contrast that elicits optokinetic responses.

With reference to FIG. 42, in certain embodiments, the OCT-based ophthalmic testing center system can be configured to use suppression stimuli 4208 (for example, small stationary features in the middle of the optokinetic field), to estimate visual acuity. For example, an OCT-based ophthalmic testing center system can be configured to increase the size of the suppression stimuli 4208 until the optokinetic response is suppressed. In certain embodiments, this threshold can be used by OCT-based ophthalmic testing center system to approximate visual acuity. Other measurements and analyses are possible without departing from the spirit and/or scope of the disclosure. For example, modification of the speed of movement for a given spatial frequency of optokinetic stimuli could be used to estimate reading speed. If processed in real-time, the OCT-based ophthalmic testing center system can be configured to use these data to augment additional test stimuli presented to the subject. For example, the OCT-based ophthalmic testing center system can be configured to first present optokinetic stimuli of progressively decreasing spatial frequency. If a subject's foveal response matches the optokinetic stimuli even at the smallest spatial frequency, the device can be configured to begin to present suppression stimuli at progressively larger sizes until the optokinetic response ceases.

As discussed in more detail above, at the conclusion of the visual acuity test for each eye, a set of reference 3D-OCT scans of each eye can advantageously be acquired that indicate the fundus position that is preferred for optimal visual acuity in each eye, or the "best fixating retina". The images of the preferred fundus position, or best fixating retina, can be stored and used as references for tests that require verification of foveal position or foveal localization, as described elsewhere. The reference images can be helpful in subjects with diseases that distort the normal anatomy of their foveal depression.

With reference to FIG. 42, the OCT-based ophthalmic testing center system can be configured to compare the visual acuity test data to a normative database to determine patterns of deviation and/or to generate risk assessments and/or clinical reports. In certain embodiments, the OCT-based ophthalmic testing center system can be configured to analyze, compare, and/or add the visual acuity test data to other data, such as the subject's ophthalmic history data that is stored on a subject's input card or retrieved from a historical database or other history-taking modules incorporated into the OCT-based ophthalmic testing center system. In certain embodiments, the OCT-based ophthalmic testing center system can be configured to automatically conduct a visual acuity test based on ophthalmic history and/or at the start of every round of ophthalmic testing to provide a set of reference images for use in eye tracking or fixation monitoring for subsequent ophthalmic tests, as discussed above. In another example, if the subject has a family history of poor visual acuity or the like, and such information is stored within the subject's ophthalmic history database, the OCT-based ophthalmic testing center system can be configured to automatically perform a visual acuity test. The OCT-based ophthalmic testing center system can be configured to generate various statistics based on the measured visual acuity test data, which may be combined with data from the normative database or historical data source.

With reference to FIG. 42, the OCT-based ophthalmic testing center system can be configured to output the results of and/or data from the visual acuity test. For example, the results can be outputted directly to the subject in a hardcopy (for example, printed card or paper) or electronic format (for example, on a display, via email, text messaged, or in a magnetic strip), stored locally on the device or on an attached computer, transmitted to a central database, or transmitted directly to the ordering or related physician.

Photostress Recovery Time Test

In general, photostress recovery time is a test that is hypothesized to differentiate retinal disease from optic nerve disease. In various embodiments, the OCT-based ophthalmic testing center system can be configured to conduct photostress recovery time testing, which is generally a functional test that can employ eye tracking methodologies, for example, tracking the foveae using foveal verification and/or foveal location. The eye tracking methodologies can also be used to determine the frequency, speed, and amplitude of foveal movements.

In various embodiments, the OCT-based ophthalmic testing center system can be configured to conduct photostress recovery time testing in either a self-operated or self-administered fashion, or in an assisted fashion, in which someone other than the subject either partially or completely administers the test. The photostress response time testing can be performed on both eyes simultaneously or, first on one eye and then on the other eye. The OCT-based ophthalmic testing center system can be configured to control the optical distance between the subject's eye and the fixation targets by adjusting the vergence of the light from the fixation display (for example, by collimation or divergence). For example, the optical distance could be set at 14 inches to simulate reading, 30 inches to simulate computer use, 20 feet to equate with conventional visual acuity measurements, infinity, or at any other distance. As discussed previously, the OCT-based ophthalmic testing center system can be configured to correct for refractive error at the various optical distances. In various embodiments, the OCT-based ophthalmic testing center system can be configured to measure visual acuity by presenting letters from a Snellen or ETDRS chart and measuring the letter accuracy based on the subject's verbal responses, as described in more detail above. The OCT-based ophthalmic testing center system can then be configured to flash one or both eyes with a bright stimulus, such as a bright white display for a predetermined exposure time (for example, at least 0.5 seconds, 1 second, 5 seconds, ten seconds, or 30 seconds), and then measure the time it takes for the subject to read one line of visual acuity above their previous best recorded visual acuity.

In another embodiment, the OCT-based ophthalmic testing center system can be configured to measure visual acuity using optokinetic stimuli, as described in more detail above. The OCT-based ophthalmic testing center system can then be configured to flash one or both eyes with a bright stimulus, such as a bright white display for a predetermined exposure time (for example, ten seconds), and then measure the time that it takes for the subject to respond to optokinetic stimuli slightly larger than the subject's threshold response from the visual acuity test. In yet another embodiment, the OCT-based ophthalmic testing center system can be configured to conduct photostress recovery time testing independently of visual acuity testing using visual acuity results stored from a previous visual acuity test. Other measurements and analyses are possible without departing from the spirit and/or scope of the disclosure. If processed in real-time, the OCT-based ophthalmic testing center system can be configured to use these measurements to augment additional test stimuli presented to the subject. For example, if, after a certain period of time, the subject is still unable to read one level above their best visual acuity, the OCT-based ophthalmic testing center system can be configured to begin to increase the size of the stimulus to determine at what point the subject will respond to the stimulus. In certain embodiments, the OCT-based ophthalmic testing center system can also be configured to repeat the test again with this larger stimulus or decrease the exposure time of the bright stimulus to the subject's eye.

In various embodiments, the OCT-based ophthalmic testing center system can be configured to compare the photostress response time test data to a normative database to determine patterns of deviation and/or to generate risk assessments and/or clinical reports. In certain embodiments, the OCT-based ophthalmic testing center system can be configured to analyze, compare, and/or add the photostress response time test data to other data, such as the subject's ophthalmic history data that is stored on a subject's input card or retrieved from a historical database or other history-taking modules incorporated into the OCT-based ophthalmic testing center system. In certain embodiments, the OCT-based ophthalmic testing center system can be configured to automatically conduct a photostress response time test based on ophthalmic history. In another example, if the subject has a family history of macular disease or the like, and such information is stored within the subject's ophthalmic history database, the OCT-based ophthalmic testing center system can be configured to automatically perform a photostress response time test. The OCT-based ophthalmic testing center system can be configured to generate various statistics based on the measured photostress response time test data, which may be combined with data from the normative database or historical data source.

The OCT-based ophthalmic testing center system can be configured to output the results of and/or data from the photostress response time test. For example, the results can be outputted directly to the subject in a hardcopy (for example, printed card or paper) or electronic format (for example, on a display, via email, text messaged, or in a magnetic strip), stored locally on the device or on an attached computer, transmitted to a central database, or transmitted directly to the ordering or related physician.

Contrast Sensitivity Test

Figure 43:
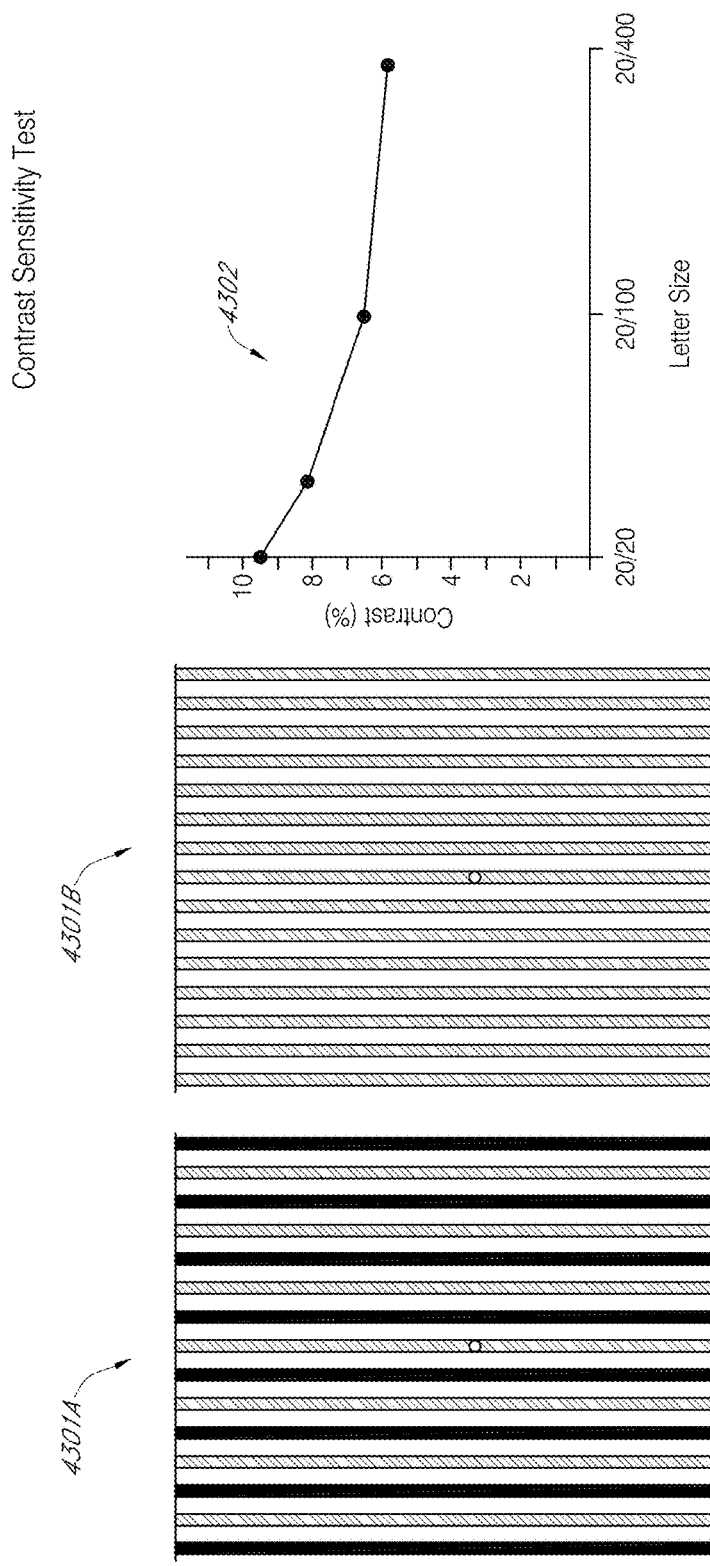
FIG. 43 illustrates an embodiment of a contrast sensitivity test conducted using the OCT-based ophthalmic testing center system as described herein and an embodiment of a graph illustrating output from the contrast sensitivity test.

With reference to FIG. 43, in general contrast sensitivity is a functional parameter that can indicate the presence of macular disease and/or progression of diseases, for example, age-related macular degeneration. Subjects with contrast sensitivity generally have difficulty distinguishing objects of similar contrast.

In reference to FIG. 43, the OCT-based ophthalmic testing center system can be configured to conduct a contrast sensitivity test by presenting objects to subjects having various contrast, for example, charts having circles with bars of alternating grays and/or specific orientations that can be identified by the user. In various embodiments, the OCT-based ophthalmic testing center system can be configured to use the same methodologies described previously for visual acuity testing except with modification of the contrast between letters and/or numbers and/or the background and/or between bars or lines on the optokinetic stimuli. The OCT-based ophthalmic testing center system can be configured to control the optical distance between the subject's eye and the fixation targets by adjusting the vergence of the light from the fixation display (for example, by collimation or divergence). For example, the optical distance could be set at 14 inches to simulate reading, 30 inches to simulate computer use, 20 feet to equate with conventional visual acuity measurements, infinity, or at any other distance. As discussed previously, the OCT-based ophthalmic testing center system can be configured to correct for refractive error at the various optical distances. In various embodiments, the OCT-based ophthalmic testing center system can be configured to use previously generated visual acuity results and/or other test data results as a starting point for contrast-based measurements. For example, the OCT-based ophthalmic testing center system can be configured to display a stimulus and/or image having light gray and/or dark gray bars instead of using black and white bars. FIG. 43 illustrates one embodiment of an image 4301A comprising bars of three varying contrasts (the hatched bar representing a middle contrast) and one image 4301B illustrating another embodiment of an image comprising bars of two varying contrasts (for example, light gray and dark gray or black and white). In various embodiments, the OCT-based ophthalmic testing center system can be configured to conduct the contrast sensitivity test using a variety of stimuli sizes, frequencies, and/or velocities. In various embodiments, the results from the contrast sensitivity test could be a multitude of visual acuity measurements at various contrast and color settings.

With reference to FIG. 43, in various embodiments the OCT-based ophthalmic testing center system can be configured to instruct (visually and/or audibly) the subject to look at the image and/or stimuli being presented on the display devices of the OCT-based ophthalmic testing center system. In various embodiments, the OCT-based ophthalmic testing center system can be configured to instruct (visually and/or audibly) the subject to either press a button and/or respond verbally by saying 'Yes' and/or the letter shown in the image when appreciated or perceived by the subject. Button presses and/or verbal response can be stored by the OCT-based ophthalmic testing center system for tabulation and/or analysis. The OCT-based ophthalmic testing center system can be configured to capture these verbalizations or verbal responses using the OCT-based ophthalmic testing center system's microphone input, and these verbalizations or voice responses can be processed using the OCT-based ophthalmic testing center system's CPU and speech recognition software to determine the nature and/or accuracy of the response, for example, did the subject say the correct letter shown in the image.

With reference to FIG. 43, measurements made with the contrast sensitivity test can include, but are not be limited to, the lowest contrast at which objects, such as bars, can be seen relative to their backgrounds; the parameters, such as spatial frequency, for the objects in each location to be seen by the subject; or incremented scores of values, such as 0.05 log units for each correctly answered letter. The OCT-based ophthalmic testing center system can be configured to tabulate and/or store the results of the contrast sensitivity test. In various embodiments, the OCT-based ophthalmic testing center can be configured to output a report and/or graphical representation of the tabulated results of the contrast sensitivity test. For example, the graph 4302 illustrates a line graphs displaying the measurements of a contrast sensitivity test conducted by the OCT-based ophthalmic testing center system. In the example, the graph 4302 illustrates contrast percentage versus letter size (using standard visual acuity designations). A user, subject, and/or patient associated with these contrast sensitivity results cannot generally see small letters without higher contrast. In general, users, subjects, and/or patients associated with graphs with substantially flat slopes can see any size letter in any contrast level. Other measurements and analyses are possible. If processed in real-time, the OCT-based ophthalmic testing center system can be configured to use these data to augment additional test stimuli presented to the subject.

With reference to FIG. 43, in various embodiments, the OCT-based ophthalmic testing center system can be configured to compare the contrast sensitivity test data to a normative database to determine patterns of deviation and/or generate risk assessments and/or clinical reports. In various embodiments, the OCT-based ophthalmic testing center system can be configured to analyze, compare, and/or add the contrast sensitivity test data to other data, such as the subject's ophthalmic history data that is stored on a subject's input card or retrieved from a historical database or other history-taking modules incorporated into the OCT-based ophthalmic testing center system. In various embodiments, the OCT-based ophthalmic testing center system can be configured to automatically conduct a contrast sensitivity test based on ophthalmic history. For example, if the subject complains of distorted vision or the like, the OCT-based ophthalmic testing center system can be configured to record and/or store such information so that the OCT-based ophthalmic testing center system can be configured to automatically perform a contrast sensitivity test based on the record. In another example, if the patient has a family history of contrast sensitivity issues or the like, and such information is stored within the subject's ophthalmic history database, the OCT-based ophthalmic testing center system can be configured to automatically perform a contrast sensitivity test. The OCT-based ophthalmic testing center system can be configured to generate various statistics based on the measured contrast sensitivity test data, which may be combined with data from the normative database or historical data source.

With reference to FIG. 43, the OCT-based ophthalmic testing center system can be configured to output the results of and/or data from the contrast sensitivity test. For example, the results can be outputted directly to the subject in a hardcopy (for example, printed card or paper) or electronic format (for example, on a display, via email, text messaged, or in a magnetic strip), stored locally on the device or on an attached computer, transmitted to a central database, or transmitted directly to the ordering or related physician.

Fixation Stability Test

Figure 44:
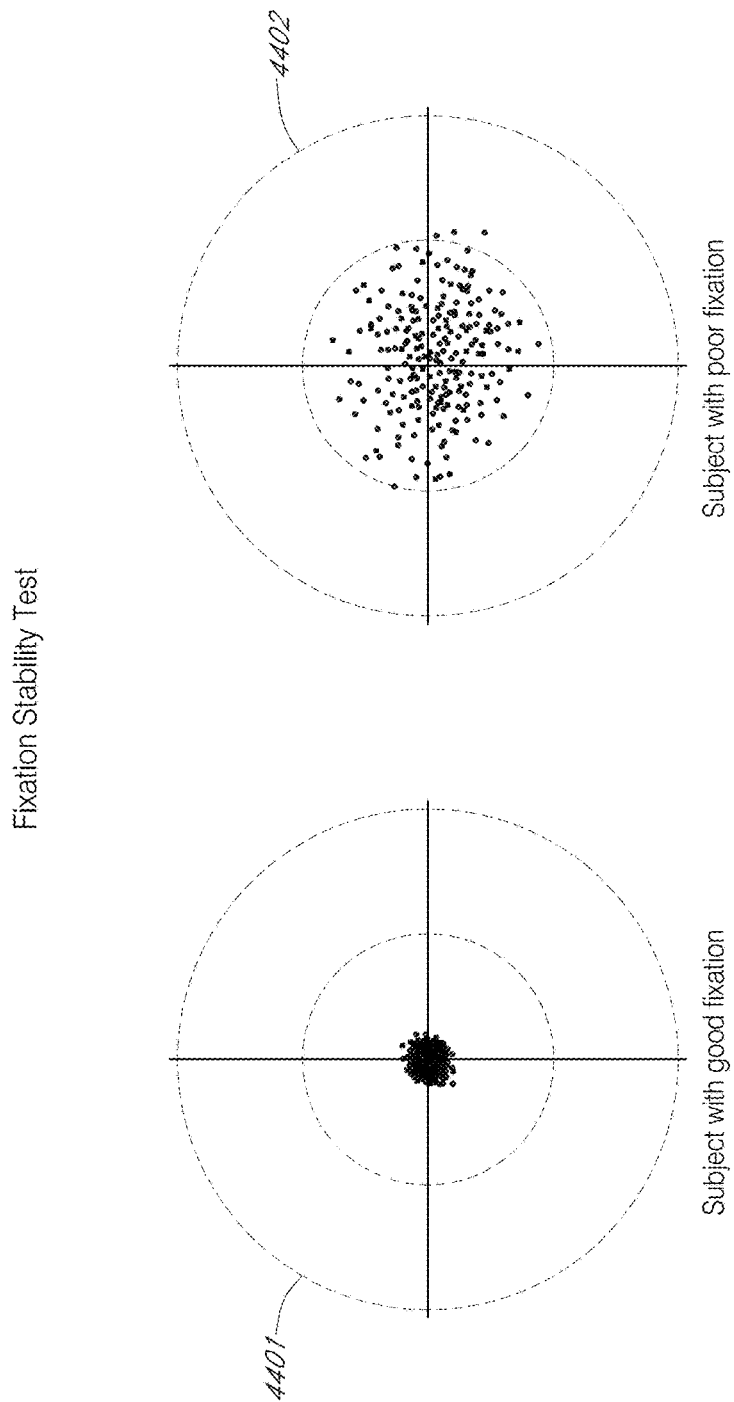
FIG. 44 illustrates various embodiments of output generated by performing fixation stability tests using the OCT-based ophthalmic testing center system as described herein.

With reference to FIG. 44, in general, fixation stability is a diagnostic test that can be correlated with underlying function. Subjects with good vision are generally able to hold steady fixation on a small target without losing track of the target and/or wandering too far afield from the target. Subjects with poor visual acuity generally have more difficulty seeing small targets and/or may have many points of equally good vision in their eye (for example, the small area with the best vision is apparently damaged), which causes their fixation to meander.

In reference to FIG. 44, in various embodiments, the OCT-based ophthalmic testing center system can be configured to conduct fixation stability testing, which generally is a functional test that can employ eye tracking methodologies, for example, tracking the fovea using foveal verification and/or foveal location. The OCT-based ophthalmic testing center system can be configured to conduct fixation stability testing in either a self-operated or self-administered fashion, or in an assisted fashion with someone other than the subject either partially or completely administers the test. The fixation stability test can be performed on both eyes simultaneously (a binocular examination) or first on one eye and then on the other eye. The OCT-based ophthalmic testing center system can comprise display devices configured to display stationary fixation targets, for example, dots, crosses, circles or other images. The OCT-based ophthalmic testing center system can be configured to control the optical distance between the subject's eye and the fixation targets by adjusting the vergence of the light from the fixation display (for example, by collimation or divergence). For example, the optical distance could be set at 14 inches to simulate reading, 30 inches to simulate computer use, 20 feet to equate with conventional visual acuity measurements, infinity, or at any other distance. As discussed previously, the OCT-based ophthalmic testing center system can be configured to correct for refractive error at the various optical distances.

With reference to FIG. 44, to conduct the fixation stability test, the OCT-based ophthalmic testing center system can be configured to instruct (visually and/or audibly) the subject to focus on the fixation target for a period of time while the OCT-based ophthalmic testing center system tracks the movement of the eye(s) during the period. In various embodiments, the OCT-based ophthalmic testing center system can be configured to conduct the fixation stability testing by presenting the subject with a steady target and instructing the subject to maintain steady fixation while simultaneously capturing high speed, small 3D-OCT scans or sparse 3D-OCT scans across the fundus as described herein. The OCT-based testing center system can be configured to capture and/or record relative movements and/or movements relative to the starting position of the fundus as a point cloud 4401, 4402 of interval movements. In various embodiments, the OCT-based ophthalmic testing center system can be configured to monitor and/or track the subject's gaze or the direction of the subject's eyes with non-OCT imaging modalities by tracking detectable structures within the eye, for example, the fovea or other features or sets of features with unique or identifiable patterns of intensity. Non-OCT imaging modalities include, without limitation, infrared (IR) imaging or scanning laser ophthalmoscopy (SLO) imaging. The OCT-based ophthalmic testing center system can also be configured to monitor the subject's gaze by tracking detectable structures within the eye using small 3D-OCT scans centered under the image of the fixation target on the retina. In various embodiments, the OCT-based ophthalmic testing center system can be configured to use foveal verification in cases where the foveal location may be known or closely approximated, and/or the OCT-based ophthalmic testing center system can be configured to use foveal location when the fovea cannot be located. For subjects suffering from retinal disease, the OCT-based ophthalmic testing center system can be configured to track other non-foveal detectable structures with OCT to the subject's fixation stability during the fixation stability test. Various statistics could be calculated from this point cloud including total distance moved per unit time, average distance from centroid, standard deviation of interval movements, or the like. Other measurements and/or analyses are possible.

In reference to FIG. 44, in various embodiments, other analyses can comprise edge detection of the vitreoretinal interface to detect the foveal depression, edge detection of the vitreoretinal interface and retinal pigment epithelium (RPE) to determine retinal thickness, edge detection of other retinal features, or topographic or thickness slope calculations followed by 2D registration to previous maps, among other analyses. In the absence of a foveal or optic nerve depression, the OCT-based ophthalmic testing center system can be configured to use relative slopes of the retinal surface to determine and/or indicate eye movement away from either the past fundus position or the position at the start of the test.

With reference to FIG. 44, in various embodiments, the OCT-based ophthalmic testing center system can be configured to compare the fixation stability test data to a normative database to determine patterns of deviation and/or generate risk assessments and/or clinical reports. In various embodiments, the OCT-based ophthalmic testing center system can be configured to analyze, compare, and/or add the fixation stability test data to other data, such as the subject's ophthalmic history data that is stored on a subject's input card or retrieved from a historical database or other history-taking modules incorporated into the OCT-based ophthalmic testing center system. In various embodiments, the OCT-based ophthalmic testing center system can be configured to automatically conduct a fixation stability test based on ophthalmic history. For example, if the subject has a history of fixation instability or the like, the OCT-based ophthalmic testing center system can be configured to record and/or store such information so that the OCT-based ophthalmic testing center system can be configured to automatically perform a fixation stability test based on the record. In another example, if the patient has a complaint of blurred vision or the like, and such information is stored within the subject's ophthalmic history database, the OCT-based ophthalmic testing center system can be configured to automatically perform a fixation stability test. The OCT-based ophthalmic testing center system can be configured to generate various statistics based on the measured fixation stability test data, which may be combined with data from the normative database or historical data source.

In reference to FIG. 44, in various embodiments, the OCT-based ophthalmic testing center system can be configured to output the results of and/or data from the fixation stability test. For example, the results can be outputted directly to the subject in a hardcopy (for example, printed card or paper) or electronic format (for example, on a display, via email, text messaged, or in a magnetic strip), stored locally on the device or on an attached computer, transmitted to a central database, or transmitted directly to the ordering or related physician.

Perimetry—Confrontation Visual Field Test

Figure 45:
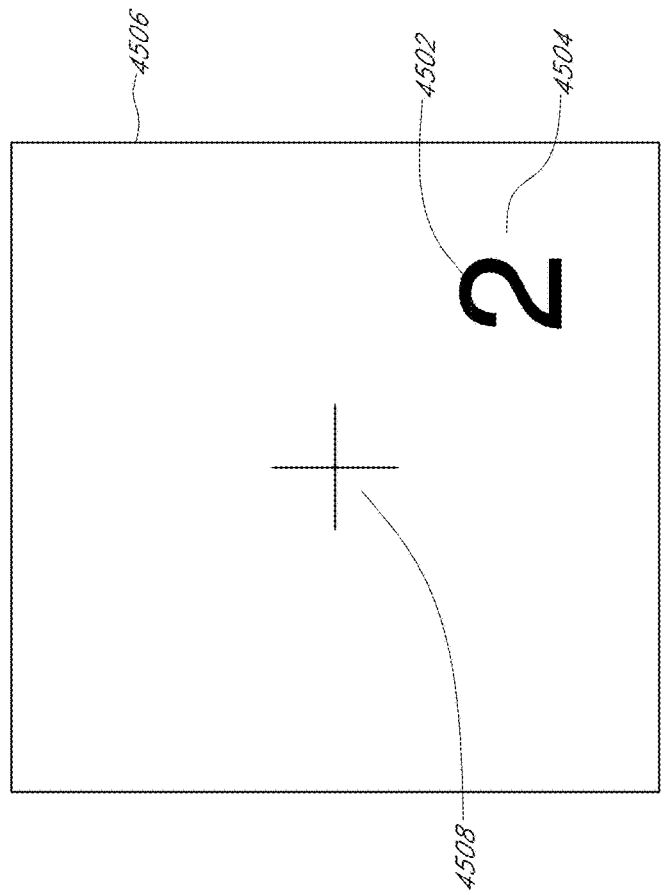
FIG. 45 illustrates an embodiment of a confrontation visual field perimetry test conducted using the OCT-based ophthalmic testing center system as described herein.
Figure 46:
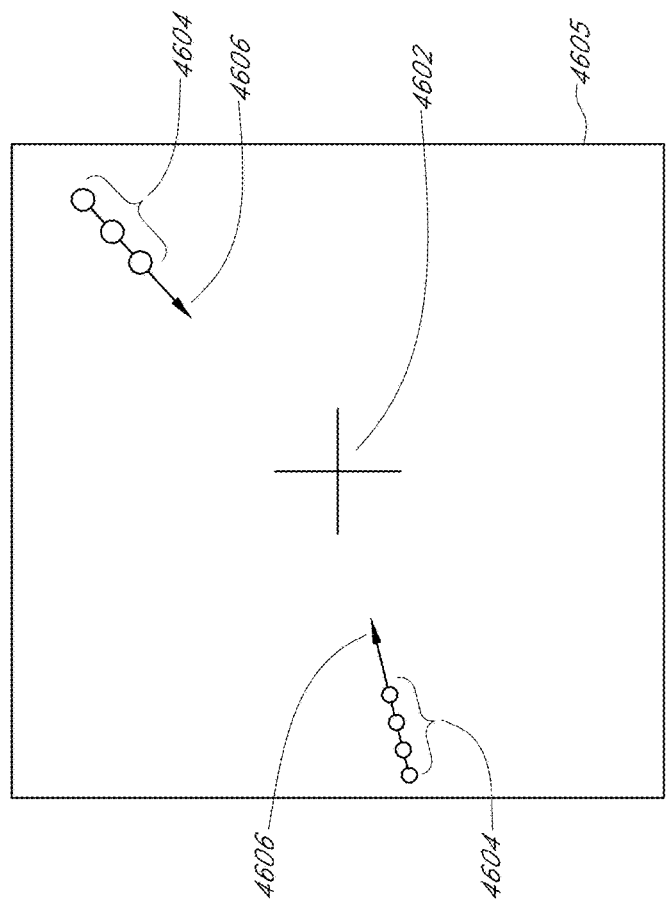
FIG. 46 illustrates an embodiment of a kinetic preimetry test conducted using the OCT-based ophthalmic testing center system as described herein.
Figure 47:
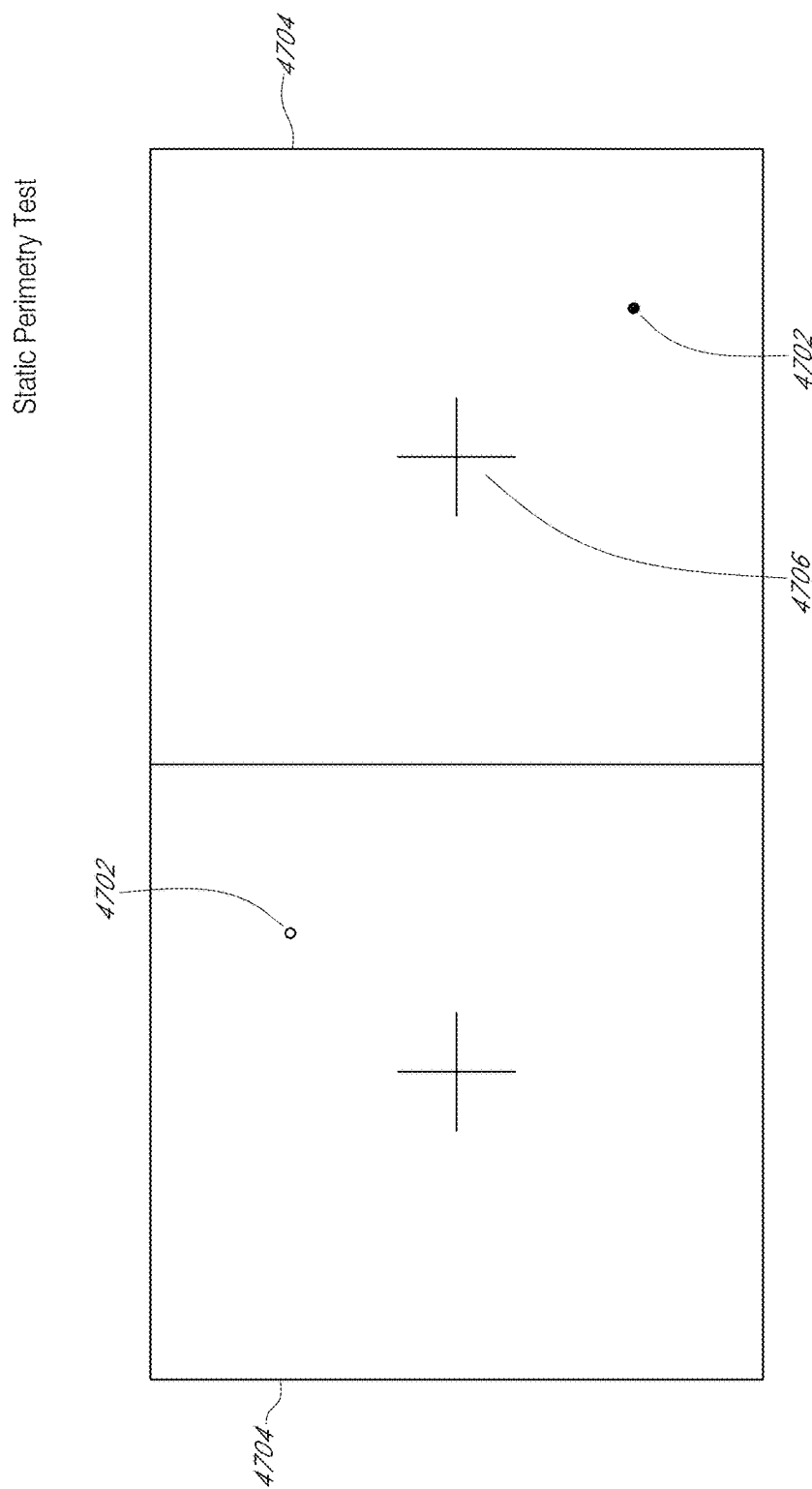
FIG. 47 illustrates an embodiment of a static perimetry test conducted using the OCT-based ophthalmic testing center system as described herein.

With reference to FIG. 45, FIG. 46 and FIG. 47, in general, perimetry, or visual field testing, can be divided into several categories. One form of perimetry is called confrontation visual fields. In various embodiments, the OCT-based ophthalmic testing center system can be configured to conduct confrontation visual fields testing, which is generally a functional test that can employ eye tracking methodologies, for, example, tracking the fovea using foveal verification and/or foveal location.

In reference to FIG. 45, in various embodiments, the OCT-based ophthalmic testing center system can be configured to conduct confrontation visual fields testing in either a self-operated or self-administered fashion, or in an assisted fashion with someone other than the subject either partially or completely administers the test. The confrontation visual fields test can be performed on both eyes simultaneously (a binocular examination) or, first on one eye and then on the other eye. The OCT-based ophthalmic testing center system can comprise display devices configured to first display stationary fixation targets 4508, for example, dots, crosses, circles, or the like. The OCT-based ophthalmic testing center system can be configured to control the optical distance between the subject's eye and the fixation targets by adjusting the vergence of the light from the fixation display (for example, by collimation or divergence). For example, the optical distance could be set at 14 inches to simulate reading, 30 inches to simulate computer use, 20 feet to equate with conventional visual acuity measurements, infinity, or at any other distance. As discussed previously, the OCT-based ophthalmic testing center system can be configured to correct for refractive error at the various optical distances.

With reference to FIG. 45, the OCT-based ophthalmic testing center system can be configured to conduct confrontation visual fields testing by displaying and/or presenting transient objects 4502, for example, dots, letters, numbers, or the like, of varying intensity, size, color and contrast, that can be displayed in, for example, one of six or more locations 4504 around the subject's visual field 4506. In various embodiments the OCT-based ophthalmic testing center system can be configured to instruct (visually and/or audibly) the subject to look straight at the fixation targets 4508 throughout the examination and/or to either press a button and/or respond verbally by saying 'Yes' or the like when a transient stimulus/object is appreciated or perceived by the subject. If transient stimuli/objects, for example, a dot, is displayed, the OCT-based ophthalmic testing center system can be configured to expect a button press and/or can be configured to store the response for tabulation. If transient stimuli/objects, for example, numbers or letters, are displayed, the OCT-based ophthalmic testing center system can be configured to expect verbal responses and/or can be configured to receive using a microphone input within and/or connected to the OCT-based ophthalmic testing center system device and/or processed by software, for example, speech recognition software, to determine the accuracy of the response.

To ensure that the subject is not merely looking at peripheral areas of the display device with their central vision but rather is using the subject's peripheral vision to detect and/or perceive the stimuli, the OCT-based ophthalmic testing center system can be configured to monitor and/or track the subject's gaze or the direction of the subject's eyes with non-OCT imaging modalities by tracking detectable structures within the eye, for example, the fovea or other features or sets of features with unique or identifiable patterns of intensity. Non-OCT imaging modalities include without limitation infrared (IR) imaging or scanning laser ophthalmoscopy (SLO) imaging. The OCT-based ophthalmic testing center system can also be configured to monitor the subject's gaze by tracking detectable structures within the eye using small 3D-OCT scans centered under the image of the central fixation target on the retina and/or by using sparse 3D-OCT scans across the fundus. In various embodiments, the OCT-based ophthalmic testing center system can be configured to use foveal verification in cases where the foveal location may be known or closely approximated, and/or the OCT-based ophthalmic testing center system can be configured to use foveal location when the fovea cannot be located. For subjects suffering from retinal disease, the OCT-based ophthalmic testing center system can be configured to track other non-foveal detectable structures with OCT to ensure their positions are unchanged during the confrontation visual fields test.

In reference to FIG. 45, in various embodiments, the OCT-based ophthalmic testing center system can be configured to conduct the eye tracking scans before each stimulus is presented to the subject, and/or analyzed either after completion of the entire test to develop a test reliability score. In various embodiments, the eye tracking scans are completed in real-time during the confrontation visual fields test so that presentation of the stimulus can be contingent upon central fixation. This analysis can comprise edge detection of the vitreoretinal interface to detect the foveal depression, edge detection of the vitreoretinal interface and retinal pigment epithelium (RPE) to determine retinal thickness, edge detection of other retinal features, or topographic or thickness slope calculations followed by 2D registration to previous maps, among other analyses. If the subject is found to be looking away from the central fixation target, the OCT-based ophthalmic testing center system can be configured to verbally or visually remind the subject to look at the fixation target. The OCT-based ophthalmic testing center system can be configured to withhold stimuli if the fovea is not found to be located centrally or an eye movement is discovered by comparison of other retinal features between stimuli. In various embodiments, the OCT-based ophthalmic testing center system can be configured to turn off a stimulus if it senses eye movement during stimulus display and movement. In the absence of a foveal or optic nerve depression, the OCT-based ophthalmic testing center system can be configured to use relative slopes of the retinal surface to determine and/or indicate eye movement away from either the past fundus position or the position at the start of the test.

With reference to FIG. 45, measurements made with the confrontation visual fields test can include, but are not be limited to, a visual field map indicating the accuracy of responses in all displayed locations, the parameters for the stimuli required in each location to be seen by the subject, the number of positive responses for displayed stimuli (true positives), the number of positive responses for undisplayed stimuli or stimuli intended to fall into the physiologic blind spot (false positives), and the number of failed responses for displayed stimuli (false negatives). Other measurements and analyses are possible. If processed in real-time, the OCT-based ophthalmic testing center system can be configured to use these data to augment additional test stimuli presented to the subject.

With reference to FIG. 45, in various embodiments, the OCT-based ophthalmic testing center system can be configured to compare the confrontation visual fields test data to a normative database to determine patterns of deviation and/or generate risk assessments and/or clinical reports. In various embodiments, the OCT-based ophthalmic testing center system can be configured to analyze, compare, and/or add the confrontation visual fields test data to other data, such as the subject's ophthalmic history data that is stored on a subject's input card or retrieved from a historical database or other history-taking modules incorporated into the OCT-based ophthalmic testing center system. In various embodiments, the OCT-based ophthalmic testing center system can be configured to automatically conduct a confrontation visual fields test based on ophthalmic history. For example, if the subject has glaucoma or the like, the OCT-based ophthalmic testing center system can be configured to record and/or store such information so that the OCT-based ophthalmic testing center system can be configured to automatically perform a confrontation visual fields test based on the record. In another example, if the patient has a family history of glaucoma or the like, and such information is stored within the subject's ophthalmic history database, the OCT-based ophthalmic testing center system can be configured to automatically perform a confrontation visual fields test. The OCT-based ophthalmic testing center system can be configured to generate various statistics based on the measured confrontation visual fields test data, which may be combined with data from the normative database or historical data source.

With reference to FIG. 45, the OCT-based ophthalmic testing center system can be configured to output the results of and/or data from the confrontation visual fields test. For example, the results can be outputted directly to the subject in a hardcopy (for example, printed card or paper) or electronic format (for example, on a display, via email, text messaged, or in a magnetic strip), stored locally on the device or on an attached computer, transmitted to a central database, or transmitted directly to the ordering or related physician.

Kinetic Perimetry Test

With reference to FIG. 46, in general, kinetic perimetry is a test used for monitoring of neurologic, neuro-ophthalmic, degenerative and/or congenital ophthalmic conditions. In various embodiments, the OCT-based ophthalmic testing center system can be configured to conduct kinetic perimetry testing, which is generally a functional test that can employ eye tracking methodologies, for example, tracking the fovea using foveal verification and/or foveal location. The OCT-based ophthalmic testing center system can conduct the kinetic perimetry testing in either a self-operated or self-administered fashion, or in an assisted fashion with someone other than the subject either partially or completely administering the test. The kinetic perimetry test can be performed on both eyes simultaneously (a binocular examination) or, first on one eye and then on the other eye. The OCT-based ophthalmic testing center system can comprise display devices configured to first display stationary fixation targets 4602, for example, dots, crosses, circles, and/or the like. The OCT-based ophthalmic testing center system can be configured to control the optical distance between the subject's eye and the fixation targets by adjusting the vergence of the light from the fixation display (for example, by collimation or divergence). For example, the optical distance could be set at 14 inches to simulate reading, 30 inches to simulate computer use, 20 feet to equate with conventional visual acuity measurements, infinity, or at any other distance. As discussed previously, the OCT-based ophthalmic testing center system can be configured to correct for refractive error at the various optical distances.

In reference to FIG. 46, the OCT-based ophthalmic testing center system can be configured to conduct the kinetic perimetry test by displaying and/or presenting transient objects 4604, for example, dots or the like, in various locations around the subject's visual field 4605. In various embodiments, the OCT-based ophthalmic testing center system can be configured to present the transient objects in varying intensity, size, color and contrast that can be shown to move, typically from the periphery to the center 4606, but also from the center to periphery in the case of blindspot testing. For example, in some embodiments, the transient objects 4606 can be presented as light objects on a darker field 4605 and in other embodiments, the transient objects 4606 can be presented as dark objects on a lighter field 4605. In various embodiments, the OCT-based ophthalmic testing center system can be configured to instruct (visually and/or audibly) the subject to look straight at the fixation targets throughout the examination and to either press a button and/or respond verbally by saying a 'Yes' when a transient stimulus is appreciated or perceived by the subject. Button presses and/or verbal response can be stored by the OCT-based ophthalmic testing center system for tabulation and/or analysis. The OCT-based ophthalmic testing center system can be configured to capture these verbalizations or verbal responses using the OCT-based ophthalmic testing center system's microphone input, and these verbalizations or voice responses can be processed using the OCT-based ophthalmic testing center system's CPU and speech recognition software to determine the nature of the response.

To ensure that the subject is not merely looking at peripheral areas of the vision area but rather is using the subject's peripheral vision to detect and/or perceive the stimuli, the OCT-based ophthalmic testing center system can be configured to monitor and/or track the subject's gaze or the direction of the subject's eyes with non-OCT imaging modalities by tracking detectable structures within the eye, for example, the fovea or other features or sets of features with unique or identifiable patterns of intensity. Non-OCT imaging modalities include without limitation infrared (IR) imaging or scanning laser ophthalmoscopy (SLO) imaging. The OCT-based ophthalmic testing center system can also be configured to monitor the subject's gaze by tracking detectable structures within the eye using small 3D-OCT centered under the image of the central fixation target on the retina and/or by using sparse 3D-OCT scans across the fundus. In various embodiments, the OCT-based ophthalmic testing center system can be configured to use foveal verification in cases where the foveal location may be known or closely approximated, and/or the OCT-based ophthalmic testing center system can be configured to use foveal location when the fovea cannot be located. For subjects suffering from retinal disease, the OCT-based ophthalmic testing center system can be configured to track other non-foveal detectable structures with OCT to ensure their positions are unchanged during the kinetic perimetry test.

In various embodiments, the OCT-based ophthalmic testing center system can be configured to conduct the eye tracking scans before each stimulus is presented to the subject, and/or analyzed either after completion of the entire test to develop a test reliability score. In various embodiments, the eye tracking scans are completed in real-time during the kinetic perimetry test so that presentation of the stimulus would be contingent upon central fixation. This analysis can comprise edge detection of the vitreoretinal interface to detect the foveal depression, edge detection of the vitreoretinal interface and retinal pigment epithelium (RPE) to determine retinal thickness, edge detection of other retinal features, or topographic or thickness slope calculations followed by 2D registration to previous maps, among other analyses. If the subject is found to be looking away from the central fixation target, the OCT-based ophthalmic testing center system can be configured to verbally or visually remind the subject to look at the fixation target. The OCT-based ophthalmic testing center system can be configured to withhold stimuli if the fovea is not found to be located centrally or an eye movement is discovered by comparison of other retinal features between stimuli. In various embodiments, the OCT-based ophthalmic testing center system can be configured to turn off a stimulus if it sensed eye movement during stimulus display and movement. In the absence of a foveal or optic nerve depression, the OCT-based ophthalmic testing center system can be configured to use relative slopes of the retinal surface to determine and/or indicate eye movement away from either the past fundus position or the position at the start of the test.

With reference to FIG. 46, measurements made with the kinetic perimetry test can include, but are not be limited to, a visual field map indicating the accuracy of responses in all displayed locations, the parameters for the stimuli required in each location to be seen by the subject, the number of positive responses for displayed stimuli (true positives), the number of positive responses for undisplayed stimuli or stimuli intended to fall into the physiologic blind spot (false positives), and the number of failed responses for displayed stimuli (false negatives). Other measurements and analyses are possible. If processed in real-time, the OCT-based ophthalmic testing center system can be configured to use these data to augment additional test stimuli presented to the subject.

With reference to FIG. 46, in various embodiments, the OCT-based ophthalmic testing center system can be configured to compare the kinetic perimetry test data to a normative database to determine patterns of deviation and/or generate risk assessments and/or clinical reports. In various embodiments, the OCT-based ophthalmic testing center system can be configured to analyze, compare, and/or add the kinetic perimetry test data to other data, such as the subject's ophthalmic history data that is stored on a subject's input card or retrieved from a historical database or other history-taking modules incorporated into the OCT-based ophthalmic testing center system. In various embodiments, the OCT-based ophthalmic testing center system can be configured to automatically conduct a kinetic perimetry test based on ophthalmic history. For example, if the subject complains of night blindness, the OCT-based ophthalmic testing center system can be configured to record and/or store such information so that the OCT-based ophthalmic testing center system can be configured to automatically perform a kinetic perimetry test based on the recorded complaint. In another example, if the patient has a family history of inherited retinal blindness or the like, and such information is stored within the subject's ophthalmic history database, the OCT-based ophthalmic testing center system can be configured to automatically perform a kinetic perimetry test. The OCT-based ophthalmic testing center system can be configured to generate various statistics based on the measured kinetic perimetry test data, which may be combined with data from the normative database or historical data source.

With reference to FIG. 46, the OCT-based ophthalmic testing center system can be configured to output the results of and/or data from the kinetic perimetry test. For example, the results can be outputted directly to the subject in a hardcopy (for example, printed card or paper) or electronic format (for example, on a display, via email, text messaged, or in a magnetic strip), stored locally on the device or on an attached computer, transmitted to a central database, or transmitted directly to the ordering or related physician.

Static Perimetry Test

With reference to FIG. 47, in general static perimetry is a test for glaucoma monitoring. In various embodiments, the OCT-based ophthalmic testing center system can be configured to conduct static perimetry testing, which is generally a functional test that can employ eye tracking methodologies, for example, tracking the fovea using foveal verification and/or foveal location. In reference to FIG. 47, in various embodiments, the OCT-based ophthalmic testing center system can be configured to conduct static perimetry testing in either a self-operated or self-administered fashion, or in an assisted fashion with someone other than the subject either partially or completely administers the test. The perimetry test can be performed on both eyes simultaneously (a binocular examination) or, first on one eye and then on the other eye. The OCT-based ophthalmic testing center system can comprise display devices that can be configured to first display stationary fixation targets, for example, dots, crosses, circles, or the like. The OCT-based ophthalmic testing center system can be configured to control the optical distance between the subject's eye and the fixation targets by adjusting the vergence of the light from the fixation display (for example, by collimation or divergence). For example, the optical distance could be set at 14 inches to simulate reading, 30 inches to simulate computer use, 20 feet to equate with conventional visual acuity measurements, infinity, or at any other distance. As discussed previously, the OCT-based ophthalmic testing center system can be configured to correct for refractive error at the various optical distances.

With reference to FIG. 47, the OCT-based ophthalmic testing center system can be configured to conduct static perimetry testing by displaying and/or presenting transient objects 4702, for example, dots, of varying intensity, size, color, contrast, or the like, that can be displayed in various locations around the subject's visual field 4704. In various embodiments the OCT-based ophthalmic testing center system can be configured to instruct (visually and/or audibly) the subject to look straight at the fixation targets 4706 throughout the examination and/or to either press a button and/or respond verbally by saying 'Yes' when a transient stimulus/object is appreciated or perceived by the subject. Button presses and/or verbal response can be stored by the OCT-based ophthalmic testing center system for tabulation and/or analysis. The OCT-based ophthalmic testing center system can be configured to capture these verbalizations or verbal responses using the OCT-based ophthalmic testing center system's microphone input, and these verbalizations or voice responses can be processed using the OCT-based ophthalmic testing center system's CPU and speech recognition software to determine the nature of the response. To ensure that the subject is not merely looking directly at peripheral areas of the display device but rather is using the subject's peripheral vision to detect and/or perceive the stimuli, the OCT-based ophthalmic testing center system can be configured to monitor and/or track the subject's gaze or the direction of the subject's eyes with non-OCT imaging modalities by tracking detectable structures within the eye, for example, the fovea or other features or sets of features with unique or identifiable patterns of intensity. Non-OCT imaging modalities include without limitation infrared (IR) imaging or scanning laser ophthalmoscopy (SLO) imaging. The OCT-based ophthalmic testing center system can also be configured to monitor the subject's gaze by tracking detectable structures within the eye using small 3D-OCT scans centered under the image of the central fixation target on the retina and/or by using sparse 3D-OCT scans across the fundus. In various embodiments, the OCT-based ophthalmic testing center system can be configured to use foveal verification in cases where the foveal location may be known or closely approximated, and/or the OCT-based ophthalmic testing center system can be configured to use foveal location when the fovea cannot be located. For subjects suffering from retinal disease, the OCT-based ophthalmic testing center system can be configured to track other non-foveal detectable structures with OCT to ensure their positions are unchanged during the static perimetry test.

In reference to FIG. 47, in various embodiments, the OCT-based ophthalmic testing center system can be configured to conduct the eye tracking scans before each stimulus is presented to the subject, and/or analyzed either after completion of the entire test to develop a test reliability score. In various embodiments, the eye tracking scans are completed in real-time during the static perimetry test so that presentation of the stimulus would be contingent upon central fixation. This analysis can comprise edge detection of the vitreoretinal interface to detect the foveal depression, edge detection of the vitreoretinal interface and retinal pigment epithelium (RPE) to determine retinal thickness, edge detection of other retinal features, or topographic or thickness slope calculations followed by 2D registration to previous maps, among other analyses. If the subject is found to be looking away from the central fixation target, the OCT-based ophthalmic testing center system can be configured to verbally or visually remind the subject to look at the fixation target. The OCT-based ophthalmic testing center system can be configured to withhold stimuli if the fovea is not found to be located centrally or an eye movement is discovered by comparison of other retinal features between stimuli. In various embodiments, the OCT-based ophthalmic testing center system can be configured to turn off a stimulus if it senses eye movement during stimulus display and movement. In the absence of a foveal or optic nerve depression, the OCT-based ophthalmic testing center system can be configured to use relative slopes of the retinal surface to determine and/or indicate eye movement away from either the past fundus position or the position at the start of the test.

With reference to FIG. 47, measurements made with the static perimetry test can include, but are not be limited to, a visual field map indicating the accuracy of responses in all displayed locations, the parameters for the stimuli required in each location to be seen by the subject, the number of positive responses for displayed stimuli (true positives), the number of positive responses for undisplayed stimuli or stimuli intended to fall into the physiologic blind spot (false positives), and the number of failed responses for displayed stimuli (false negatives). Other measurements and analyses are possible. If processed in real-time, the OCT-based ophthalmic testing center system can be configured to use these data to augment additional test stimuli presented to the subject.

With reference to FIG. 47, in various embodiments, the OCT-based ophthalmic testing center system can be configured to compare the static perimetry test data to a normative database to determine patterns of deviation and/or generate risk assessments and/or clinical reports. In various embodiments, the OCT-based ophthalmic testing center system can be configured to analyze, compare, and/or add the static perimetry test data to other data, such as the subject's ophthalmic history data that is stored on a subject's input card or retrieved from a historical database or other history-taking modules incorporated into the OCT-based ophthalmic testing center system. In various embodiments, the OCT-based ophthalmic testing center system can be configured to automatically conduct a static perimetry test based on ophthalmic history. For example, if the subject has glaucoma or the like, the OCT-based ophthalmic testing center system can be configured to record and/or store such information so that the OCT-based ophthalmic testing center system can be configured to automatically perform a static perimetry test based on the record. In another example, if the patient has a family history of glaucoma or the like, and such information is stored within the subject's ophthalmic history database, the OCT-based ophthalmic testing center system can be configured to automatically perform a static perimetry test. The OCT-based ophthalmic testing center system can be configured to generate various statistics or comparisons based on the measured static perimetry test data, which may be combined with data from the normative database or historical data source.

With reference to FIG. 47 the OCT-based ophthalmic testing center system can be configured to output the results of and/or data from the static perimetry test. For example, the results can be outputted directly to the subject in a hardcopy (for example, printed card or paper) or electronic format (for example, on a display, via email, text messaged, or in a magnetic strip), stored locally on the device or on an attached computer, transmitted to a central database, or transmitted directly to the ordering or related physician.

Corneal Topography Test

Figure 48:
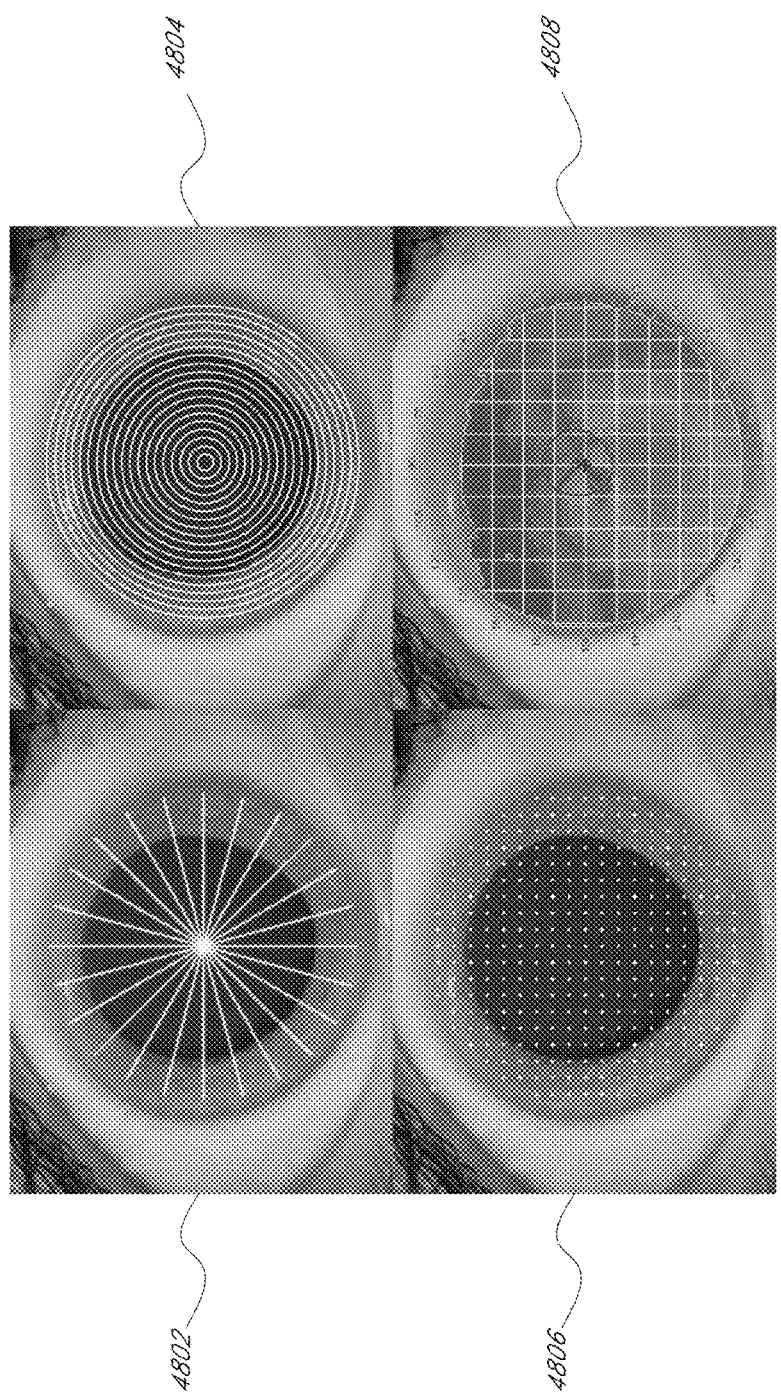
FIG. 48 illustrates various embodiments of a corneal topography test conducted using the OCT-based ophthalmic testing center system as described herein.

With reference to FIG. 48, in general, corneal topography and keratometry are used to study the sphericity and regularity of the corneal surface. Certain corneal disorders, for example, keratoconus or post-operative astigmatism, may cause the cornea to develop a non-spherical shape. In addition, the corneal curvature and power are used to predict the power of the intraocular lens needed for implantation during cataract surgery.

In reference to FIG. 48, the OCT-based ophthalmic testing center system can be configured to conduct corneal topography testing, which is generally a structural test that can employ OCT biomicroscopy. In various embodiments, the OCT-based ophthalmic testing center system can be configured to conduct corneal topography testing in either a self-operated or self-administered fashion, or in an assisted fashion with someone other than the subject either partially or completely administers the test. The corneal topography test can be performed on both eyes simultaneously (a binocular examination) or first on one eye and then on the other eye. The OCT-based ophthalmic testing center system can comprise display devices configured to display stationary fixation targets, for example, dots, crosses, circles, and/or the like. In various embodiments, the OCT-based ophthalmic testing center system can be configured to instruct (visually and/or audibly) the subject to look straight at the fixation targets throughout the examination. The OCT-based ophthalmic testing center system can be configured to control the optical distance between the subject's eye and the fixation targets by adjusting the vergence of the light from the fixation display (for example, by collimation or divergence). For example, the optical distance could be set at 14 inches to simulate reading, 30 inches to simulate computer use, 20 feet to equate with conventional visual acuity measurements, infinity, or at any other distance. As discussed previously, the OCT-based ophthalmic testing center system can be configured to correct for refractive error at the various optical distances.

With reference to FIG. 48, the OCT-based ophthalmic testing center system can be configured to scan the eye(s) of the subject using various scan patterns, including but not limited to rapid radial line 4802, circular 4804, point-based 4806 or raster line B-scans obtained while the OCT-based ophthalmic testing center system is focused on the cornea and/or anterior chamber or other area. The OCT-based ophthalmic testing center system can be configured to use edge detection software routines and/or methodologies to detect the anterior and posterior corneal interfaces to determine, for example, average curvatures (keratometry), corneal diameter, dioptric power, cylinder and axis as well as topographic maps that may depict certain pathology, for example, anterior and posterior keratoconus, in greater detail. The OCT-based ophthalmic testing center system can be configured to use the corneal topography data and measurements of corneal diameter or the like to aid surgeons in planning surgical procedures. In various embodiments, the OCT-based ophthalmic testing center system can be configured to output to a physician a recommended surgical plan, including intraocular lens power calculations, based on comparing the corneal topography data and measurements with threshold values associated with appropriate surgical plans or using known equations, such as SRK II, SRK/T, Holladay I, and Hoffer Q, to calculate the appropriate lens power for each eye. For this purpose, measurements of the axial length of the eye, conducted with the OCT-based ophthalmic testing center system, could also be incorporated into these calculations. Other measurements could also be used in these calculations.

In reference to FIG. 48, the OCT-based ophthalmic testing center system can be configured to generate various statistics, for example, fitting to expected base curves or studying eccentricity, calculated from the corneal topography data. The OCT-based ophthalmic testing center system can conduct analysis and/or measurements of irregularities on the posterior corneal surface to assess the presence of guttata or keratic precipitates. Other measurements and analyses are possible. If processed in real-time, the OCT-based ophthalmic testing center system can be configured to use these data to plan additional scans to be performed. For example, if keratic precipitates were detected by corneal OCT, the OCT-based ophthalmic testing center system could be configured to perform gonioscopy to evaluate the presence of inflammatory cells in the anterior chamber of the eye.

With reference to FIG. 48, in various embodiments, the OCT-based ophthalmic testing center system can be configured to compare the corneal topography test data to a normative database to determine patterns of deviation and/or generate risk assessments and/or clinical reports. In various embodiments, the OCT-based ophthalmic testing center system can be configured to analyze, compare, and/or add the corneal topography test data to other data, such as the subject's ophthalmic history data that is stored on a subject's input card or retrieved from a historical database or other history-taking modules incorporated into the OCT-based ophthalmic testing center system. In various embodiments, the OCT-based ophthalmic testing center system can be configured to automatically conduct a corneal topography test based on ophthalmic history. For example, if the subject complains of keratoconus-like symptoms and/or distortions, the OCT-based ophthalmic testing center system can be configured to record and/or store such information so that the OCT-based ophthalmic testing center system can be configured to automatically perform a corneal topography test based on the recorded complaint. In another example, if the patient has a family history of keratoconus, or the like, and such information is stored within the subject's ophthalmic history database, the OCT-based ophthalmic testing center system can be configured to automatically perform a corneal topography test. The OCT-based ophthalmic testing center system can be configured to generate various statistics based on the measured corneal topography test data, which may be combined with data from the normative database or historical data source.

With reference to FIG. 48, the OCT-based ophthalmic testing center system can be configured to output the results of and/or data from the corneal topography test. For example, the results can be outputted directly to the subject in a hardcopy (for example, printed card or paper) or electronic format (for example, on a display, via email, text messaged, or in a magnetic strip), stored locally on the device or on an attached computer, transmitted to a central database, or transmitted directly to the ordering or related physician.

Corneal Pachymetry Test

Figure 49:
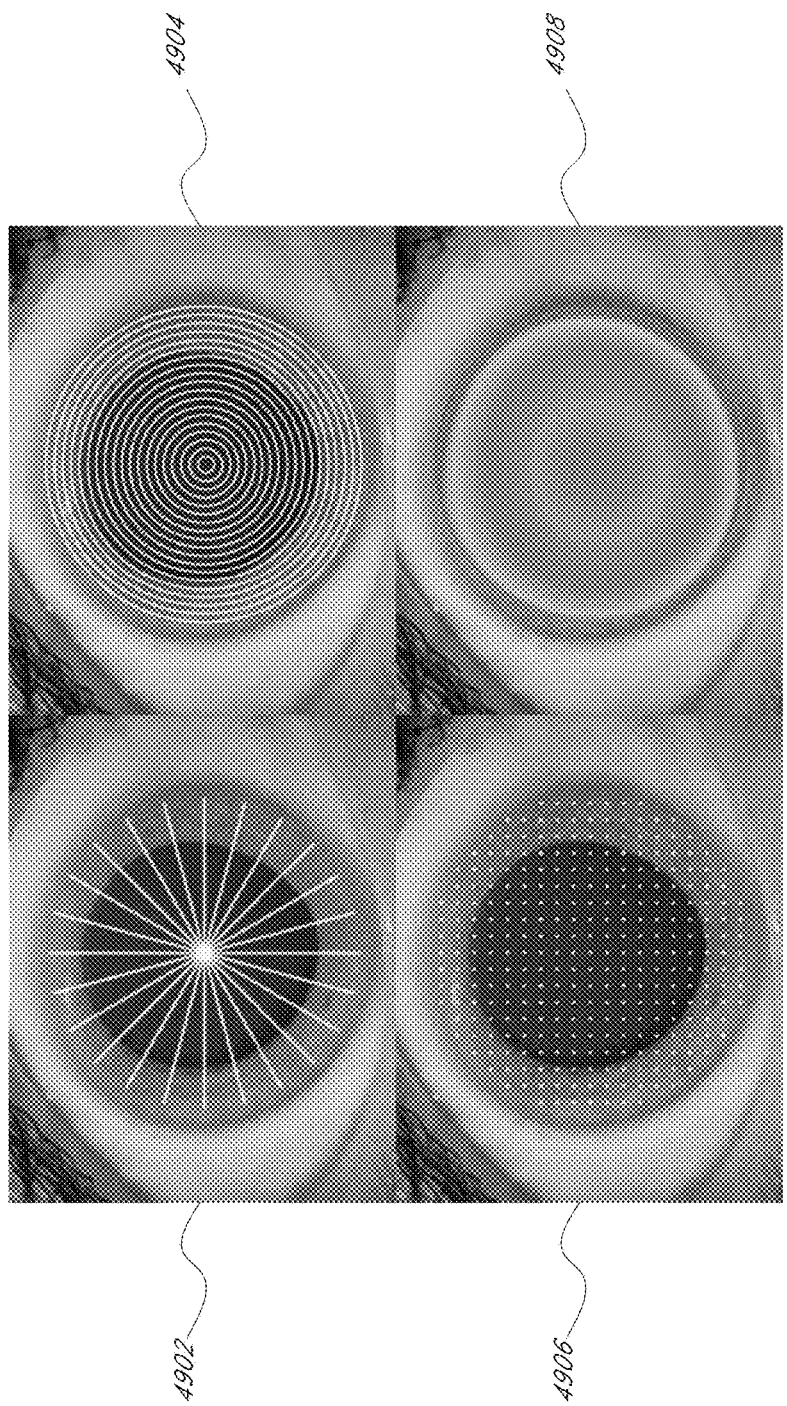
FIG. 49 illustrates an embodiment of a corneal pachymetry test conducted using the OCT-based ophthalmic testing center system as described herein.

With reference to FIG. 49, in general corneal pachymetry is a diagnostic test that determines the thickness of the cornea. Various diseases, for example Fuchs' dystrophy, lead to blurred vision due to corneal thickening. Central corneal thickness is also measured in patients with potential glaucoma.

In reference to FIG. 49, the OCT-based ophthalmic testing center system can be configured to conduct corneal pachymetry testing, which is generally a structural test that can employ OCT biomicroscopy. In various embodiments, corneal pachymetry using the OCT-based ophthalmic testing center system can be conducted in either a self-operated or self-administered fashion, or in an assisted fashion with someone other than the subject either partially or completely administers the test. The OCT-based ophthalmic testing center system can be configured to perform a corneal pachymetry test without substantially contacting the cornea. The corneal pachymetry test can be performed on both eyes simultaneously (a binocular examination) or first on one eye and then on the other eye. The OCT-based ophthalmic testing center system can comprise display devices configured to display stationary fixation targets, for example, dots, crosses, circles, and/or the like. In various embodiments, the OCT-based ophthalmic testing center system can be configured to instruct (visually and/or audibly) the subject to look straight at the fixation targets throughout the examination. The OCT-based ophthalmic testing center system can be configured to control the optical distance between the subject's eye and the fixation targets by adjusting the vergence of the light from the fixation display (for example, by collimation or divergence). For example, the optical distance could be set at 14 inches to simulate reading, 30 inches to simulate computer use, 20 feet to equate with conventional visual acuity measurements, infinity, or at any other distance. As discussed previously, the OCT-based ophthalmic testing center system can be configured to correct for refractive error at the various optical distances.

With reference to FIG. 49, the OCT-based ophthalmic testing center system can be configured to scan the eye(s) of the subject using various scan patterns, including but not limited to rapid radial line 4902, circular 4904, point-based 4906 or raster line B-scans obtained while the OCT-based ophthalmic testing center system system is focused on the cornea and/or anterior chamber. The OCT-based ophthalmic testing center system can be configured to use edge detection software routines and methodologies to detect the anterior and posterior corneal interfaces to calculate the thickness (for example, the difference or distance between interfaces) at particular points. The OCT-based ophthalmic testing center system can be configured to use the measured thicknesses to compile a 2D map 4908 describing the overall corneal thickness. In certain embodiments, the OCT-based ophthalmic testing center system can be configured to generate various statistics, for example, total volume, standard deviation of thickness, maximum thickness, or the like, that may be outputted and/or reported to the subject and/or a physician. Other measurements and analyses are possible. If processed in real-time, the OCT-based ophthalmic testing center system can be configured to use these data to plan additional scans to be performed.

With reference to FIG. 49, in various embodiments, the OCT-based ophthalmic testing center system can be configured to compare the corneal pachymetry test data to a normative database to determine patterns of deviation and/or generate risk assessments and/or clinical reports. In various embodiments, the OCT-based ophthalmic testing center system can be configured to analyze, compare, and/or add the corneal pachymetry test data to other data, such as the subject's ophthalmic history data that is stored on a subject's input card or retrieved from a historical database or other history-taking modules incorporated into the OCT-based ophthalmic testing center system. In various embodiments, the OCT-based ophthalmic testing center system can be configured to automatically conduct a corneal pachymetry test based on ophthalmic history. For example, if the subject complains of Fuchs' dystrophy-like symptoms and/or distortions, the OCT-based ophthalmic testing center system can be configured to record and/or store such information so that the OCT-based ophthalmic testing center system can be configured to automatically perform a corneal pachymetry test based on the recorded complaint. In another example, if the patient has a family history of Fuchs' dystrophy, or corneal thickening or the like, and such information is stored within the subject's ophthalmic history database, the OCT-based ophthalmic testing center system can be configured to automatically perform a corneal pachymetry test. The OCT-based ophthalmic testing center system can be configured to generate various statistics based on the measured corneal pachymetry test data, which may be combined with data from the normative database or historical data source.

With reference to FIG. 49, the OCT-based ophthalmic testing center system can be configured to output the results of and/or data from the corneal pachymetry test. For example, the results can be outputted directly to the subject in a hardcopy (for example, printed card or paper) or electronic format (for example, on a display, via email, text messaged, or in a magnetic strip), stored locally on the device or on an attached computer, transmitted to a central database, or transmitted directly to the ordering or related physician.

Virtual Gonioscopy Test

Figure 50:
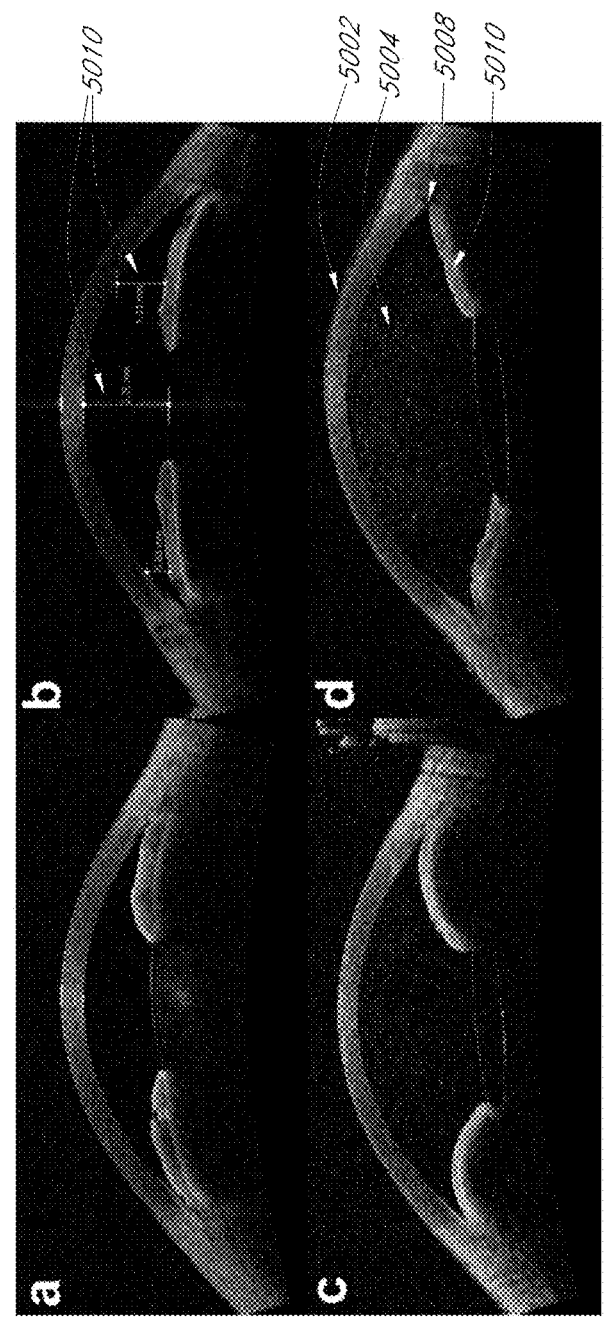
FIG. 50 illustrates an embodiment of a virtual gonioscopy test conducted using the OCT-based ophthalmic testing center system as described herein.
Figure 51:
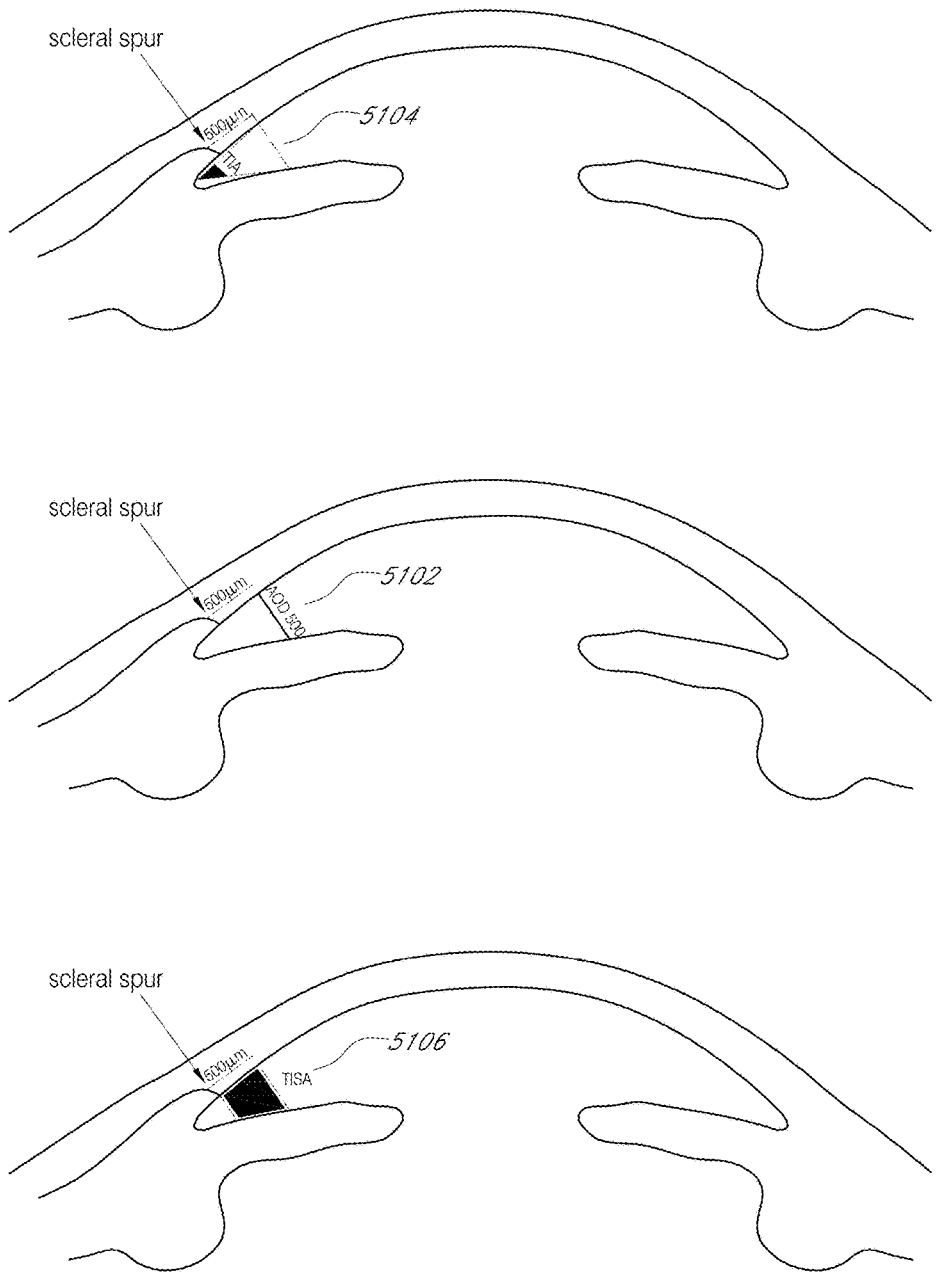
FIG. 51 illustrates various embodiments of measurements generated by a virtual gonioscopy test conducted using the OCT-based ophthalmic testing center system as described herein.

With reference to FIG. 50 and FIG. 51, gonioscopy is generally a test performed, usually in the context of glaucoma or suspicion of glaucoma, to inspect the peripheral angle of the eye which cannot be seen without a contact lens due to an optical phenomenon known as 'total internal reflection.'

With reference to FIG. 50 and FIG. 51, the OCT-based ophthalmic testing center system can be configured to conduct virtual gonioscopy testing, which is generally a structural test that can employ OCT biomicroscopy. In various embodiments, virtual gonioscopy can be conducted by the OCT-based ophthalmic testing center system without anesthetizing an eye and without placing a contact lens containing mirrors on the cornea 5002 of the eye. In various embodiments, the OCT-based ophthalmic testing center system can be configured to conduct virtual gonioscopy in either a self-operated or self-administered fashion, or in an assisted fashion with someone other than the subject either partially or completely administers the test. The virtual gonioscopy test can be performed on both eyes simultaneously (a binocular examination) or first on one eye and then on the other eye. The OCT-based ophthalmic testing center system can comprise display devices configured to display stationary fixation targets, for example, dots, crosses, circles, and/or the like. In various embodiments, the OCT-based ophthalmic testing center system can be configured to instruct (visually and/or audibly) the subject to look straight at the fixation targets throughout the examination. The OCT-based ophthalmic testing center system can be configured to control the optical distance between the subject's eye and the fixation targets by adjusting the vergence of the light from the fixation display (for example, by collimation or divergence). For example, the optical distance could be set at 14 inches to simulate reading, 30 inches to simulate computer use, 20 feet to equate with conventional visual acuity measurements, infinity, or at any other distance. As discussed previously, the OCT-based ophthalmic testing center system can be configured to correct for refractive error at the various optical distances.

In reference to FIG. 50 and FIG. 51, the OCT-based ophthalmic testing center system can be configured to scan the eye(s) of the subject using various scan patterns to obtain rapid radial line, circular, point-based and/or raster line B-scans while the OCT-based ophthalmic testing center system system is focused on the cornea 5002 and/or anterior chamber 5004 and/or other area of the eye. In various embodiments, the obtained B-scans can be sufficiently large, for example, 16 mm long with sufficient depth, to image the entire limbal-to-limbal anterior chamber from the cornea to the iris without changing the axial focus of the scanning. In various embodiments, smaller OCT B-scans may be acquired and patched together to generate a multiple sequential axial 3D-OCT scan to cover the entire limbal-to-limbal anterior chamber 5004 from the cornea 5002 to the iris 5006, or the smaller OCT B-scans may be viewed independently or individually. From the images generated by the OCT-based ophthalmic testing center system, structures, for example, the trabecular meshwork, the scleral spur, the ciliary body, and other structures, can be visually identified by a physician, a technician, or an eyecare provider, and/or manual measurements of various anterior chamber depth measurements 5010 and/or various angle geometries 5008 can be made from the images. The OCT-based ophthalmic testing center system can be configured to automatically and/or semi-automatically generate, develop, and/or measure quantitative measurements, for example, various anterior chamber depth measurements 5010, angle geometry 5008, the angle opening distance (AOD) 5102, the trabecular iris angle (TIA) 5104, and the trabecular iris space area (TISA) 5106, the anterior chamber diameter, and average and maximum lens thickness can also be made automatically and/or semi-automatically using software configured to detect the edges of these structures using edge detection algorithms or the like. In various embodiments, the OCT-based ophthalmic testing center system can be configured to use automated software to measure the depth of various portions of the anterior chamber and to generate a report showing the measured data as individual values, or as a set of values or in a 2D thickness map.

With reference to FIG. 50 and FIG. 51, the OCT-based ophthalmic testing center system can be configured to use doppler OCT to detect abnormal blood vessels (neovascularization) on the iris or in the angle. In various embodiments, the OCT-based ophthalmic testing center system can be configured to use polarization-sensitive OCT to further delineate angle structures. From the data obtained from performing a virtual gonioscopy test, the OCT-based ophthalmic testing center system can be configured use the data to identify and/or detect and/or quantify inflammatory syndromes leading to peripheral anterior synechiae. Other measurements and analyses are possible. If processed in real-time, the OCT-based ophthalmic testing center system can be configured to use these data to plan additional scans to be performed. For example, if peripheral anterior synechiae were detected, the OCT-based ophthalmic testing center system could be configured to automatically perform Doppler OCT to look for abnormal blood vessel formation.

With reference to FIG. 50 and FIG. 51, in various embodiments, the OCT-based ophthalmic testing center system can be configured to compare the virtual gonioscopy test data to a normative database to determine patterns of deviation and/or generate risk assessments and/or clinical reports. In various embodiments, the OCT-based ophthalmic testing center system can be configured to analyze, compare, and/or add the virtual gonioscopy test data to other data, such as the subject's ophthalmic history data that is stored on a subject's input card or retrieved from a historical database or other history-taking modules incorporated into the OCT-based ophthalmic testing center system. In various embodiments, the OCT-based ophthalmic testing center system can be configured to automatically conduct a virtual gonioscopy test based on ophthalmic history. For example, if the subject complains of glaucoma-like symptoms and/or distortions, the OCT-based ophthalmic testing center system can be configured to record and/or store such information so that the OCT-based ophthalmic testing center system can be configured to automatically perform a virtual gonioscopy test based on the recorded complaint. In another example, if the patient has a family history of glaucoma or the like, and such information is stored within the subject's ophthalmic history database, the OCT-based ophthalmic testing center system can be configured to automatically perform a virtual gonioscopy test. The OCT-based ophthalmic testing center system can be configured to generate various statistics based on the measured virtual gonioscopy test data, which may be combined with data from the normative database or historical data source.

With reference to FIGS. 50 and 51, the OCT-based ophthalmic testing center system can be configured to output the results of and/or data from the virtual gonioscopy test. For example, the results can be outputted directly to the subject in a hardcopy (for example, printed card or paper) or electronic format (for example, on a display, via email, text messaged, or in a magnetic strip), stored locally on the device or on an attached computer, transmitted to a central database, or transmitted directly to the ordering or related physician.

Color Vision Test

Figure 52:
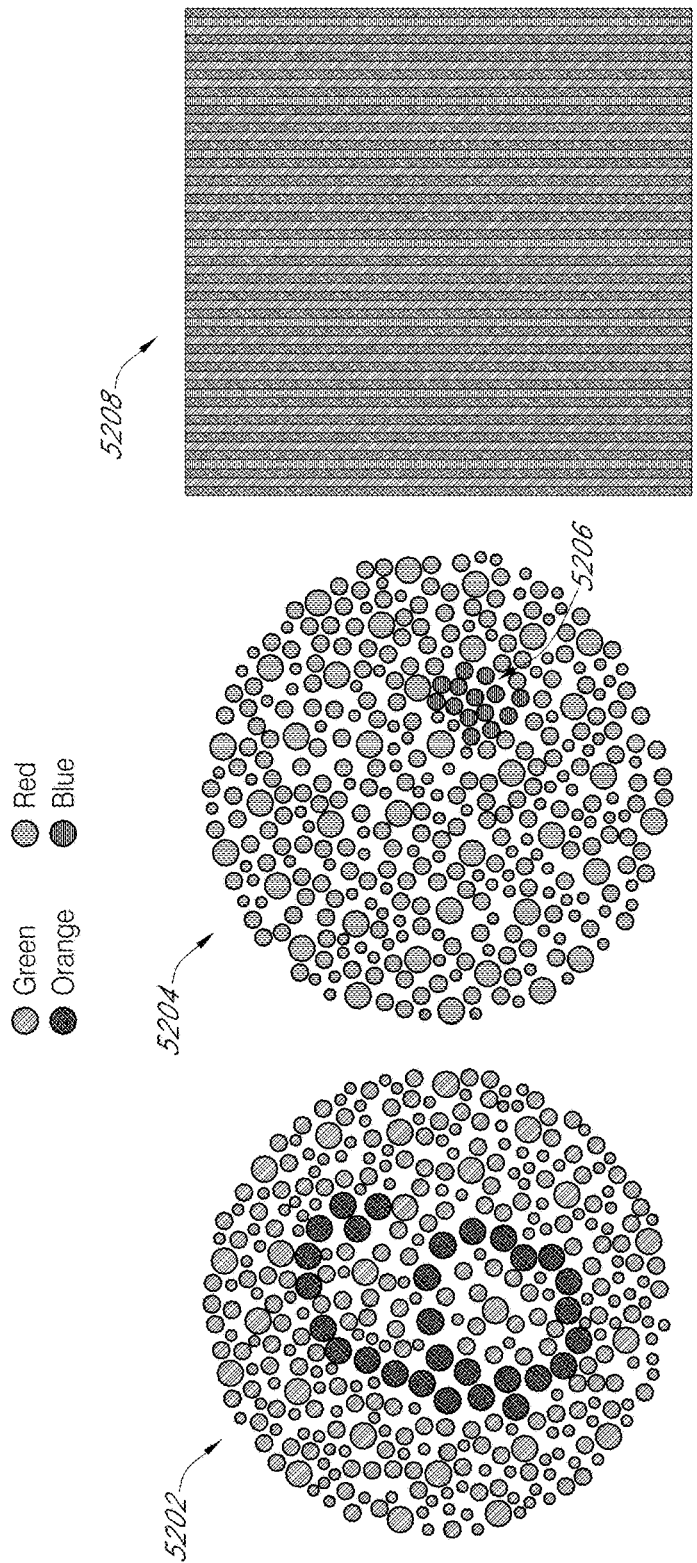
FIG. 52A-52C illustrates various embodiments of a color vision test conducted using the OCT-based ophthalmic testing center system as described herein.

In reference to FIG. 52, and in general, color vision deficits are common and may be inherited or acquired. In various embodiments, the OCT-based ophthalmic testing center system can be configured to conduct a color vision test on a subject in either a self-operated or self-administered fashion, or in an assisted fashion with someone other than the subject either partially or completely administering the test. The color vision test could be performed on both eyes simultaneously or, first on one eye and then on the other eye. The OCT-based ophthalmic testing center system can be configured to control the optical distance between the subject's eye and the fixation targets by adjusting the vergence of the light from the fixation display (for example, by collimation or divergence). For example, the optical distance could be set at 14 inches to simulate reading, 30 inches to simulate computer use, 20 feet to equate with conventional visual acuity measurements, infinity, or at any other distance. As discussed previously, the OCT-based ophthalmic testing center system can be configured to correct for refractive error at the various optical distances.

With reference to FIG. 52, in various embodiments, the OCT-based ophthalmic testing center system can comprise display devices configured to present numeric color plates to the user (for example, Ishihara plates), wherein a number is presented within a field of dots of randomized color and size. The different hatching patterns in FIGS. 52A-52C represent different colors, as shown in the legend. For example, the numeric color plate 5202 comprises a circle of dots in shades of green with the number "6" appearing in shades of orange. This coloring scheme can be used to test for protanopia. In another embodiment, the field can comprise dots in shades of red, orange and/or yellow with an image, figure, or number appearing in shades of green or blue. For example, color plate 5204 comprises a blue image 5206 in a circular field of dots in shades of red. This coloring scheme can be used to test for deuteranopia. Numerous images with different color combinations and numbers can be presented to the subject. In various embodiments, these color combinations could be configured to detect various inherited color deficits, such as achromacy, monochromacy, dichromacy, or anomalous trichromacy, or they could be configured to detect acquired color deficiency. Depending on the subject's ability to detect color, the subject may or may not be able to see the number or other image of one color type presented in the field of colored dots of another color type. The OCT-based ophthalmic testing center system can be configured to instruct (visually and/or audibly) the subject to read these numbers when visualized. The OCT-based ophthalmic testing center system can be configured to capture these verbalizations or verbal responses using the OCT-based ophthalmic testing center system's microphone input, and these verbalizations or voice responses can be processed using the OCT-based ophthalmic testing center system's CPU and speech recognition software to determine the accuracy of reading each of the several numbers. The OCT-based ophthalmic testing center system can be configured to assign scores to the verbal responses based on the accuracy of the response, and the individual scores can be added up in each eye to generate a final color vision measurement for each eye.

In reference to FIG. 52, in various embodiments, the OCT-based ophthalmic testing center system can be configured to display in either or both eyes of the subject moving fixation targets that are color-encoded in the same way as the colored numbers and/or images described above but are moving across the field of colored dots. Numerous color combinations could be presented to the subject as discrete tests or as continually changing color combinations. In various embodiments, these color combinations could be configured to detect various inherited color deficits, such as monochromacy, dichromacy, or anomalous trichromacy, or they could be configured to detect acquired color deficiency.

The OCT-based ophthalmic testing center system can be configured to instruct (visually and/or audibly) the subject to follow those moving targets when visualized. The OCT-based ophthalmic testing center system can be configured to use small 3D-OCT scans of the subject's eye(s) in the moving fixation target areaon the retian to verify the presence of the fovea. Alternatively, the OCT-based ophthalmic testing center system can be configured to detect movement of the retina using either sparse 3D-OCT scans or non-OCT imaging, such as with infrared (IR) or scanning laser ophthalmoscopy (SLO) imaging, of the retina. The OCT-based ophthalmic testing center system can be configured to measure color vision by determining the percent of time that the fovea was detected in the substantially same location as the image of the fixation target on the retina or the percent of time that the trajectory of retinal movement substantially matched the trajectory of the moving fixation stimulus.

In referring to FIG. 52, in various embodiments, the OCT-based ophthalmic testing center system can be configured to display to the subject a randomized pattern 5208 of color-coded optokinetic stimuli to conduct the color vision test. Numerous color combinations could be presented to the subject as discrete tests or as continually changing color combinations. In various embodiments, these color combinations could be configured to detect various inherited color deficits, such as monochromacy, dichromacy, or anomalous trichromacy, or they could be configured to detect acquired color deficiency. In various embodiments, the OCT-based ophthalmic testing center system can be configured to perform the color vision test without any verbal or button press response from the subject. Instead of verbal responses from the subject, foveal movements or the movements of other detectable features, could be tracked either with small foveal 3D-OCT scans, non-OCT imaging modalities, such as IR or SLO, or sparse macular 3D-OCT scans. The OCT-based ophthalmic testing center system can be configured to recognize that retinal movements with similar frequency and amplitude measurements as the optokinetic stimuli would indicate intact color vision for that particular color subtype. Failure of the fovea (or other detectable features) to move in response to these stimuli would indicate failure to visualize that color combination. Successes and failures could be tallied after presentation of numerous color combinations to determine a final color vision score.

In various embodiments, the OCT-based ophthalmic testing center system can be configured to compare the color vision test data to a normative database to determine patterns of deviation and/or generate risk assessments and/or clinical reports. In various embodiments, the OCT-based ophthalmic testing center system can be configured to analyze, compare, and/or add the color vision test data to other data, such as the subject's ophthalmic history data that is stored on a subject's input card or retrieved from a historical database or other history-taking modules incorporated into the OCT-based ophthalmic testing center system. In various embodiments, the OCT-based ophthalmic testing center system can be configured to automatically conduct a vision test based on ophthalmic history. For example, if the subject complains of color vision loss and/or distortion, the OCT-based ophthalmic testing center system can be configured to record and/or store such information so that the OCT-based ophthalmic testing center system can be configured to automatically perform a color vision test based on the recorded complaint. In another example, if the patient has a family history of color blindness or the like, and such information is stored within the subject's ophthalmic history database, the OCT-based ophthalmic testing center system can be configured to automatically perform a color vision test. The OCT-based ophthalmic testing center system can be configured to generate various statistics based on the measured color vision test data, which may be combined with data from the normative database or historical data source.

With reference to FIG. 52, the OCT-based ophthalmic testing center system can be configured to output the results of and/or data from the color vision test. For example, the results can be outputted directly to the subject in a hardcopy (for example, printed card or paper) or electronic format (for example, on a display, via email, text messaged, or in a magnetic strip), stored locally on the device or on an attached computer, transmitted to a central database, or transmitted directly to the ordering or related physician.

Central Visual Distortion Test

Figure 53:
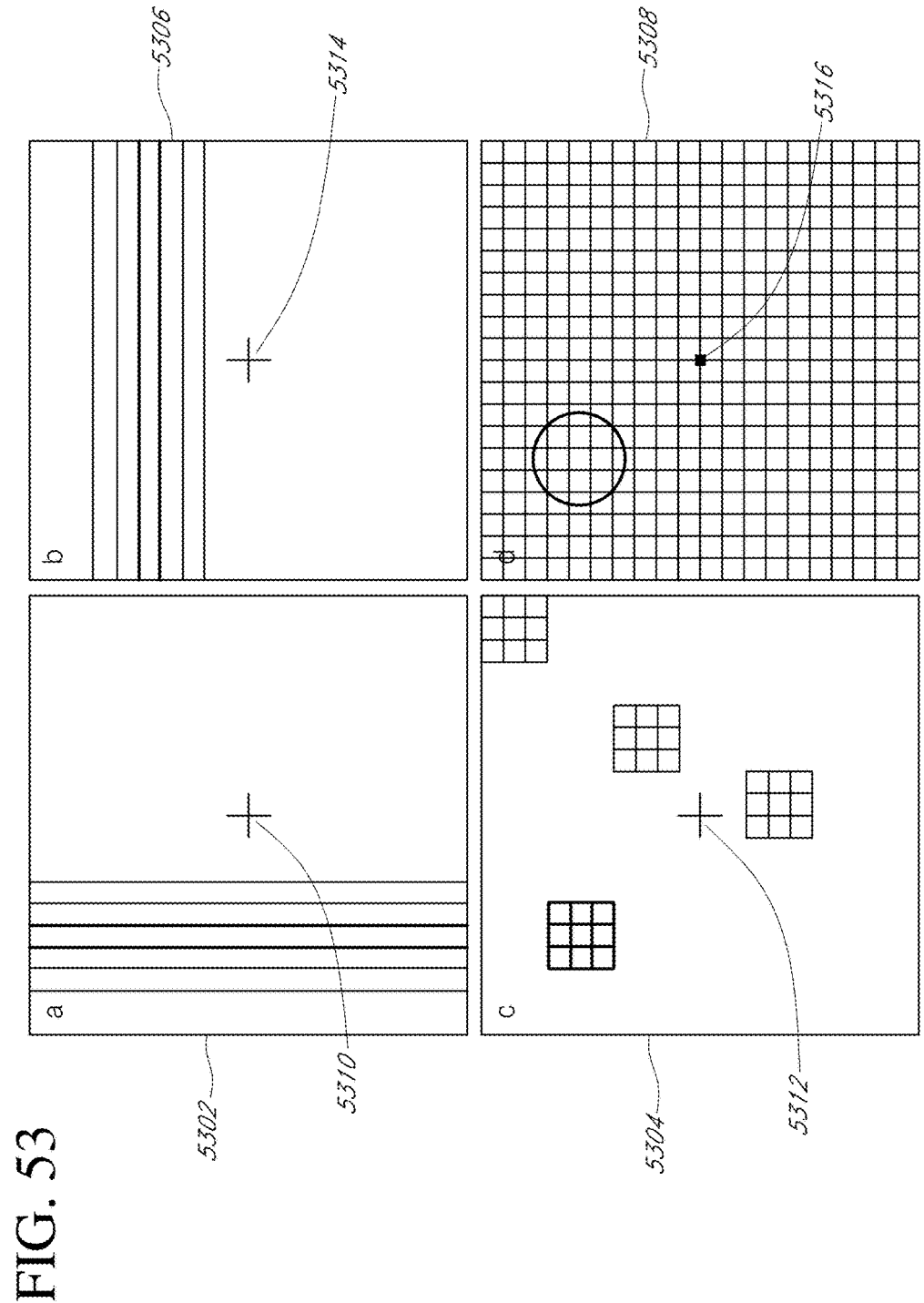
FIG. 53 illustrates various embodiments of a vision distortion test conducted using the OCT-based ophthalmic testing center system as described herein.

With reference to FIG. 53, in general, central vision refers to the high resolution vision used to read, recognize faces and see colors. Vision in this area of the retina, known as the macula, may become distorted in diseases such as macular degeneration, epiretinal membranes, and optic nerve problems.

In reference to FIG. 53, the OCT-based ophthalmic testing center system can be configured to conduct central visual distortion tests on a subject in either a self-operated or self-administered, or in an assisted fashion with someone other than the subject either partially or completely administers the test. The central visual distortion test could be performed on both eyes simultaneously or, first on one eye and then on the other eye. The OCT-based ophthalmic testing center system can comprise display devices, which can be configured to display grids 5302, 5304, 5306, 5308 with central fixation targets and/or dots 5310, 5312, 5314, 5316 at their center. The OCT-based ophthalmic testing center system can be configured to control the optical distance between the subject's eye and the fixation targets by adjusting the vergence of the light from the fixation display (for example, by collimation or divergence). For example, the optical distance could be set at 14 inches to simulate reading, 30 inches to simulate computer use, 20 feet to equate with conventional visual acuity measurements, infinity, or at any other distance. As discussed previously, the OCT-based ophthalmic testing center system can be configured to correct for refractive error at the various optical distances.

In referring to FIG. 53, the OCT-based ophthalmic testing center system can be configured to instruct (visually and/or audibly) the subject to look straight at the center of the grid or focus on the central fixation target or dot throughout the central visual distortion test. The subject's gaze or the direction of the subject's eyes can be monitored with non-OCT imaging modalities by tracking detectable structures within the eye, for example, the fovea or other features or sets of features with unique or identifiable patterns of intensity. Non-OCT imaging modalities include without limitation infrared (IR) imaging or scanning laser ophthalmoscopy (SLO) imaging. The OCT-based ophthalmic testing center system can also be configured to monitor the subject's gaze direction by tracking detectable structures within the eye using small 3D-OCT scans centered on the image of the fixation target on the retina or sparse 3D-OCT scans across the fundus to ensure that their gaze, either demonstrated by a foveal depression under the image of the fixation target or by unchanged locations for other retinal features, remains fixed on the central target. Detectable structures can include without limitation the fovea, other depressions or protrusions within the eye, or unique or identifiable patterns or combinations of protrusions and/or depressions that signify the point of preferred fixation in the retina.

With reference to FIG. 53, the OCT-based ophthalmic testing center system can be configured to conduct the eye tracking scans before each stimulus or grid image is presented to the subject and analyzed after completion of the entire test to develop a reliability score to determine the reliability of the central visual distortion. In various embodiments, the reliability is determined by how often the fovea was located under the image of the central fixation target or dot or point. In various embodiments, the OCT-based ophthalmic testing center system can be configured to conduct reliability testing (for example, determining when the fovea is located under the image of the fixation target or dot or point) in real-time or in substantially real-time so that presentation or display of the stimulus or grid image is presented to the subject only when the eye(s) is focused on the central fixation target or dot.

In referring to FIG. 53, this analysis can comprise edge detection of the vitreoretinal interface to detect the foveal depression, edge detection of the vitreoretinal interface and retinal pigment epithelium (RPE) to determine retinal thickness, edge detection of other retinal features, or topographic or thickness slope calculations followed by 2D registration to previous maps, among other analyses. If the subject is found to be looking away from the central fixation target, the OCT-based ophthalmic testing center system can be configured to verbally and/or visually remind the subject to look at and/or focus on the central fixation target. The OCT-based ophthalmic testing center system can be configured to withhold or not display the stimuli and/or grid if the fovea is not detected or found to be located centrally or an eye movement is discovered by comparison of retinal features between stimuli. In various embodiments, the OCT-based ophthalmic testing center system can be configured to turn off a stimulus if the device sensed eye movement during stimulus/grid display and movement. In the absence of a foveal or optic nerve depression, the OCT-based ophthalmic testing center system can be configured to use the relative slopes of the retinal surface to indicate eye movement away from either the past fundus position or the position at the start of the central visual distortion test.

With reference to FIG. 53, in various embodiments, the OCT-based testing center system can be configured to instruct (visually and/or audibly) the user to press a button or to say 'Yes' whenever the subject perceives any grid lines in the subject's central visual field are distorted or wavy. The OCT-based ophthalmic testing center system can be configured to display and/or add individual horizontal and/or vertical lines of varying color, thickness, and/or contrast to the image until the whole area of the grid is covered. By testing for distortion with both horizontal and/or vertical lines, the OCT-based ophthalmic testing center system can be configured to detect and/or identify and/or localize the locations of maximal distortion, and the OCT-based ophthalmic testing center system can be configured to map these locations and/or areas in a 2D map of the eye(s). In various embodiments, the OCT-based ophthalmic testing center system can be configured to use a speaker output and/or a visual display to instruct the user to press a button and/or to say 'Yes' whenever a small distorted grid is seen or perceived. The OCT-based ophthalmic testing center system can be configured to display small grids, instead of horizontal and vertical lines, of varying color, thickness, and/or contrast to either or both eyes. With these inputs, the OCT-based ophthalmic testing center system can be configured to detect, map and/or identify the areas of greater and/or greatest distortion.

With reference to FIG. 53, measurements made with central visual distortion test can include, but are not be limited to, a visual distortion map indicating the presence of responses in all displayed locations and/or the parameters for the stimuli required in each location to be seen by the subject. Other measurements and/or analyses are possible. If processed in real-time, the OCT-based ophthalmic testing center system can be configured to use these data to augment additional test stimuli and/or grids presented to the subject.

With reference to FIG. 53, in various embodiments, the OCT-based ophthalmic testing center system can be configured to compare the central visual distortion test data to a normative database to determine patterns of deviation and/or to generate risk assessments and/or clinical reports. In various embodiments, the OCT-based ophthalmic testing center system can be configured to analyze, compare, and/or add the central visual distortion test data to other data, such as the subject's ophthalmic history data that is stored on a subject's input card or retrieved from a historical database or other history-taking modules incorporated into the OCT-based ophthalmic testing center system. In various embodiments, the OCT-based ophthalmic testing center system can be configured to automatically conduct a central visual distortion test based on ophthalmic history. For example, if the subject complains of distortions in the peripheral view, the OCT-based ophthalmic testing center system can be configured to record and/or store such information so that the OCT-based ophthalmic testing center system can be configured to automatically perform a central visual distortion test based on the recorded complaint. In another example, if the patient has a family history of peripheral vision issues or the like, and such information is stored within the subject's ophthalmic history database, the OCT-based ophthalmic testing center system can be configured to automatically perform a central visual distortion test. The OCT-based ophthalmic testing center system can be configured to generate various statistics based on the measured central visual distortion data, which may be combined with data from the normative database or historical data source.

With reference to FIG. 53, the OCT-based ophthalmic testing center system can be configured to output the results of and/or data from the central visual distortion test. For example, the results can be outputted directly to the subject in a hardcopy (for example, printed card or paper) or electronic format (for example, on a display, via email, text messaged, or in a magnetic strip), stored locally on the device or on an attached computer, transmitted to a central database, or transmitted directly to the ordering or related physician.

Reading Speed Testing

Figure 54:
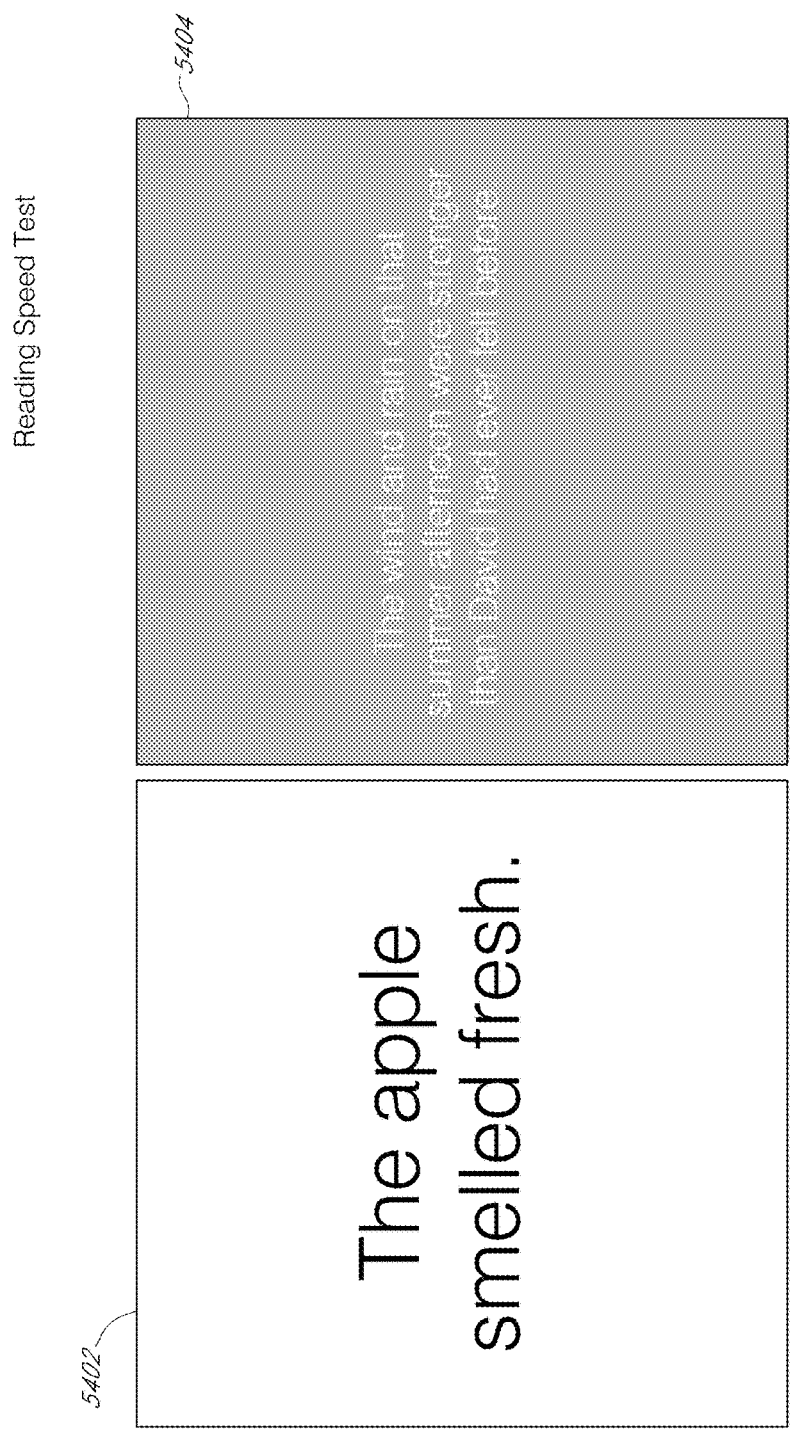
FIG. 54 illustrates an embodiment of a reading speed test conducted using the OCT-based ophthalmic testing center system as described herein.

With reference to FIG. 54, in general visual acuity tests may not describe the day-to-day visual dysfunction experienced by patients with macular diseases, for example, age-related macular degeneration or the like. The speed, cadence and accuracy of reading regular text can be a good measure of small changes in visual function that fall between the larger Snellen visual acuity categories such as 20/200 and 20/100. Accordingly, it may be preferred to conduct a reading speed test.

In reference to FIG. 54, an OCT-based ophthalmic testing center system could accomplish reading speed testing, which is a functional test that can employ eye tracking methodologies, for example, tracking the fovea using foveal verification and/or foveal location. In various embodiments, the reading speed test can be performed by the OCT-based ophthalmic testing center system in either a self-operated or self-administered fashion, or in an assisted fashion with someone other than the subject either partially or completely administering the test. This reading speed test could be performed on both eyes simultaneously or, first on one eye and then on the other eye. The OCT-based ophthalmic testing center system can comprise display devices, which can be configured to present sentences or paragraphs 5402, 5404 using letters with various fonts, type style, sizes, contrast, color and/or backgrounds. The OCT-based ophthalmic testing center system can be configured to control the optical distance between the subject's eye and the fixation targets by adjusting the vergence of the light from the fixation display (for example, by collimation or divergence). For example, the optical distance could be set at 14 inches to simulate reading, 30 inches to simulate computer use, 20 feet to equate with conventional visual acuity measurements, infinity, or at any other distance. As discussed previously, the OCT-based ophthalmic testing center system can be configured to correct for refractive error at the various optical distances.

In referring to FIG. 54, the OCT-based ophthalmic testing center system can be configured to instruct (visually and/or audibly) the subject to read text presented during the reading speed test. The OCT-based ophthalmic testing center system can be configured to capture these verbalizations or verbal responses using the OCT-based ophthalmic testing center system's microphone input, and these verbalizations or voice responses can be processed using the OCT-based ophthalmic testing center system's CPU and speech recognition software to determine the reading accuracy. The subject's gaze or the direction of the subject's eyes can be monitored with non-OCT imaging modalities by tracking detectable structures within the eye, for example, the fovea or other features or sets of features with unique or identifiable patterns of intensity. Non-OCT imaging modalities include without limitation infrared (IR) imaging or scanning laser ophthalmoscopy (SLO) imaging.

The OCT-based ophthalmic testing center system can also be configured to monitor the subject's gaze direction, speed, and/or consistency of movement by tracking detectable structures within the eye using small 3D-OCT (for example, foveal verification) and/or sparse 3D-OCT (for example, foveal location) scans across the fundus. In various embodiments, the OCT-based ophthalmic testing center system can be configured to use foveal verification in cases where the foveal location may be known or closely approximated, and/or the OCT-based ophthalmic testing center system can be configured to use foveal location when the fovea cannot be located. In general, reading speed tests are ordered for people with retinal disease. Accordingly, for subjects suffering from retinal disease, the OCT-based ophthalmic testing center system can be configured to track other non-foveal detectable structures with OCT.

With reference to FIG. 54, other non-foveal detectable structures can include without limitation other depressions or protrusions within the eye, or unique or identifiable patterns or combinations of protrusions and/or depressions that signify the point of preferred fixation in the retina. In various embodiments, this analysis can comprise edge detection of the vitreoretinal interface to detect the foveal depression, edge detection of the vitreoretinal interface and retinal pigment epithelium (RPE) to determine retinal thickness, edge detection of other retinal features, or topographic or thickness slope calculations followed by 2D registration to previous maps, among other analyses. In the absence of a foveal or optic nerve depression, the relative slopes of the retinal surface could be used to indicate eye movement away from either the past fundus position or the position at the start of the test.

With reference to FIG. 54, measurements made with the reading speed test can include, but not be limited to, the total time spent reading a given sentence, the accuracy of word recognition and the kinetics of retinal/eye movements. Other measurements and analyses are also possible. If processed in real-time, the OCT-based ophthalmic testing center system can be configured to use the reading speed test data in conjunction with or to augment additional test stimuli presented to the subject. For example, if the subject demonstrates uncertainty in reading the letters displayed, the OCT-based ophthalmic testing center system device can be configured to switch the font of the content, for example from script to a Times New Roman, to see if that is easier for the subject to see. If not, the device could present the paragraph using larger letters than are typically used in standard testing. In various embodiments, the OCT-based ophthalmic testing center system can be configured to compare the reading speed test data to a normative database to determine patterns of deviation and/or generate risk assessments and/or clinical reports. In various embodiments, the OCT-based ophthalmic testing center system can be configured to analyze, compare, and/or add the reading speed test data to other data, such as the subject's ophthalmic history data that is stored on a subject's input card or retrieved from a historical database or other history-taking modules incorporated into the OCT-based ophthalmic testing center system. The OCT-based ophthalmic testing center system can be configured to generate various statistics based on the measured reading speed data, which may be combined with data from the normative database or historical data source.

With reference to FIG. 54, the OCT-based ophthalmic testing center system can be configured to output the results of and/or data from the reading speed test. For example, the results can be outputted directly to the subject in a hardcopy (for example, printed card or paper) or electronic format (for example, on a display, via email, text messaged, or in a magnetic strip), stored locally on the device or on an attached computer, transmitted to a central database, or transmitted directly to the ordering or related physician.

Stereoacuity Testing

Figure 55:
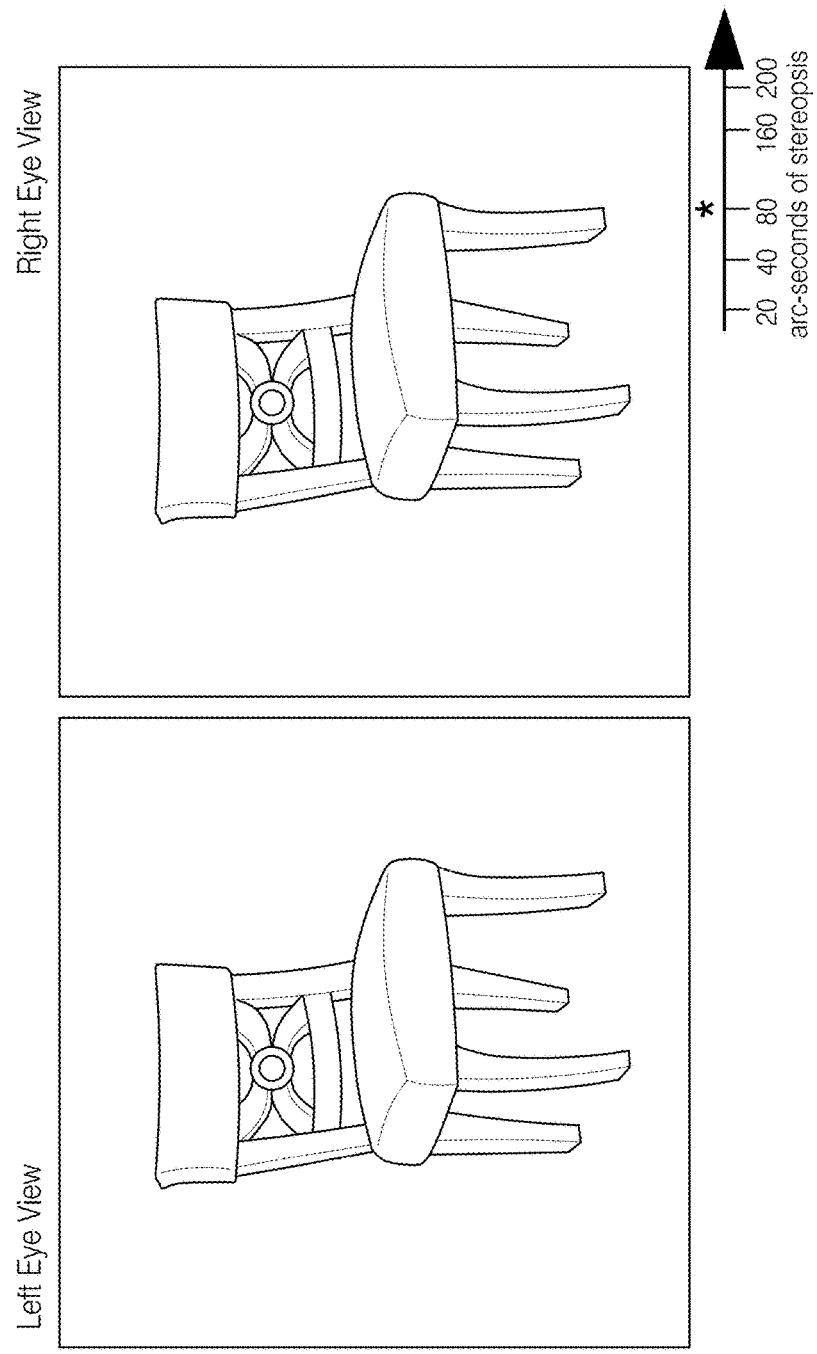
FIGS. 55 and 56 illustrate an embodiment of a stereoacuity test conducted using the OCT-based ophthalmic testing center system as described herein.
Figure 56:
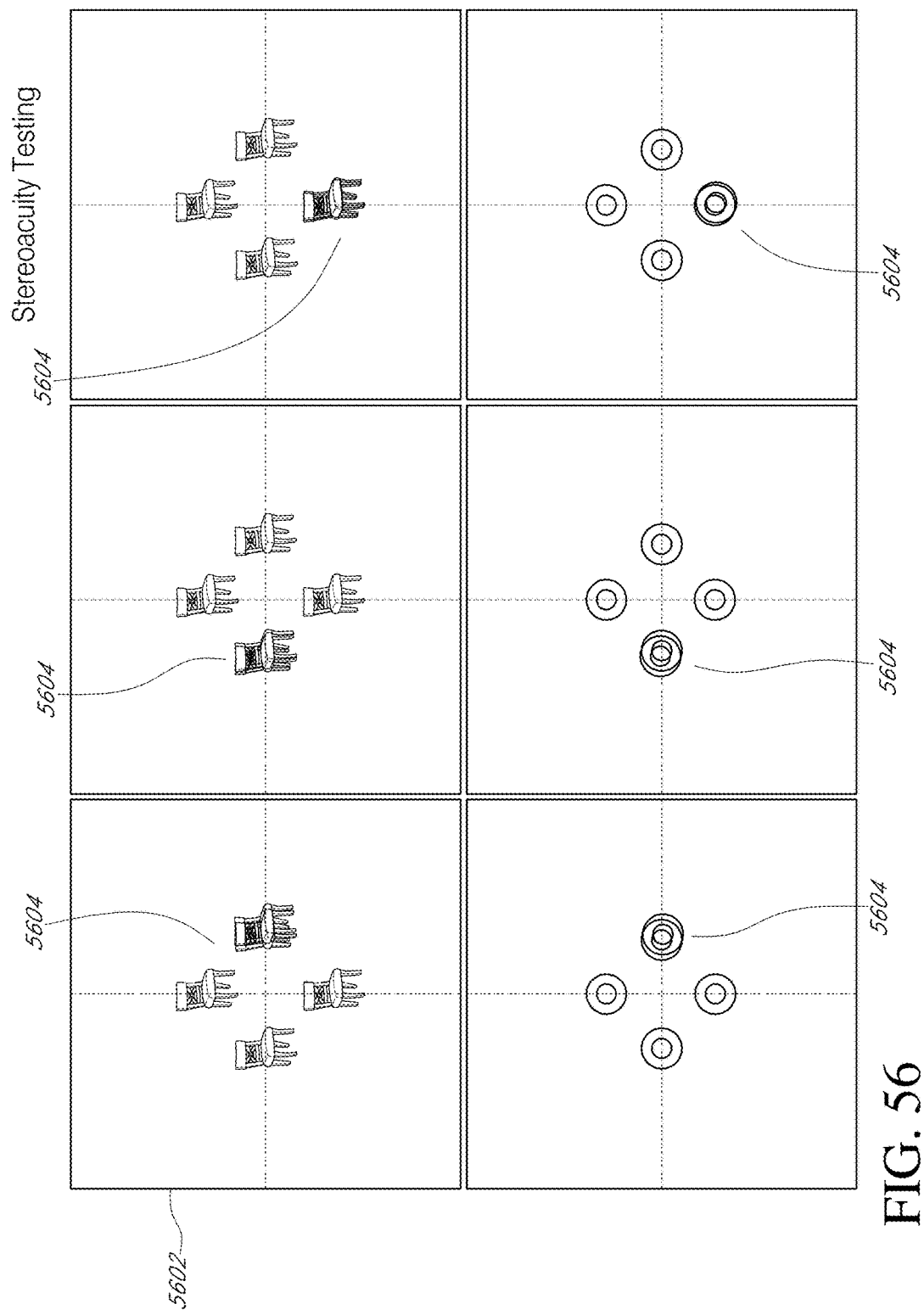

With reference to FIG. 55 and FIG. 56, stereopsis is generally a measure of depth perception, and stereoacuity testing of the eyes can be used to detect a loss of stereopsis when viewing paired stereo images. Stereoacuity testing can be performed on children and adults. Levels of stereopsis are measured in arc seconds, and can be detected by presenting a subject with a sequence of sets of image pairs with progressively increasing stereo disparity. Out of all of the images presented at each level of stereoacuity, the subject must choose the single image that looks three dimensional. If they answer correctly, the examiner moves onto image sets with finer levels of disparity until the subject no longer answers correctly or reaches the end of the test. At this point, the subject's level of stereoacuity, measured in arc seconds, is listed as the value associated with the last set of stereoimages that the subject identified correctly.

In reference to FIG. 55 and FIG. 56, an OCT-based ophthalmic testing center system could accomplish stereoacuity testing in either a self-operated or self-administered fashion, or in an assisted fashion where someone other than the subject either partially or completely administers the test. The stereoacuity test is a functional test that can employ eye tracking methodologies, for example, tracking the fovea using foveal verification and/or foveal location. The stereoacuity test is also a binocular test where the two internal display devices present stereo paired images or movies to a test subject. In various embodiments, the OCT-based ophthalmic testing center system can use polarized or colored targets. The OCT-based ophthalmic testing center system can be configured to control the optical distance between the subject's eye and the fixation targets by adjusting the vergence of the light from the fixation display (for example, by collimation or divergence). For example, the optical distance could be set at 14 inches to simulate reading, 30 inches to simulate computer use, 20 feet to equate with conventional visual acuity measurements, infinity, or at any other distance. As discussed previously, the OCT-based ophthalmic testing center system can be configured to correct for refractive error at the various optical distances.

In various embodiments, the OCT-based ophthalmic testing center system can be configured to instruct (visually and/or audibly) the subject to click a button on the device or to verbally say 'Yes' whenever the subject appreciates, sees, views, identifies, or perceives images in stereo. The OCT-based ophthalmic testing center system can be configured to process the subject's verbal responses by using speech recognition software within the device. After providing those instructions, the OCT-based ophthalmic testing center system device can be configured to present images to the subject. The OCT-based ophthalmic testing center system can be configured to progressively increase the stereodisparity between paired images by shifting these images outwards, for example along the epipolar line that relates the two images, until the subject presses the button to indicate stereopsis or verbally says 'Yes.' Real world images, movies or simple targets, such as circles or the like, could be used as stereo paired images.

With reference to FIG. 56, the OCT-based ophthalmic testing center system can be configured to instruct (visually and/or audibly) the subject, via its speaker device, display, or other output device, to review four concurrently displayed images 5602 (or other number of images) and focus or gaze or direct the eyes of the subject toward the single image out of the four (or other number of images) in each set that appears in 3D 5604. The OCT-based ophthalmic testing center system can be configured to present sets of objects 5602, either line drawings or real-world images or the like, where only one of the image pairs would have stereo disparity 5604. The subject's gaze or the direction of the subject's eyes can be monitored with non-OCT imaging modalities by tracking detectable structures within the eye, for example, the fovea or other features or sets of features with unique or identifiable patterns of intensity. Non-OCT imaging modalities include without limitation infrared (IR) imaging or scanning laser ophthalmoscopy (SLO) imaging. The OCT-based ophthalmic testing center system can also be configured to monitor the subject's gaze by tracking detectable structures within the eye using small 3D-OCT scans centered on the four images in each set that could potentially be seen in stereo. Detectable structures can include without limitation the fovea, other depressions or protrusions within the eye, or unique or identifiable patterns or combinations of protrusions and/or depressions that signify the point of preferred fixation in the retina.

In reference to FIG. 56, the OCT-based ophthalmic testing center system can be configured to analyze and/or survey all four image locations to measure or detect or determine the subject's degree of uncertainty (as they glance back and forth between potential options). For example, if all four image locations were scanned several times per second for several seconds, the number of times the fovea (or other feature for tracking) appeared in each of those image locations could be counted. If the fovea only appeared in a particular image location during that survey, this could imply that the user had high confidence that this was the image displayed in 3D. If, on the other hand, the fovea appeared in more than one image location on many foveal verification scans, this could indicate that the subject was unsure which one was the image displayed in 3D and was shifting fixation back and forth between the choices.

In reference to FIG. 55 and FIG. 56, a button input or a plurality of buttons could be used in addition or instead of verbal responses to enable the subject to indicate that the subject is looking at the subject's final guess or choice, or that the subject could not see any objects in 3D. Measurements made with this test can include, but not be limited to, the arc seconds of disparity between the last image pair set answered correctly. If processed in real-time, the OCT-based ophthalmic testing center system can be configured to use the stereoacuity test data in conjunction with or to augment additional test stimuli presented to the subject. For example, if the subject demonstrates uncertainty about which image is displayed in stereo with the largest stereodisparity value, the OCT-based ophthalmic testing center system device could switch the image content, for example from a chair to a disc, to see if that is easier for the subject to see. If not, the device could present the subject with larger stereodisparity image pairs than are typically used in standard testing or switch to the test demonstrated in FIG. 55. In various embodiments, the OCT-based ophthalmic testing center system can be configured to compare the stereoacuity test data to a normative database to determine patterns of deviation and/or generate risk assessments and/or clinical reports. In various embodiments, the OCT-based ophthalmic testing center system can be configured to analyze, compare, and/or add the stereoacuity test data to other data, such as the subject's ophthalmic history data that is stored on a subject's input card or retrieved from a historical database or other history-taking modules incorporated into the OCT-based ophthalmic testing center system. In various embodiments, the OCT-based ophthalmic testing center system can be configured to automatically conduct a stereoacuity test based on ophthalmic history. For example, if the subject complains of not being able to see depths, the OCT-based ophthalmic testing center system can be configured to record and/or store such information so that the OCT-based ophthalmic testing center system can be configured to automatically perform a stereoacuity test based on the recorded complaint. In another example, if the patient has a family history of color depth-perception issues or the like, and such information is stored within the subject's ophthalmic history database, the OCT-based ophthalmic testing center system can be configured to automatically perform a stereoacuity test. The OCT-based ophthalmic testing center system can be configured to generate various statistics based on the measured stereoacuity data, which may be combined with data from the normative database or historical data source.

With reference to FIG. 55 and FIG. 56 the OCT-based ophthalmic testing center system can be configured to output the results of and/or data from the stereoacuity test. For example, the results can be outputted directly to the subject in a hardcopy (for example, printed card or paper) or electronic format (for example, on a display, via email, text messaged, or in a magnetic strip), stored locally on the device or on an attached computer, transmitted to a central database, or transmitted directly to the ordering or related physician.

Foveal Suppression Testing

Foveal suppression can occur in children having amblyopia and can also arise in other circumstances in adults. In instances where the eyes of a person project two images to the brain having discrepancies and/or having varying focus, the brain may in some cases suppress the image from one of the eyes, thereby reducing confusion for the brain due to conflicting images. This phenomenon is known as foveal suppression.

Figure 57:
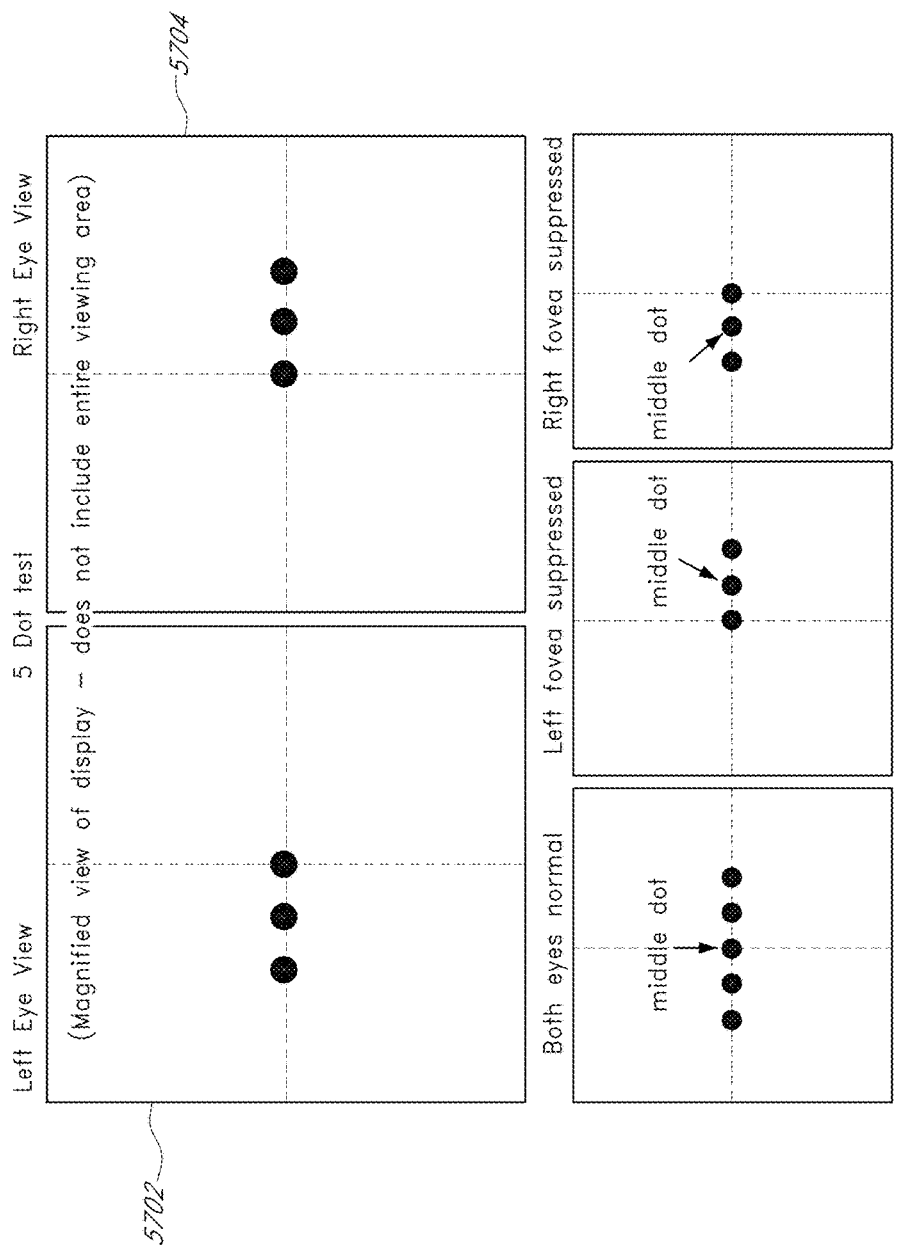
FIGS. 57 and 58 illustrate various embodiments of a foveal suppresion test conducted using the OCT-based ophthalmic testing center system as described herein.

With reference to FIG. 57, the OCT-based ophthalmic testing center system can also be configured to conduct foveal suppression testing in either a self-operated or self-administered fashion, or in an assisted fashion where someone other than the subject either partially or completely administers the test. The foveal suppression test is a functional test that can employ eye tracking methodologies, for example, tracking the fovea using foveal verification and/or foveal location. This test can be a binocular test where the two internal display devices of the OCT-based testing center system present two different test images 5702 and 5704. In various embodiments, the OCT-based ophthalmic testing center system comprises two internal display devices that can be configured to present polarized or colored targets to conduct the test. The optical distance between the subject's eye and the fixation targets could be controlled by adjusting the vergence of the light from the fixation display (for example, by collimation or divergence). For example, the optical distance could be set at 14 inches to simulate reading, 30 inches to simulate computer use, 20 feet to equate with conventional visual acuity measurements, infinity, or at any other distance. As discussed previously, the OCT-based ophthalmic testing center system can be configured to correct for refractive error at the various optical distances.

With reference to FIG. 57, in various embodiments, the OCT-based ophthalmic testing center system can be configured to instruct (visually and/or audibly) the subject to look at the center dot in all of the dots displayed. The OCT-based ophthalmic testing center system can be configured to display a five-dot pattern (a first image 5702 showing three dots left justified on the left and a second image 5704 showing three dots right justified on the right with exactly one dot overlapping). Although six dots are being presented to the user, people without foveal suppression will generally see a five-dot pattern because two of the dots overlap and appear as one. People with foveal suppression will generally see a three-dot pattern or some other number of dots. Although a five-dot pattern is discussed here, other dot patterns and/or other numbers of dots could be used as well. While the subject is focusing on what the subject perceives as the center dot, the OCT-based ophthalmic testing center system can be configured to monitor and/or determine the subject's gaze to detect foveal suppression. The subject's gaze can be monitored with non-OCT imaging modalities by tracking detectable structures within the eye, for example, the fovea or other depressions or protrusions. Non-OCT imaging modalities include without limitation infrared (IR) imaging or scanning laser ophthalmoscopy (SLO) imaging. The OCT-based ophthalmic testing center system can also be configured to monitor the subject's gaze by tracking detectable structures within the eye using small 3D-OCT scans centered on the three potential central dot areas. Detectable structures can include without limitation the fovea, other depressions or protrusions within the eye, or unique or identifiable patterns or combinations of protrusions and/or depressions that signify the point of preferred fixation in the retina.

In reference to FIG. 57, the OCT-based ophthalmic testing center system can be configured to track movement of, for example, the fovea; however, other retinal features can be used. Before commencing a foveal suppression test, the OCT-based ophthalmic testing center system is configured to detect the location of the fovea in both eyes by using, for example, the foveal location and foveal verification methodologies and techniques disclosed above. After detecting the fovea, the OCT-based ophthalmic testing center system can be configured to display the five-dot pattern 5702, 5704 discussed above and instruct the subject to look at the center dot. By verifying the location of the fovea as the subject gazes at what the subject perceives as the center dot in the group of visualized dots, the OCT-based ophthalmic testing center system can detect the direction of the subject's gaze. Based on the direction of the subject's gaze, the OCT-based ophthalmic testing center system can be configured to detect foveal suppression. For example, a gaze direction that is left of center would indicate right foveal suppression, and a gaze direction that is right of center would indicate left foveal suppression. If the eyes exhibit a central gaze direction during the foveal suppression test, then the OCT-based testing center system would generally detect no foveal suppression. In various embodiments, all three dot locations could be surveyed rapidly to measure the subject's degree of uncertainty which may reflect partial or subclinical foveal suppression. For example, if all three potential middle dot locations were scanned several times per second for several seconds, the number of times the fovea (or other feature for tracking) appeared in each of those dot locations could be counted. If the fovea only appeared in one dot location during that survey, this could imply that the user had high confidence that this was the middle dot. If, on the other hand, the fovea appeared in more than one dot location on many foveal verification scans, this could indicate that the subject was unsure which one was the middle dot and was shifting fixation back and forth between these choices. Verbal inputs indicating the number of dots visualized could also be used in place of gaze detection.

Figure 58:
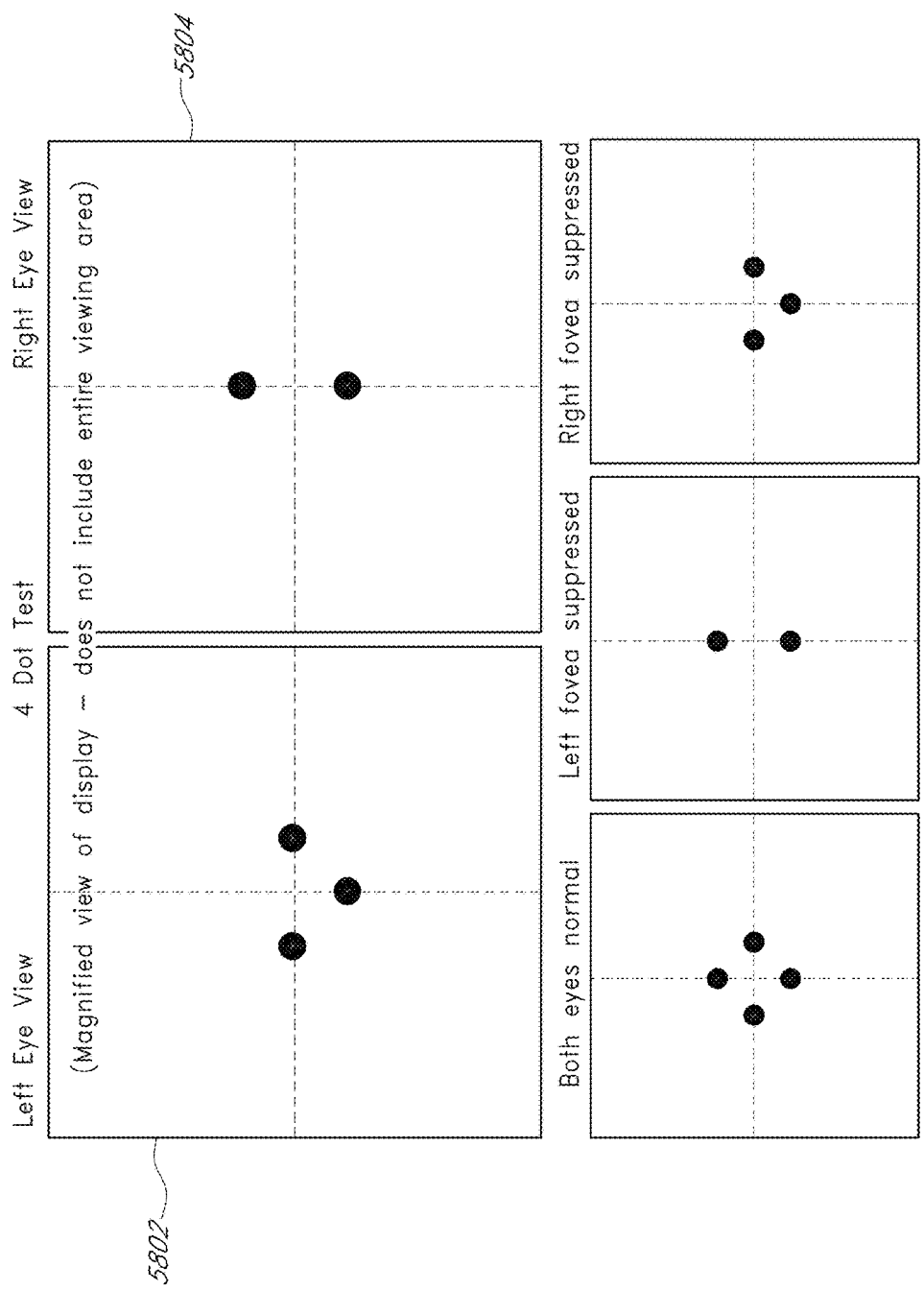

With reference to FIG. 58, in various embodiments, the OCT-based ophthalmic testing center system can be configured to display two different test images 5802 and 5804 on the two internal display devices. The OCT-based ophthalmic testing center system can be configured to instruct (audibly and/or visually) the user to report the number of dots visualized while the instrument presented the dot patterns 5802, 5804. The subject's verbal response, such as 2, 3, 4, or 5, would be received by the OCT-based ophthalmic testing center system's microphone and would be interpreted by speech recognition software. The OCT-based ophthalmic testing center system can be configured to verify the response, for example, by outputting (visually and/or audibly) the detected verbal response and instructing the subject to confirm the correctness of the response by, for example, clicking a button. Based on the verbal response, the OCT-based ophthalmic testing center system can be configured to detect foveal suppression. For example, a response of two would indicate left foveal suppression, a response of three would indicate right foveal suppression, a response of 4 would indicate bilaterally intact foveae and a response beyond those would be unreliable.

With reference to FIG. 58, in various embodiments, the OCT-based ophthalmic testing center system can be configured to compare the foveal suppression test data to a normative database to determine patterns of deviation and/or to generate risk assessments and/or clinical reports. In various embodiments, the OCT-based ophthalmic testing center system can be configured to analyze, compare, and/or add the foveal suppression test data to other data, such as the subject's ophthalmic history data that is stored on a subject's input card or retrieved from a historical database or other history-taking modules incorporated into the OCT-based ophthalmic testing center system. In various embodiments, the OCT-based ophthalmic testing center system can be configured to automatically conduct a foveal suppression test based on ophthalmic history. For example, if the subject complains of confusion and/or distortion, the OCT-based ophthalmic testing center system can be configured to record and/or store such information so that the OCT-based ophthalmic testing center system can be configured to automatically perform a foveal suppression test based on the recorded complaint. In another example, if the patient has a family history of foveal misalignment or the like, and such information is stored within the subject's ophthalmic history database, the OCT-based ophthalmic testing center system can be configured to automatically perform a foveal suppression test. The OCT-based ophthalmic testing center system can be configured to generate various statistics based on the measured central visual distortion data, which may be combined with data from the normative database or historical data source.

With reference to FIG. 58, the OCT-based ophthalmic testing center system can be configured to output the results of and/or data from the foveal suppression test. For example, the results can be outputted directly to the subject in a hardcopy (for example, printed card or paper) or electronic format (for example, on a display, via email, text messaged, or in a magnetic strip), stored locally on the device or on an attached computer, transmitted to a central database, or transmitted directly to the ordering or related physician.

A wide variety of variations to the devices, systems, methods, etc. described herein are possible. For example, the optical layout of the OCT instrument may vary widely.

Figure 59:
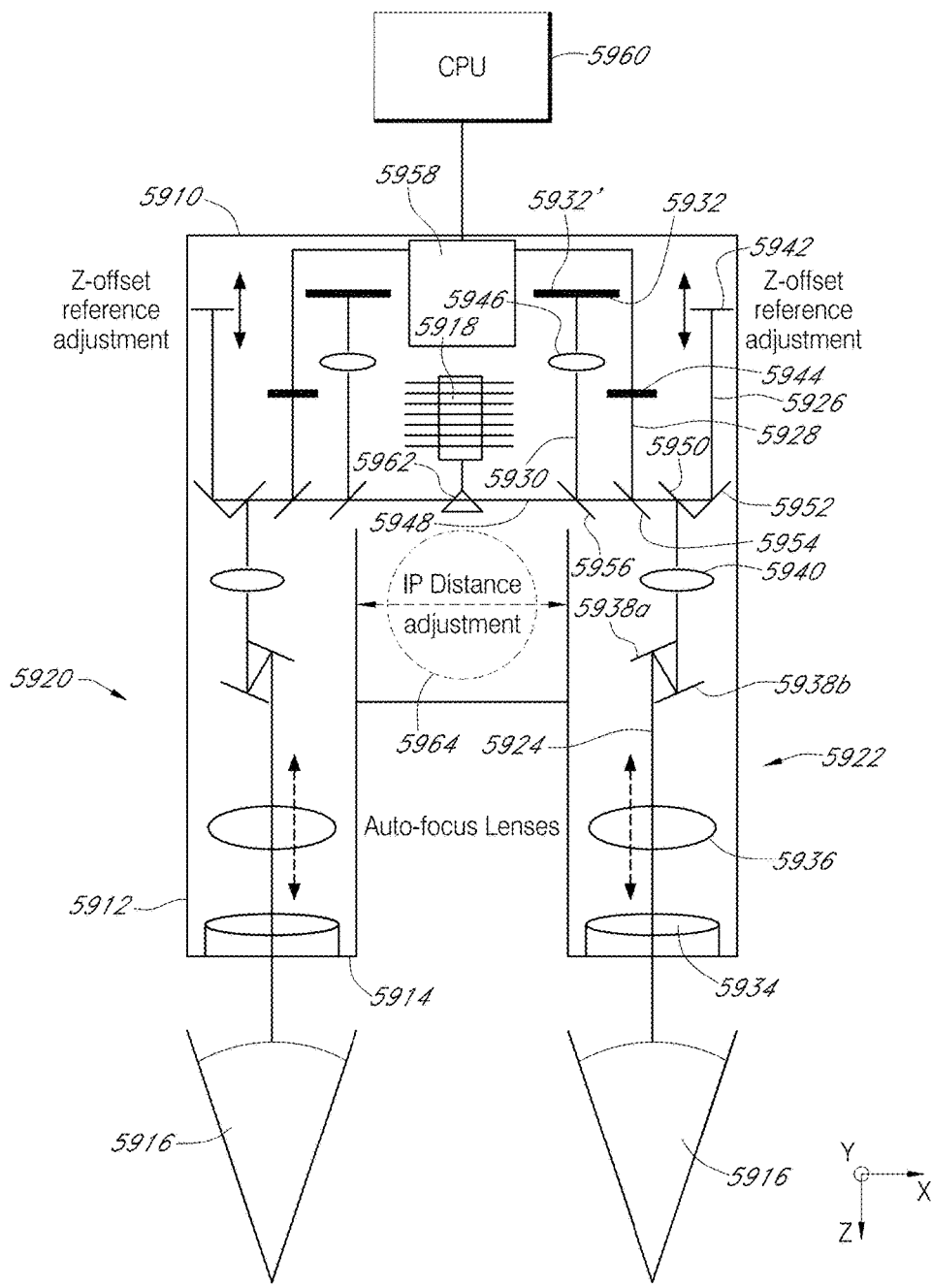
FIG. 59 is a schematic diagram of one embodiment of an OCT device as described herein.

An alternative configuration, for example, is shown in FIG. 59. This embodiment includes a housing 5910 including a pair of eyepieces 5912 having light-occluding, hygienic eyepiece covers 5914 that receive the subject's eyes 5916. Within the housing 5910 is a light source 5918, which may comprise for example a swept light source that directs light into left and right hand portions 5920, 5922 of the system for left and right eyes 5916, respectively. Each of the left and right hand portions 5920, 5922 includes an interferometer comprising a test arm 5924 that extends into the eyepiece 5912 and through to the eye 5916 as well as a reference arm 5926 and a light detection arm 5928. Each of the left and right hand portions 5920, 5922 also includes an arm 5930 having a fixation target 5932 therein.

The test arm 5924 includes an ocular lens 5934 proximal to the eye 5916, auto-focus optics 5936 that is adjustable so as to selectively vary the shape of the beam directed into the eye 5916. The auto-focus optics 5936 may include an auto-focus lens system comprising one or more lenses. In certain embodiments, at least one lens is mounted to a translation stage, which may, for example, be longitudinally translatable, so as to vary the position of the lens and possibly the optical power of the auto-focus optics 5936 and/or the vergence of the light exiting the ocular 5934. The auto-focus optics 5936 may additionally include variable astigmatic correction optics that can be selectively adjusted to alter the astigmatism, and thus astigmatic correction, introduced into the test arm. Stokes' lenses or other types of optical element(s) having variable astigmatism that can be selectively controlled, for example, by altering the position or orientation of the astigmatism correction optics, may be used. In this manner, the magnitude and axis of cylinder may be adjusted so as to offset and/or correct astigmatism in the eye 5916 of the subject. As described above, adjustments to the auto-focus optics 5936 may permit a more focused beam to be directed into the eye 5916 and may also be used to determine the refractive error (including, e.g., sphere, cylinder, and/or axis) of the subject.

The test arm 5924 additionally includes scanners 5938*a*, 5938*b* such as galvanometers. These scanners 5938*a*, 5938*b* may comprise mirrors that are moved in different (for example, orthogonal) directions to scan the beam, for example, in x and y directions (with z being the longitudinal direction along the optical axis of the eye 5916). The test arm 5924 may further comprise one or more lenses 5940 that can alter the vergence of light from the light source 5918 and/or the fixation target 5932 to simulate variations in distance to the fixation target. For example, the one or more lenses 5940 can be configured to transmit collimated light to simulate distance viewing conditions or can be configured to diverge the light to simulate near target viewing.

The reference arm 5926 can include a mirror/reflector 5942 (or other mechanism to modify the optical path length) that is translatable along the z-direction to provide a z-offset reference adjustment. Translation of this reflector 5942 adjusts the z-offset of the OCT system.

A detector 5944 is included in the light detection arm 5928. This detector 5944 may comprise a single photodetector in some embodiments, for example, when a swept light source is used. In alternative embodiments, a detector array, linear or 2-D, may be employed. Examples include CCD and CMOS detector arrays.

The fixation target arm 5930 includes a lens 5946 and a display 5932' for displaying the fixation target 5932. The display 5932' may comprise a FLCOS, LCD, or other display device. This display 5932' may display text, graphics, images, movies, etc. for viewing by the subject while the exam is being performed.

In the embodiment shown in FIG. 59, the light source 5918, test and reference arms 5924, 5926, as well as light detection arm 5928 and fixation target arm 5930 are coupled to a common optical path 5948, although other arrangements and configurations are possible. A series of beam splitters are used to couple the different arms to the common optical path 5948. A test arm beam splitter 5950 couples the test arm 5924 to the common optical path 5948 and thus to the light source 5918. A reference arm beam splitter 5952 also couples the reference arm 5926 to the common optical path 5948 and to the light source 5918. A light detection arm beam splitter 5954 couples the light detection arm 5928 to the common optical path 5948 and thus to the test and reference arms 5924, 5926. Additionally, a fixation target arm beam splitter 5956 couples the fixation target arm 5930 to the common optical path 5948 and to the test arm 5924 through which the eye 5916 of the subject views the fixation target 5932.

Accordingly, a light beam emitted by the light source 5918 is directed by the test arm beam splitter 5950 into the test arm 5924 wherein the beam is scanned, e.g., in orthogonal x and y directions using the scanning galvanometers 5938*a*, 5938*b*. The beam passes through the auto-focus optics 5936 and the ocular 5934 into the subject's eye 5916. The light beam is reflected from the subject's eye 5916 and returns along the test arm 5924. The beam is coupled into the common optical path 5948 by the test arm beam splitter 5950.

Light from the light source 5918 is also is directed by the reference arm beam splitter 5952 into the reference arm 5926 wherein the beam is reflected from the mirror 5942 and returned to the common optical path 5948 via the reference arm beam splitter 5952. The mirror 5942 is scanned, for example, in the z-direction, to produce an A-scan (for example, using time-domain OCT) and/or to determine the depth into the eye 5916 that is probed/imaged by the OCT instrument.

The light returned from the test arm 5924 and the reference arm 5926 combines and interferes. The light from the test arm 5924 and the reference arm 5926 are directed into the light detection arm 5928 by the light detection arm beam splitter 5954. The interference can thus be monitored by the detector 5944, which is electrically coupled to a digital signal processor 5958 in the embodiment shown in FIG. 59. A CPU 5960 is also shown electrically connected to and in communication with the digital signal processor 5958.

Light from the fixation target 5932' is also coupled by the fixation target arm beam splitter 5956 into the common optical path 5948. This light is then coupled into the test arm 5924 via the test arm beam splitter 5950 such that the subject can view the fixation target 5932. The lens 5946 disposed with respect to the fixation target 5932 may, in some embodiments, collimate the light.

The left and the right portions 5920, 5922 may include similar optical components in certain embodiments. In various embodiments, a beam splitter 5962 is disposed with respect to the light source 5918 to couple some of the light from the light source to the left portion 5920 and to the subject's left eye 5916 and some of the light to the right portion 5922 and to the subject's right eye. An interpupillary adjustment control 5964 may be provided to adjust the interpupillary distance of the eyepieces 5912.

The optical layout can vary from that shown in FIG. 59. The system can be configured differently. For example, optical fiber (e.g., microfibers) may be used to provide the optical paths with optical fiber couplers coupling paths together. Integrated optics may be used. Additionally, different optical and electrical components can be employed. Additional components can be added or components can be removed. The methods used to test the eye 5916 may vary as well.

All of the methods and processes described above may be embodied in, and fully automated via, software code modules executed by one or more general purpose computers or processors. The code modules may be stored in any type of computer-readable medium or other computer storage device. Some or all of the methods may alternatively be embodied in specialized computer hardware.

Conditional language, for example, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

While the invention has been discussed in terms of certain embodiments, it should be appreciated that the invention is not so limited. The embodiments are explained herein by way of example, and there are numerous modifications, variations and other embodiments that may be employed that would still be within the scope of the present invention.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Additionally, the skilled artisan will recognize that any of the above-described methods can be carried out using any appropriate apparatus. Further, the disclosure herein of any particular feature, aspect, method, property, characteristic, quality, attribute, element, or the like in connection with various embodiments can be used in all other embodiments set forth herein. Additionally, processing steps may be added, removed, or reordered. A wide variety of designs and approaches are possible.

For purposes of this disclosure, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

What is claimed is:

1. An optical coherence tomography instrument comprising:
   an eyepiece for receiving at least one eye of a user;
   at least one target display visible through said eyepiece;
   a light source that outputs light that is directed through the eyepiece to the user's eye;
   an interferometer configured to produce optical interference using light reflected from the user's eye;
   an optical detector disposed so as to detect said optical interference; and
   electronics coupled to the target display and said detector and configured to provide an output based on optical coherence tomography measurements obtained using said interferometer,
   wherein said electronics are further configured to produce features on said target display of varying size and receive user responses to test the user's visual acuity, and
   wherein the optical coherence tomography instrument is configured to allow the user to self-administer the visual acuity test.

2. The optical coherence tomography instrument of claim 1, further comprising a voice recognition interface to receive user responses.

3. The optical coherence tomography instrument of claim 1, further comprising a keypad to receive user responses.

4. The optical coherence tomography instrument of claim 1, further comprising a toggle to receive user responses.

5. The optical coherence tomography instrument of claim 1, further comprising a button to receive user responses.

6. The optical coherence tomography instrument of claim 1, further comprising a touch pad to receive user responses.

7. The optical coherence tomography instrument of claim 1, further comprising a touch sensor to receive user responses.

8. The optical coherence tomography instrument of claim 1, further comprising a foot pedal to receive user responses.

9. The optical coherence tomography instrument of claim 1, further comprising a knob to receive user responses.

10. The optical coherence tomography instrument of claim 1, further comprising a rotating handle to receive user responses.

11. The optical coherence tomography instrument of claim 1, further comprising a microphone to receive user responses.

12. The optical coherence tomography instrument of claim 1, wherein the detector comprises a CCD or CMOS detector array and the electronics comprises a microprocessor.

13. The optical coherence tomography instrument of claim 1, wherein the electronics are configured to test the user's visual acuity in both eyes simultaneously.

14. The optical coherence tomography instrument of claim 1, wherein the electronics are configured to test the user's visual acuity in one eye at a time.

15. The optical coherence tomography instrument of claim 1, wherein the electronics are configured to perform an assessment of visual acuity and output the assessment of visual acuity through an output device.

16. The optical coherence tomography instrument of claim 15, wherein the output device comprises a printer or a display.

17. The optical coherence tomography instrument of claim 1, wherein the at least one target display comprises a first target display and a second target display.

18. The optical coherence tomography instrument of claim 1, further comprising a fixation marker control system configured to display a fixation marker visible by the user.

19. The optical coherence tomography instrument of claim 18, wherein the fixation marker can be configured to move.

* * * * *